US006835824B1

(12) United States Patent
Burks, Jr. et al.

(10) Patent No.: US 6,835,824 B1
(45) Date of Patent: Dec. 28, 2004

(54) PEANUT ALLERGENS AND METHODS

(75) Inventors: A. Wesley Burks, Jr., Little Rock, AR (US); J. Steven Stanley, Little Rock, AR (US); Gary A. Bannon, Little Rock, AR (US); Gael Cockrell, Cabot, AR (US); Ricki M. Helm, Little Rock, AR (US)

(73) Assignee: University of Arkansas, Little Rock, AR (US)

( * ) Notice: Subject to any disclaimer, the term of this patent is extended or adjusted under 35 U.S.C. 154(b) by 0 days.

(21) Appl. No.: 09/191,593

(22) Filed: Nov. 13, 1998

Related U.S. Application Data

(63) Continuation of application No. 08/717,933, filed on Sep. 23, 1996, now abandoned.
(60) Provisional application No. 60/009,455, filed on Dec. 29, 1995.

(51) Int. Cl.[7] ............................................. C07H 21/04
(52) U.S. Cl. ................ 536/23.6; 536/25.32; 424/275.1; 435/320.1
(58) Field of Search .............................. 536/23.1, 23.6, 536/25.32; 424/275.1, 184.1; 435/69.1, 320.1

(56) References Cited

U.S. PATENT DOCUMENTS

| 3,645,852 A | 2/1972 | Axen et al. ..................... 195/68 |
| 3,720,760 A | 3/1973 | Bennich et al. ................. 424/1 |
| 4,535,010 A | 8/1985 | Axen et al. .................. 427/246 |

OTHER PUBLICATIONS

Phadebas Rast® Radioimmunoassay Reagents for 100 or 300 Tubes, Pharmacia Diagnostics AB, Uppsala Sweden 1985, Revised Jan. 1988.
G. Cockrell BS, C Connaughton BS, RM Helm, Ph.D., AW Burks, MD, Monoclonal Antibody Enzyme–Linked Immunosorbent Assay (ELISA) for ARA H 1, A Major Peanut Allergen, Abstract 613, The Journal of Allergy and Clinical Immunology, vol. 89, No. 1, Part 2, Jan. 1992, The American Acadamy of Allergy and Immunology.
S.L. Hefle, M.S., J. P. Folgert, B.S., F.S., Chu, PHD, R.K. Bush, M.D., Abstract 209, Isolation of Peanut Allergens Using Monoclonal Antibodies.
A.W. Burks, M.D., L.W. Williams, M.D., R.M. Helm, PH.D., Abstract 210, Production of Murine Monoclonal (mAb) Antibodies to ARA h I, A 63.5 kD Allergen in Peanuts.
A.W. Burks, M.D., R.M. Helm, PHD, L.W. Williams, M.D., T. O'Brien, PH.D., Abstract 211, Identification of a Second Major Peanut Allergen in Patients with Atopic Dermatitis and Peanut Hypersensitivity. The Journal of Allergy and Clinical Immunology, vol. 87, No. 1, Part 2, Jan. 1991, The American Acadamy of Allergy and Immunology.

Directions For Use, Pharmacia Diagnostics AB, Uppsala, Sweden 1985, Revised May 1988.
Susan M. Pollart, M.D. et al., Identification, Quantitation, and Purification of Cockroach Allergens Using Monoclonal Antibodies, J. Allergy Clin. Immunol., Feb. 1991; 87:511–521.
M.U. Keating, M.D., et al., Immunoassay of Peanut Allergens in Food–Processin Material and Finished Foods, J. Allergy Clin. Immunol., Jul. 1990; 86:41–44.
Martin D. Chapman, Monoclonal Antibodies as Structural Probes for Mite, Cat, and Cockroach Allergens, Advances in the Biosciences, vol. 74, © 1989.
A. Wesley Burks, et al., Identification of a Major Peanut Allergen, ARA H I, in Patients With Atopic Dermatitis and Positive Peanut Challenges; Reprinted from The Journal of Allergy and Clinical Immunology, St. Louis, vol. 88, No. 2, pp. 172–179, Aug. 1991.
A. Wesley Burks, M.D., et al., Identification and Characterization of a Second Major Peanut Allergen, ARA H II, With use of the SERA of Patients with Atopic Dermatitis and Positive Peanut Challenge, Reprinted from The Journal of Allergy and Clinical Immunology, St. Louis, vol. 90, No. 6, pp. 962–969, Dec., 1992.
Alister Voller et al., Enzyme–Linked Immunosorbent Assay, Chapter 17 in N.R. Rose ed. Manual of Clinical Laboratory Immunology, Third Edition, 1986, Chapter 17, p. 99–109.
Donald Barnett et al., Partial Characterization of an Allergenic Glycoprotein from Peanut (*Arachis Hypogaea* L.), Biochimica et Biophysica Acta 882:97–105, 1986.
Thomas C. Thomas et al., Purification of Membrane Proteins, Methods in Enzymology, vol. 182:499–520, 1990.
Sevier et al., Monoclonal Antibodies in Clinical Immunology, Clinical Chemistry, 27:11, 1797–1806, 1981.
Kohler et al., Continuous Cultures of Fused Cells Secreting Antibody of Predefined Specificity, Nature, 256, 495–497, 1975.
A. Wesley Burks et al., Isolation, Identification, and Characterization of Clones Encoding Antigens Responsible for Peanut Hypersensitivity, Allergens, Immunotherapy and Management, Int. Arch. Allergy Immunol 506 1995.

(List continued on next page.)

*Primary Examiner*—Laurie Scheiner
(74) *Attorney, Agent, or Firm*—Choate, Hall & Stewart; Brenda H. Jarrell; Charles E. Lyon

(57) ABSTRACT

One of the major peanut allergens, Ara h I, was selected from cDNA expression library clones using Ara h I specific oligo-nucleotides and polymerase chain reaction technology. The Ara h I clone identified a 2.3 kb mRNA species on a Northern blot containing peanut poly A+RNA. DNA sequence analysis of the cloned inserts revealed that the Ara h I allergen has significant homology with the vicilin seed storage protein family found in most higher plants. The isolation of the Ara h I clones allowed the synthesis of this protein in *E. coli* cells and subsequent recognition of this recombinant protein in immunoblot analysis using serum IgE from patients with peanut hypersensitivity.

6 Claims, 36 Drawing Sheets

OTHER PUBLICATIONS

Figure 1:
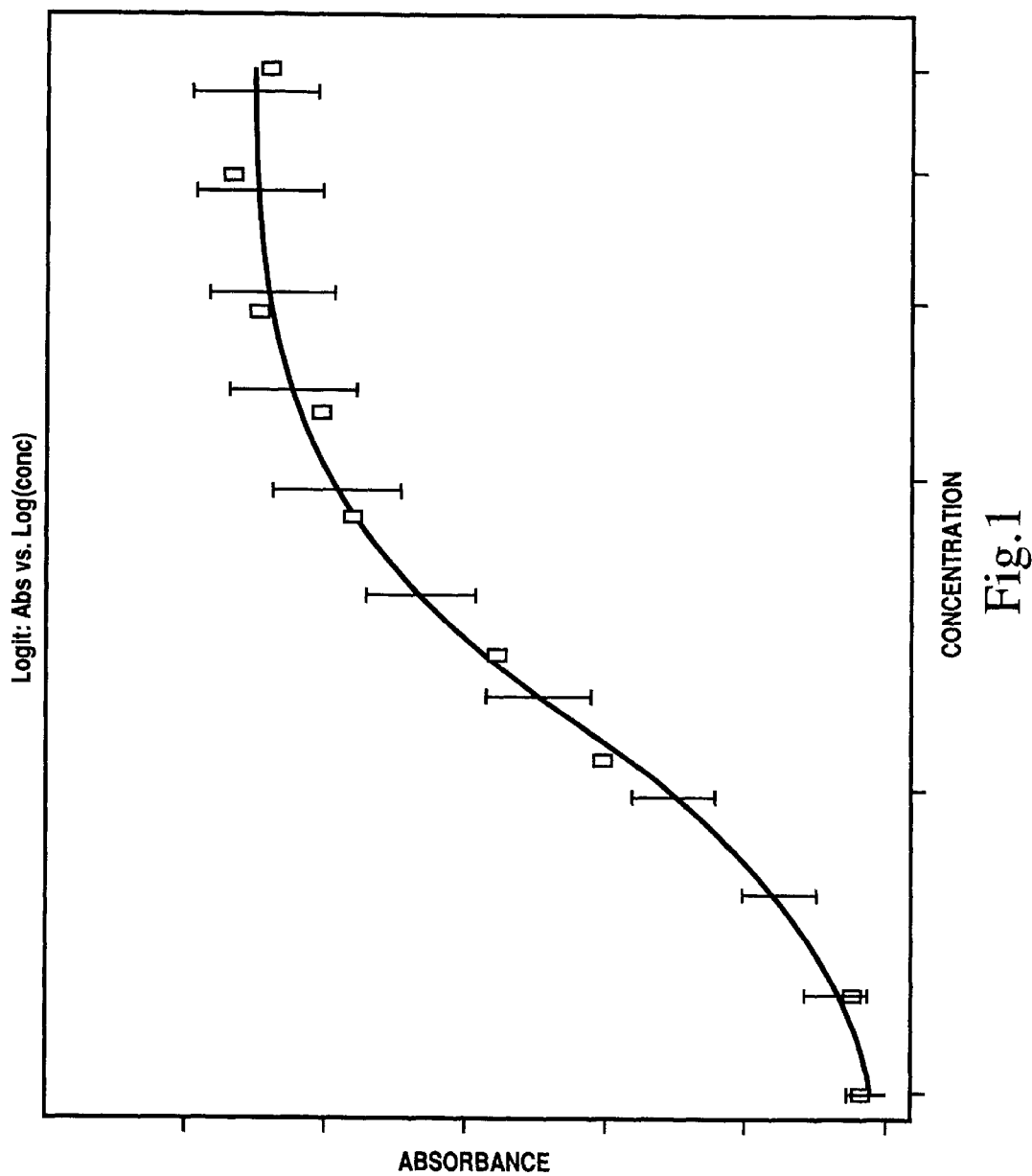

A. Wesley Burks et al., Recombinant Peanut Allergen ARA H 1 Expression and IGE Binding in Patients With Peanut Hypersensitivity, J. Clin. Invest., vol. 96, Oct. 1995, 1715–1721.

A. Wesley Burks et al., Epitope Specificity of the Major Peanut Allergen, ARA H II, J. Allergy Clin. Immunol, Feb. 1995, 607–611.

Abstracts 765–772, The Journal of Allergy and Clinical Immunology, vol. 95, No. 1, Part 2, Jan. 1995.

Abstracts 585–592, The Journal of Allergy and Clinical Immunology, vol. 97, No. 1, Part 3, Jan. 1996.

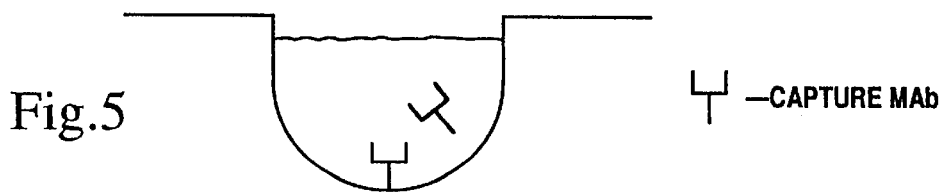
Fig.5 — CAPTURE MAb
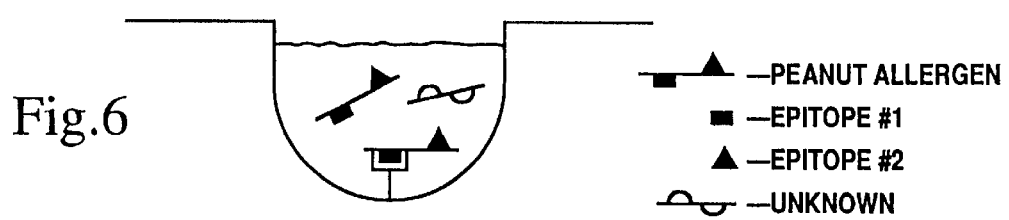
Fig.6
— PEANUT ALLERGEN
■ — EPITOPE #1
▲ — EPITOPE #2
— UNKNOWN
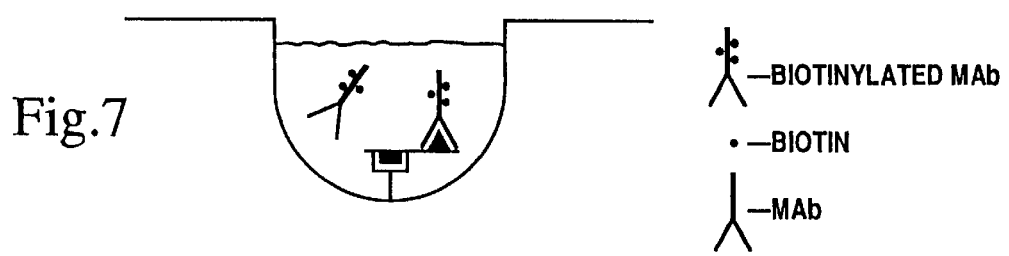
Fig.7
— BIOTINYLATED MAb
• — BIOTIN
— MAb
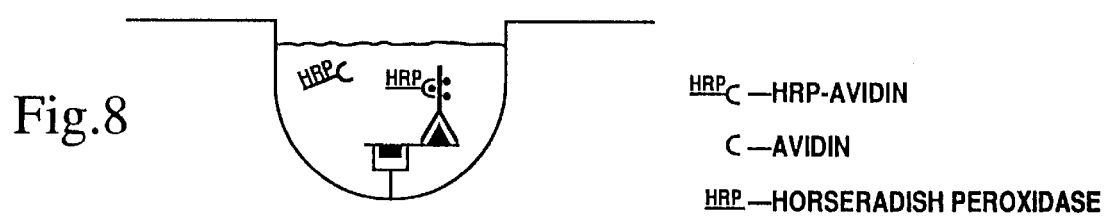
Fig.8
HRPC — HRP-AVIDIN
C — AVIDIN
HRP — HORSERADISH PEROXIDASE
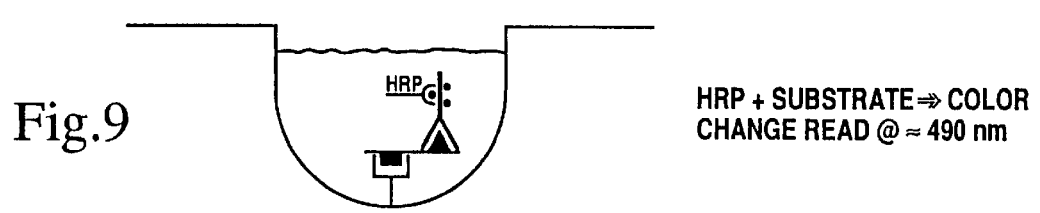
Fig.9
HRP + SUBSTRATE ⇒ COLOR
CHANGE READ @ ≈ 490 nm AATAATCATATATATTCATCAATCATCTATATAAGTAGTAGCAGGAGCAATGAGAGGGAG 60
------------------------------------------------------------.............

GGTTTCTCCACTGATGCTGTTGCTAGGGATCCTTGTCCTGGCTTCAGTTTCTGCAACGCA 120
............................................................

TGCCAAGTCATCACCTTACCAGAAGAAAACAGAGAACCCCTGCGCCCAGAGGTGCCTCCA 180
G.........C.------TT.CCG....................................

GAGTTGTCAACAGGAACCGGATGACTTGAAGCAAAAGGCATGCGAGTCTCGCTGCACCAA 240
............................................................

GCTCGAGTATGATCCTCGTTGTGTCTATGATCCTCGAGGACACACTGGCACCACCAACCA 300
................................-----------.........G.........

ACGTTCCCCTCCAGGGGAGCGGACACGTGGCCGCCAACCCGGAGACTACGATGATGACCG 360
....CA......................................................

CCGTCAACCCCGAAGAGAGGAAGGAGGCCGATGGGGACCAGCTGGACCGAGGGAGCGTGA 420
...........................................A................

AAGAGAAGAAGACTGGAGACAACCAAGAGAAGATTGGAGGCGACCAAGTCATCAGCAGCC 480
............................................................

ACGGAAAATAAGGCCCGAAGGAAGAGAAGGAGAACAAGAGTGGGGAACACCAGGTAGCCA 540
...........................................................G.

TGTGAGGGAAGAAACATCTCGGAACAACCCTTTCTACTTCCCGTCAAGGCGGTTTAGCAC 600
G.............A.............................................

CCGCTACGGGAACCAAAACGGTAGGATCCGGGTCCTGCAGAGGTTTGACCAAAGGTCAAG 660
.................................C.........................A

GCAGTTTCAGAATCTCCAGAATCACCGTATTGTGCAGATCGAGGCCAAACCTAACACTCT 720
.......................................G...................

TGTTCTTCCCAAGCACGCTGATGCTGATAACATCCTTGTTATCCAGCAAGGGCAAGCCAC 780
..................................................A........

CGTGACCGTAGCAAATGGCAATAACAGAAAGAGCTTTAATCTTGACGAGGGCCATGCACT 840
............................................................

CAGAATCCCATCCGGTTTCATTTCCTACATCTTGAACCGCCATGACAACCAGAACCTCAG 900
.............................................T..A...........

AGTAGCTAAAATCTCCATGCCCGTTAACACACCCGGCCAGTTTGAGGATTTCTTCCCGGC 960
..............G.............................................

GAGCAGCCGAGACCAATCATCCTACTTGCAGGGCTTCAGCAGGAATACGTTGGAGGCCGC 1020
....................A..............T.......................

CTTCAATGCGGAATTCAATGAGATACGGAGGGTGCTGTTAGAAGAGAATGCAGGAGGTGA 1080
...........................................................A..

FIG. 16

```
GCAAGAGGAGAGAGGGCAGAGGCGATGGAGTACTCGGAGTAGTGAGAACAATGAAGGAGT 1140
.............................C.....................---.T...........

GATAGTCAAAGTGTCAAAGGAGCACGTTGAAGAACTTACTAAGCACGCTAAATCCGTCTC 1200
...................................C............................

AAAGAAAGGCTCCGAAGAAGAGGGAGATATCACCAACCCAATCAACTTGAGAGAAGGCGA 1260
....................A---.........................T.....

GCCCGATCTTTCTAACAACTTTGGGAAGTTATTTGAGGTGAAGCCAGACAAGAAGAACCC 1320
...........................G..................................

CCAGCTTCAGGACCTGGACATGATGCTCACCTGTGTAGAGATCAAAGAAGGAGCTTTGAT 1380
................................................................

GCTCCCACACTTCAACTCAAAGGCCATGGTTATCGTCGTCGTCAACAAAGGAACTGGAAA 1440
................................C...............................

CCTTGAACTCGTGGCTGTAAGAAAAGAGCAACAACAGAGGGGACGGCGGGAA-------- 1492
............A.....................................CAAGAGTG

-GAAGAGGAGGACGAAGACGAAGAAGAGGAGGGAAGTAACAGAGAGGTGCGTAGGTACAC 1551
G.....A.....G.....T...........................................

AGCGAGGTTGAAGGAAGGCGATGTGTTCATCATGCCAGCAGCTCATCCAGTAGCCATCAA 1611
................................................................

CGCTTCCTCCGAACTCCATCTGCTTGGCTTCGGTATCAACGCTGAAAACAACCACAGAAT 1671
................................................................

CTTCCTTGCAGGTGATAAGGACAATGTGATAGACCAGATAGAGAAGCAAGCGAAGGATTT 1731
................................................................

AGCATTCCCTGGGTCGGGTGAACAAGTTGAGAAGCTCATCAAAAACCAGAAGGAATCTCA 1791
............T.................................G...G.....

CTTTGTGAGTGCTCGTCCTCAATCTCAATCTCAATCTCCGTCGTCTCCTGAGAAAGAGTC 1851
............................CG..----------------------...

TCCTGAGAAAGAGGATCAAGAGGAGGAAAACCAAGGAGGGAAGGGTCCACTCCTTTCAAT 1911
......A.........................................................

TTTGAAGGCTTTTAACTGAGAATGGAGGCAACTTGTTATGTATCGATAATAAGATCACGC 1971
................................A.................C..............

TTTTGTACTCTACTATCCAAAAACTTATCAATAAATAAAAACGTTTGTGCGTTGTTTCTC 2031
.......A..........................................................

CAAAAAAAA 2040
.........
```

FIG. 16 (Continued)

```
MRGRVSPLMLLLGILVLASVSATHAKSSPYQKKTENPCAQRCLQSCQQEPDDLKQKACESRCTKLEYDPR      70
CVYDPRGHTGTTNQRSPPGERTRGRQPGDYDDDRRQPRREEGGRWGPAGPREREREEDWRQPREDWRRPS     140
HQQPRKIRPEGREGEQEWGTPGSHVREETSRNNPFYFPSRRFSTRYGNQNGRIRVLQRFDQRSRQFQNLQ 210
NHRIVQIEAKPNTLVLPKHADADNILVIQQGQATVTVANGNNRKSFNLDEGHALRIPSGFISYILNRHDN    280
QNLRVAKISMPVNTPGQFEDFFPASSRDQSSYLQGFSRNTLEAAFNAEFNEIRRVLLEENAGGEQEERGQ    350
RRWSTRSSENNEGVIVKVSKEHVEELTKHAKSVSKKGSEEEGDITNPINLREGEPDLSNNFGKLFEVKPD  420
KKNPQLQDLDMMLTCVEIKEGALMLPHFNSKAMVIVVVNKGTGNLELVAVRKEQQQRGRREEEEDEDEEE    490
EGSNREVRRYTARLKEGDVFIMPAAHPVAINASSELHLLGFGINAENNHRIFLAGDKDNVIDQIEKQAKD 560
LAFPGSGEQVEKLIKNQKESHFVSARPQSQSQSPSSPEKESPEKEDQEEENQGGKGPLLSILKAFN
```

FIG. 16 (Continued)

```
                         D1
MRGRVSPLMLLLGILVLASV SATHAKSSPYQKKTENRCAQRLLGSQQEPRDL KQKACPSRCTELEXDRR  70
                    P1                P2

D2                                    D3
GVY DPRGHTGTTNQRSPP EEKTKQRQTQEDSEHQEKAEI GRWGPAGPR ERERREDRRQPRELRRRS  140
P3                                              P4

HQCPS CIKPEQRECECENQIEEEMYREETCRNNPYY PSRRFSTRYGNQNGRIRVLQRFDQRSRQFQNLQ  210
    P5

NHRIVQIEAK PNTLVLPKHA DADNILVIQQGQATVTVANGNNRKSFYLDEGHALRIPSGPISYILNRH DN  280
          P6                                            P7
  D4                                        D5
QNLRVAKI SMPYNTPQPEDRPPASSEDQSSYLQGFSRNELEAAFN AEFNEIRRVL HENAGGEQRERGQ  350
        P8

D6                              D7
RRWSTRSSENM EGVIVKVREEHYES LTKHAKSV SKKGSEESGDITNPINLRSGPDESNN EGKLESVKFD  420
                                   P9                         P10

D8                                    D9
KKNPQLQDLDMMLTCVEIKEGALMLPHFNSKAMVIVY NEGTGHLELVAVR KEQQQRGRREEEEDEDEER  490

D10              D11
EGSNREVRRYIASLEEGDVEIMPAAHPVAI NSSELRLGEGIRA ENNKRIPL AGPNPTEDQIERIAKD  560

D12
LAFPNGEQVERLIKNQKSHY VSARPQSQSQ RSSPEKESPREEDEEENQGGKGPLL SILKAFN  626
                                P11

[ ] Predicted (P1-P11)
░░ Determined (D1-D12)
```

FIG. 23B

```
                    4         5         6         7
          90       100       110       120       130
           |         |         |         |         |
     TNQRSPPGERTRGRQPGDYDDDRRQPRREEGGRWGPAGPREREREEDWRQPR
     TNQRSPPGER
       QRSPPGERTR
         SPPGERTRGR
           PGERTRGRQP
             ERTRGRQPGD
               TRGRQPGDYD
                 GRQPGDYDDD
                   QPGDYDDDRR
                     GDYDDDRRQP
                       YDDDRRQPRR
                         DDRRQPRREE
                           RRQPRREEGG
                             QPRREEGGRW
                               RREEGGRWGP
                                 EEGGRWGPAG
                                   GGRWGPAGPR
                                     RWGPAGPRER
                                       GPAGPRERER
                                         AGPRERERER
                                           PRERERERED W
                                             ERERBEDWRQ
                                               ERBEDWRQPR
```

FIG. 24B

```
ACG AGG CTC ACC ATA CTA GTA GCC CTC GCC CTT TTC CTC CTC GCT GCC   48
Thr Arg Leu Thr Ile Leu Val Ala Leu Ala Leu Phe Leu Leu Ala Ala

CAC GCA TCT GCG AGG CAG CAG TGG GAA CTC CAA GGA GAC AGA AGA TGC   95
His Ala Ser Ala Arg Gln Gln Trp Glu Leu Gln Gly Asp Arg Arg Cys

CAG AGC CAG CTC GAG AGG GCG AAC CTG AGG CCC TGC GAG CAA CAT CTC  144
Gln Ser Gln Leu Glu Arg Ala Asn Leu Arg Pro Cys Glu Gln His Leu

ATG CAG AAG ATC CAA CGT GAC GAG GAT TCA TAT GAA CGG GAC CCG TAC  192
Met Gln Lys Ile Gln Arg Asp Glu Asp Ser Tyr Glu Arg Asp Pro Tyr

AGC CCT AGT CAG GAT CCG TAC AGC CCT AGT CCA TAT GAT CGG AGA GGC  240
Ser Pro Ser Gln Asp Pro Tyr Ser Pro Ser Pro Tyr Asp Arg Arg Gly

GCT GGA TCC TCT CAG CAC CAA GAG AGG TGT TGC AAT GAG CTG AAC GAG  288
Ala Gly Ser Ser Gln His Gln Glu Arg Cys Cys Asn Glu Leu Asn Glu

TTT GAG AAC AAC CAA AGG TGC ATG TGC GAG GCA TTG CAA CAG ATC ATG  336
Phe Glu Asn Asn Gln Arg Cys Met Cys Glu Ala Leu Gln Gln Ile Met

GAG AAC CAG AGC GAT AGG TTG CAG GGG AGG CAA CAG GAG CAA CAG TTC  384
Glu Asn Gln Ser Asp Arg Leu Gln Gly Arg Gln Gln Glu Gln Gln Phe

AAG AGG GAG CTC AGG AAC TTG CCT CAA CAG TGC GGC CTT AGG GCA CCA  432
Lys Arg Glu Leu Arg Asn Leu Pro Gln Gln Cys Gly Leu Arg Ala Pro

CAG CGT TGC GAC TTG GAC GTC GAA AGT GGC GGC AGA GAC AGA TAC TAA  480
Gln Arg Cys Asp Leu Asp Val Glu Ser Gly Gly Arg Asp Arg Tyr
```

FIG. 27

FIG. 30
*Ara h II*
```
D1
TRLTILVALALFLLAAHASARQQWELQGDRRCQSQLERANLRPCEQHLMQ    50
                              P1
    D2                        D3
KIQRDEDSYERDPYSPSQDPYSPSPYDRRGAGSSQHQERCCNELNEFENN    100
    P2
QRCMCEALQQIMENQSDRLQGRQQEQQFKRELRNLPQQCGLRAPQRCDLD    150
    P3
D4
VESGGRDRY                                             159
P4
```
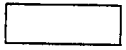 Predicted (P1-P4)
 Determined (D1-D4)

A

3

B

```
       50           60           70
        |            |            |
    MQKIQRDEDSYERDPYSPSQDP
    MQKIQRDEDS
       KIQRDEDSYE
          QRDEDSYERD
             DEDSYERDPY
                DSYERDPYSP
                   YERDPYSPSQ
                      RDPYSPSQDP
```

Control

● Y 59A
● E 60A
● R 61A
  D 62A
  P 63A
  Y 64A    Epitope 3
● S 65A
  P 66A
● S 67A
● Q 68A
● WT

FIG. 33

```
AATAATCATATATATTCATCAATCATCTATATAAGTAGTAGCAGGAGCAATGAGAGGGAG  60
----------------------------------------------..............

GGTTTCTCCACTGATGCTGTTGCTAGGGATCCTTGTCCTGGCTTCAGTTTCTGCAACGCA 120
............................................................

TGCCAAGTCATCACCTTACCAGAAGAAAACAGAGAACCCCTGCGCCCAGAGGTGCCTCCA 180
G.........C.------TT.CCG....................................

GAGTTGTCAACAGGAACCGGATGACTTGAAGCAAAAGGCATGCGAGTCTCGCTGCACCAA 240
............................................................

GCTCGAGTATGATCCTCGTTGTGTCTATGATCCTCGAGGACACACTGGCACCACCAACCA 300
.................................------------......G......

ACGTTCCCCTCCAGGGGAGCGGACACGTGGCCGCCAACCCGGAGACTACGATGATGACCG 360
....CA......................................................

CCGTCAACCCCGAAGAGAGGAAGGAGGCCGATGGGGACCAGCTGGACCGAGGGAGCGTGA 420
..................................................A........

AAGAGAAGAAGACTGGAGACAACCAAGAGAAGATTGGAGGCGACCAAGTCATCAGCAGCC 480
............................................................

ACGGAAAATAAGGCCCGAAGGAAGAGAAGGAGAACAAGAGTGGGGAACACCAGGTAGCCA 540
...........................................................G.

TGTGAGGGAAGAAACATCTCGGAACAACCCTTTCTACTTCCCGTCAAGGCGGTTTAGCAC 600
G................A..........................................

CCGCTACGGGAACCAAAACGGTAGGATCCGGGTCCTGCAGAGGTTTGACCAAAGGTCAAG 660
......................C...................................A

GCAGTTTCAGAATCTCCAGAATCACCGTATTGTGCAGATCGAGGCCAAACCTAACACTCT 720
..................................................G........

TGTTCTTCCCAAGCACGCTGATGCTGATAACATCCTTGTTATCCAGCAAGGGCAAGCCAC 780
..........................................................A........

CGTGACCGTAGCAAATGGCAATAACAGAAAGAGCTTTAATCTTGACGAGGGCCATGCACT 840
............................................................

CAGAATCCCATCCGGTTTCATTTCCTACATCTTGAACCGCCATGACAACCAGAACCTCAG 900
...........................................T..A.............

AGTAGCTAAAATCTCCATGCCCGTTAACACACCCGGCCAGTTTGAGGATTTCTTCCCGGC 960
...................................G.......................

GAGCAGCCGAGACCAATCATCCTACTTGCAGGGCTTCAGCAGGAATACGTTGGAGGCCGC 1020
.......................A................T..................

CTTCAATGCGGAATTCAATGAGATACGGAGGGTGCTGTTAGAAGAGAATGCAGGAGGTGA 1080
............................................................A..
```

FIG. 34

```
GCAAGAGGAGAGAGGGCAGAGGCGATGGAGTACTCGGAGTAGTGAGAACAATGAAGGAGT 1140
...............................C.....................---.T............

GATAGTCAAAGTGTCAAAGGAGCACGTTGAAGAACTTACTAAGCACGCTAAATCCGTCTC 1200
...............................C............................

AAAGAAAGGCTCCGAAGAAGAGGGAGATATCACCAACCCAATCAACTTGAGAGAAGGCGA 1260
.........................A---...........................T.....

GCCCGATCTTTCTAACAACTTTGGGAAGTTATTTGAGGTGAAGCCAGACAAGAAGAACCC 1320
..............................G..............................

CCAGCTTCAGGACCTGGACATGATGCTCACCTGTGTAGAGATCAAAGAAGGAGCTTTGAT 1380
..............................................................

GCTCCCACACTTCAACTCAAAGGCCATGGTTATCGTCGTCGTCAACAAAGGAACTGGAAA 1440
................................C.............................

CCTTGAACTCGTGGCTGTAAGAAAAGAGCAACAACAGAGGGGACGGCGGGAA-------- 1492
............A..................................CAAGAGTG

-GAAGAGGAGGACGAAGACGAAGAAGAGGAGGGAAGTAACAGAGAGGTGCGTAGGTACAC 1551
G.....A.....G.....T............................................

AGCGAGGTTGAAGGAAGGCGATGTGTTCATCATGCCAGCAGCTCATCCAGTAGCCATCAA 1611
..............................................................

CGCTTCCTCCGAACTCCATCTGCTTGGCTTCGGTATCAACGCTGAAAACAACCACAGAAT 1671
..............................................................

CTTCCTTGCAGGTGATAAGGACAATGTGATAGACCAGATAGAGAAGCAAGCGAAGGATTT 1731
..............................................................

AGCATTCCCTGGGTCGGGTGAACAAGTTGAGAAGCTCATCAAAAACCAGAAGGAATCTCA 1791
............T.................................G...G.....

CTTTGTGAGTGCTCGTCCTCAATCTCAATCTCAATCTCCGTCGTCTCCTGAGAAAGAGTC 1851
................................CG..---------------------...

TCCTGAGAAAGAGGATCAAGAGGAGGAAAACCAAGGAGGGAAGGGTCCACTCCTTTCAAT 1911
......A.........................................................

TTTGAAGGCTTTTAACTGAGAATGGAGGCAACTTGTTATGTATCGATAATAAGATCACGC 1971
................___..........A................C................

TTTTGTACTCTACTATCCAAAAACTTATCAATAAATAAAAACGTTTGTGCGTTGTTTCTC 2031
.......A..........................___.........................

CAAAAAAAA 2040
.........
```

FIG. 34 (Continued)

MRGRVSPLMLLLGILVLASVSATHAKSSPYQKKTENPCAQRCLQSCQQEPDDLKQKACESRCTKLEYDPR 70

CVYDPRGHTGTTNQRSPPGERTRGRQPGDYDDDRRQPRREEGGRWGPAGPREREREEDWRQPREDWRRPS 140

HQQPRKIRPEGREGEQEWGTPGSHVREETSR<u>NNPFYFPSRR</u>FSTRYGNQNGRIRVLQRFDQRSRQFQNLQ 210
                                                 Peptide III

NHRIVQIEAKPNTLVLPKHADADNILVIQQGQATVTVANGNNRKSFNLDEGHALRIPSGFISYILNRHDN 280

QNLRVAKISMPVNTPGQFEDFFPASSRDQSSYLQGFSRNTLEAAFNAEFNEIRRVLLEENAGGEQEERGQ 350

RRWSTRSSENNEGVIVKVSKEHVEELTKHAKSVSK<u>KGSEEEGDITNPINLR</u>EGEPDLSNNFGKLFEVKPD 420
                                                      Peptide II

KKNPQLQDLDMMLTCVEIKEGALMLPHFNSKAMVIVVVNKGTGNLELVAVRKEQQQRGRREEEEDEDEEE 490

EGSNREVRRYTARLKEGDVFIMPAAHPVAINASSELHLLGFGINAENNHR<u>IFLAGDKDNVIDQIEK</u>QAKD 560
                                                                           Peptide I

LAFPGSGEQVEKLIKNQKESHFVSARPQSQSQSPSSPEKESPEKEDQEEENQGGKGPLLSILKAFN

FIG. 34 (Continued)

SEQUENCE LISTING (1) GENERAL INFORMATION:

(iii) NUMBER OF SEQUENCES:  67

(2) INFORMATION FOR SEQ ID NO:  1:

(i) SEQUENCE CHARACTERISTICS:
       (A) LENGTH:  32 amino acid residues
       (B) TYPE:  Amino acid sequence
       (C) STRANDEDNESS: Not Applicable
       (D) TOPOLOGY:  Unknown (ii) MOLECULE TYPE:  Glycoprotein
       (A) DESCRIPTION: 32 N-terminal amino acid residue
           sequence of a 17 kD protein/allergen (upper band)
           isolated from a crude extract of peanuts (Arachis
           hypogaea L.) identified as Ara h II (IUIS/WHO)

(iii) HYPOTHETICAL:  No (iv) ANTI-SENSE:  Not applicable (v) FRAGMENT TYPE:  N-terminal fragment

```
       (vi) ORIGINAL SOURCE:
            (A) ORGANISM:  Arachis hypogaea L.
            (B) STRAIN:  Southeastern runners
            (C) INDIVIDUAL ISOLATE:  Commercial lots North
                Carolina State Univ.
            (D) DEVELOPMENTAL STAGE:  Mature raw peanuts
            (E) HAPLOTYPE:  Not applicable
            (F) TISSUE TYPE:  Mature peanuts
            (G) CELL TYPE:  Not applicable
            (H) CELL LINE:  Not applicable
            (I) ORGANELLE:  Not applicable (vii) IMMEDIATE SOURCE:  Crude soluble whole peanut extract
            (A) LIBRARY:  Not applicable
            (B) CLONE:  Not applicable (viii) POSITION IN GENOME:  Not applicable (ix) FEATURE:
            (A) NAME/KEY:
            (B) LOCATION:  Not registered
            (C) IDENTIFICATION METHOD:  Not completed
            (D) OTHER INFORMATION:  Ara h II allergen isolated
                from crude extract of Arachis hypogaea L with an
                apparent molecular wt of 17 kD that binds to IgE
                in human serum from patients with peanut
                immediate hypersensitivity (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:  1:

Xaa  Gln  Gln  Xaa  Glu  Leu  Gln  Xaa  Asp  Xaa  Xaa
1                   5                        10

Xaa  Gln  Ser  Gln  Leu  Glu  Arg  Ala  Asp  Leu  Arg
          15                       20

Pro  Gly  Glu  Gln  Xaa  Leu  Met  Xaa  Lys  Ile
          25                  30

(2) INFORMATION FOR SEQ ID NO:  2:

(i) SEQUENCE CHARACTERISTICS:
            (A) LENGTH:  32 amino acid residues
            (B) TYPE:  Amino acid sequence
            (C) STRANDEDNESS: Not Applicable
            (D) TOPOLOGY:  Unknown (ii) MOLECULE TYPE:  Glycoprotein
            (A) DESCRIPTION: 32 N-terminal amino acid residue
                sequence of a 17 kD protein/allergen (lower band)
                isolated from a crude extract of peanuts (Arachis
                hypogaea L.) identified as Ara h II (IUIS/WHO)

(iii) HYPOTHETICAL:  No (iv) ANTI-SENSE:  Not applicable (v) FRAGMENT TYPE:  N-terminal fragment (vi) ORIGINAL SOURCE:
            (A) ORGANISM:  Arachis hypogaea L.
            (B) STRAIN:  Southeastern runners
            (C) INDIVIDUAL ISOLATE:  Commercial lots North
                Carolina State Univ.
            (D) DEVELOPMENTAL STAGE:  Mature raw peanuts
```

```
            (E) HAPLOTYPE:  Not applicable
            (F) TISSUE TYPE:  Mature peanuts
            (G) CELL TYPE:  Not applicable
            (H) CELL LINE:  Not applicable
            (I) ORGANELLE:  Not applicable (vii) IMMEDIATE SOURCE:  Crude soluble whole peanut extract
            (A) LIBRARY:  Not applicable
            (B) CLONE:  Not applicable (viii) POSITION IN GENOME:  Not applicable (ix) FEATURE:
            (A) NAME/KEY:
            (B) LOCATION:  Not registered
            (C) IDENTIFICATION METHOD:  Not completed
            (D) OTHER INFORMATION:  Ara h II allergen isolated
                from crude extract of Arachis hypogaea L with an
                apparent molecular wt of 17 kD that binds to IgE
                in human serum from patients with peanut
                immediate hypersensitivity (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:  2:

Xaa  Gln  Gln  Xaa  Glu  Leu  Gln  Asp  Leu  Glu  Xaa
 1              5                             10

Xaa  Gln  Ser  Gln  Leu  Glu  Asp  Ala  Asn  Leu  Arg
               15                        20

Pro  Arg  Glu  Gln  Xaa  Leu  Met  Xaa  Lys  Ile
          25                   30

(2) INFORMATION FOR SEQ ID NO:  3:

(i) SEQUENCE CHARACTERISTICS:
            (A) LENGTH:  9 amino acid residues
            (B) TYPE:  Amino acid sequence
            (C) STRANDEDNESS: Not Applicable
            (D) TOPOLOGY:  Unknown (ii) MOLECULE TYPE:  Glycoprotein
            (A) DESCRIPTION: 9 N-terminal amino acid residue
                sequence of a 17 kD protein/allergen (lower band)
                isolated from a crude extract of peanuts (Arachis
                hypogaea L.) identified as Ara h II (IUIS/WHO)

(iii) HYPOTHETICAL:  No (iv) ANTI-SENSE:  Not applicable (v) FRAGMENT TYPE:  N-terminal fragment (vi) ORIGINAL SOURCE:
            (A) ORGANISM:  Arachis hypogaea L.
            (B) STRAIN:  Southeastern runners
            (C) INDIVIDUAL ISOLATE:  Commercial lots North
                Carolina State Univ.
            (D) DEVELOPMENTAL STAGE:  Mature raw peanuts
            (E) HAPLOTYPE:  Not applicable
            (F) TISSUE TYPE:  Mature peanuts
            (G) CELL TYPE:  Not applicable
            (H) CELL LINE:  Not applicable
            (I) ORGANELLE:  Not applicable
```

```
    (vii) IMMEDIATE SOURCE:  Crude soluble whole peanut extract
          (A) LIBRARY:  Not applicable
          (B) CLONE:  Not applicable (viii) POSITION IN GENOME:  Not applicable (ix) FEATURE:
          (A) NAME/KEY:
          (B) LOCATION:  Not registered
          (C) IDENTIFICATION METHOD:  Not completed
          (D) OTHER INFORMATION:  Ara h II allergen isolated
              from crude extract of Arachis hypogaea L with an
              apparent molecular wt of 17 kD that binds to IgE
              in human serum from patients with peanut
              immediate hypersensitivity (x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO:  3:

Xaa  Gln  Gln  Xaa  Glu  Leu  Gln  Asp  Leu
1                   5

(2) INFORMATION FOR SEQ ID NO:  4:

(i) SEQUENCE CHARACTERISTICS:
          (A) LENGTH:  1949 bases
          (B) TYPE:  nucleic acid
          (C) STRANDEDNESS:  double
          (D) TOPOLOGY:  linear (ii) MOLECULE TYPE:  cDNA to mRNA
          (A) DESCRIPTION: identified as Ara h I Alpha P17

(iii) HYPOTHETICAL:  No (iv) ANTI-SENSE:  No (v) FRAGMENT TYPE:  Not applicable (vi) ORIGINAL SOURCE:
          (A) ORGANISM:  Arachis hypogaea
          (B) STRAIN:  Florunner
          (C) INDIVIDUAL ISOLATE:  Clone P17
          (D) DEVELOPMENTAL STAGE:  Seed
          (E) HAPLOTYPE:  Not applicable
          (F) TISSUE TYPE:  Seed mRNA, cDNA library
          (G) CELL TYPE:  Not applicable
          (H) CELL LINE:  Not applicable
          (I) ORGANELLE:  Not applicable (vii) IMMEDIATE SOURCE:
          (A) LIBRARY:  Florunner seed cDNA expression
              library in Uni-ZAP  XR vector
          (B) CLONE:  P17

(viii) POSITION IN GENOME:
          (A) CHROMOSOME/SEGMENT:  Not applicable
          (B) MAP POSITION:  Not applicable
          (C) UNITS:  Not applicable (ix) FEATURE:
          (A) NAME/KEY:  CDS
          (B) LOCATION:  3..1847
          (C) IDENTIFICATION METHOD:  By agreement with
              protein information and established
              consensus sequence
```

(D) OTHER INFORMATION: Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 4:

| | | |
|---|---|---|
| CAATGAGAGG GAGGGTTTCT CCACTGATGC TGTTGCTTGG GATCCTTGTC | 50 |
| CTGGCTTCAG TTTCTGCAAC GCAGGCCAAG TCACCTTACC GGAAAACAGA | 100 |
| GAACCCCTGC GCCCAGAGGT GCCTCCAGAG TTGTCAACAG GAACCGGACG | 150 |
| ACTTGAAGCA AAAGGCATGC GAGTCTCGCT GCACCAAGCT CGAGTATGAT | 200 |
| CCTCGTTGTG TCTATGACAC TGGCGCCACC AACCAACGTC ACCCTCCAGG | 250 |
| GGAGCGGACA CGTGGCCGCC AACCCGGAGA CTACGATGAT GACCGCCGTC | 300 |
| AACCCCGAAG AGAGGAAGGA GGCCGATGGG GACCAGCTGA ACCGAGGGAG | 350 |
| CGTGAAAGAG AAGAAGACTG GAGACAACCA AGAGAAGATT GGAGGCGACC | 400 |
| AAGTCATCAG CAGCCACGGA AAATAAGGCC CGAAGGAAGA GAAGGAGAAC | 450 |
| AAGAGTGGGG AACACCAGGT AGCGAGGTGA GGGAAGAAAC ATCACGGAAC | 500 |
| AACCCTTTCT ACTTCCCGTC AAGGCGGTTT AGCACCCGCT ACGGGAACCA | 550 |
| AAACGGTAGG ATCCGCGTCC TGCAGAGGTT TGACCAAAGG TCAAAGCAGT | 600 |
| TTCAGAATCT CCAGAATCAC CGTATTGTGC AGATCGAGGC CAGACCTAAC | 650 |
| ACTCTTGTTC TTCCCAAGCA CGCTGATGCT GATAACATCC TTGTTATCCA | 700 |
| GCAAGGACAA GCCACCGTGA CCGTAGCAAA TGGCAATAAC AGAAAGAGCT | 750 |
| TTAATCTTGA CGAGGGCCAT GCACTCAGAA TCCCATCCGG TTTCATTTCC | 800 |
| TACATCTTGA ATCGACATGA CAACCAGAAC CTCAGAGTAG CTAAAATCTC | 850 |
| CATGCCCGTT AACACGCCCG GCCAGTTTGA GGATTTCTTC CCGGCGAGCA | 900 |
| GCCGAGACCA ATCATCCTAC TTGCAGGGAT TCAGCAGGAA TACTTTGGAG | 950 |
| GCCGCCTTCA ATGCGGAATT CAATGAGATA CGGAGGGTGC TGTTAGAAGA | 1000 |
| GAATGCAGGA GGAGAGCAAG AGGAGAGAGG GCAGAGGCGA CGGAGTACTC | 1050 |
| GGAGTAGTGA TAATGAAGGA GTGATAGTCA AAGTGTCAAA GGAGCACGTT | 1100 |
| CAAGAACTTA CTAAGCACGC TAAATCCGTC TCAAAGAAAG GCTCCGAAGA | 1150 |
| GGAAGATATC ACCAACCCAA TCAACTTGAG AGATGGCGAG CCCGATCTTT | 1200 |
| CTAACAACTT TGGGAGGTTA TTTGAGGTGA AGCCAGACAA GAAGAACCCC | 1250 |
| CAGCTTCAGG ACCTGGACAT GATGCTCACC TGTGTAGAGA TCAAAGAAGG | 1300 |
| AGCTTTGATG CTCCCACACT TCAACTCAAA GGCCATGGTC ATCGTCGTCG | 1350 |
| TCAACAAAGG AACTGGAAAC CTTGAACTCG TAGCTGTAAA AAAAGAGCAA | 1400 |
| CAACAGAGGG GACGGCGGGA ACAAGAGTGG AAGAAGAGG AGGAAGATGA | 1450 |
| AGAAGAGGAG GGAAGTAACA GAGAGGTGCG TAGGTACACA GCGAGGTTGA | 1500 |
| AGGAAGGCGA TGTGTTCATC ATGCCAGCAG CTCATCCAGT AGCCATCAAC | 1550 |

```
GCTTCCTCCG AACTCCATCT GCTTGGCTTC GGTATCAACG CTGAAAACAA            1600

CCACAGAATC TTCCTTGCAG GTGATAAGGA CAATGTGATA GACCAGATAG            1650

AGAAGCAAGC GAAGGATTTA GCATTCCCTG GTTCGGGTGA ACAAGTTGAG            1700

AAGCTCATCA AAAACCAGAG GGAGTCTCAC TTTGTGAGTG CTCGTCCTCA            1750

ATCTCAATCT CCGTCGTCTC CTGAAAAAGA GGATCAAGAG GAGGAAAACC            1800

AAGGAGGGAA GGGTCCACTC CTTTCAATTT TGAAGGCTTT TAACTGAGAA            1850

TGGAGGAAAC TTGTTATGTA TCCATAATAA GATCACGCTT TTGTAATCTA            1900

CTATCCAAAA ACTTATCAAT AAATAAAAAC GTTTGTGCGT TGTTTCTCC             1949

(2) INFORMATION FOR SEQ ID NO: 5:

(i) SEQUENCE CHARACTERISTICS:
        (A) LENGTH:  2032 bases
        (B) TYPE:  nucleic acid
        (C) STRANDEDNESS:  double
        (D) TOPOLOGY:  linear (ii) MOLECULE TYPE:  cDNA to mRNA
        (A) DESCRIPTION: identified as Ara h I Beta P41b (iii) HYPOTHETICAL:  No (iv) ANTI-SENSE:  No (v) FRAGMENT TYPE:  Not applicable (vi) ORIGINAL SOURCE:
        (A) ORGANISM:  Arachis hypogaea
        (B) STRAIN:  Florunner
        (C) INDIVIDUAL ISOLATE:  Clone P41b
        (D) DEVELOPMENTAL STAGE:  Seed
        (E) HAPLOTYPE:  Not applicable
        (F) TISSUE TYPE:  Seed mRNA, cDNA library
        (G) CELL TYPE:  Not applicable
        (H) CELL LINE:  Not applicable
        (I) ORGANELLE:  Not applicable (vii) IMMEDIATE SOURCE:
        (A) LIBRARY:  Florunner seed cDNA expression
            library in Uni-ZAP XR vector
        (B) CLONE:  P41b (viii) POSITION IN GENOME:
        (A) CHROMOSOME/SEGMENT:  Not applicable
        (B) MAP POSITION:  Not applicable
        (C) UNITS:  Not applicable (ix) FEATURE:
        (A) NAME/KEY:  CDS
        (B) LOCATION:  50..1930
        (C) IDENTIFICATION METHOD:  By agreement with
            protein information and established
            consensus sequence
        (D) OTHER INFORMATION:  Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 5:
```

```
AATAATCATA TATATTCATC AATCATCTAT ATAAGTAGTA GCAGGAGCAA        50

TGAGAGGGAG GGTTTCTCCA CTGATGCTGT TGCTAGGGAT CCTTGTCCTG       100

GCTTCAGTTT CTGCAACGCA TGCCAAGTCA TCACCTTACC AGAAGAAAAC       150

AGAGAACCCC TGCGCCCAGA GGTGCCTCCA GAGTTGTCAA CAGGAACCGG       200

ATGACTTGAA GCAAAAGGCA TGCGAGTCTC GCTGCACCAA GCTCGAGTAT       250

GATCCTCGTT GTGTCTATGA TCCTCGAGGA CACACTGGCA CCACCAACCA       300

ACGTTCCCCT CCAGGGGAGC GGACACGTGG CCGCCAACCC GGAGACTACG       350

ATGATGACCG CCGTCAACCC CGAAGAGAGG AAGGAGGCCG ATGGGGACCA       400

GCTGGACCGA GGGAGCGTGA AAGAGAAGAA GACTGGAGAC AACCAAGAGA       450

AGATTGGAGG CGACCAAGTC ATCAGCAGCC ACGGAAAATA AGGCCCGAAG       500

GAAGAGAAGG AGAACAAGAG TGGGGAACAC CAGGTAGCCA TGTGAGGGAA       550

GAAACATCTC GGAACAACCC TTTCTACTTC CCGTCAAGGC GGTTTAGCAC       600

CCGCTACGGG AACCAAAACG GTAGGATCCG GGTCCTGCAG AGGTTTGACC       650

AAAGGTCAAG GCAGTTTCAG AATCTCCAGA ATCACCGTAT TGTGCAGATC       700

GAGGCCAAAC CTAACACTCT TGTTCTTCCC AAGCACGCTG ATGCTGATAA       750

CATCCTTGTT ATCCAGCAAG GGCAAGCCAC CGTGACCGTA GCAAATGGCA       800

ATAACAGAAA GAGCTTTAAT CTTGACGAGG GCCATGCACT CAGAATCCCA       850

TCCGGTTTCA TTTCCTACAT CTTGAACCGC CATGACAACC AGAACCTCAG       900

AGTAGCTAAA ATCTCCATGC CCGTTAACAC ACCCGGCCAG TTTGAGGATT       950

TCTTCCCGGC GAGCAGCCGA GACCAATCAT CCTACTTGCA GGGCTTCAGC      1000

AGGAATACGT TGGAGGCCGC CTTCAATGCG GAATTCAATG AGATACGGAG      1050

GGTGCTGTTA AAGAGAATG CAGGAGGTGA GCAAGAGGAG AGAGGGCAGA       1100

GGCGATGGAG TACTCGGAGT AGTGAGAACA ATGAAGGAGT GATAGTCAAA      1150

GTGTCAAAGG AGCACGTTGA AGAACTTACT AAGCACGCTA AATCCGTCTC      1200

AAAGAAAGGC TCCGAAGAAG AGGGAGATAT CACCAACCCA ATCAACTTGA      1250

GAGAAGGCGA GCCCGATCTT TCTAACAACT TTGGGAAGTT ATTTGAGGTG      1300

AAGCCAGACA AGAAGAACCC CCAGCTTCAG GACCTGGACA TGATGCTCAC      1350

CTGTGTAGAG ATCAAAGAAG GAGCTTTGAT GCTCCCACAC TTCAACTCAA      1400

AGGCCATGGT TATCGTCGTC GTCAACAAAG GAACTGGAAA CCTTGAACTC      1450

GTGGCTGTAA GAAAAGAGCA ACAACAGAGG GGACGGCGGG AAGAAGAGGA      1500

GGACGAAGAC GAAGAAGAGG AGGGAAGTAA CAGAGAGGTG CGTAGGTACA      1550

CAGCGAGGTT GAAGGAAGGC GATGTGTTCA TCATGCCAGC AGCTCATCCA      1600

GTAGCCATCA ACGCTTCCTC CGAACTCCAT CTGCTTGGCT TCGGTATCAA      1650

CGCTGAAAAC AACCACAGAA TCTTCCTTGC AGGTGATAAG GACAATGTGA      1700

TAGACCAGAT AGAGAAGCAA GCGAAGGATT TAGCATTCCC TGGGTCGGGT      1750

GAACAAGTTG AGAAGCTCAT CAAAAACCAG AAGGAATCTC ACTTTGTGAG      1800

TGCTCGTCCT CAATCTCAAT CTCAATCTCC GTCGTCTCCT GAGAAAGAGT      1850

CTCCTGAGAA AGAGGATCAA GAGGAGGAAA ACCAAGGAGG GAAGGGTCCA      1900

CTCCTTTCAA TTTTGAAGGC TTTTAACTGA GAATGGAGGC AACTTGTTAT      1950
```

```
GTATCGATAA TAAGATCACG CTTTTGTACT CTACTATCCA AAAACTTATC            2000

AATAAATAAA AACGTTTGTG CGTTGTTTCT CC                              2032

(2) INFORMATION FOR SEQ ID NO: 6:

(i) SEQUENCE CHARACTERISTICS:
        (A) LENGTH:  717 bases
        (B) TYPE:  nucleic acid
        (C) STRANDEDNESS:  double
        (D) TOPOLOGY:  linear (ii) MOLECULE TYPE:  cDNA to mRNA
        (A) DESCRIPTION: identified as Ara h II P38

(iii) HYPOTHETICAL:  No (iv) ANTI-SENSE:  No (v) FRAGMENT TYPE:  Not applicable (vi) ORIGINAL SOURCE:
        (A) ORGANISM:  Arachis hypogaea
        (B) STRAIN:  Florunner
        (C) INDIVIDUAL ISOLATE:  Clone P38
        (D) DEVELOPMENTAL STAGE:  Seed
        (E) HAPLOTYPE:  Not applicable
        (F) TISSUE TYPE:  Seed mRNA, cDNA library
        (G) CELL TYPE:  Not applicable
        (H) CELL LINE:  Not applicable
        (I) ORGANELLE:  Not applicable (vii) IMMEDIATE SOURCE:
        (A) LIBRARY:  Florunner seed cDNA expression
            library in Uni-ZAP  XR vector
        (B) CLONE:  P38

(viii) POSITION IN GENOME:
        (A) CHROMOSOME/SEGMENT:  Not applicable
        (B) MAP POSITION:  Not applicable
        (C) UNITS:  Not applicable (ix) FEATURE:
        (A) NAME/KEY:  CDS
        (B) LOCATION:  2..475
        (C) IDENTIFICATION METHOD:  By agreement with
            protein information and established
            consensus sequence
        (D) OTHER INFORMATION:  Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 6:

GCTCACCATA CTAGTAGCCC TCGCCCTTTT CCTCCTCGCT GCCCACGCAT              50

CTGCGAGGCA GCAGTGGGAA CTCCAAGGAG ACAGAAGATG CCAGAGCCAG             100

CTCGAGAGGG CGAACCTGAG GCCCTGCGAG CAACATCTCA TGCAGAAGAT             150

CCAACGTGAC GAGGATTCAT ATGAACGGGA CCCGTACAGC CCTAGTCAGG             200

ATCCGTACAG CCCTAGTCCA TATGATCGGA GAGGCGCTGG ATCCTCTCAG             250

CACCAAGAGA GGTGTTGCAA TGAGCTGAAC GAGTTTGAGA ACAACCAAAG             300
```

```
GTGCATGTGC GAGGCATTGC AACAGATCAT GGAGAACCAG AGCGATAGGT            350

TGCAGGGGAG GCAACAGGAG CAACAGTTCA AGAGGGAGCT CAGGAACTTG            400

CCTCAACAGT GCGGCCTTAG GGCACCACAG CGTTGCGACT TGGACGTCGA            450

AAGTGGCGGC AGAGACAGAT ACTAAACACC TATCTCAAAA AAAGAAAAGA            500

AAAGAAAAGA AAATAGCTTA TATATAAGCT ATTATCTATG GTTATGTTTA            550

GTTTTGGTAA TAATAAAGAT CATCACTATA TGAATGTGTT GATCGTGTTA            600

ACTAAGGCAA GCTTAGGTTA TATGAGCACC TTTAGAGTGC TTTTATGGCG            650

TTGTCTATGT TTTGTTGCTG CAGAGTTGTA ACCATCTTGA AATAATATAA            700

AAAGATCATG TTTTGTT                                                717

(2) INFORMATION FOR SEQ ID NO: 7:

(i) SEQUENCE CHARACTERISTICS:
        (A) LENGTH: 18 amino acid residues
        (B) TYPE: amino acid
        (C) STRANDEDNESS: Not Applicable
        (D) TOPOLOGY: Unknown (ii) MOLECULE TYPE: glycoprotein
        (A) DESCRIPTION: identified as Ara h 2 Peptide I.
            The amino acid sequence of the amino terminus (I)
            and a tryptic peptide (II) derived from Ara h 2
            protein.

(iii) HYPOTHETICAL: No (iv) ANTI-SENSE: Not applicable (v) FRAGMENT TYPE: amino terminus (vi) ORIGINAL SOURCE:
        (A) ORGANISM: Arachis hypogaea
        (B) STRAIN: Florunner
        (C) INDIVIDUAL ISOLATE:
        (D) DEVELOPMENTAL STAGE: seed
        (E) HAPLOTYPE: Not applicable
        (F) TISSUE TYPE: seed
        (G) CELL TYPE: Not applicable
        (H) CELL LINE: Not applicable
        (I) ORGANELLE: Not applicable (vii) IMMEDIATE SOURCE:
        (A) LIBRARY:
        (B) CLONE:

(viii) POSITION IN GENOME:
        (A) CHROMOSOME/SEGMENT: Not applicable
        (B) MAP POSITION: Not applicable
        (C) UNITS: Not applicable (ix) FEATURE:
        (A) NAME/KEY:
        (B) LOCATION:
        (C) IDENTIFICATION METHOD: By agreement with
            protein information and established
            consensus sequence
        (D) OTHER INFORMATION: Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
```

-continued (K) RELEVANT RESIDUES IN SEQ ID NO:

(xi) SEQUENCE DESCRIPTION: SEQ ID NO: 7:

Xaa Gln Gln Trp Glu Leu Gln Gly Asp Arg Arg Gln Ser Gln
1               5                   10                  15

Leu Glu Arg (2) INFORMATION FOR SEQ ID NO:  8:

(i) SEQUENCE CHARACTERISTICS:
          (A) LENGTH:  13 amino acid residues
          (B) TYPE:  amino acid
          (C) STRANDEDNESS: Not Applicable
          (D) TOPOLOGY:  Unknown (ii) MOLECULE TYPE:  glycoprotein
          (A) DESCRIPTION: identified as Ara h 2 Peptide II. The
              amino acid sequence of the amino terminus (I) and a
              tryptic peptide (II) derived from Ara h 2 protein.

(iii) HYPOTHETICAL:  No (iv) ANTI-SENSE:  Not applicable (v) FRAGMENT TYPE:  peptide (vi) ORIGINAL SOURCE:
          (A) ORGANISM:  Arachis hypogaea
          (B) STRAIN:  Florunner
          (C) INDIVIDUAL ISOLATE:
          (D) DEVELOPMENTAL STAGE:  seed
          (E) HAPLOTYPE:  Not applicable
          (F) TISSUE TYPE:  seed
          (G) CELL TYPE:  Not applicable
          (H) CELL LINE:  Not applicable
          (I) ORGANELLE:  Not applicable (vii) IMMEDIATE SOURCE:
          (A) LIBRARY:
          (B) CLONE:

(viii) POSITION IN GENOME:
          (A) CHROMOSOME/SEGMENT:  Not applicable
          (B) MAP POSITION:  Not applicable
          (C) UNITS:  Not applicable (ix) FEATURE:
          (A) NAME/KEY:
          (B) LOCATION:
          (C) IDENTIFICATION METHOD:  By agreement with
              protein information and established
              consensus sequence
          (D) OTHER INFORMATION:  Seed storage protein and
              allergen (x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO: 8:

Ala Asn Leu Arg Pro Cys Glu Gln His Leu Met Gln Lys
1               5                   10

(2) INFORMATION FOR SEQ ID NO:  9:

-continued

```
    (i) SEQUENCE CHARACTERISTICS:
        (A) LENGTH:  717 nucleotides
        (B) TYPE:  nucleic acid
        (C) STRANDEDNESS:  double
        (D) TOPOLOGY:  linear (ii) MOLECULE TYPE:  cDNA
        (A) DESCRIPTION:  identified as Ara h II cDNA clone (iii) HYPOTHETICAL:  No (iv) ANTI-SENSE:  No (v) FRAGMENT TYPE:  Not applicable (vi) ORIGINAL SOURCE:
        (A) ORGANISM:  Arachis hypogaea
        (B) STRAIN:  Florunner
        (C) INDIVIDUAL ISOLATE:
        (D) DEVELOPMENTAL STAGE:  seed
        (E) HAPLOTYPE:  Not applicable
        (F) TISSUE TYPE:  seed cDNA
        (G) CELL TYPE:  Not applicable
        (H) CELL LINE:  Not applicable
        (I) ORGANELLE:  Not applicable (vii) IMMEDIATE SOURCE:
        (A) LIBRARY:  florunner seed cDNA expression
            library in Uni-ZAP  XR vector
        (B) CLONE:

(viii) POSITION IN GENOME:
        (A) CHROMOSOME/SEGMENT:  Not applicable
        (B) MAP POSITION:  Not applicable
        (C) UNITS:  Not applicable (ix) FEATURE:
        (A) NAME/KEY:
        (B) LOCATION:
        (C) IDENTIFICATION METHOD:  By agreement with
            protein information and established
            consensus sequence
        (D) OTHER INFORMATION:  Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 9:
```

| | |
|---|---|
| G CTC ACC ATA CTA GTA GCC CTC GCC CTT TTC CTC CTC GCT GCC | 43 |
| CAC GCA TCT GCG AGG CAG CAG TGG GAA CTC CAA GGA GAC AGA AGA | 88 |
| TGC CAG AGC CAG CTC GAG AGG GCG AAC CTG AGG CCC TGC GAG CAA | 133 |
| CAT CTC ATG CAG AAG ATC CAA CGT GAC GAG GAT TCA TAT GAA CGG | 178 |
| GAC CCG TAC AGC CCT AGT CAG GAT CCG TAC AGC CCT AGT CCA TAT | 223 |
| GAT CGG AGA GGC GCT GGA TCC TCT CAG CAC CAA GAG AGG TGT TGC | 268 |
| AAT GAG CTG AAC GAG TTT GAG AAC AAC CAA AGG TGC ATG TGC GAG | 313 |
| GCA TTG CAA CAG ATC ATG GAG AAC CAG AGC GAT AGG TTG CAG GGG | 358 |
| AGG CAA CAG GAG CAA CAG TTC AAG AGG GAG CTC AGG AAC TTG CCT | 403 |
| CAA CAG TGC GGC CTT AGG GCA CCA CAG CGT TGC GAC TTG GAC GTC | 448 |

```
GAA AGT GGC GGC AGA GAC AGA TAC TAA                              475

ACACCTATCT CAAAAAAAGA AAAGAAAAGA AAAGAAAATA GCTTATATAT            525

AAGCTATTAT CTATGGTTAT GTTTAGTTTT GGTAATAATA AAGATCATCA            575

CTATATGAAT GTGTTGATCG TGTTAACTAA GGCAAGCTTA GGTTATATGA            625

GCACCTTTAG AGTGCTTTTA TGGCGTTGTC TATGTTTTGT TGCTGCAGAG            675

TTGTAACCAT CTTGAAATAA TATAAAAAGA TCATGTTTTG TT                   717

(2) INFORMATION FOR SEQ ID NO: 10:

(i) SEQUENCE CHARACTERISTICS:
        (A) LENGTH: 157 amino acids
        (B) TYPE: amino acid
        (C) STRANDEDNESS: Not Applicable
        (D) TOPOLOGY: Unknown (ii) MOLECULE TYPE: cDNA
        (A) DESCRIPTION: identified as Ara h II cDNA clone
            derived amino acid sequence (iii) HYPOTHETICAL: No (iv) ANTI-SENSE: No (v) FRAGMENT TYPE: Not applicable (vi) ORIGINAL SOURCE:
        (A) ORGANISM: Arachis hypogaea
        (B) STRAIN: Florunner
        (C) INDIVIDUAL ISOLATE:
        (D) DEVELOPMENTAL STAGE: seed
        (E) HAPLOTYPE: Not applicable
        (F) TISSUE TYPE: seed cDNA
        (G) CELL TYPE: Not applicable
        (H) CELL LINE: Not applicable
        (I) ORGANELLE: Not applicable (vii) IMMEDIATE SOURCE:
        (A) LIBRARY:
        (B) CLONE:

(viii) POSITION IN GENOME:
        (A) CHROMOSOME/SEGMENT: Not applicable
        (B) MAP POSITION: Not applicable
        (C) UNITS: Not applicable (ix) FEATURE:
        (A) NAME/KEY:
        (B) LOCATION:
        (C) IDENTIFICATION METHOD: By agreement with
            protein information and established
            consensus sequence
        (D) OTHER INFORMATION: Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 10:

Leu Thr Ile Leu Val Ala Leu Ala Leu Phe Leu Leu Ala Ala
 1               5                  10
```

-continued

```
His Ala Ser Ala Arg Gln Gln Trp Glu Leu Gln Gly Asp Arg Arg Cys
 15                  20                  25                  30

Gln Ser Gln Leu Glu Arg Ala Asn Leu Arg Pro Cys Glu Gln His Leu
                 35                  40                  45

Met Gln Lys Ile Gln Arg Asp Glu Asp Ser Tyr Glu Arg Asp Pro Tyr
             50                  55                  60

Ser Pro Ser Gln Asp Pro Tyr Ser Pro Ser Pro Tyr Asp Arg Arg Gly
             65                  70                  75

Ala Gly Ser Ser Gln His Gln Glu Arg Cys Cys Asn Glu Leu Asn Glu
 80                  85                  90

Phe Glu Asn Asn Gln Arg Cys Met Cys Glu Ala Leu Gln Gln Ile Met
 95                 100                 105                 110

Glu Asn Gln Ser Asp Arg Leu Gln Gly Arg Gln Gln Glu Gln Gln Phe
                115                 120                 125

Lys Arg Glu Leu Arg Asn Leu Pro Gln Gln Cys Gly Leu Arg Ala Pro
                130                 135                 140

Gln Arg Cys Asp Leu Asp Val Glu Ser Gly Gly Arg Asp Arg Tyr
                145                 150                 155
```

(2) INFORMATION FOR SEQ ID NO: 11:

(i) SEQUENCE CHARACTERISTICS:
        (A) LENGTH: 10 amino acids
        (B) TYPE: amino acid
        (C) STRANDEDNESS: Not Applicable
        (D) TOPOLOGY: unknown (ii) MOLECULE TYPE: glycoprotein
        (A) DESCRIPTION: identified as Ara h 2 IgE binding epitope
            peptide 1 Ara h 2 position 15-24, epitope represents
            synthesized amino acid sequence derived from the amino
            acid sequence of the translated nucleotide sequence
            reading frame of the clone.

(iii) HYPOTHETICAL: No (iv) ANTI-SENSE: Not applicable (v) FRAGMENT TYPE: Not applicable (vi) ORIGINAL SOURCE:
        (A) ORGANISM: Arachis hypogaea
        (B) STRAIN: Florunner
        (C) INDIVIDUAL ISOLATE: Ara h II
        (D) DEVELOPMENTAL STAGE:
        (E) HAPLOTYPE: Not applicable
        (F) TISSUE TYPE:
        (G) CELL TYPE: Not applicable
        (H) CELL LINE: Not applicable
        (I) ORGANELLE: Not applicable (vii) IMMEDIATE SOURCE:
        (A) LIBRARY:
        (B) CLONE:

(viii) POSITION IN GENOME:
        (A) CHROMOSOME/SEGMENT: Not applicable
        (B) MAP POSITION: Not applicable
        (C) UNITS: Not applicable (ix) FEATURE:
        (A) NAME/KEY:
        (B) LOCATION:
        (C) IDENTIFICATION METHOD: By agreement with
            protein information and established
            consensus sequence
        (D) OTHER INFORMATION: Seed storage protein and
            allergen (x) PUBLICATION INFORMATION:

```
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 11:

His Ala Ser Ala Arg Gln Gln Trp Glu Leu
 1               5                  10

(2) INFORMATION FOR SEQ ID NO:  12:

(i) SEQUENCE CHARACTERISTICS:
            (A) LENGTH:  10 amino acids
            (B) TYPE:  amino acid
            (C) STRANDEDNESS: Not Applicable
            (D) TOPOLOGY:  unknown (ii) MOLECULE TYPE:  glycoprotein
            (A) DESCRIPTION: identified as Ara h 2 IgE binding epitope
                peptide 2 Ara h 2 position 21-30, epitope represents
                synthesized amino acid sequence derived from the amino
                acid sequence of the translated nucleotide sequence
                reading frame of the clone.

(iii) HYPOTHETICAL:  No (iv) ANTI-SENSE:  Not applicable (v) FRAGMENT TYPE:  Not applicable (vi) ORIGINAL SOURCE:
            (A) ORGANISM:  Arachis hypogaea
            (B) STRAIN:  Florunner
            (C) INDIVIDUAL ISOLATE:  Ara h II
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:

(viii) POSITION IN GENOME:
            (A) CHROMOSOME/SEGMENT:  Not applicable
            (B) MAP POSITION:  Not applicable
            (C) UNITS:  Not applicable (ix) FEATURE:
            (A) NAME/KEY:
            (B) LOCATION:
            (C) IDENTIFICATION METHOD:  By agreement with
                protein information and established
                consensus sequence
            (D) OTHER INFORMATION:  Seed storage protein and
                allergen (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
```

-continued

```
        (K) RELEVANT RESIDUES IN SEQ ID NO:

(xi) SEQUENCE DESCRIPTION: SEQ ID NO: 12:

Gln Trp Glu Leu Gln Gly Asp Arg Arg Cys
1               5                   10

(2) INFORMATION FOR SEQ ID NO:13:

(i) SEQUENCE CHARACTERISTICS:
        (A) LENGTH: 10 amino acids
        (B) TYPE: amino acid
        (C) STRANDEDNESS: Not Applicable
        (D) TOPOLOGY: unknown (ii) MOLECULE TYPE: glycoprotein
        (A) DESCRIPTION: identified as Ara h 2 IgE binding epitope
            peptide 3 Ara h 2 position 27-36, epitope represents
            synthesized amino acid sequence derived from the amino
            acid sequence of the translated nucleotide sequence
            reading frame of the clone.

(iii) HYPOTHETICAL: No (iv) ANTI-SENSE: Not applicable (v) FRAGMENT TYPE: Not applicable (vi) ORIGINAL SOURCE:
        (A) ORGANISM: Arachis hypogaea
        (B) STRAIN: Florunner
        (C) INDIVIDUAL ISOLATE: Ara h II
        (D) DEVELOPMENTAL STAGE:
        (E) HAPLOTYPE: Not applicable
        (F) TISSUE TYPE:
        (G) CELL TYPE: Not applicable
        (H) CELL LINE: Not applicable
        (I) ORGANELLE: Not applicable (vii) IMMEDIATE SOURCE:
        (A) LIBRARY:
        (B) CLONE:

(viii) POSITION IN GENOME:
        (A) CHROMOSOME/SEGMENT: Not applicable
        (B) MAP POSITION: Not applicable
        (C) UNITS: Not applicable (ix) FEATURE:
        (A) NAME/KEY:
        (B) LOCATION:
        (C) IDENTIFICATION METHOD: By agreement with
            protein information and established
            consensus sequence
        (D) OTHER INFORMATION: Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 13:

Asp Arg Arg Cys Gln Ser Gln Leu Glu Arg
1               5                   10

(2) INFORMATION FOR SEQ ID NO: 14:
```

```
    (i) SEQUENCE CHARACTERISTICS:
        (A) LENGTH:  10 amino acids
        (B) TYPE:  amino acid
        (C) STRANDEDNESS: Not Applicable
        (D) TOPOLOGY:  unknown (ii) MOLECULE TYPE:  glycoprotein
        (A) DESCRIPTION: identified as Ara h 2 IgE binding epitope
            peptide 4 Ara h 2 position 39-48, epitope represents
            synthesized amino acid sequence derived from the amino
            acid sequence of the translated nucleotide sequence
            reading frame of the clone.

(iii) HYPOTHETICAL:  No (iv) ANTI-SENSE:  Not applicable (v) FRAGMENT TYPE:  Not applicable (vi) ORIGINAL SOURCE:
        (A) ORGANISM:  Arachis hypogaea
        (B) STRAIN:  Florunner
        (C) INDIVIDUAL ISOLATE:  Ara h II
        (D) DEVELOPMENTAL STAGE:
        (E) HAPLOTYPE:  Not applicable
        (F) TISSUE TYPE:
        (G) CELL TYPE:  Not applicable
        (H) CELL LINE:  Not applicable
        (I) ORGANELLE:  Not applicable (vii) IMMEDIATE SOURCE:
        (A) LIBRARY:
        (B) CLONE:

(viii) POSITION IN GENOME:
        (A) CHROMOSOME/SEGMENT:  Not applicable
        (B) MAP POSITION:  Not applicable
        (C) UNITS:  Not applicable (ix) FEATURE:
        (A) NAME/KEY:
        (B) LOCATION:
        (C) IDENTIFICATION METHOD:  By agreement with
            protein information and established
            consensus sequence
        (D) OTHER INFORMATION:  Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 14:

Leu Arg Pro Cys Glu Gln His Leu Met Gln
 1               5                   10

(2) INFORMATION FOR SEQ ID NO:  15:

(i) SEQUENCE CHARACTERISTICS:
        (A) LENGTH:  10 amino acids
        (B) TYPE:  amino acid
        (C) STRANDEDNESS: Not Applicable
        (D) TOPOLOGY:  unknown (ii) MOLECULE TYPE:  glycoprotein
        (A) DESCRIPTION: identified as Ara h 2 IgE binding epitope
            peptide 5 Ara h 2 position 49-58, epitope represents
            synthesized amino acid sequence derived from the amino
```

```
                    acid sequence of the translated nucleotide sequence
                    reading frame of the clone.

(iii) HYPOTHETICAL: No (iv) ANTI-SENSE: Not applicable (v) FRAGMENT TYPE: Not applicable (vi) ORIGINAL SOURCE:
             (A) ORGANISM: Arachis hypogaea
             (B) STRAIN: Florunner
             (C) INDIVIDUAL ISOLATE: Ara h II
             (D) DEVELOPMENTAL STAGE:
             (E) HAPLOTYPE: Not applicable
             (F) TISSUE TYPE:
             (G) CELL TYPE: Not applicable
             (H) CELL LINE: Not applicable
             (I) ORGANELLE: Not applicable (vii) IMMEDIATE SOURCE:
             (A) LIBRARY:
             (B) CLONE:

(viii) POSITION IN GENOME:
             (A) CHROMOSOME/SEGMENT: Not applicable
             (B) MAP POSITION: Not applicable
             (C) UNITS: Not applicable (ix) FEATURE:
             (A) NAME/KEY:
             (B) LOCATION:
             (C) IDENTIFICATION METHOD: By agreement with
                 protein information and established
                 consensus sequence
             (D) OTHER INFORMATION: Seed storage protein and
                 allergen (x) PUBLICATION INFORMATION:
             (A) AUTHORS:
             (B) TITLE:
             (C) JOURNAL:
             (D) VOLUME:
             (E) ISSUE:
             (F) PAGES:
             (G) DATE:
             (H) DOCUMENT NUMBER:
             (I) FILING DATE:
             (J) PUBLICATION DATE:
             (K) RELEVANT RESIDUES IN SEQ ID NO:

(xi) SEQUENCE DESCRIPTION: SEQ ID NO: 15:

Lys Ile Gln Arg Asp Glu Asp Ser Tyr Glu
 1               5                  10

(2) INFORMATION FOR SEQ ID NO: 16:

(i) SEQUENCE CHARACTERISTICS:
             (A) LENGTH: 10 amino acids
             (B) TYPE: amino acid
             (C) STRANDEDNESS: Not Applicable
             (D) TOPOLOGY: unknown (ii) MOLECULE TYPE: glycoprotein
             (A) DESCRIPTION: identified as Ara h 2 IgE binding epitope
                 peptide 6 Ara h 2 position 57-66, epitope represents
                 synthesized amino acid sequence derived from the amino
                 acid sequence of the translated nucleotide sequence
                 reading frame of the clone.

(iii) HYPOTHETICAL: No (iv) ANTI-SENSE: Not applicable (v) FRAGMENT TYPE: Not applicable (vi) ORIGINAL SOURCE:
```

```
            (A) ORGANISM:  Arachis hypogaea
            (B) STRAIN:  Florunner
            (C) INDIVIDUAL ISOLATE:  Ara h II
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:

(viii) POSITION IN GENOME:
            (A) CHROMOSOME/SEGMENT:  Not applicable
            (B) MAP POSITION:  Not applicable
            (C) UNITS:  Not applicable (ix) FEATURE:
            (A) NAME/KEY:
            (B) LOCATION:
            (C) IDENTIFICATION METHOD:  By agreement with
                protein information and established
                consensus sequence
            (D) OTHER INFORMATION:  Seed storage protein and
                allergen (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 16:

Tyr Glu Arg Asp Pro Tyr Ser Pro Ser Gln
1               5                   10

(2) INFORMATION FOR SEQ ID NO:  17:

(i) SEQUENCE CHARACTERISTICS:
            (A) LENGTH:  10 amino acids
            (B) TYPE:  amino acid
            (C) STRANDEDNESS: Not Applicable
            (D) TOPOLOGY:  unknown (ii) MOLECULE TYPE:  glycoprotein
            (A) DESCRIPTION: identified as Ara h 2 IgE binding epitope
                peptide 7 Ara h 2 position 65-74, epitope represents
                synthesized amino acid sequence derived from the amino
                acid sequence of the translated nucleotide sequence
                reading frame of the clone.

(iii) HYPOTHETICAL:  No (iv) ANTI-SENSE:  Not applicable (v) FRAGMENT TYPE:  Not applicable (vi) ORIGINAL SOURCE:
            (A) ORGANISM:  Arachis hypogaea
            (B) STRAIN:  Florunner
            (C) INDIVIDUAL ISOLATE:  Ara h II
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable
```

```
    (vii) IMMEDIATE SOURCE:
          (A) LIBRARY:
          (B) CLONE:

(viii) POSITION IN GENOME:
          (A) CHROMOSOME/SEGMENT: Not applicable
          (B) MAP POSITION: Not applicable
          (C) UNITS: Not applicable (ix) FEATURE:
          (A) NAME/KEY:
          (B) LOCATION:
          (C) IDENTIFICATION METHOD: By agreement with
              protein information and established
              consensus sequence
          (D) OTHER INFORMATION: Seed storage protein and
              allergen (x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO: 17:

Ser Gln Asp Pro Tyr Ser Pro Ser Pro Tyr
 1               5                   10

(2) INFORMATION FOR SEQ ID NO: 18:

(i) SEQUENCE CHARACTERISTICS:
          (A) LENGTH: 10 amino acids
          (B) TYPE: amino acid
          (C) STRANDEDNESS: Not Applicable
          (D) TOPOLOGY: unknown (ii) MOLECULE TYPE: glycoprotein
          (A) DESCRIPTION:identified as Ara h 2 IgE binding epitope
              peptide 8 Ara h 2 position 115-124, epitope represents
              synthesized amino acid sequence derived from the amino
              acid sequence of the translated nucleotide sequence
              reading frame of the clone.

(iii) HYPOTHETICAL: No (iv) ANTI-SENSE: Not applicable (v) FRAGMENT TYPE: Not applicable (vi) ORIGINAL SOURCE:
          (A) ORGANISM: Arachis hypogaea
          (B) STRAIN: Florunner
          (C) INDIVIDUAL ISOLATE: Ara h II
          (D) DEVELOPMENTAL STAGE:
          (E) HAPLOTYPE: Not applicable
          (F) TISSUE TYPE:
          (G) CELL TYPE: Not applicable
          (H) CELL LINE: Not applicable
          (I) ORGANELLE: Not applicable (vii) IMMEDIATE SOURCE:
          (A) LIBRARY:
          (B) CLONE:

(viii) POSITION IN GENOME:
          (A) CHROMOSOME/SEGMENT: Not applicable
          (B) MAP POSITION: Not applicable
          (C) UNITS: Not applicable (ix) FEATURE:
```

```
            (A) NAME/KEY:
            (B) LOCATION:
            (C) IDENTIFICATION METHOD:  By agreement with
                protein information and established
                consensus sequence
            (D) OTHER INFORMATION:  Seed storage protein and
                allergen (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 18:

Asp Arg Leu Gln Gly Arg Gln Gln Glu Gln
1               5                   10

(2) INFORMATION FOR SEQ ID NO:  19:

(i) SEQUENCE CHARACTERISTICS:
            (A) LENGTH:  10 amino acids
            (B) TYPE:  amino acid
            (C) STRANDEDNESS: Not Applicable
            (D) TOPOLOGY:  unknown (ii) MOLECULE TYPE:  glycoprotein
            (A) DESCRIPTION:identified as Ara h 2 IgE binding epitope
                peptide 9 Ara h 2 position 127-136, epitope represents
                synthesized amino acid sequence derived from the amino
                acid sequence of the translated nucleotide sequence
                reading frame of the clone.

(iii) HYPOTHETICAL:  No (iv) ANTI-SENSE:  Not applicable (v) FRAGMENT TYPE:  Not applicable (vi) ORIGINAL SOURCE:
            (A) ORGANISM:  Arachis hypogaea
            (B) STRAIN:  Florunner
            (C) INDIVIDUAL ISOLATE:  Ara h II
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:

(viii) POSITION IN GENOME:
            (A) CHROMOSOME/SEGMENT:  Not applicable
            (B) MAP POSITION:  Not applicable
            (C) UNITS:  Not applicable (ix) FEATURE:
            (A) NAME/KEY:
            (B) LOCATION:
            (C) IDENTIFICATION METHOD:  By agreement with
                protein information and established
                consensus sequence
            (D) OTHER INFORMATION:  Seed storage protein and
                allergen (x) PUBLICATION INFORMATION:
            (A) AUTHORS:
```

```
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 19:

Lys Arg Glu Leu Arg Asn Leu Pro Gln Gln
 1               5                  10

(2) INFORMATION FOR SEQ ID NO: 20:

(i) SEQUENCE CHARACTERISTICS:
        (A) LENGTH:  10 amino acids
        (B) TYPE:  amino acid
        (C) STRANDEDNESS: Not Applicable
        (D) TOPOLOGY:  unknown (ii) MOLECULE TYPE: glycoprotein
        (A) DESCRIPTION:identified as Ara h 2 IgE binding epitope
            peptide 10 Ara h 2 position 143-152, epitope represents
            synthesized amino acid sequence derived from the amino
            acid sequence of the translated nucleotide sequence
            reading frame of the clone.

(iii) HYPOTHETICAL:  No (iv) ANTI-SENSE:  Not applicable (v) FRAGMENT TYPE:  Not applicable (vi) ORIGINAL SOURCE:
        (A) ORGANISM:  Arachis hypogaea
        (B) STRAIN:  Florunner
        (C) INDIVIDUAL ISOLATE:  Ara h II
        (D) DEVELOPMENTAL STAGE:
        (E) HAPLOTYPE:  Not applicable
        (F) TISSUE TYPE:
        (G) CELL TYPE:  Not applicable
        (H) CELL LINE:  Not applicable
        (I) ORGANELLE:  Not applicable (vii) IMMEDIATE SOURCE:
        (A) LIBRARY:
        (B) CLONE:

(viii) POSITION IN GENOME:
        (A) CHROMOSOME/SEGMENT:  Not applicable
        (B) MAP POSITION:  Not applicable
        (C) UNITS:  Not applicable (ix) FEATURE:
        (A) NAME/KEY:
        (B) LOCATION:
        (C) IDENTIFICATION METHOD:  By agreement with
            protein information and established
            consensus sequence
        (D) OTHER INFORMATION:  Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:
```

(xi) SEQUENCE DESCRIPTION: SEQ ID NO: 20:

Gln Arg Cys Asp Leu Asp Val Glu Ser Gly
 1               5                  10

(2) INFORMATION FOR SEQ ID NO:  21:

(i) SEQUENCE CHARACTERISTICS:
         (A) LENGTH:  157 amino acids
         (B) TYPE:  amino acid
         (C) STRANDEDNESS: Not Applicable
         (D) TOPOLOGY:  unknown (ii) MOLECULE TYPE: glycoprotein
         (A) DESCRIPTION: identified as Ara h 2 P38 deduced
             sequence from nucleotide sequence reading frame.

(iii) HYPOTHETICAL:  No (iv) ANTI-SENSE:  Not applicable (v) FRAGMENT TYPE:  Not applicable (vi) ORIGINAL SOURCE:
         (A) ORGANISM:  Arachis hypogaea
         (B) STRAIN:  Florunner
         (C) INDIVIDUAL ISOLATE:  Ara h II
         (D) DEVELOPMENTAL STAGE:
         (E) HAPLOTYPE:  Not applicable
         (F) TISSUE TYPE:
         (G) CELL TYPE:  Not applicable
         (H) CELL LINE:  Not applicable
         (I) ORGANELLE:  Not applicable (vii) IMMEDIATE SOURCE:
         (A) LIBRARY:
         (B) CLONE:

(viii) POSITION IN GENOME:
         (A) CHROMOSOME/SEGMENT:  Not applicable
         (B) MAP POSITION:  Not applicable
         (C) UNITS:  Not applicable (ix) FEATURE:
         (A) NAME/KEY:  final check
         (B) LOCATION:  4..480
         (C) IDENTIFICATION METHOD:  By agreement with
             protein information and established
             consensus sequence
         (D) OTHER INFORMATION:  Seed storage protein and
             allergen (x) PUBLICATION INFORMATION:
         (A) AUTHORS:
         (B) TITLE:
         (C) JOURNAL:
         (D) VOLUME:
         (E) ISSUE:
         (F) PAGES:
         (G) DATE:
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO: 21:

Leu Thr Ile Leu Val Ala Leu Ala Leu Phe
 1               5                  10

Leu Leu Ala Ala His Ala Ser Ala Arg Gln
                15                  20

Gln Trp Glu Leu Gln Gly Asp Arg Arg Cys
                25                  30

Gln Ser Gln Leu Glu Arg Ala Asn Leu Arg

```
                         35                      40
Pro Cys Glu Gln His Leu Met Gln Lys Ile
                     45                  50

Gln Arg Asp Glu Asp Ser Tyr Glu Arg Asp
                     55                  60

Pro Ser Tyr Pro Ser Gln Asp Pro Tyr Ser
                     65                  70

Pro Ser Pro Tyr Asp Arg Arg Gly Ala Gly
                     75                  80

Ser Ser Gln His Gln Glu Arg Cys Cys Asn
                     85                  90

Glu Leu Asn Glu Phe Glu Asn Asn Gln Arg
                     95                 100

Cys Met Cys Glu Ala Leu Gln Gln Ile Met
                    105                 110

Glu Asn Gln Ser Asp Arg Leu Gln Gly Arg
                    115                 120

Gln Gln Glu Gln Gln Phe Lys Arg Glu Leu
                    125                 130

Arg Asn Leu Pro Gln Gln Cys Gly Leu Arg
                    135                 140

Ala Pro Gln Arg Cys Asp Leu Asp Val Glu
                    145                 150

Ser Gly Gly Arg Asp Arg Tyr
                    155

(2) INFORMATION FOR SEQ ID NO: 22:

(i) SEQUENCE CHARACTERISTICS:
        (A) LENGTH: 26 nucleotides
        (B) TYPE: nucleotide
        (C) STRANDEDNESS: unknown
        (D) TOPOLOGY: unknown (ii) MOLECULE TYPE: OLIGONUCLEOTIDE
        (A) DESCRIPTION: identified as amino terminus of
            Ara h 2 peanut allergen (peptide I).

(iii) HYPOTHETICAL: No (iv) ANTI-SENSE: Not applicable (v) FRAGMENT TYPE: amino terminus (vi) ORIGINAL SOURCE:
        (A) ORGANISM: Arachis hypogaea
        (B) STRAIN: Florunner
        (C) INDIVIDUAL ISOLATE:
        (D) DEVELOPMENTAL STAGE:
        (E) HAPLOTYPE: Not applicable
        (F) TISSUE TYPE:
        (G) CELL TYPE: Not applicable
        (H) CELL LINE: Not applicable
        (I) ORGANELLE: Not applicable (vii) IMMEDIATE SOURCE:
        (A) LIBRARY:
        (B) CLONE:

(viii) POSITION IN GENOME:
        (A) CHROMOSOME/SEGMENT: Not applicable
        (B) MAP POSITION: Not applicable
        (C) UNITS: Not applicable (ix) FEATURE:
        (A) NAME/KEY:
```

```
           (B) LOCATION:
           (C) IDENTIFICATION METHOD:  By agreement with
                 protein information and established
                 consensus sequence
           (D) OTHER INFORMATION:  Seed storage protein and
                 allergen, the GA(TC) represent two different
                 forms of a trinucleotide sequence: GAT or GAC;
                 therefore the correct nucleotide sequence is
                 numbered differently.

(x) PUBLICATION INFORMATION:
           (A) AUTHORS:
           (B) TITLE:
           (C) JOURNAL:
           (D) VOLUME:
           (E) ISSUE:
           (F) PAGES:
           (G) DATE:
           (H) DOCUMENT NUMBER:
           (I) FILING DATE:
           (J) PUBLICATION DATE:
           (K) RELEVANT RESIDUES IN SEQ ID NO:

(xi) SEQUENCE DESCRIPTION: SEQ ID NO: 22:

CARCARTGGG ARTTRCARGG NGAYAG                                              26

(2) INFORMATION FOR SEQ ID NO:  23:

(i) SEQUENCE CHARACTERISTICS:
           (A) LENGTH:  23 nucleotides
           (B) TYPE: nucleotide
           (C) STRANDEDNESS:  unknown
           (D) TOPOLOGY:  unknown (ii) MOLECULE TYPE:  oligonucleotide
           (A) DESCRIPTION: identified as oligonucleotide
                 derived from amino acid sequence within
                 peptide I of Ara h I (63.5 KD).

(iii) HYPOTHETICAL:  No (iv) ANTI-SENSE:  Not applicable (v) FRAGMENT TYPE:

(vi) ORIGINAL SOURCE:
           (A) ORGANISM:  Arachis hypogaea
           (B) STRAIN:
           (C) INDIVIDUAL ISOLATE:
           (D) DEVELOPMENTAL STAGE: mature raw peanut
           (E) HAPLOTYPE:  Not applicable
           (F) TISSUE TYPE:  mature peanut
           (G) CELL TYPE:  Not applicable
           (H) CELL LINE:  Not applicable
           (I) ORGANELLE:  Not applicable (vii) IMMEDIATE SOURCE:  crude soluble whole peanut
                 extract
           (A) LIBRARY:  Not applicable
           (B) CLONE:  Not applicable (viii) POSITION IN GENOME:
           (A) CHROMOSOME/SEGMENT:  Not applicable
           (B) MAP POSITION:  Not applicable
           (C) UNITS:  Not applicable (ix) FEATURE:
           (A) NAME/KEY:
           (B) LOCATION:
           (C) IDENTIFICATION METHOD:  By agreement with
                 protein information and established
                 consensus sequence
           (D) OTHER INFORMATION:  Seed storage protein and
                 allergen, the GA(TC) represent two different
                 forms of a trinucleotide sequence: GAT or GAC;
                 therefore the correct nucleotide sequence is
                 numbered differently.
```

```
    (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 23:

GAYAARGAYA AYGTNATHGA YCA                                            23

(2) INFORMATION FOR SEQ ID NO:  24:

(i) SEQUENCE CHARACTERISTICS:
        (A) LENGTH:  10 amino acids
        (B) TYPE:  amino acid
        (C) STRANDEDNESS: Not Applicable
        (D) TOPOLOGY:  unknown (ii) MOLECULE TYPE:  glycoprotein
        (A) DESCRIPTION: identified as Ara h I IgE binding
            epitope peptide 1 Ara h I position 25-34.

(iii) HYPOTHETICAL:  No (iv) ANTI-SENSE:  Not applicable (v) FRAGMENT TYPE:  Not applicable (vi) ORIGINAL SOURCE:
        (A) ORGANISM:  Arachis hypogaea
        (B) STRAIN:  Florunner
        (C) INDIVIDUAL ISOLATE:  Ara h I
        (D) DEVELOPMENTAL STAGE:
        (E) HAPLOTYPE:  Not applicable
        (F) TISSUE TYPE:
        (G) CELL TYPE:  Not applicable
        (H) CELL LINE:  Not applicable
        (I) ORGANELLE:  Not applicable (vii) IMMEDIATE SOURCE:
        (A) LIBRARY:
        (B) CLONE:

(viii) POSITION IN GENOME:
        (A) CHROMOSOME/SEGMENT:  Not applicable
        (B) MAP POSITION:  Not applicable
        (C) UNITS:  Not applicable (ix) FEATURE:
        (A) NAME/KEY:
        (B) LOCATION:
        (C) IDENTIFICATION METHOD:  By agreement with
            protein information and established
            consensus sequence
        (D) OTHER INFORMATION:  Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:
```

(xi) SEQUENCE DESCRIPTION: SEQ ID NO: 24:

Ala Lys Ser Ser Pro Tyr Gln Lys Lys Thr
1               5                   10

(2) INFORMATION FOR SEQ ID NO: 25:

(i) SEQUENCE CHARACTERISTICS:
        (A) LENGTH:  10 amino acids
        (B) TYPE:  amino acid
        (C) STRANDEDNESS: Not Applicable
        (D) TOPOLOGY:  unknown (ii) MOLECULE TYPE:  glycoprotein
         (A) DESCRIPTION: identified as Ara h I IgE binding
             epitope peptide 2 Ara h I position 48-57.

(iii) HYPOTHETICAL:  No (iv) ANTI-SENSE:  Not applicable (v) FRAGMENT TYPE:  Not applicable (vi) ORIGINAL SOURCE:
         (A) ORGANISM:  Arachis hypogaea
         (B) STRAIN:  Florunner
         (C) INDIVIDUAL ISOLATE:  Ara h I
         (D) DEVELOPMENTAL STAGE:
         (E) HAPLOTYPE:  Not applicable
         (F) TISSUE TYPE:
         (G) CELL TYPE:  Not applicable
         (H) CELL LINE:  Not applicable
         (I) ORGANELLE:  Not applicable (vii) IMMEDIATE SOURCE:
          (A) LIBRARY:
          (B) CLONE:

(viii) POSITION IN GENOME:
           (A) CHROMOSOME/SEGMENT:  Not applicable
           (B) MAP POSITION:  Not applicable
           (C) UNITS:  Not applicable (ix) FEATURE:
         (A) NAME/KEY:
         (B) LOCATION:
         (C) IDENTIFICATION METHOD:  By agreement with
             protein information and established
             consensus sequence
         (D) OTHER INFORMATION:  Seed storage protein and
             allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 25:

Gln Glu Pro Asp Asp Leu Lys Gln Lys Ala
1               5                   10

(2) INFORMATION FOR SEQ ID NO:  26:

(i) SEQUENCE CHARACTERISTICS:
        (A) LENGTH:  10 amino acids
        (B) TYPE:  amino acid
        (C) STRANDEDNESS: Not Applicable
        (D) TOPOLOGY:  unknown

```
        (ii) MOLECULE TYPE: glycoprotein
             (A) DESCRIPTION: identified as Ara h I IgE binding
                 epitope peptide 3 Ara h I position 65-74.

(iii) HYPOTHETICAL: No (iv) ANTI-SENSE: Not applicable (v) FRAGMENT TYPE: Not applicable (vi) ORIGINAL SOURCE:
             (A) ORGANISM: Arachis hypogaea
             (B) STRAIN: Florunner
             (C) INDIVIDUAL ISOLATE: Ara h I
             (D) DEVELOPMENTAL STAGE:
             (E) HAPLOTYPE: Not applicable
             (F) TISSUE TYPE:
             (G) CELL TYPE: Not applicable
             (H) CELL LINE: Not applicable
             (I) ORGANELLE: Not applicable (vii) IMMEDIATE SOURCE:
             (A) LIBRARY:
             (B) CLONE:

(viii) POSITION IN GENOME:
             (A) CHROMOSOME/SEGMENT: Not applicable
             (B) MAP POSITION: Not applicable
             (C) UNITS: Not applicable (ix) FEATURE:
             (A) NAME/KEY:
             (B) LOCATION:
             (C) IDENTIFICATION METHOD: By agreement with
                 protein information and established
                 consensus sequence
             (D) OTHER INFORMATION: Seed storage protein and
                 allergen (x) PUBLICATION INFORMATION:
             (A) AUTHORS:
             (B) TITLE:
             (C) JOURNAL:
             (D) VOLUME:
             (E) ISSUE:
             (F) PAGES:
             (G) DATE:
             (H) DOCUMENT NUMBER:
             (I) FILING DATE:
             (J) PUBLICATION DATE:
             (K) RELEVANT RESIDUES IN SEQ ID NO:

(xi) SEQUENCE DESCRIPTION: SEQ ID NO: 26:

Leu Glu Tyr Pro Pro Arg Cys Val Tyr Asp
 1               5                   10

(2) INFORMATION FOR SEQ ID NO: 27:

(i) SEQUENCE CHARACTERISTICS:
             (A) LENGTH: 10 amino acids
             (B) TYPE: amino acid
             (C) STRANDEDNESS: Not Applicable
             (D) TOPOLOGY: unknown (ii) MOLECULE TYPE: glycoprotein
             (A) DESCRIPTION: identified as Ara h I IgE binding
                 epitope peptide 4 Ara h I position 89-98.

(iii) HYPOTHETICAL: No (iv) ANTI-SENSE: Not applicable (v) FRAGMENT TYPE: Not applicable (vi) ORIGINAL SOURCE:
             (A) ORGANISM: Arachis hypogaea
```

```
            (B) STRAIN:  Florunner
            (C) INDIVIDUAL ISOLATE:  Ara h I
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:

(viii) POSITION IN GENOME:
            (A) CHROMOSOME/SEGMENT:  Not applicable
            (B) MAP POSITION:  Not applicable
            (C) UNITS:  Not applicable (ix) FEATURE:
            (A) NAME/KEY:
            (B) LOCATION:
            (C) IDENTIFICATION METHOD:  By agreement with
                protein information and established
                consensus sequence
            (D) OTHER INFORMATION:  Seed storage protein and
                allergen (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 27:

Gly Glu Arg Thr Arg Gly Arg Gln Pro Gly
 1               5                  10

(2) INFORMATION FOR SEQ ID NO:  28:

(i) SEQUENCE CHARACTERISTICS:
            (A) LENGTH:  10 amino acids
            (B) TYPE:  amino acid
            (C) STRANDEDNESS: Not Applicable
            (D) TOPOLOGY:  unknown (ii) MOLECULE TYPE:  glycoprotein
            (A) DESCRIPTION: identified as Ara h I IgE binding
                epitope peptide 5 Ara h I position 97-105.

(iii) HYPOTHETICAL:  No (iv) ANTI-SENSE:  Not applicable (v) FRAGMENT TYPE:  Not applicable (vi) ORIGINAL SOURCE:
            (A) ORGANISM:  Arachis hypogaea
            (B) STRAIN:  Florunner
            (C) INDIVIDUAL ISOLATE:  Ara h I
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:
```

```
     (viii) POSITION IN GENOME:
           (A) CHROMOSOME/SEGMENT:  Not applicable
           (B) MAP POSITION:  Not applicable
           (C) UNITS:  Not applicable (ix) FEATURE:
           (A) NAME/KEY:
           (B) LOCATION:
           (C) IDENTIFICATION METHOD:  By agreement with
               protein information and established
               consensus sequence
           (D) OTHER INFORMATION:  Seed storage protein and
               allergen (x) PUBLICATION INFORMATION:
           (A) AUTHORS:
           (B) TITLE:
           (C) JOURNAL:
           (D) VOLUME:
           (E) ISSUE:
           (F) PAGES:
           (G) DATE:
           (H) DOCUMENT NUMBER:
           (I) FILING DATE:
           (J) PUBLICATION DATE:
           (K) RELEVANT RESIDUES IN SEQ ID NO:

(xi) SEQUENCE DESCRIPTION: SEQ ID NO: 28:

Pro Gly Asp Tyr Asp Asp Asp Arg Arg Gln
 1               5                  10

(2) INFORMATION FOR SEQ ID NO:  29:

(i) SEQUENCE CHARACTERISTICS:
           (A) LENGTH:  10 amino acids
           (B) TYPE:  amino acid
           (C) STRANDEDNESS: Not Applicable
           (D) TOPOLOGY:  unknown (ii) MOLECULE TYPE:  glycoprotein
           (A) DESCRIPTION: identified as Ara h I IgE binding
               epitope peptide 6 Ara h I position 107-116.

(iii) HYPOTHETICAL:  No (iv) ANTI-SENSE:  Not applicable (v) FRAGMENT TYPE:  Not applicable (vi) ORIGINAL SOURCE:
           (A) ORGANISM:  Arachis hypogaea
           (B) STRAIN:  Florunner
           (C) INDIVIDUAL ISOLATE:  Ara h I
           (D) DEVELOPMENTAL STAGE:
           (E) HAPLOTYPE:  Not applicable
           (F) TISSUE TYPE:
           (G) CELL TYPE:  Not applicable
           (H) CELL LINE:  Not applicable
           (I) ORGANELLE:  Not applicable (vii) IMMEDIATE SOURCE:
           (A) LIBRARY:
           (B) CLONE:

(viii) POSITION IN GENOME:
           (A) CHROMOSOME/SEGMENT:  Not applicable
           (B) MAP POSITION:  Not applicable
           (C) UNITS:  Not applicable (ix) FEATURE:
           (A) NAME/KEY:
           (B) LOCATION:
           (C) IDENTIFICATION METHOD:  By agreement with
               protein information and established
               consensus sequence
           (D) OTHER INFORMATION:  Seed storage protein and
               allergen
```

-continued (x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO: 29:

```
Pro Arg Arg Glu Glu Gly Gly Arg Trp Gly
 1               5                  10
```

(2) INFORMATION FOR SEQ ID NO: 30:

(i) SEQUENCE CHARACTERISTICS:
(A) LENGTH: 10 amino acids
(B) TYPE: amino acid
(C) STRANDEDNESS: Not Applicable
(D) TOPOLOGY: unknown (ii) MOLECULE TYPE: glycoprotein
(A) DESCRIPTION: identified as Ara h I IgE binding epitope peptide 7 Ara h I position 123-132.

(iii) HYPOTHETICAL: No (iv) ANTI-SENSE: Not applicable (v) FRAGMENT TYPE: Not applicable (vi) ORIGINAL SOURCE:
(A) ORGANISM: Arachis hypogaea
(B) STRAIN: Florunner
(C) INDIVIDUAL ISOLATE: Ara h I
(D) DEVELOPMENTAL STAGE:
(E) HAPLOTYPE: Not applicable
(F) TISSUE TYPE:
(G) CELL TYPE: Not applicable
(H) CELL LINE: Not applicable
(I) ORGANELLE: Not applicable (vii) IMMEDIATE SOURCE:
(A) LIBRARY:
(B) CLONE:

(viii) POSITION IN GENOME:
(A) CHROMOSOME/SEGMENT: Not applicable
(B) MAP POSITION: Not applicable
(C) UNITS: Not applicable (ix) FEATURE:
(A) NAME/KEY:
(B) LOCATION:
(C) IDENTIFICATION METHOD: By agreement with protein information and established consensus sequence
(D) OTHER INFORMATION: Seed storage protein and allergen (x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO: 30:

Arg Glu Arg Glu Glu Asp Trp Arg Glu Pro
1               5                   10

(2) INFORMATION FOR SEQ ID NO: 31:

(i) SEQUENCE CHARACTERISTICS:
        (A) LENGTH: 10 amino acids
        (B) TYPE: amino acid
        (C) STRANDEDNESS: Not Applicable
        (D) TOPOLOGY: unknown (ii) MOLECULE TYPE: glycoprotein
        (A) DESCRIPTION: identified as Ara h I IgE binding
            epitope peptide 8 Ara h I position 134-143.

(iii) HYPOTHETICAL: No (iv) ANTI-SENSE: Not applicable (v) FRAGMENT TYPE: Not applicable (vi) ORIGINAL SOURCE:
        (A) ORGANISM: Arachis hypogaea
        (B) STRAIN: Florunner
        (C) INDIVIDUAL ISOLATE: Ara h I
        (D) DEVELOPMENTAL STAGE:
        (E) HAPLOTYPE: Not applicable
        (F) TISSUE TYPE:
        (G) CELL TYPE: Not applicable
        (H) CELL LINE: Not applicable
        (I) ORGANELLE: Not applicable (vii) IMMEDIATE SOURCE:
        (A) LIBRARY:
        (B) CLONE:

(viii) POSITION IN GENOME:
        (A) CHROMOSOME/SEGMENT: Not applicable
        (B) MAP POSITION: Not applicable
        (C) UNITS: Not applicable (ix) FEATURE:
        (A) NAME/KEY:
        (B) LOCATION:
        (C) IDENTIFICATION METHOD: By agreement with
            protein information and established
            consensus sequence
        (D) OTHER INFORMATION: Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 31:

Glu Asp Trp Arg Arg Pro Ser His Gln Gln
1               5                   10

(2) INFORMATION FOR SEQ ID NO: 32:

(i) SEQUENCE CHARACTERISTICS:
        (A) LENGTH: 10 amino acids
        (B) TYPE: amino acid sequence
        (C) STRANDEDNESS: Not Applicable

```
          (D) TOPOLOGY:  unknown (ii) MOLECULE TYPE:  glycoprotein
         (A) DESCRIPTION: identified as Ara h I IgE binding
             epitope peptide 9 Ara h I position 143-152.

(iii) HYPOTHETICAL:  No (iv) ANTI-SENSE:  Not applicable (v) FRAGMENT TYPE:  Not applicable (vi) ORIGINAL SOURCE:
         (A) ORGANISM:  Arachis hypogaea
         (B) STRAIN:  Florunner
         (C) INDIVIDUAL ISOLATE:  Ara h I
         (D) DEVELOPMENTAL STAGE:
         (E) HAPLOTYPE:  Not applicable
         (F) TISSUE TYPE:
         (G) CELL TYPE:  Not applicable
         (H) CELL LINE:  Not applicable
         (I) ORGANELLE:  Not applicable (vii) IMMEDIATE SOURCE:
         (A) LIBRARY:
         (B) CLONE:

(viii) POSITION IN GENOME:
         (A) CHROMOSOME/SEGMENT:  Not applicable
         (B) MAP POSITION:  Not applicable
         (C) UNITS:  Not applicable (ix) FEATURE:
         (A) NAME/KEY:
         (B) LOCATION:
         (C) IDENTIFICATION METHOD:  By agreement with
             protein information and established
             consensus sequence
         (D) OTHER INFORMATION:  Seed storage protein and
             allergen (x) PUBLICATION INFORMATION:
         (A) AUTHORS:
         (B) TITLE:
         (C) JOURNAL:
         (D) VOLUME:
         (E) ISSUE:
         (F) PAGES:
         (G) DATE:
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO: 32:

Gln Pro Arg Lys Ile Arg Pro Glu Gly Arg
 1               5                  10

(2) INFORMATION FOR SEQ ID NO:  33:

(i) SEQUENCE CHARACTERISTICS:
         (A) LENGTH:  10 amino acids
         (B) TYPE:  amino acid
         (C) STRANDEDNESS: Not Applicable
         (D) TOPOLOGY:  unknown (ii) MOLECULE TYPE:  glycoprotein
         (A) DESCRIPTION: identified as Ara h I IgE binding
             epitope peptide 10 Ara h I position 294-303.

(iii) HYPOTHETICAL:  No (iv) ANTI-SENSE:  Not applicable (v) FRAGMENT TYPE:  Not applicable (vi) ORIGINAL SOURCE:
```

```
            (A) ORGANISM:  Arachis hypogaea
            (B) STRAIN:  Florunner
            (C) INDIVIDUAL ISOLATE:  Ara h I
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:

(viii) POSITION IN GENOME:
            (A) CHROMOSOME/SEGMENT:  Not applicable
            (B) MAP POSITION:  Not applicable
            (C) UNITS:  Not applicable (ix) FEATURE:
            (A) NAME/KEY:
            (B) LOCATION:
            (C) IDENTIFICATION METHOD:  By agreement with
                protein information and established
                consensus sequence
            (D) OTHER INFORMATION:  Seed storage protein and
                allergen (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 33:

Thr Pro Gly Gln Phe Glu Asp Phe Phe Pro
1               5                   10

(2) INFORMATION FOR SEQ ID NO:  34:

(i) SEQUENCE CHARACTERISTICS:
            (A) LENGTH:  10 amino acids
            (B) TYPE:  amino acid
            (C) STRANDEDNESS: Not Applicable
            (D) TOPOLOGY:  unknown (ii) MOLECULE TYPE:  glycoprotein
            (A) DESCRIPTION: identified as Ara h I IgE binding
                epitope peptide 11 Ara h I position 311-320.

(iii) HYPOTHETICAL:  No (iv) ANTI-SENSE:  Not applicable (v) FRAGMENT TYPE:  Not applicable (vi) ORIGINAL SOURCE:
            (A) ORGANISM:  Arachis hypogaea
            (B) STRAIN:  Florunner
            (C) INDIVIDUAL ISOLATE:  Ara h I
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:
```

-continued

```
  (viii) POSITION IN GENOME:
         (A) CHROMOSOME/SEGMENT:  Not applicable
         (B) MAP POSITION:  Not applicable
         (C) UNITS:  Not applicable (ix) FEATURE:
         (A) NAME/KEY:
         (B) LOCATION:
         (C) IDENTIFICATION METHOD:  By agreement with
             protein information and established
             consensus sequence
         (D) OTHER INFORMATION:  Seed storage protein and
             allergen (x) PUBLICATION INFORMATION:
         (A) AUTHORS:
         (B) TITLE:
         (C) JOURNAL:
         (D) VOLUME:
         (E) ISSUE:
         (F) PAGES:
         (G) DATE:
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO: 34:

Ser Tyr Leu Gln Glu Phe Ser Arg Asn Thr
 1               5                  10

(2) INFORMATION FOR SEQ ID NO:  35:

(i) SEQUENCE CHARACTERISTICS:
         (A) LENGTH:  10 amino acids
         (B) TYPE:  amino acid
         (C) STRANDEDNESS: Not Applicable
         (D) TOPOLOGY:  unknown (ii) MOLECULE TYPE:  glycoprotein
         (A) DESCRIPTION: identified as Ara h I IgE binding
             epitope peptide 12 Ara h I position 325-334.

(iii) HYPOTHETICAL:  No (iv) ANTI-SENSE:  Not applicable (v) FRAGMENT TYPE:  Not applicable (vi) ORIGINAL SOURCE:
         (A) ORGANISM:  Arachis hypogaea
         (B) STRAIN:  Florunner
         (C) INDIVIDUAL ISOLATE:  Ara h I
         (D) DEVELOPMENTAL STAGE:
         (E) HAPLOTYPE:  Not applicable
         (F) TISSUE TYPE:
         (G) CELL TYPE:  Not applicable
         (H) CELL LINE:  Not applicable
         (I) ORGANELLE:  Not applicable (vii) IMMEDIATE SOURCE:
         (A) LIBRARY:
         (B) CLONE:

(viii) POSITION IN GENOME:
         (A) CHROMOSOME/SEGMENT:  Not applicable
         (B) MAP POSITION:  Not applicable
         (C) UNITS:  Not applicable (ix) FEATURE:
         (A) NAME/KEY:
         (B) LOCATION:
         (C) IDENTIFICATION METHOD:  By agreement with
             protein information and established
             consensus sequence
         (D) OTHER INFORMATION:  Seed storage protein and
```

```
               allergen (x) PUBLICATION INFORMATION:
         (A) AUTHORS:
         (B) TITLE:
         (C) JOURNAL:
         (D) VOLUME:
         (E) ISSUE:
         (F) PAGES:
         (G) DATE:
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO: 35:

Phe Asn Ala Glu Phe Asn Glu Ile Arg Arg
1               5                   10

(2) INFORMATION FOR SEQ ID NO:  36:

(i) SEQUENCE CHARACTERISTICS:
         (A) LENGTH:   10 amino acids
         (B) TYPE:   amino acid
         (C) STRANDEDNESS: Not Applicable
         (D) TOPOLOGY:   unknown (ii) MOLECULE TYPE:  glycoprotein
         (A) DESCRIPTION: identified as Ara h I IgE binding
             epitope peptide 13 Ara h I position 344-353.

(iii) HYPOTHETICAL:  No (iv) ANTI-SENSE:  Not applicable (v) FRAGMENT TYPE:  Not applicable (vi) ORIGINAL SOURCE:
         (A) ORGANISM:  Arachis hypogaea
         (B) STRAIN:  Florunner
         (C) INDIVIDUAL ISOLATE:  Ara h I
         (D) DEVELOPMENTAL STAGE:
         (E) HAPLOTYPE:  Not applicable
         (F) TISSUE TYPE:
         (G) CELL TYPE:  Not applicable
         (H) CELL LINE:  Not applicable
         (I) ORGANELLE:  Not applicable (vii) IMMEDIATE SOURCE:
         (A) LIBRARY:
         (B) CLONE:

(viii) POSITION IN GENOME:
         (A) CHROMOSOME/SEGMENT:  Not applicable
         (B) MAP POSITION:  Not applicable
         (C) UNITS:  Not applicable (ix) FEATURE:
         (A) NAME/KEY:
         (B) LOCATION:
         (C) IDENTIFICATION METHOD:  By agreement with
             protein information and established
             consensus sequence
         (D) OTHER INFORMATION:  Seed storage protein and
             allergen (x) PUBLICATION INFORMATION:
         (A) AUTHORS:
         (B) TITLE:
         (C) JOURNAL:
         (D) VOLUME:
         (E) ISSUE:
         (F) PAGES:
         (G) DATE:
         (H) DOCUMENT NUMBER:
         (I) FILING DATE:
         (J) PUBLICATION DATE:
```

-continued

```
        (K) RELEVANT RESIDUES IN SEQ ID NO:

(xi) SEQUENCE DESCRIPTION: SEQ ID NO: 36:

Glu Gln Glu Glu Arg Gly Gln Arg Arg Trp
1               5                   10

(2) INFORMATION FOR SEQ ID NO: 37:

(i) SEQUENCE CHARACTERISTICS:
         (A) LENGTH: 10 amino acids
         (B) TYPE: amino acid
         (C) STRANDEDNESS: Not Applicable
         (D) TOPOLOGY: unknown (ii) MOLECULE TYPE: glycoprotein
         (A) DESCRIPTION: identified as Ara h I IgE binding
             epitope peptide 14 Ara h I position 393-402.

(iii) HYPOTHETICAL: No (iv) ANTI-SENSE: Not applicable (v) FRAGMENT TYPE: Not applicable (vi) ORIGINAL SOURCE:
         (A) ORGANISM: Arachis hypogaea
         (B) STRAIN: Florunner
         (C) INDIVIDUAL ISOLATE: Ara h I
         (D) DEVELOPMENTAL STAGE:
         (E) HAPLOTYPE: Not applicable
         (F) TISSUE TYPE:
         (G) CELL TYPE: Not applicable
         (H) CELL LINE: Not applicable
         (I) ORGANELLE: Not applicable (vii) IMMEDIATE SOURCE:
         (A) LIBRARY:
         (B) CLONE:

(viii) POSITION IN GENOME:
         (A) CHROMOSOME/SEGMENT: Not applicable
         (B) MAP POSITION: Not applicable
         (C) UNITS: Not applicable (ix) FEATURE:
         (A) NAME/KEY:
         (B) LOCATION:
         (C) IDENTIFICATION METHOD: By agreement with
             protein information and established
             consensus sequence
         (D) OTHER INFORMATION: Seed storage protein and
             allergen (x) PUBLICATION INFORMATION:
         (A) AUTHORS:
         (B) TITLE:
         (C) JOURNAL:
         (D) VOLUME:
         (E) ISSUE:
         (F) PAGES:
         (G) DATE:
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO: 37:

Asp Ile Thr Asn Pro Ile Asn Leu Arg Glu
1               5                   10

(2) INFORMATION FOR SEQ ID NO: 38:

(i) SEQUENCE CHARACTERISTICS:
         (A) LENGTH: 10 amino acids
         (B) TYPE: amino acid
```

-continued (C) STRANDEDNESS: Not Applicable
(D) TOPOLOGY: unknown (ii) MOLECULE TYPE: glycoprotein
(A) DESCRIPTION: identified as Ara h I IgE binding epitope peptide 15 Ara h I position 409-418.

(iii) HYPOTHETICAL: No (iv) ANTI-SENSE: Not applicable (v) FRAGMENT TYPE: Not applicable (vi) ORIGINAL SOURCE:
(A) ORGANISM: Arachis hypogaea
(B) STRAIN: Florunner
(C) INDIVIDUAL ISOLATE: Ara h I
(D) DEVELOPMENTAL STAGE:
(E) HAPLOTYPE: Not applicable
(F) TISSUE TYPE:
(G) CELL TYPE: Not applicable
(H) CELL LINE: Not applicable
(I) ORGANELLE: Not applicable (vii) IMMEDIATE SOURCE:
(A) LIBRARY:
(B) CLONE:

(viii) POSITION IN GENOME:
(A) CHROMOSOME/SEGMENT: Not applicable
(B) MAP POSITION: Not applicable
(C) UNITS: Not applicable (ix) FEATURE:
(A) NAME/KEY:
(B) LOCATION:
(C) IDENTIFICATION METHOD: By agreement with protein information and established consensus sequence
(D) OTHER INFORMATION: Seed storage protein and allergen (x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO: 38:

```
Asn Asn Phe Gly Lys Leu Phe Glu Val Lys
 1               5                  10
```

(2) INFORMATION FOR SEQ ID NO: 39:

(i) SEQUENCE CHARACTERISTICS:
(A) LENGTH: 10 amino acids
(B) TYPE: amino acid
(C) STRANDEDNESS: Not Applicable
(D) TOPOLOGY: unknown (ii) MOLECULE TYPE: glycoprotein
(A) DESCRIPTION: identified as Ara h I IgE binding epitope peptide 16 Ara h I position 461-470.

(iii) HYPOTHETICAL: No (iv) ANTI-SENSE: Not applicable (v) FRAGMENT TYPE: Not applicable -continued

```
       (vi) ORIGINAL SOURCE:
                (A) ORGANISM:  Arachis hypogaea
                (B) STRAIN:  Florunner
                (C) INDIVIDUAL ISOLATE:  Ara h I
                (D) DEVELOPMENTAL STAGE:
                (E) HAPLOTYPE:  Not applicable
                (F) TISSUE TYPE:
                (G) CELL TYPE:  Not applicable
                (H) CELL LINE:  Not applicable
                (I) ORGANELLE:  Not applicable (vii) IMMEDIATE SOURCE:
                (A) LIBRARY:
                (B) CLONE:

(viii) POSITION IN GENOME:
                (A) CHROMOSOME/SEGMENT:  Not applicable
                (B) MAP POSITION:  Not applicable
                (C) UNITS:  Not applicable (ix) FEATURE:
                (A) NAME/KEY:
                (B) LOCATION:
                (C) IDENTIFICATION METHOD:  By agreement with
                    protein information and established
                    consensus sequence
                (D) OTHER INFORMATION:  Seed storage protein and
                    allergen (x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO: 39:

Gly Thr Gly Asn Leu Glu Leu Val Ala Val
 1               5                  10

(2) INFORMATION FOR SEQ ID NO:  40:

(i) SEQUENCE CHARACTERISTICS:
                (A) LENGTH:  10 amino acids
                (B) TYPE:  amino acid
                (C) STRANDEDNESS: Not Applicable
                (D) TOPOLOGY:  unknown (ii) MOLECULE TYPE:  glycoprotein
                (A) DESCRIPTION: identified as Ara h I IgE binding
                    epitope peptide 17 Ara h I position 498-507.

(iii) HYPOTHETICAL:  No (iv) ANTI-SENSE:  Not applicable (v) FRAGMENT TYPE:  Not applicable (vi) ORIGINAL SOURCE:
                (A) ORGANISM:  Arachis hypogaea
                (B) STRAIN:  Florunner
                (C) INDIVIDUAL ISOLATE:  Ara h I
                (D) DEVELOPMENTAL STAGE:
                (E) HAPLOTYPE:  Not applicable
                (F) TISSUE TYPE:
                (G) CELL TYPE:  Not applicable
                (H) CELL LINE:  Not applicable
                (I) ORGANELLE:  Not applicable (vii) IMMEDIATE SOURCE:
                (A) LIBRARY:
```

```
            (B) CLONE:

(viii) POSITION IN GENOME:
            (A) CHROMOSOME/SEGMENT:  Not applicable
            (B) MAP POSITION:  Not applicable
            (C) UNITS:  Not applicable (ix) FEATURE:
            (A) NAME/KEY:
            (B) LOCATION:
            (C) IDENTIFICATION METHOD:  By agreement with
                protein information and established
                consensus sequence
            (D) OTHER INFORMATION:  Seed storage protein and
                allergen (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 40:

Arg Arg Tyr Thr Ala Arg Leu Lys Glu Gly
 1               5                  10

(2) INFORMATION FOR SEQ ID NO:  41:

(i) SEQUENCE CHARACTERISTICS:
            (A) LENGTH:  10 amino acids
            (B) TYPE:  amino acid
            (C) STRANDEDNESS: Not Applicable
            (D) TOPOLOGY:  unknown (ii) MOLECULE TYPE:  glycoprotein
            (A) DESCRIPTION: identified as Ara h I IgE binding
                epitope peptide 18 Ara h I position 525-534.

(iii) HYPOTHETICAL:  No (iv) ANTI-SENSE:  Not applicable (v) FRAGMENT TYPE:  Not applicable (vi) ORIGINAL SOURCE:
            (A) ORGANISM:  Arachis hypogaea
            (B) STRAIN:  Florunner
            (C) INDIVIDUAL ISOLATE:  Ara h I
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:

(viii) POSITION IN GENOME:
            (A) CHROMOSOME/SEGMENT:  Not applicable
            (B) MAP POSITION:  Not applicable
            (C) UNITS:  Not applicable (ix) FEATURE:
            (A) NAME/KEY:
            (B) LOCATION:
            (C) IDENTIFICATION METHOD:  By agreement with
                protein information and established
                consensus sequence
```

```
            (D) OTHER INFORMATION:  Seed storage protein and
                allergen (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 41:

Glu Leu His Leu Leu Gly Phe Gly Ile Asn
 1               5                  10

(2) INFORMATION FOR SEQ ID NO:  42:

(i) SEQUENCE CHARACTERISTICS:
            (A) LENGTH:  10 amino acids
            (B) TYPE:  amino acid
            (C) STRANDEDNESS: Not Applicable
            (D) TOPOLOGY:  unknown (ii) MOLECULE TYPE:  glycoprotein
            (A) DESCRIPTION: identified as Ara h I IgE binding
                epitope peptide 19 Ara h I position 539-548.

(iii) HYPOTHETICAL:  No (iv) ANTI-SENSE:  Not applicable (v) FRAGMENT TYPE:  Not applicable (vi) ORIGINAL SOURCE:
            (A) ORGANISM:  Arachis hypogaea
            (B) STRAIN:  Florunner
            (C) INDIVIDUAL ISOLATE:  Ara h I
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:

(viii) POSITION IN GENOME:
            (A) CHROMOSOME/SEGMENT:  Not applicable
            (B) MAP POSITION:  Not applicable
            (C) UNITS:  Not applicable (ix) FEATURE:
            (A) NAME/KEY:
            (B) LOCATION:
            (C) IDENTIFICATION METHOD:  By agreement with
                protein information and established
                consensus sequence
            (D) OTHER INFORMATION:  Seed storage protein and
                allergen (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
```

```
        (J) PUBLICATION DATE:
        (K) RELEVANT RESIDUES IN SEQ ID NO:

(xi) SEQUENCE DESCRIPTION: SEQ ID NO: 42:

His Arg Ile Phe Leu Ala Gly Asp Lys Asp
 1               5                  10

(2) INFORMATION FOR SEQ ID NO:  43:

(i) SEQUENCE CHARACTERISTICS:
        (A) LENGTH:  10 amino acids
        (B) TYPE:  amino acid
        (C) STRANDEDNESS: Not Applicable
        (D) TOPOLOGY:  unknown (ii) MOLECULE TYPE:  glycoprotein
        (A) DESCRIPTION: identified as Ara h I IgE binding
            epitope peptide 20 Ara h I position 551-560.

(iii) HYPOTHETICAL:  No (iv) ANTI-SENSE:  Not applicable (v) FRAGMENT TYPE:  Not applicable (vi) ORIGINAL SOURCE:
        (A) ORGANISM:  Arachis hypogaea
        (B) STRAIN:  Florunner
        (C) INDIVIDUAL ISOLATE:  Ara h I
        (D) DEVELOPMENTAL STAGE:
        (E) HAPLOTYPE:  Not applicable
        (F) TISSUE TYPE:
        (G) CELL TYPE:  Not applicable
        (H) CELL LINE:  Not applicable
        (I) ORGANELLE:  Not applicable (vii) IMMEDIATE SOURCE:
        (A) LIBRARY:
        (B) CLONE:

(viii) POSITION IN GENOME:
        (A) CHROMOSOME/SEGMENT:  Not applicable
        (B) MAP POSITION:  Not applicable
        (C) UNITS:  Not applicable (ix) FEATURE:
        (A) NAME/KEY:
        (B) LOCATION:
        (C) IDENTIFICATION METHOD:  By agreement with
            protein information and established
            consensus sequence
        (D) OTHER INFORMATION:  Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 43:

Ile Asp Gln Ile Glu Lys Gln Ala Lys Asp
 1               5                  10

(2) INFORMATION FOR SEQ ID NO:  44:

(i) SEQUENCE CHARACTERISTICS:
        (A) LENGTH:  10 amino acids
```

-continued (B) TYPE: amino acid
(C) STRANDEDNESS: Not Applicable
(D) TOPOLOGY: unknown (ii) MOLECULE TYPE: glycoprotein
(A) DESCRIPTION: identified as Ara h I IgE binding epitope peptide 21 Ara h I position 559-568.

(iii) HYPOTHETICAL: No (iv) ANTI-SENSE: Not applicable (v) FRAGMENT TYPE: Not applicable (vi) ORIGINAL SOURCE:
(A) ORGANISM: Arachis hypogaea
(B) STRAIN: Florunner
(C) INDIVIDUAL ISOLATE: Ara h I
(D) DEVELOPMENTAL STAGE:
(E) HAPLOTYPE: Not applicable
(F) TISSUE TYPE:
(G) CELL TYPE: Not applicable
(H) CELL LINE: Not applicable
(I) ORGANELLE: Not applicable (vii) IMMEDIATE SOURCE:
(A) LIBRARY:
(B) CLONE:

(viii) POSITION IN GENOME:
(A) CHROMOSOME/SEGMENT: Not applicable
(B) MAP POSITION: Not applicable
(C) UNITS: Not applicable (ix) FEATURE:
(A) NAME/KEY:
(B) LOCATION:
(C) IDENTIFICATION METHOD: By agreement with protein information and established consensus sequence
(D) OTHER INFORMATION: Seed storage protein and allergen (x) PUBLICATION INFORMATION:
(A) AUTHORS:
(B) TITLE:
(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO: 44:

```
Lys Asp Leu Ala Phe Pro Gly Ser Gly Glu
 1               5                   10
```

(2) INFORMATION FOR SEQ ID NO: 45:

(i) SEQUENCE CHARACTERISTICS:
(A) LENGTH: 10 amino acids
(B) TYPE: amino acid
(C) STRANDEDNESS: Not Applicable
(D) TOPOLOGY: unknown (ii) MOLECULE TYPE: glycoprotein
(A) DESCRIPTION: identified as Ara h I IgE binding epitope peptide 22 Ara h I position 578-587.

(iii) HYPOTHETICAL: No (iv) ANTI-SENSE: Not applicable (v) FRAGMENT TYPE: Not applicable

```
        (vi) ORIGINAL SOURCE:
             (A) ORGANISM:  Arachis hypogaea
             (B) STRAIN:  Florunner
             (C) INDIVIDUAL ISOLATE:  Ara h I
             (D) DEVELOPMENTAL STAGE:
             (E) HAPLOTYPE:  Not applicable
             (F) TISSUE TYPE:
             (G) CELL TYPE:  Not applicable
             (H) CELL LINE:  Not applicable
             (I) ORGANELLE:  Not applicable (vii) IMMEDIATE SOURCE:
             (A) LIBRARY:
             (B) CLONE:

(viii) POSITION IN GENOME:
             (A) CHROMOSOME/SEGMENT:  Not applicable
             (B) MAP POSITION:  Not applicable
             (C) UNITS:  Not applicable (ix) FEATURE:
             (A) NAME/KEY:
             (B) LOCATION:
             (C) IDENTIFICATION METHOD:  By agreement with
                 protein information and established
                 consensus sequence
             (D) OTHER INFORMATION:  Seed storage protein and
                 allergen (x) PUBLICATION INFORMATION:
             (A) AUTHORS:
             (B) TITLE:
             (C) JOURNAL:
             (D) VOLUME:
             (E) ISSUE:
             (F) PAGES:
             (G) DATE:
             (H) DOCUMENT NUMBER:
             (I) FILING DATE:
             (J) PUBLICATION DATE:
             (K) RELEVANT RESIDUES IN SEQ ID NO:

(xi) SEQUENCE DESCRIPTION: SEQ ID NO: 45:

Lys Glu Ser His Phe Val Ser Ala Arg Pro
1               5                   10

(2) INFORMATION FOR SEQ ID NO:  46:

(i) SEQUENCE CHARACTERISTICS:
             (A) LENGTH:  10 amino acids
             (B) TYPE:  amino acid
             (C) STRANDEDNESS: Not Applicable
             (D) TOPOLOGY:  unknown (ii) MOLECULE TYPE:  glycoprotein
             (A) DESCRIPTION: identified as Ara h I IgE binding
                 epitope peptide 23 Ara h I position 597-606.

(iii) HYPOTHETICAL:  No (iv) ANTI-SENSE:  Not applicable (v) FRAGMENT TYPE:  Not applicable (vi) ORIGINAL SOURCE:
             (A) ORGANISM:  Arachis hypogaea
             (B) STRAIN:  Florunner
             (C) INDIVIDUAL ISOLATE:  Ara h I
             (D) DEVELOPMENTAL STAGE:
             (E) HAPLOTYPE:  Not applicable
             (F) TISSUE TYPE:
             (G) CELL TYPE:  Not applicable
             (H) CELL LINE:  Not applicable
             (I) ORGANELLE:  Not applicable (vii) IMMEDIATE SOURCE:
```

```
          (A) LIBRARY:
          (B) CLONE:

(viii) POSITION IN GENOME:
          (A) CHROMOSOME/SEGMENT: Not applicable
          (B) MAP POSITION: Not applicable
          (C) UNITS: Not applicable (ix) FEATURE:
          (A) NAME/KEY:
          (B) LOCATION:
          (C) IDENTIFICATION METHOD: By agreement with
              protein information and established
              consensus sequence
          (D) OTHER INFORMATION: Seed storage protein and
              allergen (x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO: 46:

Pro Glu Lys Glu Ser Pro Glu Lys Glu Asp
 1               5                  10

(2) INFORMATION FOR SEQ ID NO: 47:

(i) SEQUENCE CHARACTERISTICS:
          (A) LENGTH: 10 amino acids
          (B) TYPE: amino acid
          (C) STRANDEDNESS: Not Applicable
          (D) TOPOLOGY: unknown (ii) MOLECULE TYPE: glycoprotein
          (A) DESCRIPTION: identified as Ara h II IgE binding
              epitope peptide 1 Ara h II position 14-23.

(iii) HYPOTHETICAL: No (iv) ANTI-SENSE: Not applicable (v) FRAGMENT TYPE: Not applicable (vi) ORIGINAL SOURCE:
          (A) ORGANISM: Arachis hypogaea
          (B) STRAIN: Florunner
          (C) INDIVIDUAL ISOLATE: Ara h I
          (D) DEVELOPMENTAL STAGE:
          (E) HAPLOTYPE: Not applicable
          (F) TISSUE TYPE:
          (G) CELL TYPE: Not applicable
          (H) CELL LINE: Not applicable
          (I) ORGANELLE: Not applicable (vii) IMMEDIATE SOURCE:
          (A) LIBRARY:
          (B) CLONE:

(viii) POSITION IN GENOME:
          (A) CHROMOSOME/SEGMENT: Not applicable
          (B) MAP POSITION: Not applicable
          (C) UNITS: Not applicable (ix) FEATURE:
          (A) NAME/KEY:
          (B) LOCATION:
          (C) IDENTIFICATION METHOD: By agreement with
              protein information and established
```

```
                consensus sequence
        (D) OTHER INFORMATION: Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 47:

Leu Leu Ala Ala His Ala Ser Ala Arg Gln
 1               5                  10

(2) INFORMATION FOR SEQ ID NO:  48:

(i) SEQUENCE CHARACTERISTICS:
        (A) LENGTH:  10 amino acids
        (B) TYPE:  amino acid
        (C) STRANDEDNESS: Not Applicable
        (D) TOPOLOGY:  unknown (ii) MOLECULE TYPE:  glycoprotein
         (A) DESCRIPTION: identified as Ara h II IgE binding
             epitope peptide 2 Ara h II position 27-36.

(iii) HYPOTHETICAL:  No (iv) ANTI-SENSE:  Not applicable (v) FRAGMENT TYPE:  Not applicable (vi) ORIGINAL SOURCE:
        (A) ORGANISM:  Arachis hypogaea
        (B) STRAIN:  Florunner
        (C) INDIVIDUAL ISOLATE:  Ara h I
        (D) DEVELOPMENTAL STAGE:
        (E) HAPLOTYPE:  Not applicable
        (F) TISSUE TYPE:
        (G) CELL TYPE:  Not applicable
        (H) CELL LINE:  Not applicable
        (I) ORGANELLE:  Not applicable (vii) IMMEDIATE SOURCE:
        (A) LIBRARY:
        (B) CLONE:

(viii) POSITION IN GENOME:
        (A) CHROMOSOME/SEGMENT:  Not applicable
        (B) MAP POSITION:  Not applicable
        (C) UNITS:  Not applicable (ix) FEATURE:
        (A) NAME/KEY:
        (B) LOCATION:
        (C) IDENTIFICATION METHOD:  By agreement with
            protein information and established
            consensus sequence
        (D) OTHER INFORMATION: Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
```

```
            (I) FILING DATE:
            (J) PUBLICATION DATE:
            (K) RELEVANT RESIDUES IN SEQ ID NO:

(xi) SEQUENCE DESCRIPTION: SEQ ID NO: 48:

Gln Gly Asp Arg Arg Cys Gln Ser Gln Leu
 1               5                  10

(2) INFORMATION FOR SEQ ID NO:  49:

(i) SEQUENCE CHARACTERISTICS:
            (A) LENGTH:  10 amino acids
            (B) TYPE:  amino acid
            (C) STRANDEDNESS: Not Applicable
            (D) TOPOLOGY:  unknown (ii) MOLECULE TYPE:  glycoprotein
            (A) DESCRIPTION: identified as Ara h II IgE binding
                epitope peptide 3 Ara h II position 60-69.

(iii) HYPOTHETICAL:  No (iv) ANTI-SENSE:  Not applicable (v) FRAGMENT TYPE:  Not applicable (vi) ORIGINAL SOURCE:
            (A) ORGANISM:  Arachis hypogaea
            (B) STRAIN:  Florunner
            (C) INDIVIDUAL ISOLATE:  Ara h I
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:

(viii) POSITION IN GENOME:
            (A) CHROMOSOME/SEGMENT:  Not applicable
            (B) MAP POSITION:  Not applicable
            (C) UNITS:  Not applicable (ix) FEATURE:
            (A) NAME/KEY:
            (B) LOCATION:
            (C) IDENTIFICATION METHOD:  By agreement with
                protein information and established
                consensus sequence
            (D) OTHER INFORMATION:  Seed storage protein and
                allergen (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 49:

Tyr Glu Arg Asp Pro Tyr Ser Pro Ser Gln
 1               5                  10

(2) INFORMATION FOR SEQ ID NO:  50:

(i) SEQUENCE CHARACTERISTICS:
```

(A) LENGTH:  10 amino acids
            (B) TYPE:  amino acid
            (C) STRANDEDNESS: Not Applicable
            (D) TOPOLOGY:  unknown (ii) MOLECULE TYPE:  glycoprotein
            (A) DESCRIPTION: identified as Ara h II IgE binding
                epitope peptide 4 Ara h II position 81-90.

(iii) HYPOTHETICAL:  No (iv) ANTI-SENSE:  Not applicable (v) FRAGMENT TYPE:  Not applicable (vi) ORIGINAL SOURCE:
            (A) ORGANISM:  Arachis hypogaea
            (B) STRAIN:  Florunner
            (C) INDIVIDUAL ISOLATE:  Ara h I
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:

(viii) POSITION IN GENOME:
            (A) CHROMOSOME/SEGMENT:  Not applicable
            (B) MAP POSITION:  Not applicable
            (C) UNITS:  Not applicable (ix) FEATURE:
            (A) NAME/KEY:
            (B) LOCATION:
            (C) IDENTIFICATION METHOD:  By agreement with
                protein information and established
                consensus sequence
            (D) OTHER INFORMATION:  Seed storage protein and
                allergen (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 50:

Ala Gly Ser Ser Gln His Gln Glu Arg Cys
 1               5                  10

(2) INFORMATION FOR SEQ ID NO:  51:

(i) SEQUENCE CHARACTERISTICS:
            (A) LENGTH:  10 amino acids
            (B) TYPE:  amino acid
            (C) STRANDEDNESS: Not Applicable
            (D) TOPOLOGY:  unknown (ii) MOLECULE TYPE:  glycoprotein
            (A) DESCRIPTION: identified as Ara h II IgE binding
                epitope peptide 5 Ara h II position 91-100.

(iii) HYPOTHETICAL:  No (iv) ANTI-SENSE:  Not applicable

```
        (v) FRAGMENT TYPE:  Not applicable (vi) ORIGINAL SOURCE:
            (A) ORGANISM:  Arachis hypogaea
            (B) STRAIN:  Florunner
            (C) INDIVIDUAL ISOLATE:  Ara h I
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:

(viii) POSITION IN GENOME:
            (A) CHROMOSOME/SEGMENT:  Not applicable
            (B) MAP POSITION:  Not applicable
            (C) UNITS:  Not applicable (ix) FEATURE:
            (A) NAME/KEY:
            (B) LOCATION:
            (C) IDENTIFICATION METHOD:  By agreement with
                protein information and established
                consensus sequence
            (D) OTHER INFORMATION:  Seed storage protein and
                allergen (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 51:

Cys Asn Glu Leu Asn Glu Phe Glu Asn Asn
1               5                   10

(2) INFORMATION FOR SEQ ID NO:  52:

(i) SEQUENCE CHARACTERISTICS:
            (A) LENGTH:  10 amino acids
            (B) TYPE:  amino acid
            (C) STRANDEDNESS: Not Applicable
            (D) TOPOLOGY:  unknown (ii) MOLECULE TYPE:  glycoprotein
            (A) DESCRIPTION: identified as Ara h II IgE binding
                epitope peptide 6 Ara h II position 105-159.

(iii) HYPOTHETICAL:  No (iv) ANTI-SENSE:  Not applicable (v) FRAGMENT TYPE:  Not applicable (vi) ORIGINAL SOURCE:
            (A) ORGANISM:  Arachis hypogaea
            (B) STRAIN:  Florunner
            (C) INDIVIDUAL ISOLATE:  Ara h I
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable
```

```
    (vii) IMMEDIATE SOURCE:
         (A) LIBRARY:
         (B) CLONE:

(viii) POSITION IN GENOME:
         (A) CHROMOSOME/SEGMENT:  Not applicable
         (B) MAP POSITION:  Not applicable
         (C) UNITS:  Not applicable (ix) FEATURE:
         (A) NAME/KEY:
         (B) LOCATION:
         (C) IDENTIFICATION METHOD:  By agreement with
             protein information and established
             consensus sequence
         (D) OTHER INFORMATION:  Seed storage protein and
             allergen (x) PUBLICATION INFORMATION:
         (A) AUTHORS:
         (B) TITLE:
         (C) JOURNAL:
         (D) VOLUME:
         (E) ISSUE:
         (F) PAGES:
         (G) DATE:
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO: 52:

Gln Arg Cys Asp Leu Asp Val Glu Ser Gly
 1               5                   10

(2) INFORMATION FOR SEQ ID NO: 53:

(i) SEQUENCE CHARACTERISTICS:
         (A) LENGTH:  28 amino acids
         (B) TYPE:  amino acid
         (C) STRANDEDNESS: Not Applicable
         (D) TOPOLOGY:  unknown (ii) MOLECULE TYPE:  glycoprotein
         (A) DESCRIPTION: identified as derived N-terminal
             sequence of Ara h 2 p38.

(iii) HYPOTHETICAL:  No (iv) ANTI-SENSE:  Not applicable (v) FRAGMENT TYPE:  N-terminal fragment (vi) ORIGINAL SOURCE:
         (A) ORGANISM:  Arachis hypogaea
         (B) STRAIN:  Florunner
         (C) INDIVIDUAL ISOLATE:  P38
         (D) DEVELOPMENTAL STAGE:
         (E) HAPLOTYPE:  Not applicable
         (F) TISSUE TYPE:
         (G) CELL TYPE:  Not applicable
         (H) CELL LINE:  Not applicable
         (I) ORGANELLE:  Not applicable (vii) IMMEDIATE SOURCE:
         (A) LIBRARY:
         (B) CLONE:  P38

(viii) POSITION IN GENOME:
         (A) CHROMOSOME/SEGMENT:  Not applicable
         (B) MAP POSITION:  Not applicable
         (C) UNITS:  Not applicable (ix) FEATURE:
         (A) NAME/KEY:
         (B) LOCATION:
         (C) IDENTIFICATION METHOD:  By agreement with
```

```
                protein information and established
                consensus sequence
        (D) OTHER INFORMATION:  Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 53:

Gln Gln Trp Glu Leu Gln Gly Asp Arg Arg
 1               5                  10

Cys Gln Ser Gln Leu Glu Arg Ala Asn Leu
                15                  20

Arg Pro Cys Glu Gln His Leu Met
                25

(2) INFORMATION FOR SEQ ID NO:  54:

(i) SEQUENCE CHARACTERISTICS:
         (A) LENGTH:  13 amino acids
         (B) TYPE:  amino acid
         (C) STRANDEDNESS: Not Applicable
         (D) TOPOLOGY:  unknown (ii) MOLECULE TYPE:  peptide
         (A) DESCRIPTION: identified as peptide 45 of Ara h 2
             p38.

(iii) HYPOTHETICAL:  No (iv) ANTI-SENSE:  Not applicable (v) FRAGMENT TYPE:  amino terminus (vi) ORIGINAL SOURCE:
         (A) ORGANISM:  Arachis hypogaea
         (B) STRAIN:  Florunner
         (C) INDIVIDUAL ISOLATE:  P38
         (D) DEVELOPMENTAL STAGE:
         (E) HAPLOTYPE:  Not applicable
         (F) TISSUE TYPE:
         (G) CELL TYPE:  Not applicable
         (H) CELL LINE:  Not applicable
         (I) ORGANELLE:  Not applicable (vii) IMMEDIATE SOURCE:
         (A) LIBRARY:
         (B) CLONE:  P38

(viii) POSITION IN GENOME:
         (A) CHROMOSOME/SEGMENT:  Not applicable
         (B) MAP POSITION:  Not applicable
         (C) UNITS:  Not applicable (ix) FEATURE:
         (A) NAME/KEY:
         (B) LOCATION:
         (C) IDENTIFICATION METHOD:  By agreement with
             protein information and established
             consensus sequence
         (D) OTHER INFORMATION:  Seed storage protein and
             allergen (x) PUBLICATION INFORMATION:
         (A) AUTHORS:
```

```
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO: 54:

Ala Asn Leu Arg Pro Cys Glu Gln His Leu Met Gln Lys
 1               5                  10

(2) INFORMATION FOR SEQ ID NO: 55:

(i) SEQUENCE CHARACTERISTICS:
          (A) LENGTH:  17 amino acids
          (B) TYPE:  amino acid
          (C) STRANDEDNESS: Not Applicable
          (D) TOPOLOGY:  unknown (ii) MOLECULE TYPE:  peptide
          (A) DESCRIPTION: identified as peptide 37
              of Ara h 2 p38.

(iii) HYPOTHETICAL:  No (iv) ANTI-SENSE:  Not applicable (v) FRAGMENT TYPE:  amino terminus (vi) ORIGINAL SOURCE:
          (A) ORGANISM:  Arachis hypogaea
          (B) STRAIN:  Florunner
          (C) INDIVIDUAL ISOLATE:  P38
          (D) DEVELOPMENTAL STAGE:
          (E) HAPLOTYPE:  Not applicable
          (F) TISSUE TYPE:
          (G) CELL TYPE:  Not applicable
          (H) CELL LINE:  Not applicable
          (I) ORGANELLE:  Not applicable (vii) IMMEDIATE SOURCE:
          (A) LIBRARY:
          (B) CLONE:  P38

(viii) POSITION IN GENOME:
          (A) CHROMOSOME/SEGMENT:  Not applicable
          (B) MAP POSITION:  Not applicable
          (C) UNITS:  Not applicable (ix) FEATURE:
          (A) NAME/KEY:
          (B) LOCATION:
          (C) IDENTIFICATION METHOD:  By agreement with
              protein information and established
              consensus sequence
          (D) OTHER INFORMATION:  Seed storage protein and
              allergen (x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO: 55:
```

```
Asp Pro Tyr Ser Pro Ser Gln Asp Pro Tyr Ser Pro
  1               5                  10

Ser Pro Tyr Asp Arg
            15
```

(2) INFORMATION FOR SEQ ID NO: 56:

(i) SEQUENCE CHARACTERISTICS:
        (A) LENGTH: 8 amino acids
        (B) TYPE: amino acid
        (C) STRANDEDNESS: Not Applicable
        (D) TOPOLOGY: unknown (ii) MOLECULE TYPE: peptide
        (A) DESCRIPTION: identified as peptide 20
            of Ara h 2 p38.

(iii) HYPOTHETICAL: No (iv) ANTI-SENSE: Not applicable (v) FRAGMENT TYPE: amino terminus (vi) ORIGINAL SOURCE:
        (A) ORGANISM: Arachis hypogaea
        (B) STRAIN: Florunner
        (C) INDIVIDUAL ISOLATE: P38
        (D) DEVELOPMENTAL STAGE:
        (E) HAPLOTYPE: Not applicable
        (F) TISSUE TYPE:
        (G) CELL TYPE: Not applicable
        (H) CELL LINE: Not applicable
        (I) ORGANELLE: Not applicable (vii) IMMEDIATE SOURCE:
        (A) LIBRARY:
        (B) CLONE: P38

(viii) POSITION IN GENOME:
        (A) CHROMOSOME/SEGMENT: Not applicable
        (B) MAP POSITION: Not applicable
        (C) UNITS: Not applicable (ix) FEATURE:
        (A) NAME/KEY:
        (B) LOCATION:
        (C) IDENTIFICATION METHOD: By agreement with
            protein information and established
            consensus sequence
        (D) OTHER INFORMATION: Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 56:

```
Gln Gln Glu Gln Gln Phe Lys Arg
  1               5
```

(2) INFORMATION FOR SEQ ID NO: 57:

(i) SEQUENCE CHARACTERISTICS:
        (A) LENGTH: 30 amino acids
        (B) TYPE: amino acid
        (C) STRANDEDNESS: Not Applicable

```
            (D) TOPOLOGY:  unknown (ii) MOLECULE TYPE:  peptide
           (A) DESCRIPTION: identified as 17.5 kD N-terminal
               peptide sequence of Ara h 2 p38 (gene sequence
               19..48).

(iii) HYPOTHETICAL:  No (iv) ANTI-SENSE:  Not applicable (v) FRAGMENT TYPE:  amino terminus (vi) ORIGINAL SOURCE:
           (A) ORGANISM:  Arachis hypogaea
           (B) STRAIN:  Florunner
           (C) INDIVIDUAL ISOLATE:  P38
           (D) DEVELOPMENTAL STAGE:
           (E) HAPLOTYPE:  Not applicable
           (F) TISSUE TYPE:
           (G) CELL TYPE:  Not applicable
           (H) CELL LINE:  Not applicable
           (I) ORGANELLE:  Not applicable (vii) IMMEDIATE SOURCE:
           (A) LIBRARY:
           (B) CLONE:  P38

(viii) POSITION IN GENOME:
           (A) CHROMOSOME/SEGMENT:  Not applicable
           (B) MAP POSITION:  Not applicable
           (C) UNITS:  Not applicable (ix) FEATURE:
           (A) NAME/KEY:
           (B) LOCATION:
           (C) IDENTIFICATION METHOD:  By agreement with
               protein information and established
               consensus sequence
           (D) OTHER INFORMATION:  Seed storage protein and
               allergen (x) PUBLICATION INFORMATION:
           (A) AUTHORS:
           (B) TITLE:
           (C) JOURNAL:
           (D) VOLUME:
           (E) ISSUE:
           (F) PAGES:
           (G) DATE:
           (H) DOCUMENT NUMBER:
           (I) FILING DATE:
           (J) PUBLICATION DATE:
           (K) RELEVANT RESIDUES IN SEQ ID NO:

(xi) SEQUENCE DESCRIPTION: SEQ ID NO: 57:

Gly Gln Gln Trp Glu Leu Gln Gly Asp Arg Arg Gln
  1               5                  10

Ser Gln Leu Glu Arg Ala Asn Leu Xaa Pro Xaa Glu Gln
      15                  20                  25

Xaa Leu Met Xaa
            30

(2) INFORMATION FOR SEQ ID NO: 58:

(i) SEQUENCE CHARACTERISTICS:
           (A) LENGTH:  28 amino acids
           (B) TYPE:  amino acid
           (C) STRANDEDNESS: Not Applicable
           (D) TOPOLOGY:  unknown (ii) MOLECULE TYPE:  peptide
           (A) DESCRIPTION: identified as 17.5 kD N-terminal
                sequence of Ara h 2 p38 (gene sequence 20..47).
```

```
    (iii) HYPOTHETICAL:  No (iv) ANTI-SENSE:  Not applicable (v) FRAGMENT TYPE:  amino terminus (vi) ORIGINAL SOURCE:
          (A) ORGANISM:  Arachis hypogaea
          (B) STRAIN:  Florunner
          (C) INDIVIDUAL ISOLATE:  P38
          (D) DEVELOPMENTAL STAGE:
          (E) HAPLOTYPE:  Not applicable
          (F) TISSUE TYPE:
          (G) CELL TYPE:  Not applicable
          (H) CELL LINE:  Not applicable
          (I) ORGANELLE:  Not applicable (vii) IMMEDIATE SOURCE:
          (A) LIBRARY:
          (B) CLONE:  P38

(viii) POSITION IN GENOME:
          (A) CHROMOSOME/SEGMENT:  Not applicable
          (B) MAP POSITION:  Not applicable
          (C) UNITS:  Not applicable (ix) FEATURE:
          (A) NAME/KEY:
          (B) LOCATION:
          (C) IDENTIFICATION METHOD:  By agreement with
              protein information and established
              consensus sequence
          (D) OTHER INFORMATION:  Seed storage protein and
              allergen (x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO: 58:

Gln Gln Trp Glu Leu Gln Gly Asp Arg Arg Arg Gln Ser
 1               5                  10

Gln Leu Glu Arg Ala Asn Leu Arg Pro Cys Glu Gln His
     15                  20                  25

Lys Met (2) INFORMATION FOR SEQ ID NO:  59:

(i) SEQUENCE CHARACTERISTICS:
          (A) LENGTH:  8 amino acids
          (B) TYPE:  amino acid
          (C) STRANDEDNESS: Not Applicable
          (D) TOPOLOGY:  unknown (ii) MOLECULE TYPE:  peptide
          (A) DESCRIPTION: identified as peptide 20
              of Ara h 2 p38 (gene sequence 121..128).

(iii) HYPOTHETICAL:  No (iv) ANTI-SENSE:  Not applicable (v) FRAGMENT TYPE:  amino terminus (vi) ORIGINAL SOURCE:
          (A) ORGANISM:  Arachis hypogaea
```

```
         (B) STRAIN:  Florunner
         (C) INDIVIDUAL ISOLATE:  Ara h II p38
         (D) DEVELOPMENTAL STAGE:
         (E) HAPLOTYPE:  Not applicable
         (F) TISSUE TYPE:
         (G) CELL TYPE:  Not applicable
         (H) CELL LINE:  Not applicable
         (I) ORGANELLE:  Not applicable (vii) IMMEDIATE SOURCE:
         (A) LIBRARY:
         (B) CLONE:  P38

(viii) POSITION IN GENOME:
         (A) CHROMOSOME/SEGMENT:  Not applicable
         (B) MAP POSITION:  Not applicable
         (C) UNITS:  Not applicable (ix) FEATURE:
         (A) NAME/KEY:
         (B) LOCATION:
         (C) IDENTIFICATION METHOD:  By agreement with
             protein information and established
             consensus sequence
         (D) OTHER INFORMATION:  Seed storage protein and
             allergen (x) PUBLICATION INFORMATION:
         (A) AUTHORS:
         (B) TITLE:
         (C) JOURNAL:
         (D) VOLUME:
         (E) ISSUE:
         (F) PAGES:
         (G) DATE:
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO: 59:

Gln Gln Glu Gln Gln Phe Lys Arg
 1               5

(2) INFORMATION FOR SEQ ID NO:  60:

(i) SEQUENCE CHARACTERISTICS:
         (A) LENGTH:  8 amino acids
         (B) TYPE:  amino acid
         (C) STRANDEDNESS: Not Applicable
         (D) TOPOLOGY:  unknown (ii) MOLECULE TYPE:  peptide
         (A) DESCRIPTION: identified as Ara h 2 p38
             peptide 20 (gene sequence 121..128).

(iii) HYPOTHETICAL:  No (iv) ANTI-SENSE:  Not applicable (v) FRAGMENT TYPE:  Not applicable (vi) ORIGINAL SOURCE:
         (A) ORGANISM:  Arachis hypogaea
         (B) STRAIN:  Florunner
         (C) INDIVIDUAL ISOLATE:  Ara h II p38
         (D) DEVELOPMENTAL STAGE:
         (E) HAPLOTYPE:  Not applicable
         (F) TISSUE TYPE:
         (G) CELL TYPE:  Not applicable
         (H) CELL LINE:  Not applicable
         (I) ORGANELLE:  Not applicable (vii) IMMEDIATE SOURCE:
         (A) LIBRARY:
         (B) CLONE:  P38
```

-continued

```
    (viii) POSITION IN GENOME:
          (A) CHROMOSOME/SEGMENT:  Not applicable
          (B) MAP POSITION:  Not applicable
          (C) UNITS:  Not applicable (ix) FEATURE:
          (A) NAME/KEY:
          (B) LOCATION:
          (C) IDENTIFICATION METHOD:  By agreement with
              protein information and established
              consensus sequence
          (D) OTHER INFORMATION:  Seed storage protein and
              allergen (x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO: 60:

Gln Gln Glu Gln Gln Phe Lys Arg
1               5

(2) INFORMATION FOR SEQ ID NO:  61:

(i) SEQUENCE CHARACTERISTICS:
          (A) LENGTH:  17 amino acids
          (B) TYPE:  amino acid
          (C) STRANDEDNESS: Not Applicable
          (D) TOPOLOGY:  unknown (ii) MOLECULE TYPE:  peptide
          (A) DESCRIPTION: identified as Ara h 2 p38 peptide
              37 (gene sequence 60-76).

(iii) HYPOTHETICAL:  No (iv) ANTI-SENSE:  Not applicable (v) FRAGMENT TYPE:  amino terminus (vi) ORIGINAL SOURCE:
          (A) ORGANISM:  Arachis hypogaea
          (B) STRAIN:  Florunner
          (C) INDIVIDUAL ISOLATE:  P38
          (D) DEVELOPMENTAL STAGE:
          (E) HAPLOTYPE:  Not applicable
          (F) TISSUE TYPE:
          (G) CELL TYPE:  Not applicable
          (H) CELL LINE:  Not applicable
          (I) ORGANELLE:  Not applicable (vii) IMMEDIATE SOURCE:
          (A) LIBRARY:
          (B) CLONE:  P38

(viii) POSITION IN GENOME:
          (A) CHROMOSOME/SEGMENT:  Not applicable
          (B) MAP POSITION:  Not applicable
          (C) UNITS:  Not applicable (ix) FEATURE:
          (A) NAME/KEY:
          (B) LOCATION:
          (C) IDENTIFICATION METHOD:  By agreement with
              protein information and established
              consensus sequence
          (D) OTHER INFORMATION:  Seed storage protein and
              allergen
```

```
        (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 61:

Asp Pro Tyr Ser Pro Ser Gln Asp Pro Tyr Ser Pro Ser
  1               5                  10

Pro Tyr Asp Arg
     15

(2) INFORMATION FOR SEQ ID NO:  62:

(i) SEQUENCE CHARACTERISTICS:
           (A) LENGTH:   17 amino acids
           (B) TYPE:  amino acid
           (C) STRANDEDNESS: Not Applicable
           (D) TOPOLOGY:  unknown (ii) MOLECULE TYPE:  peptide
           (A) DESCRIPTION: identified as Ara h 2 p38 peptide
               37 (gene sequence 60-76).

(iii) HYPOTHETICAL:  No (iv) ANTI-SENSE:  Not applicable (v) FRAGMENT TYPE:  Not Applicable (vi) ORIGINAL SOURCE:
           (A) ORGANISM:  Arachis hypogaea
           (B) STRAIN:  Florunner
           (C) INDIVIDUAL ISOLATE:  Ara h II P38
           (D) DEVELOPMENTAL STAGE:
           (E) HAPLOTYPE:  Not applicable
           (F) TISSUE TYPE:
           (G) CELL TYPE:  Not applicable
           (H) CELL LINE:  Not applicable
           (I) ORGANELLE:  Not applicable (vii) IMMEDIATE SOURCE:
           (A) LIBRARY:
           (B) CLONE:  P38

(viii) POSITION IN GENOME:
           (A) CHROMOSOME/SEGMENT:  Not applicable
           (B) MAP POSITION:  Not applicable
           (C) UNITS:  Not applicable (ix) FEATURE:
           (A) NAME/KEY:
           (B) LOCATION:
           (C) IDENTIFICATION METHOD:  By agreement with
               protein information and established
               consensus sequence
           (D) OTHER INFORMATION:  Seed storage protein and
               allergen (x) PUBLICATION INFORMATION:
           (A) AUTHORS:
           (B) TITLE:
           (C) JOURNAL:
           (D) VOLUME:
           (E) ISSUE:
           (F) PAGES:
           (G) DATE:
           (H) DOCUMENT NUMBER:
```

-continued

```
            (I) FILING DATE:
            (J) PUBLICATION DATE:
            (K) RELEVANT RESIDUES IN SEQ ID NO:

(xi) SEQUENCE DESCRIPTION: SEQ ID NO: 62:

Asp Pro Tyr Ser Pro Ser Gln Asp Pro Tyr
 1               5                  10

Ser Pro Ser Pro Tyr Asp Arg
                15

(2) INFORMATION FOR SEQ ID NO:  63:

(i) SEQUENCE CHARACTERISTICS:
            (A) LENGTH:  13 amino acids
            (B) TYPE:  amino acid
            (C) STRANDEDNESS: Not Applicable
            (D) TOPOLOGY:  unknown (ii) MOLECULE TYPE:  peptide
            (A) DESCRIPTION: identified as Ara h 2 p38 peptide
                45 (gene sequence 37-49).

(iii) HYPOTHETICAL:  No (iv) ANTI-SENSE:  Not applicable (v) FRAGMENT TYPE:  Not Applicable (vi) ORIGINAL SOURCE:
            (A) ORGANISM:  Arachis hypogaea
            (B) STRAIN:  Florunner
            (C) INDIVIDUAL ISOLATE:  Ara h II P38
            (D) DEVELOPMENTAL STAGE:
            (E) HAPLOTYPE:  Not applicable
            (F) TISSUE TYPE:
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:  P38

(viii) POSITION IN GENOME:
            (A) CHROMOSOME/SEGMENT:  Not applicable
            (B) MAP POSITION:  Not applicable
            (C) UNITS:  Not applicable (ix) FEATURE:
            (A) NAME/KEY:
            (B) LOCATION:
            (C) IDENTIFICATION METHOD:  By agreement with
                protein information and established
                consensus sequence
            (D) OTHER INFORMATION:  Seed storage protein and
                allergen (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 63:

Ala Asn Leu Arg Pro Cys Glu Gln His Leu Met Gln Lys
 1               5                  10
```

```
(2) INFORMATION FOR SEQ ID NO: 64:

(i) SEQUENCE CHARACTERISTICS:
        (A) LENGTH: 13 amino acids
        (B) TYPE: amino acid
        (C) STRANDEDNESS: Not Applicable
        (D) TOPOLOGY: unknown (ii) MOLECULE TYPE: peptide
        (A) DESCRIPTION: identified as Ara h 2 peptide 45
            (gene sequence 37-49).

(iii) HYPOTHETICAL: No (iv) ANTI-SENSE: Not applicable (v) FRAGMENT TYPE: Not Applicable (vi) ORIGINAL SOURCE:
        (A) ORGANISM: Arachis hypogaea
        (B) STRAIN: Florunner
        (C) INDIVIDUAL ISOLATE: Ara h II P38
        (D) DEVELOPMENTAL STAGE:
        (E) HAPLOTYPE: Not applicable
        (F) TISSUE TYPE:
        (G) CELL TYPE: Not applicable
        (H) CELL LINE: Not applicable
        (I) ORGANELLE: Not applicable (vii) IMMEDIATE SOURCE:
        (A) LIBRARY:
        (B) CLONE: P38

(viii) POSITION IN GENOME:
        (A) CHROMOSOME/SEGMENT: Not applicable
        (B) MAP POSITION: Not applicable
        (C) UNITS: Not applicable (ix) FEATURE:
        (A) NAME/KEY:
        (B) LOCATION:
        (C) IDENTIFICATION METHOD: By agreement with
            protein information and established
            consensus sequence
        (D) OTHER INFORMATION: Seed storage protein and
            allergen (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO: 64:

Ala Asn Leu Arg Pro Cys Glu Gln His Leu Met Gln Lys
 1               5                  10

(2) INFORMATION FOR SEQ ID NO: 65:

(i) SEQUENCE CHARACTERISTICS:
        (A) LENGTH: 16 amino acids
        (B) TYPE: amino acid
        (C) STRANDEDNESS: Not Applicable
        (D) TOPOLOGY: unknown (ii) MOLECULE TYPE: peptide
        (A) DESCRIPTION: identified as Ara h I peptide I.

(iii) HYPOTHETICAL: No
```

```
        (iv) ANTI-SENSE:  Not applicable (v) FRAGMENT TYPE:  Not Applicable (vi) ORIGINAL SOURCE:
             (A) ORGANISM:  Arachis hypogaea
             (B) STRAIN:  Florunner
             (C) INDIVIDUAL ISOLATE:  Ara h I
             (D) DEVELOPMENTAL STAGE:
             (E) HAPLOTYPE:  Not applicable
             (F) TISSUE TYPE:  cDNA
             (G) CELL TYPE:  Not applicable
             (H) CELL LINE:  Not applicable
             (I) ORGANELLE:  Not applicable (vii) IMMEDIATE SOURCE:
             (A) LIBRARY:
             (B) CLONE:  P38

(viii) POSITION IN GENOME:
             (A) CHROMOSOME/SEGMENT:  Not applicable
             (B) MAP POSITION:  Not applicable
             (C) UNITS:  Not applicable (ix) FEATURE:
             (A) NAME/KEY:
             (B) LOCATION:
             (C) IDENTIFICATION METHOD:  By agreement with
                 protein information and established
                 consensus sequence
             (D) OTHER INFORMATION:  Seed storage protein and
                 allergen (x) PUBLICATION INFORMATION:
             (A) AUTHORS:
             (B) TITLE:
             (C) JOURNAL:
             (D) VOLUME:
             (E) ISSUE:
             (F) PAGES:
             (G) DATE:
             (H) DOCUMENT NUMBER:
             (I) FILING DATE:
             (J) PUBLICATION DATE:
             (K) RELEVANT RESIDUES IN SEQ ID NO:

(xi) SEQUENCE DESCRIPTION: SEQ ID NO: 65:

Ile Phe Leu Ala Gly Asp Lys Asp Asn Val Ile
 1               5                  10

Asp Gln Ile Glu Lys
             15

(2) INFORMATION FOR SEQ ID NO:  66:

(i) SEQUENCE CHARACTERISTICS:
             (A) LENGTH:  16 amino acids
             (B) TYPE:  amino acid
             (C) STRANDEDNESS: Not Applicable
             (D) TOPOLOGY:  unknown (ii) MOLECULE TYPE:  peptide
             (A) DESCRIPTION: identified as Ara h I peptide II.

(iii) HYPOTHETICAL:  No (iv) ANTI-SENSE:  Not applicable (v) FRAGMENT TYPE:  Not Applicable (vi) ORIGINAL SOURCE:
             (A) ORGANISM:  Arachis hypogaea
             (B) STRAIN:  Florunner
             (C) INDIVIDUAL ISOLATE:  Ara h I
             (D) DEVELOPMENTAL STAGE:
             (E) HAPLOTYPE:  Not applicable
             (F) TISSUE TYPE:  cDNA
```

```
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:  P38

(viii) POSITION IN GENOME:
            (A) CHROMOSOME/SEGMENT:  Not applicable
            (B) MAP POSITION:  Not applicable
            (C) UNITS:  Not applicable (ix) FEATURE:
            (A) NAME/KEY:
            (B) LOCATION:
            (C) IDENTIFICATION METHOD:  By agreement with
                protein information and established
                consensus sequence
            (D) OTHER INFORMATION:  Seed storage protein and
                allergen (x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO: 66:

Lys Gly Ser Glu Glu Glu Gly Asp Ile Thr
 1               5                   10

Asn Pro Ile Asn Leu Arg
                15

(2) INFORMATION FOR SEQ ID NO:  67:

(i) SEQUENCE CHARACTERISTICS:
            (A) LENGTH:  10 amino acids
            (B) TYPE:  amino acid
            (C) STRANDEDNESS: Not Applicable
            (D) TOPOLOGY:  unknown (ii) MOLECULE TYPE:  peptide
            (A) DESCRIPTION: identified as Ara h I peptide III.

(iii) HYPOTHETICAL:  No (iv) ANTI-SENSE:  Not applicable (v) FRAGMENT TYPE:  Not Applicable (vi) ORIGINAL SOURCE:
            (A) ORGANISM:  Arachis hypogaea
            (B) STRAIN:  Florunner
            (C) INDIVIDUAL ISOLATE:  Ara h I
            (D) DEVELOPMENTAL STAGE:
            (E) HAPLOTYPE:  Not applicable
            (F) TISSUE TYPE:  cDNA
            (G) CELL TYPE:  Not applicable
            (H) CELL LINE:  Not applicable
            (I) ORGANELLE:  Not applicable (vii) IMMEDIATE SOURCE:
            (A) LIBRARY:
            (B) CLONE:  P38

(viii) POSITION IN GENOME:
            (A) CHROMOSOME/SEGMENT:  Not applicable
            (B) MAP POSITION:  Not applicable
```

```
        (C) UNITS:  Not applicable (ix) FEATURE:
      (A) NAME/KEY:
      (B) LOCATION:
      (C) IDENTIFICATION METHOD:  By agreement with
           protein information and established
           consensus sequence
      (D) OTHER INFORMATION:  Seed storage protein and
           allergen (x) PUBLICATION INFORMATION:
      (A) AUTHORS:
      (B) TITLE:
      (C) JOURNAL:
      (D) VOLUME:
      (E) ISSUE:
      (F) PAGES:
      (G) DATE:
      (H) DOCUMENT NUMBER:
      (I) FILING DATE:
      (J) PUBLICATION DATE:
      (K) RELEVANT RESIDUES IN SEQ ID NO:

(xi) SEQUENCE DESCRIPTION: SEQ ID NO: 67:

Asn Asn Pro Phe Tyr Phe Pro Ser Arg Arg
 1               5                  10
```

PEANUT ALLERGENS AND METHODS

CROSS-REFERENCE TO RELATED APPLICATIONS

This application is a continuation of U.S. patent application Ser. No. 08/717,933, filed Sep. 23, 1996 now abandoned, which claimed benefit of U.S. provisional application Serial No. 60/009,455, filed Dec. 29, 1995, now abandoned.

BACKGROUND OF THE INVENTION

The present invention is directed to methods and apparatus for detecting and quantifying allergens in foodstuffs, and, more particularly, concerns peanut allergens, antigens, monoclonal antibodies having specificity for peanut allergens, hybridoma cell lines which produce the monoclonal antibodies and immunoassay methods and apparatus including the monoclonal antibodies for detecting and quantifying peanut allergens in food-processing equipment and materials as well as natural, processed, and finished foods.

The ingestion of peanuts is a common cause of food hypersensitivity reactions. Symptoms can vary from mild abdominal discomfort to severe anaphylaxis. In a recent report by Yunginger et al., "Fatal Food-Induced Anaphylaxis", *Journal of the American Medical Association* 1988; 260:1450–2, four of seven patients who experienced fatal anaphylaxis died after peanut ingestion. All four of these patients unknowingly had eaten peanut in food prepared and consumed away from home. In the most recent studies involving children and food challenges, peanut is among the three leading foods that cause food hypersensitivity reactions.

The increasing use of peanut products in our food supply has served to aggravate the problem of peanut allergy. Peanuts, generally in the form of peanut butter, are introduced into the American diet at a very young age. Some children react on challenge to peanut on their first known exposure, indicating that they had been sensitized in utero, by breast feeding, or by an unknown exposure. Unlike other food sensitivities in children, long-term follow-up studies of up to fourteen years indicate that peanut hypersensitivity is rarely outgrown.

It is important for peanut-sensitive individuals to have a means of recognizing and avoiding peanut-containing products. Unfortunately, peanut allergens have been identified in non-peanut foodstuffs manufactured on common processing equipment that were inadequately cleaned. Peanut products that serve as substitutes for other nuts in candies are not uncommon. In patients suffering from extrinsic asthma, hayfever, or atopic eczema, symptoms develop immediately after exposure to specific allergens. This immediate type of allergy is a function of a special type of serum antibodies called reagins. These reagins have been identified as belonging to the IgE class of immunoglobulins. Radioimmunoassays (RIA) have been developed to measure the level of circulating allergen specific IgE in human blood samples.

For example, Pharmacia Diagnostics AB, Uppsala, Sweden, manufactures a Phadebas RAST® radioimmunoassay (U.S. Pat. Nos. 3,645,852 and 3,720,760). The Phadebas Rast® radioimmunoassay is an in vitro test system based on the Radio Allegro Sorbent Test principle for determination of circulating specific IgE antibodies. The allergen of interest is covalently coupled to a solid phase. The allergen is reacted with a patient serum sample containing both allergen specific and non-specific IgE. The allergen reacts with the specific IgE in the patient sample. After washing away non-specific IgE, radioactively labeled antibodies against IgE are added forming a complex. Then unbound radioactively labeled anti-IgE is washed away. Next, the radioactivity of the bound complex is measured in a gamma counter. The more bound radioactivity found, the more specific IgE present in the sample. To classify the test results, patient counts are compared directly with counts of reference sera run in parallel. This system is designed for use in testing allergens including grass, tree, weed pollens, house dust, mites, foods, insects, epidermals, molds, drugs, occupational allergens, and parasites.

Pharmacia Diagnostics AB, Uppsala, Sweden also manufactures a Pharmacia IgE RIA Ultra solid-phase, sandwich radioimmunoassay for quantitative determination of total IgE in human serum. The serum concentration of IgE is significantly elevated in most patients with allergic diseases, such as extrinsic asthma, hayfever, and atopic disease. In this system, a monoclonal anti-IgE is covalently coupled to a test tube wall. This monoclonal reacts with the IgE in the samples during a first incubation. The tubes are then washed and radioactively labeled anti-IgE reacts with the bound IgE during a second incubation. After the second incubation, unbound radioactively labeled anti-IgE is washed away. The radioactivity in the tube is then measured and is directly proportional to the concentration of the IgE in the sample.

The use of a radioimmunoassay to detect peanut allergens in food processing materials and finished foods is described in a Keating et al. article entitled "Immunoassay of Peanut Allergens in Food Processing Materials and Finished Foods", appearing in the *Journal of Allergy Clinical Immunology* 1990; 86:41–4. To quantitate trace amounts of peanut allergens in food processing materials and finished foods, there was established a solid-phase radioimmunoassay inhibition using pooled sera from five peanut-sensitive subjects and roasted peanut meal extract covalently linked to polyacrylamide beads. Test samples were extracted, dialyzed, lyophilized, and reconstituted at 10 to 125 mg of dry weight per ml concentrations. The peanut allergen content of test samples was expressed relative to a reference extract of roasted peanut meal that was assigned an arbitrary potency of 100,000 U/ml. In confectionary products spiked with varying quantities of peanut, the recovery of peanut allergen ranged from 31% to 94%. The sensitivity of the assay was 2.5 U/mg of dry weight from the samples. Peanut allergens were undetectable in virgin vegetable oil used to roast peanuts, but 600 to 760 U/mg of dry weight were present in oil after varying periods of use. The allergen content of used oil was reduced to 8 U/mg of dry weight by filtration and steam cleaning. The availability of such a radioimmunoassay provides a way of monitoring finished food products for potential allergens.

In light of the foregoing, there is a need for an improved immunoassay for detecting and quantifying specific peanut allergens in food processing materials, equipment, and raw, processed, and finished foods.

BRIEF SUMMARY OF THE INVENTION

In accordance with the present invention, specific peanut allergens are identified and a monoclonal antibody based assay is provided for detecting and quantifying the specific peanut allergens.

The identification of a major peanut allergen, Ara h I, is described in an article "Identification of a Major Peanut Allergen In Patients With Atopic Dermatitis and Positive Peanut Challenges" by Burks et al., *The Journal of Clinical Immunology*, August 1991; Vol. 88, No. 2, pp 172–179.

Serum from nine patients with atopic dermatitis in a positive double-blind, placebo-controlled -food challenge to peanut was used to begin the process of identification and purification of the major peanut allergens. Identification of a major peanut allergen was accomplished by use of anion-exchange column chromatography, sodium dodecyl sulphate-polyacrylamide gel electrophoresis, ELISA, thin layer isoelectric focusing, and IgE-specific immunoblotting. Anion-exchange chromatography revealed several fractions that bound IgE from the serum of the challenged positive patient pool. By measuring anti-peanut-specific IgE in the ELISA and IgE-specific immunoblotting, there was identified an allergenic component with two Coomassie brilliant blue staining bands by sodium dodecyl sulphate-polyacrylamide gel electrophoresis with a mean molecular weight of 63.5 kD. Examination of this fraction by the IgE anti-peanut ELISA with individual serum and by the ELISA-inhibition assay with pooled serum, lead to its identification as a major allergen. Thin layer isoelectric focusing and immunoblotting of the 63.5 kD fraction revealed it to have an isoelectric point (pI) of 4.55. Based on allergen nomenclature of the IUIS subcommittee for allergen nomenclature, this allergen was designated Ara h I (*Arachis hypogaea*).

Burks et al. also identified and characterized a second major peanut allergen, Ara h II, as described in an article entitled "Identification and Characterization of A Second Major Peanut Allergen, Ara h II, With Use of the Sera of Patients with Atopic Dermatitis in Positive Peanut Challenge", *Journal of Allergy and Clinical Immunology*, December 1992; Vol. 90. Again, serum from nine patients with atopic dermatitis in a positive double-blind, placebo controlled, food challenge to peanut was used in the process of identification and purification of the peanut allergen. Identification of a second major peanut allergen was accomplished with the use of various biochemical and molecular techniques. Anion exchange chromatography of the crude peanut extract produced several fractions that bound IgE from the serum of the patient pool with positive challenges. By measuring anti-peanut specific IgE and by IgE specific immunoblotting, there was identified an allergic component that has two closely migrating bands with a mean molecular weight of 17 kD. Two-dimensional gel electrophoresis of this fraction revealed it to have a mean isoelectric point of 5.2. According to allergen nomenclature of the IUIS subcommittee for allergen nomenclature, this allergen is designated, Ara h II (*Arachis hypogaea*).

The Ara h I allergen bound IgE in over 90% of a group of six patients with peanut hypersensitivity as shown in Table 1. Multiple monoclonal antibodies were made to this peanut allergen as shown in Table 2. Two of these monoclonal antibodies recognizing distinct epitopes were chosen to prepare a two-site immunometric ELISA for quantitating the 63.5 kD peanut allergen in food products. One was chosen as the capture monoclonal antibody and the other was biotinylated and used as the detection monoclonal antibody in an avidin-biotin assay.

In accordance with one embodiment of the present invention, defatted roasted Florunner peanuts were used as the peanut standard. A microtiter plate was coated with 1 $\mu$g/ml of the capture monoclonal antibody 8F10. After incubation for one hour, the plate was washed three times and either the peanut standard or an unknown sample was added. The Florunner standard extract ranged from 0.01 ng/ml to 10 ng/ml total protein. Following incubation at 25° C. for one hour, the plates were washed and then the biotinylated second antibody 8D9 was added at a concentration of 1:500 v/v. The plates were again incubated at 25° C. for one hour and developed by the addition of a horse-radish peroxidase-avidin (HRP-avidin) conjugate, followed by citric acid substrate and stopped by the addition of 2N hydrochloric acid. The microtiter plates were read at 495 nm on a Titertek Multiscan. The results were plotted on a log-logit paper to obtain 63.5 kD allergen concentration from the standard curve (see FIG. 1). The assay had an inter-assay coefficient of variation of less than 6%. In each sample run, the linear correlation coefficient was greater than or equal to 0.98.

As shown in Table 3, test samples included commercially purchased candies and oils. Candies that included peanut on the label and other candies that did not have peanut as a listed ingredient were tested. Also, oils made from either peanut or vegetable oils were tested. Samples were prepared by weighing out 2.5 gms of each candy and then extracting each in 50 ml of 1 M NaCl, 20 mM $NaH_2PO_4$ and 8 M urea with constant agitation overnight at 4° C. Particulate material was removed by filtration through 4×4 rayon polyester gauze (Johnson & Johnson). The sample was then centrifuged at 18,000 rpm for one hour and the supernatant collected. After dialysis, all fractions were lyophilized and stored at 4° C. until used in the assay.

Table 4 shows the results of the monoclonal antibody ELISA with the different candy products. The first column shows the results of the candies with peanut listed on the label. The results range from Peanut Butter M&M's® with 299 ng/ml of allergen to plain M&M's® with 7.35 ng/ml of allergen. The second column shows the results of the five candies tested with no peanut listed on the label. No peanut allergen could be detected in any of these candies.

Table 5 shows the results of the monoclonal antibody ELISA for the various oils tested. No Ara h I could be detected in any of the oils tested from peanut, vegetable, canola, or soybean oil. No oil was tested that had previously been used for roasting peanuts. The lower limits of detection of added peanut to a candy product in this assay appears to be approximately 1% peanut.

The ELISA assay of the present invention differs from the radioimmunoassay (RIA) developed by Yunginger et al. in several ways. The Yunginger RIA is an RIA-inhibition assay with pooled human IgE serum from peanut-sensitive patients as the detection antibody. In the RIA-inhibition assay the serum IgE pool from peanut positive individuals would contain IgE antibody against more allergens than just Ara h I. In contrast, the present ELISA assay can be used to determine the concentration of a specific peanut allergen (Ara h I) in extracted peanut products.

With the use of the present monoclonal antibody ELISA, questions regarding threshold exposure levels in highly allergic patients can be answered and can provide a way to correlate quantities of ingested allergens with the development of clinical symptoms. Contamination of products with other food proteins occurs more frequently than probably appreciated. The ability to monitor food products with the potential to be contaminated is important. The present assay provides a new level of sophistication in the study of peanut hypersensitivity.

The principle object of the present invention is the provision of a monoclonal antibody enzyme-linked immunosorbent assay for peanut allergen. Another object of the present invention is the isolation and purification of peanut allergens. A still further object of the present invention is the provision of peanut allergen antigens and monoclonal antibodies having specificity for a selected peanut allergen antigen. Yet another object of the present invention is the provision of hybridomas which produce monoclonal antibodies specific for peanut allergen.

Still yet another object of the present invention is the provision of a two-site monoclonal antibody based enzyme-linked immunosorbent assay that can be used to detect and determine the concentration of a specific peanut allergen such as Ara h I in a food product or food processing and producing equipment or materials.

Another object of the present invention is the provision of a process for producing monoclonal antibodies specific to a selected peanut allergen, hybridoma cell lines which produce such monoclonal antibodies, and an immunoassay which utilizes the monoclonal antibodies for detecting the presence and concentration of a selected peanut allergen. And, still yet another object of the present invention is the provision of a monoclonal antibody based enzyme-linked immunosorbent assay which does not contain human blood derivatives or radioactively labeled antibodies.

Other objects and further scope of the applicability of the present invention will become apparent from the detailed description to follow taken in conjunction with the accompanying drawings wherein like parts are designated by like reference numerals.

BRIEF DESCRIPTION OF THE SEVERAL VIEWS OF THE DRAWING

FIG. 1 is a graphical representation of absorbance relative to allergen concentration;

FIG. 2 is an illustration of the anion-exchange chromatogram of the crude peanut extract;

FIG. 3 is a bar graph representation of the amount of antipeanut IgE related to the crude peanut extract and each of the pooled fractions;

FIG. 4 is a graphical illustration of inhibition relative to concentration of crude peanut extract and fraction 3;

FIGS. 5–9 are schematic illustrations of a two-site monoclonal antibody enzyme-linked immunosorbent assay in accordance with one embodiment of the present invention;

FIG. 10 is a graphical representation of absorbance relative to time;

FIG. 11 is an illustration of SDS-PAGE and immunoblotting of the defatted crude peanut extract;

FIG. 12 is a bar graph representation of the amount of antipeanut IgE related to defatted crude peanut extract and pooled fractions;

FIG. 13 is a graphical illustration of inhibition relative to concentration of crude peanut extract and anion-exchange fraction 4; and FIG. 14 is a representation of blue stain of 2-dimensional gel with fraction 4 containing the 17 kD allergen.

DETAILED DESCRIPTION OF THE INVENTION

In accordance with a preferred embodiment of the present invention, a monoclonal antibody (MAb) based enzyme-linked immunosorbent assay (ELISA) and method is provided for detecting and quantifying a major peanut allergen, Ara h I, in food products. The Ara h I peanut allergen (63.5 kD fraction) was used as an immunogen to produce monoclonal antibodies (MAbs) having specificity for the selected peanut allergen. The Ara h I allergen was isolated as described in the Burks et al. article entitled "Identification of a Major Peanut Allergen, Ara h I, In Patients With Atopic Dermatitis and Positive Peanut Challenges", *Journal of Allergy Clinical Immunology* 1991; 88:172–9.

Patients with atopic dermatitis (AD) who had positive double-blind, placebo controlled, food challenge to peanut were used in the process of identification and purification of the peanut allergens. A major peanut allergen, Ara h I, was identified by use of anion-exchange column chromatography, sodium dodecyl sulphate polyacrylamide gel electrophoresis (SDS-PAGE), ELISA, thin layer isoelectric focusing (TLIEF) and IgE-specific immunoblotting. The Ara h I allergen is a glycoprotein from a pure strain of Florunner peanuts that has a mean molecular weight of 63.5 kD and a mean isoelectric point (pI) of 4.55.

Nine patients (mean age 4.2 years) with AD and a positive immediate prick skin test to peanut had either a positive DBPCFC or a convincing history of peanut anaphylaxis. (The allergic reaction was potentially life-threatening, that is, laryngeal edema, severe wheezing and/or hypotension.) Five milliliters of venous blood was obtained from each patient and allowed to clot, and then the serum was collected. An equal volume of serum from each donor was mixed to prepare a nine-person, peanut-specific, IgE antibody (Ab) pool.

Three commercial lots of southeastern runners (*Arachis hypogaea*) (Florunner), medium grade peanuts from the 1979 crop (North Carolina State University), were used in this study. The peanuts were stored in the freezer at −18° C. until they were roasted. The three lots were combined in equal proportions and blended before defatting. The defatting process (defatted with hexane after roasting for 13 to 16 minutes at 163° to 177° C.) was done in the laboratory of Dr. Clyde Young (North Carolina State University). The powdered crude peanut was extracted according to the recommendations of Yunginger (Yunginger J W, Jones R T. A review of peanut chemistry: implications for the standardization of peanut extracts. In Proceedings of the Fourth International Paul Ehrlich Seminar on the Regulatory Control and Standardization of Allergenic Extracts, Bethesda, Md., Oct. 16–17, 1985, Stuttgart: Gustav Fischer Verlag, 1987:251–64) in 1 mol/L of NaCl to 20 mmol/L of sodium phosphate (pH 7.0), with the addition of 8 mol/L of urea for 4 hours at 4° C. The extract was isolated by centrifugation at 20,000 g for 60 minutes at 4° C.

Analytic and preparative anion-exchange chromatography was performed with the fast protein liquid chromatography (FPLC) system (Pharmacia, Piscataway, N.J.). Anion-exchange chromatography was used with the Mono Q 5/5 and 10/10 columns (Pharmacia). The crude peanut extract was dialyzed against 20 mmol/L of Tris-bis-propane (pH 7.2) and 8 mol/L of urea, and 40 mg was loaded onto the Mono Q 10/10 column. A stepwise salt gradient of 0 to 1.5 mol/L of NaCl was applied. All fractions of each resolved peak were pooled, dialyzed, and lyophilized.

Dot blotting was done to determine which fractions from the anion-exchange column chromatogram contained IgE-binding material. The collected fractions (200 μl) were blotted with the Mini Blot apparatus (Schleicher & Schuell Inc., Keene, N.H.) onto 0.45 micron nitrocellulose membranes (Bio-Rad Laboratories, Richmond, Calif.). After membranes were dried, the remaining active sites were blocked with 20 ml of blocking solution (0.5% gelatin with 0.001% thimerosol in 500 ml of PBS) for 1 hour. The procedure is then identical to the immunoblotting for IgE described below.

The electrophoresis procedure was a modification of the method of Sutton et al. (Sutton R, Wrigley C W, Baldo B A. Detection of IgE and IgG binding proteins after electrophoresis transfer from polyacrylamide gels. *Journal of*

*Immunological Methods*, 1982; 52:183–6.) SDS-PAGE was performed with a 12.5% polyacrylamide separating gel and a stacking gel of 3%. Twenty microliters of a 1 mg/ml solution of each protein was applied to each well. Replicate samples were applied for independent analysis. Electrophoresis was performed for 4 hours at 0.030 A per gel (E-C Apparatus Corp., St. Petersburg, Fla.) for the 14 cm by 12 cm gels, and for 1 hour at 175 V per gel for the 8 cm by 7.5 cm gels (Mini-Protean II system, Bio-Rad Laboratories). To assure proper protein separation and visualization, Coomassie brilliant blue (Sigma Chemical Co., St. Louis, Mo.) stains were done on the gels. For detection of carbohydrate staining material, gels were stained with the modified PAS stain according to the method of Kapitany (Kapitany R, Zebrowski E J. A high resolution PAS stain for polyacrylamide gel electrophoresis. *Anal Biochem* 1973; 56:361–9).

Proteins were electrophoretically transferred from the separating gel to a nitrocellulose membrane in a transfer buffer (Tris-glycine) with 10% SDS and 40% methanol. The procedure was done in a transblot apparatus (Bio-Rad Laboratories) for 2 hours (0.150 A) (regular size transfer apparatus for crude peanut and minitransfer apparatus for fraction 3). An amido black stain (Bio-Rad Laboratories) was done to assure transfer of the protein.

After removal from the transblot apparatus, the nitrocellulose was placed in blocking solution overnight at 4° C. The nitrocellulose blot was then washed three times with PBS (PBS with 0.05% Tween 20) and incubated with the pooled serum (1:20 vol/vol dilution) for 2 hours at 4° C. with rocking. After the nitrocellulose blot was again washed with PBS three times, alkaline phosphatase-conjugated goat anti-human IgE (1:1000 vol/vol of PBS, Bio-Rad Laboratories) was added and incubated at room temperature with rocking for 2 hours. After an additional wash with PBS three times, the blot was developed with 250 μl of 30 mg of nitro blue tetrazolium in 70% dimethylformamide and 250 μl of 15 mg of 5-bromo-4-chloro-3-indolyl-phosphate in 70% dimethylformamide (Bio-Rad Laboratories) solutions in 25 ml of carbonate buffer (0.2 mol/L, pH 9.8) at room temperature for 15 minutes. The reaction was then stopped by decanting the 30 mg of nitro blue tetrazolium in 70% dimethylformamide/ 15 mg of 5-bromo-4-chloro-3-indolyl-phosphate in 70% dimethylformamide solution and incubating the nitrocellulose for 10 minutes with distilled water. The blot was then air-dried.

A biotin-avidin ELISA was developed to quantify IgE antipeanut protein Abs with modifications from an assay previously published. The upper two rows of a 96-well microtiter plate (Gibco, Santa Clara, Calif.) were coated with 100 μl each of equal amounts (1 μg/ml) of antihuman IgE MAbs, 7.12 and 4.15 (kindly provided by Dr. A. Saxon) in coating buffer (0.1 mol/L of sodium carbonate-bicarbonate buffer, pH 9. 5). The remainder of the plate was coated with one of the peanut extracts at a concentration of 1 μg/ml in coating buffer. The plate was incubated at 37° C. for 1 hour and then was washed five times with rinse buffer (PBS, pH 7.4, containing 0.05% Tween 20; Sigma Chemical Co.) immediately and between subsequent incubations. In the upper two rows we used a secondary standard IgE reference to generate a curve for IgE, ranging from 0.05 to 25 ng/ml.

The serum pool and individual patient serum samples were diluted (1:20 vol/vol) and dispensed in duplicate in the lower portion of the plate. After incubation for 1 hour at 37° C. and a subsequent washing, biotinylated, affinity-purified, goat antihuman IgE (KPL, Gaithersburg, Md.) (1:1000 vol/vol of PBS) was added to all wells. Plates were incubated again for 1 hour at 37° C. and washed, and 100 μl of horseradish peroxidase-avidin conjugate (Vector Laboratories, Burlingame, Calif.) was added for 30 minutes. After plates were washed, they were developed by the addition of a buffer containing o-phenylenediamine (Sigma Chemical Co.). The reaction was stopped by the addition of 100 μl of 2-N-hydrochloric acid to each well, and absorbance was read at 492 nm (Titertek Multiscan, Flow Laboratories, McLean, Va.). The standard curve was plotted on a log-logit scale by means of simple linear regression, and values for the pool and individual patient samples were read from the curve as "nanogram-equivalent units" per milliliter (nanogram per milliliter).

A competitive ELISA-inhibition analysis was done with the FPLC fractions. One hundred microliters of pooled serum (1:20 vol/vol) from the positive-challenge patients was incubated with various concentrations of the FPLC protein fractions (0.00005 to 50 ng/ml) for 18 hours at 4° C. The inhibited pooled serum was used in the ELISA described above. The percent inhibition was calculated by taking the food-specific IgE value divided by the food-specific IgE value. The number is multiplied by 100 to get the percentage of inhibition.

The samples were focused with the LKB Multiphor system with LKB PAG plates, pH gradient, 3.5 to 6.85 (LKB, Bromma, Sweden) Five microliters of sample (100 μg of protein) was applied, and an electric current of 200 V was applied for 30 minutes. The gel was fixed and stained with Coomassie brilliant blue following the standard protocol (LKB). For IgE immunoblotting, the protein was transferred to nitrocellulose by capillary transfer and stained as described in the immunoblotting section above.

Pilot experiments were conducted with the analytical Mono Q 5/5 anion-exchange column to determine the optimal buffer system and salt gradient. Scale up and optimization was completed with the Mono Q 10/10, with a stepwise salt gradient (0 to 1.5 mol/L of NaCl). The procedure separated the crude peanut extract into seven peaks (see FIG. 2). Preliminary dot blotting from the separation identified IgE-binding material in each peak. Multiple runs of this fractionation procedure were performed, and each isolated peak was pooled, dialyzed against 100 mmol/L of $NH_4HCO_3$, and lyophilized. Preliminary separation of crude peanut extract with gel filtration (Superose) did not significantly enrich the purification process.

Initial SDS-PAGE and immunoblotting of the crude peanut extract revealed multiple protein fractions with several IgE-staining bands. Aliquots of the seven lyophilized fractions from the anion-exchange column were analyzed by SDS-PAGE. Immunoblotting for specific IgE with the pooled serum revealed two closely migrating bands that bound significant IgE. Preliminary blots with normal control serum and with serum from patients with elevated serum IgE values revealed no non-specific binding to this fraction. The two bands in fraction 3 stained positive for PAS. In addition, this fraction did not bind to Con A (after staining with biotinylated Con A and alkaline phosphatase-conjugated anti-biotin).

Figure 3:
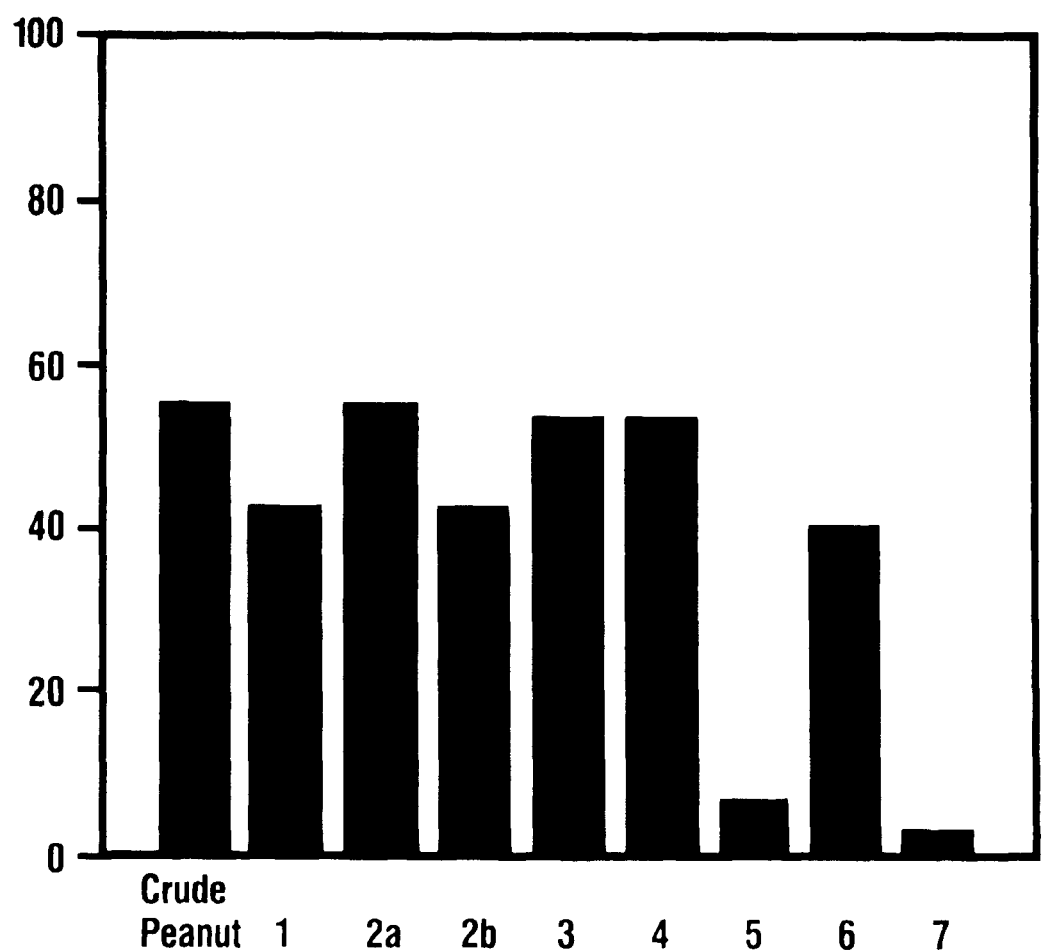

ELISA results comparing the crude peanut extract to each isolated fraction are illustrated in FIG. 3. Mono Q 10/10 fractions 2a, 3, and 4 had significant amounts (>50 ng/ml) of IgE binding compared to the crude peanut extract. We additionally tested the serum of six patients (members of the pooled serum) to determine the relative IgE binding to both the crude and the enriched allergen fraction containing the 63.5 kD component (fraction 3). The results are presented in Table 6. Each patient's serum had measurable amounts of peanut-specific IgE to both the crude extract and the 63.5 kD fraction. Serum from patients with AD, elevated serum IgE values, and positive DBPCFCs to milk (patient No. 7) and from healthy normal controls (patient No. 8) did not have detectable peanut-specific IgE to this allergen.

Figure 4:
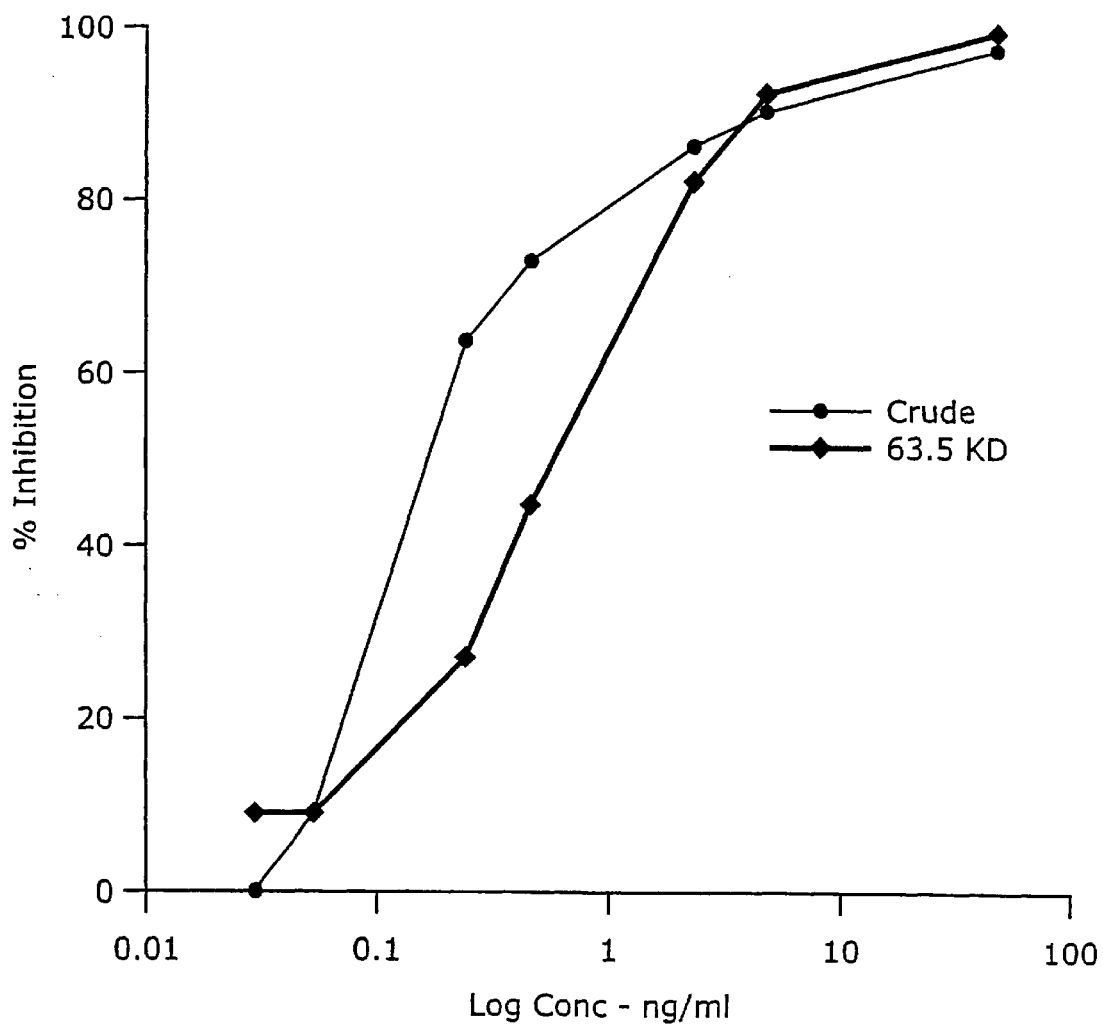

The ELISA-inhibition results are illustrated in FIG. 4. The concentration of the 63.5 kD fraction required to produce 50% inhibition was 5.5 ng/ml compared to 1.4 ng/ml of the crude peanut extract. Control experiments with other food proteins did not demonstrate significant inhibition, demonstrating the specificity of the inhibition assay.

Because immunoblotting and ELISAs of the various anion-exchange fractions demonstrated that fraction 3 contained a major allergen, isoelectric focusing (IEF) and immunoblotting were done on this fraction. Two bands were observed in this allergen that migrated closely together at 63.5 kD on SDS-PAGE, stained with Coomassie brilliant blue, and had a mean pI of 4.55. This protein fraction readily binds IgE from the pooled serum.

Monoclonal antibodies (MAbs) specific to the Ara h I peanut allergen were produced as follows. BALB/c mice were given 3 intraperitoneal injections of 25 μg of the 63.5 kD fraction at 2-week intervals. Two weeks after the final injection the sera were screened for IgG antipeanut antibodies using a peanut-specific IgG ELISA. The positive mice were sacrificed and spleen cells from the sacrificed mice were fused with 8-azaguanine resistant P3X63-Ag8.653 mouse myeloma cells using 50% polyethylene glycol.

Hybrids, which were selected on the basis of the IgG binding assay, were cloned by limiting dilution. Positive clones were selectively expanded and injected intraperitoneally into pristane-primed female BALB/c mice. The resulting ascites was purified by a Protein G column on the FPLC system (Pharmacia).

Four MAbs identified as 8D9, 8F10, 2E9, and 7B3 were used in two-site immunometric assays to measure peanut and other legume antigens by solid phase ELISA. To determine the epitope specificity of each MAb, ELISA-inhibition studies were done with the biotinylated MAb. For detection of specific binding of the MAbs to the 63.5 kD allergen, electrophoresis and immunoblotting were done.

Monoclonal antibody 8F10 was used to affinity purify the allergen identified. Monoclonal antibody 8F10 (approximately 300 mg of purified MAb) was coupled to 8 grams of CNBr-activated Sepharose 4B according to the manufacturer's instructions. Two hundred milliliters of crude peanut extract were absorbed over the column at a flow rate of 20 ml/hr. After adsorption, the column was washed with digestion buffer and the bound allergen eluted using 4 mM HCL, pH 3.0. The collected fractions were screened for peanut-specific allergen by the previously described ELISA and assessed for purity by SDS-PAGE.

Four of the MAbs (subtyped as lambda chain IgG1) were used for immunoblotting against the 63.5 kD allergen. In a two-site immunometric assay each MAb was used as the capture antibody and the serum pool, either the peanut positive IgE serum pool or normal serum pool, was used as the second antibody. The results show that each MAb had significant amounts of binding to the crude peanut material, the 63.5 kD peanut allergen (Ara h I), and the 17 kD peanut allergen (Ara h II) but no significant binding to other legumes, including soy, peas, chick peas, green beans, and lima beans (Table 7). The assays using the normal serum pool showed no significant binding.

In the next ELISA the MAbs were again used as the capture antibody with individual serum used as the second antibody (Table 8). Some individual variation occurred among the individual patients, but each patient included in the peanut positive pool had significant amounts of binding while the patients with normal serum had less than 8.0%.

ELISA-inhibition studies were done with seven MAbs to determine the epitope specificity of each. Biotinylated MAb was incubated with differing concentrations of each of the other MAbs (including a MAb for Altl, the primary allergen from Alternaria). The inhibition was graded from 0+ (none) to 4+ (significant) (Table 2). Monoclonal antibodies 8D9 and 8F10 had the least amount of cross-inhibition between the 4 MAbs.

The allergen purified by MAb 8F10 was isolated from Florunner peanut extract by MAb affinity chromatography. The eluted fraction has 2 major bands on SDS-PAGE at a mean MW of 63.5 kD. The radiolabeled IgE immunoblot with the pooled peanut positive serum showed significant IgE binding.

Since over 90% of six patients with documented food hypersensitivity reactions to peanut demonstrate specific-IgE to the Ara h I allergen (63.5 kD fraction), an ELISA assay which would detect this allergen in food products was developed.

A total of thirty hybridoma subclones were identified for screening. The number of subclones was reduced to twenty by ELISA and SDS-PAGE/Western blotting to determine the binding affinity and specificity using whole peanut extracts. From the twenty subclones the following thirteen were frozen in liquid nitrogen for further testing: hybridoma cell lines 2H9, 2G10, 10B3, 2E9, 4HB, 10A3, 6B5, 7D9, 1B6, 7B3, 8F10, 6F9, and 8D9.

Seven cell lines producing high titer immunoglobulins (MAbs) and having a considerable amount of ascites fluid in mice providing for the recovery of a significant amount of immunoglobulin were selected for further testing (8F10, 8D9, 6B5, 7B3, 2E9, 6F9, and 1B6). The MAbs 8F10 and 8D9 were isolated from the hybridoma cell lines 8F10 and 8D9 supernatants and used as the standard two-site ELISA assay. Cell culture supernatants from the five remaining cell lines were tested to determine their specificity and binding inhibition in the assays. Small quantities of ascites were also tested by ELISA to determine capture and detection MAb pairings.

Based on the above testing, the preferred capture and detection (biotinylated) MAb pairs include 8F10 and 8D9, 7B3 and 1B6, 2E9 and 6B5, and 2E9 and 8D9. In these monoclonal antibody pairs, either antibody can be used as the capture or detection antibody in the two-site monoclonal antibody enzyme-linked immunosorbent assay of the present invention. For example, assays have been developed using the MAb 8F10 as the capture Ab and MAb 8D9 as the detection Ab or with MAb 8D9 as the capture Ab and MAb 8F10 as the detection (biotinylated) Ab. Other possible MAb pairings include MAbs 7B3 and 2E9, 7B3 and 6B5, 7B3 and 6F9, and 2E9 and 6F9. As shown in Table 2, each of the MAbs 8F10, 8D9, 2E9, 7B3, 1B6, 6B5, and 6F9 were tested as the capture and detection antibody in combination with each of the other antibodies.

Table 9 shows the results of site specificity testing for each of seven MAbs with respect to four binding sites (epitopes) on the Ara h I peanut allergen. The results relating to specificity for the four sites labeled A, B, C, and D are based on the use of capture and detection MAbs, while the results relating to the three sites labeled X, Y and Z are based on the use of MAbs in combination with peanut positive serum pool IgE antibody. It is not known whether the three sites A, B, and D are the same three sites X, Y and Z.

IgG1 products from hybridoma cell lines produced against Ara h I were used to develop a 2-site monoclonal antibody ELISA. In one example, monoclonal antibody 8D9 was used as the capture antibody, and monoclonal antibody 8F10 was biotinylated to use as the second antibody.

A crude Florunner peanut extract was used as the standard. Five food products with peanuts on the label (including plain M&M's®, which contain peanuts), five food products without peanuts on the labels, three commercial peanut oils and two commercial soybean oils were used as extract source material. The amount of Ara h I in the peanut-labeled products varied from 1.4 µg/ml to 1777 µg/ml. No Ara h I allergen could be detected in peanut oil, soybean oil or in any of the nonpeanut food extracts. The present ELISA for Ara h I is useful for screening food products for this peanut allergen and. for correlating the amount of peanut allergen which might cause significant clinical reactions.

With reference to FIGS. 5–9 of the drawings and in accordance with an exemplary embodiment of the present invention, an ELISA for peanut allergen is produced and analyzed as follows. The 8F10 monoclonal antibody is diluted 1:1000 v/v in coating buffer; concentration is approximately 1–5 µg/ml in 0.1 M sodium carbonate/sodium bicarbonate buffer, pH 9.2. One hundred microliters is added to each well of a 96-well microtiter plate and incubated overnight at 4° C. (FIG. 5).

The coating buffer with monoclonal antibody 8F10 is thoroughly washed from the wells with phosphate buffer containing 0.05% Tween 20.

Dilutions of a known peanut extract (0.05–50 µg) and the 63.5 kD allergen are prepared to establish a standard curve. Dilutions of the unknown are prepared to determine if they contain the 63.5 kD allergen. One hundred microliters of the known and unknowns are then added to the individual wells and incubated one hour at 37° C. (FIG. 6).

The solutions are washed from the wells. Only the antigens/allergens that have receptors (epitopes) to the specific monoclonal antibody bind to the capture monoclonal antibody 8F10.

A second monoclonal antibody having a different epitope specificity than that of the capture monoclonal antibody is biotinylated and used as the detection antibody. Monoclonal antibody 8D9 is diluted to a concentration of 1 mg/ml in 0.1 M sodium bicarbonate and dialyzed overnight in the same buffer, A 0.1 ml of biotin-X-NHS per ml (Calbiochem) of antibody solution is added and rocked for two hours at room temperature. The coupling reaction is stopped with 0.1 ml of 1 M ammonium chloride per ml of antibody solution and rocked an additional ten minutes at room temperature. The biotinylated 8D9 monoclonal antibody (Biotin-8D9) is then dialyzed against 500 ml of phosphate buffered saline with 0.01% thimersol, pH 7.4, at 4° C. with stirring. The 500 ml buffer is replaced the next day and dialysis is allowed to continue for an additional 4 hours. The biotinylated antibody solution is adjusted to 2% with bovine serum albumin as a stabilizer; aliquoted into 0.5 ml fractions; and stored frozen at −70 C. One hundred microliters of the biotinylated 8D9 antibody is then added to each well and incubated overnight at 4° C. (FIG. 7). The wells are again washed to remove all of the unbound antibody.

One hundred microliters of a 1:1000 dilution of avidin conjugated horseradish peroxidase enzyme (Vector) is then added to each well for 5 minutes at room temperature (FIG. 8). The biotin on the biotinylated monoclonal antibody and the avidin on the enzyme bind at this stage. The unbound conjugate is washed from the wells.

One hundred microliters of horseradish peroxidase substrate (Citrate buffer, OPD (Sigma), $H_2O_2$; prepared fresh) is added to each well and incubated at room temperature until a color change develops signified by a colorless solution to a brown/orange/yellow color in the wells (approximately 5–10 minutes). The color development is stopped with the addition of 100 µl of 2N HCL (FIG. 9).

The degree of color development is measured spectrophotometrically (OD490; BioRad plate reader) to determine the absorption. A standard curve is calculated by plotting the concentration of the known peanut concentration versus the optical density of the reaction in the individual wells. The concentrations of the unknown can then be calculated from this curve by interpolation from the curve reading the optical density and determining the concentration from algebraic equations (Software program with the BioRad plate reader, FIG. 1).

Other examples of two-site monoclonal antibody enzyme-linked immunosorbent assays in accordance with the present invention include assays using the following MAb pairs: 7B3 and 1B6, 7B3 and 2E9, 7B3 and 6B5, 7B3 and 6F9, 2E9 and 6B5, 2E9 and 6F9, and 2E9 and 8D9. It should be understood that these seven pairs represent fourteen assay examples since each of the MAbs in these pairs can be used as either the capture or detection antibody.

Because each of the above-described monoclonal antibodies is derived from living hybridoma cells which may perish and since the above description provides one skilled in the art the methodology to produce other hybridoma cells and monoclonal antibodies to the Ara h I peanut allergen, the scope of the present invention is not limited to the named. hybridoma cell lines and monoclonal antibodies derived therefrom.

The two-site monoclonal antibody enzyme-linked immunosorbent assay (ELISA) has many advantages as compared to the conventional radioimmunoassay (RIA). For example, no isotopes or scintillation counters are required, and the readout may be by eye. The tedious cutting up of trays, loading into tubes, and loading and unloading the counter are all avoided. If a quantitative readout is needed (unnecessary for hybridoma screening) automated reading devices are available which will scan 96 wells in a minute or so, compared to 1–2 h for scintillation counting. Finally, the reagents for ELISA are inexpensive and have a long shelf life. Enzyme-conjugated anti-immunoglobulin or protein A are available commercially from many suppliers. The most commonly used enzymes are horseradish peroxidase and alkaline phosphatase. Both are capable of giving good results, providing that no endogenous enzyme is present.

IDENTIFICATION OF ARA H II

Identification and purification of allergens is crucial to the understanding of IgE-mediated disease. Immunologic and structural studies with these purified allergens are the next steps in unraveling this process. Several allergens have been identified that stimulate IgE production and cause IgE-mediated disease in humans. In comparison with the body of work done to identify and purify inhaled allergens, significantly less work has been done on the food allergens.[1-3] Because peanuts are a relatively common and often fatal cause of food hypersensitivity reactions we chose to use this model to study IgE-mediated reactions.[4]

Approximately 60% of children with severe atopic dermatitis (AD) have food hypersensitivity reactions.[5,6] The ability to document food hypersensitivity reactions by double-blind, placebo-controlled, food; challenges (DBPCFCs) in this group has allowed appropriate scientific work to be done on the identification of the allergens causing disease.

With the sera of patients who had positive DBPCFCs to peanut, we were able to begin the process of identification and purification of the major peanut allergens. In our previous study we identified and purified Ara h I, a protein with a mean molecular weight of 63.5 kD and a mean isoelectric point (pI) of 4.55.[7] Identification of a second major peanut allergen, Ara h II, was accomplished by use of anion-exchange column chromatography, sodium dodecyl sulfate-polyacrylamide gel electrophoresis (SDS-PAGE), enzyme-linked immunosorbent assays (ELISAs), thin-layer isoelectric focusing (TLIEF), two-dimensional gel immunoelectrophoresis, IgE-specific immunoblotting, carbohydrate analysis, amino acid analysis, and sequencing. This protein has a mean molecular weight of 17 kD and a mean pI of 5.2.

Patients Sensitive to Peanuts

Approval for this study was obtained from the Human Use Committee at the University of Arkansas for Medical Sciences. Nine patients (mean age, 4.2 years) with AD and a positive immediate prick skin test to peanut had either a positive DBPCFC or a convincing history of peanut anaphylaxis (the allergic reaction was potentially life threatening, that is with laryngeal edema, severe wheezing, and/or hypotension) (7 patients had positive DBPCFCs). Details of the challenge procedure and interpretation have been previously discussed.[8] Five milli-liters of venous blood were drawn from each patient, allowed to clot, and the serum was collected. An equal volume of serum from each donor was mixed to prepare a nine-person peanut-specific IgE antibody pool.

Crude Peanut Extract

Three commercial lots of southeastern runner (Arachis hypogaea), medium grade, from the 1979 crop (North Carolina State University) were used in this study. The peanuts were stored in the freezer at −18° C. until roasted. The three lots were combined in equal proportions and blended before defatting. The defatting process (defatted with hexane after roasting for 13 to 16 minutes at 163° to 177° C.) was done in the laboratory of Dr. Clyde Young (North Carolina State University). The powdered crude peanut was extracted per the recommendations of Yunginger and Jones[9] in 1 mol/L NaCl to 20 mmol/L sodium phosphate (pH 7.0) with the addition of 8 mol/L urea for 4 hours at 4° C. The extract was isolated by centrifugation at 20,000 g for 60 minutes at 4° C. The total protein determination was done by the (BCA) method (Bio-Rad Laboratories, Richmond, Calif.).

Chromatography

Analytic and preparative anion-exchange chromatography was performed with the FPLC system (Pharmacia, Piscataway, N.J.). Anion-exchange chromatography used the PL-SAX column (Anion exchange column, Polymer Laboratories, Amherst, Mass.). The crude peanut extract was dialyzed against 20 mmol/L Tris-bis-propane (pH 7.2) without urea and 40 mg loaded on the PL-SAX column. A stepwise salt gradient of 0 to 1.5 mol/L NaCl was applied. All fractions of each resolved peak were pooled, dialyzed and lyophilized.

Dot blotting was done to determine which fractions from the anion-exchange column chromatogram contained IgE-binding material. Two hundred microliters of each fraction were blotted with the Mini Blot apparatus (Schleicher and Schuell, Keene, N.H.) onto 0.45 um nitrocellulose membranes (Bio-Rad). After the membranes were dried, the remaining active sites were blocked with 20 ml of blocking solution (0.5% gelatin with 0.001% thimerosal in 500 ml of phosphate-buffered saline [PBS]) for 1 hour. The procedure is then identical to the immunoblotting for IgE.

Electrophoresis and Immunoblotting

The electrophoresis procedure is a modification of Sutton et al.[10,11] SDS-PAGE was carried out with a 12.5% polyacrylamide separating gel and a stacking gel of 3%. Twenty microliters of a 1 mg/ml solution of each fraction was applied to each well. Replicate samples were applied for independent analysis. Electrophoresis was performed for 4 hours at 0.030 A per gel (E-C Apparatus Corp., St. Petersburg, Fla.) for the 14 cm by 12 cm gels, and for 1 hour at 175 V per gel for the 8 cm by 7.5 cm gels (Mini-Protean II system, Bio-Rad Laboratories). To assure proper protein separation and visualization, Coomassie brilliant blue (Sigma Chemical Co., St. Louis, Mo.) stains were done on gels. For detection of carbohydrate staining material, gels were stained with the modified PAS stain according to the method of Kapitany et al.[12]

Proteins were transferred from the separating gel to a nitrocellulose membrane in a transfer buffer (tris-glycine) with 10% SDS and 40% methanol.[13] The procedure was done in a transblot apparatus (Bio-Rad Laboratories) for 2 hours (0.150 A). An amido black stain (Bio-Rad Laboratories) was done to assure transfer of the protein.

After removal from the transblot apparatus, the nitrocellulose was placed in blocking solution overnight. The nitrocellulose blot was then washed three times with PBS (PBS with 0.05% Tween 20) and incubated with the pooled peanut-sensitive IgE serum (1:20 dilution) for 2 hours at 4° C. with rocking. After washing again with PBS three times, alkaline phosphatase-conjugated goat antihuman IgE (1:1000 vol/vol of PBS, Bio-Rad Laboratories) was added and incubated at room temperature with rocking for 2 hours. After again washing with PBS three times, the blot was developed with 250 μl of 30 mg nitro blue tetrazolium in 70% dimethylformamide (NBT) (Bio-Rad Laboratories) and 250 μl of 15 mg of 5-bromo-4-chloro-3-indolyl-phosphate in 70% dimethylformamide (BCIP) (Bio-Rad Laboratories) solutions in 25 ml carbonate buffer (0.2 mol/L, pH 9.8) at room temperature for 15 minutes. The reaction was then stopped by decanting the NBT/BCIP solution and incubating the nitrocellulose for 10 minutes with distilled water. The blot was air-dried for visual analysis.

ELISA for IgE

A biotin-avidin ELISA was developed to quantify IgE antipeanut protein antibodies with modifications from an assay previously published.[14] The upper two rows of a 96-well microtiter plate (Gibco, Santa Clara, Calif.) were coated with 100 μl each of equal amounts (1 μg/ml) of antihuman IgE monoclonal antibodies, 7.12 and 4.15 (kindly provided by Dr. A. Saxon). The remainder of the plate was coated with one of the peanut products at a concentration of 1 μg/ml in coating buffer (0.1 mol/L sodium carbonate-bicarbonate buffer, pH 9.5). The plate was incubated at 37° C. for 1 hour and then was washed five times with rinse buffer (PBS, pH 7.4, containing 0.05% Tween 20; Sigma Chemicals Co.) immediately and between subsequent incubations. The upper two rows used a secondary standard reference to generate a curve for IgE, ranging from 0.05 to 25 ng/ml.

The serum pool and patient serum samples were diluted (1:20 vol/vol) and dispensed in duplicate in the lower portion of the plate. After incubation for 1 hour at 37° C. and washing, biotinylated, affinity-purified goat antihuman IgE (KPL, Gaithersburg, Md.) (1:1000 vol/vol PBS) was added to all wells. Plates were incubated for 1 hour at 37° C., washed, and 100 μl horseradish peroxidase-avidin conjugate (Vector Laboratories, Burlingame, Calif.) added for 30 minutes. After washing, the plates were developed by addition of a buffer containing O-phenylenediamine (Sigma Chemical Co.). The reaction was stopped by the addition of 100 μl 2-N-hydrochloric acid to each well, and absorbance was read at 492 nm (Titertek Multiscan, Flow Laboratories, McLean, Va.). The standard curve was plotted on log-logit scale by means of simple linear regression, and values for the pool and individual patient samples were read from the curve as "nanogram-equivalent units" per milliliter (nanogram per milliliter).[15,16]

ELISA Inhibition

A competitive ELISA inhibition was done with the FPLC fractions. One hundred microliters of pooled serum (1:20) from the patients with positive challenges was incubated with various concentrations of the FPLC protein fractions (0.00005 to 50 ng/ml) for 18 hours. The inhibited pooled serum was then used in the ELISA described above. The percent inhibition was calculated by taking the food-specific IgE value minus the incubated food-specific IgE value divided by the food-specific IgE value. This number is multiplied by 100 to get the percentage of inhibition.

Isoelectric Focusing

The samples were focused with the LKB Multiphor system using LKB PAG plates, pH gradient 3.5 to 9.5 (LKB, Bromma, Sweden). Five microliters of sample (1 mg/ml). was applied, and an electric current of 200 V was applied for 30 minutes and then increased to 900 to 1200 V for 30 minutes. The gel was fixed and stained with Coomassie brilliant blue following the standard protocol (LKB).

Two-dimensional Gel Electrophoresis

The samples were run according to the method of O'Farrell et al.[17] The first dimension is an isoelectric focusing gel in glass tubing. After making the gel mixture the samples are loaded with overlay solution and 0.02 mol/L NaOH. The samples are run at 400 V for 12 hours and at 800 V for 1 hour. After removing the gel from the tube, the isoelectric focusing gel is equilibrated for 2 hours in SDS sample buffer. The second dimension is 14 cm by 12 cm, 12.5% polyacrylamide gel described in the electrophoresis section. The gels were stained with the pooled peanut-positive serum for IgE-specific bands as above.

Amino Acid Analysis, Amino Acid Sequencing, and Carbohydrate Analysis

The 17 kD fraction was run on a 10% mini-gel (Bio-Rad Laboratories) in Tris-glycine buffer and stained with Rapid Reversible Stain (Diversified Biotech, Newton Centre, Mass.). The two bands were cut separately from the gel and electroluted in tris-glycine SDS buffer. After lyophilization the bands were sequenced individually. Automated gas-phase sequencing was performed on an Applied Biosystems model 475A sequencing system (Dr. Bill Lewis, University of Wyoming, Laramie, Wyo.). Amino acid analysis was done with a Hitachi (Hitachi Instruments, Inc., Danbury, Conn.) HPLC L5000 LC controller with a C18 reverse-phase column.

The electroluted 17 kD fraction was analyzed for carbohydrate analysis (Dr. Russell Carlson, Complex Carbohydrate Research Center, University of Georgia, Athens, Ga.). Glycosyl composition analysis on these samples was performed by the preparation and analysis of trimethylsiyl methylglycosides.

RESULTS

Chromotography

Figure 10:
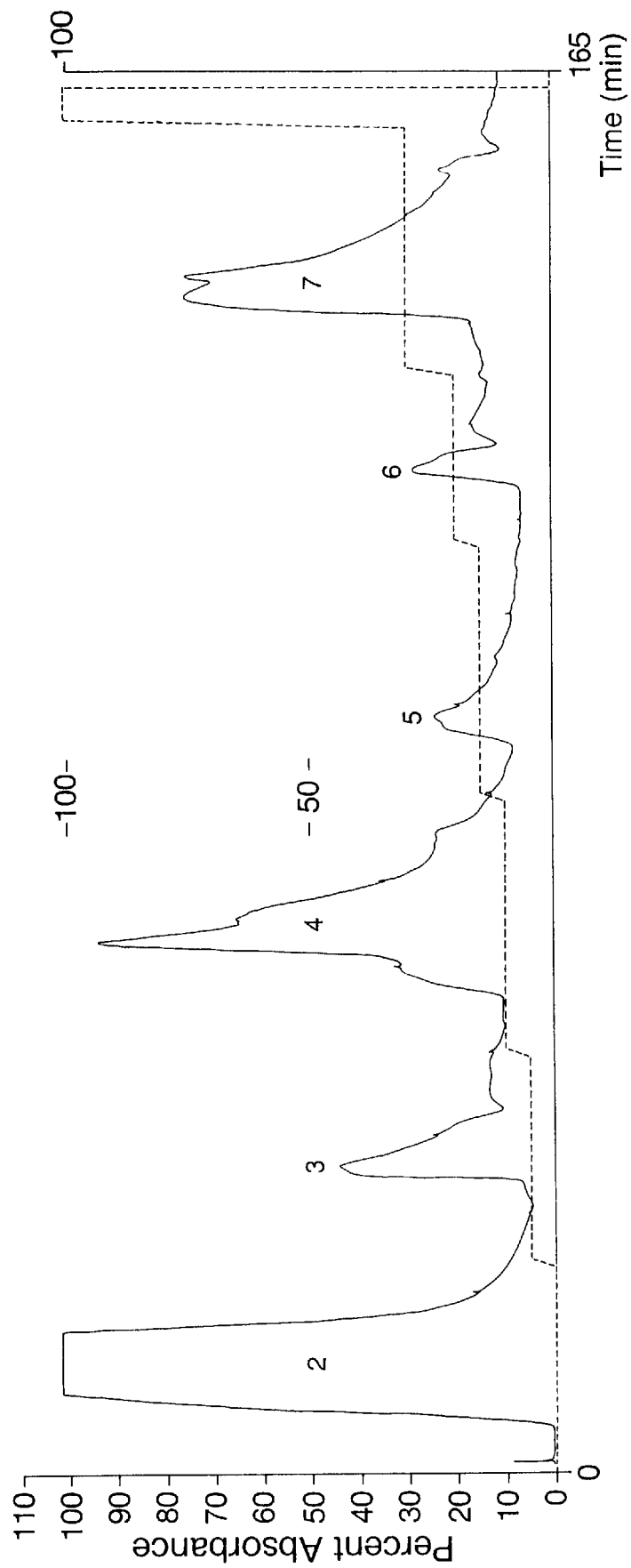

Pilot experiments were conducted with the analytical Mono Q 5/5 (Pharmacia) anion-exchange column to determine the optimal buffer system and salt gradient. Screening for IgE-specific peanut binding components was done by dot blotting of these factions. Scale up and optimization was completed with the PL-SAX column (anion-exchange), with a stepwise salt gradient (0 to 1.5 mol/L NaCl). This procedure separated the crude peanut extract into seven major peaks (FIG. 10). Preliminary dot blotting from this separation identified IgE-binding material in each peak (picture not shown). Multiple runs of this fractionation procedure were performed, and each isolated peak was pooled, dialyzed against 100 mmol/L $NH_4HCO_3CO_3$, and lyophilized.

Electrophoresis and Immunoblotting

Initial SDS-PAGE and immunoblotting of the crude peanut extract revealed multiple fractions with several IgE-staining bands.[7] Aliquots of the seven lyophilized fractions from the anion-exchange column were analyzed by SDS-PAGE (date not shown). Each fraction showed 2 to 5 Coomassie brilliant blue staining protein bands. Immunoblotting for specific IgE with the pooled serum revealed IgE-staining bands in each fraction. Fraction 4 showed two large, closely migrating, IgE-specific bands with a mean molecular weight of 17 kD (FIG. 11) (6% by weight of crude peanut extract).

ELISA and ELISA Inhibition

Figure 12:
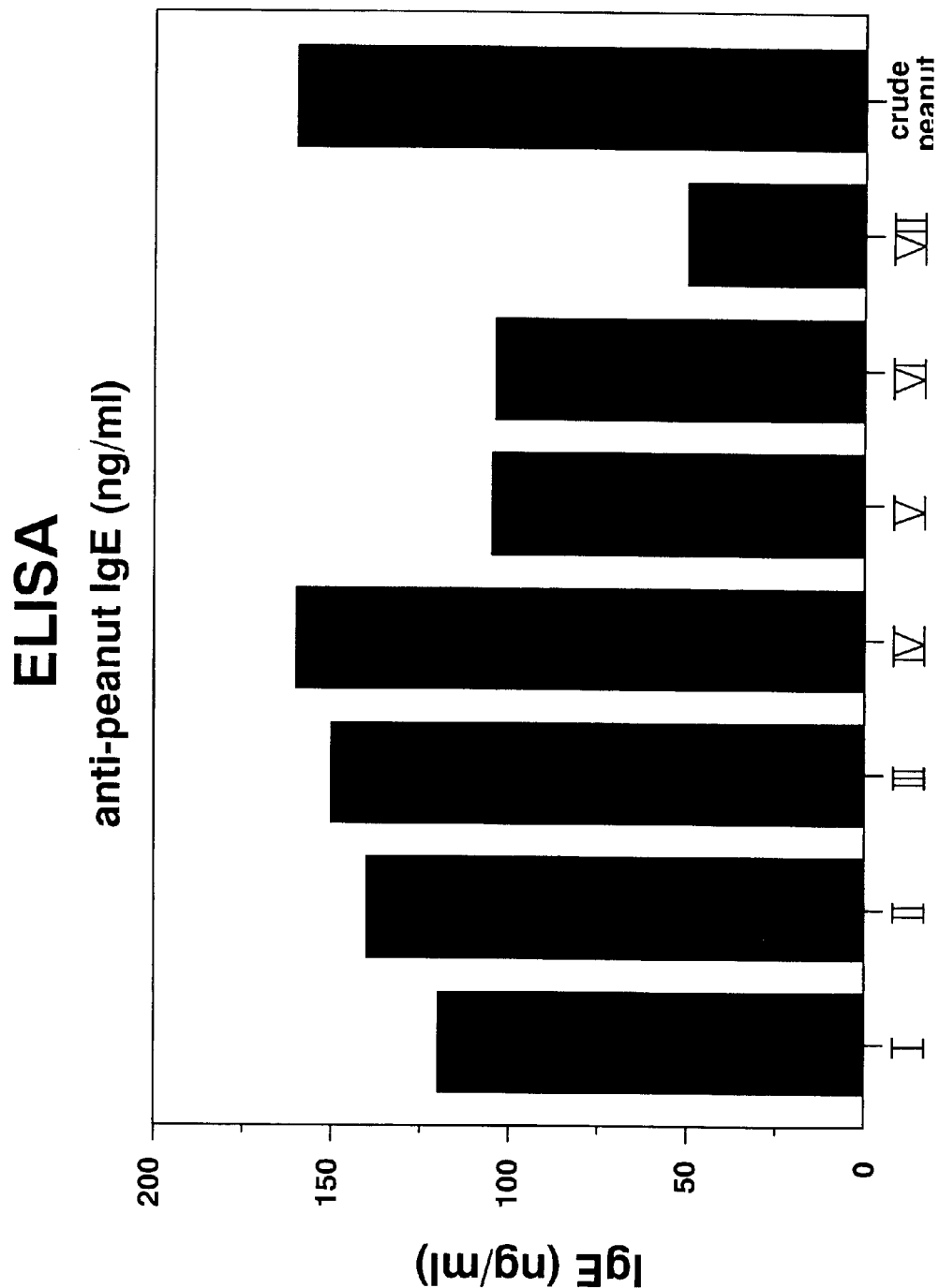

ELISA results comparing the crude peanut extract with each isolated fraction are shown in FIG. 12. Fractions 1 through 7 all had IgE-binding from the peanut-positive serum pool. We tested individually the serum of six patients (members of pooled serum) to determine the relative IgE-binding material to both the crude peanut, fraction 4 (which contained the 17 kD component), and Ara h I (major component, 63.5 kD fraction). Each patient's serum had measurable amounts of peanut-specific IgE to each. Three of the patients had more peanut-specific IgE (nanogram/milliliter) to the 17 kD fraction than to the 63.5 kD fraction (Table 10).

Figure 13:
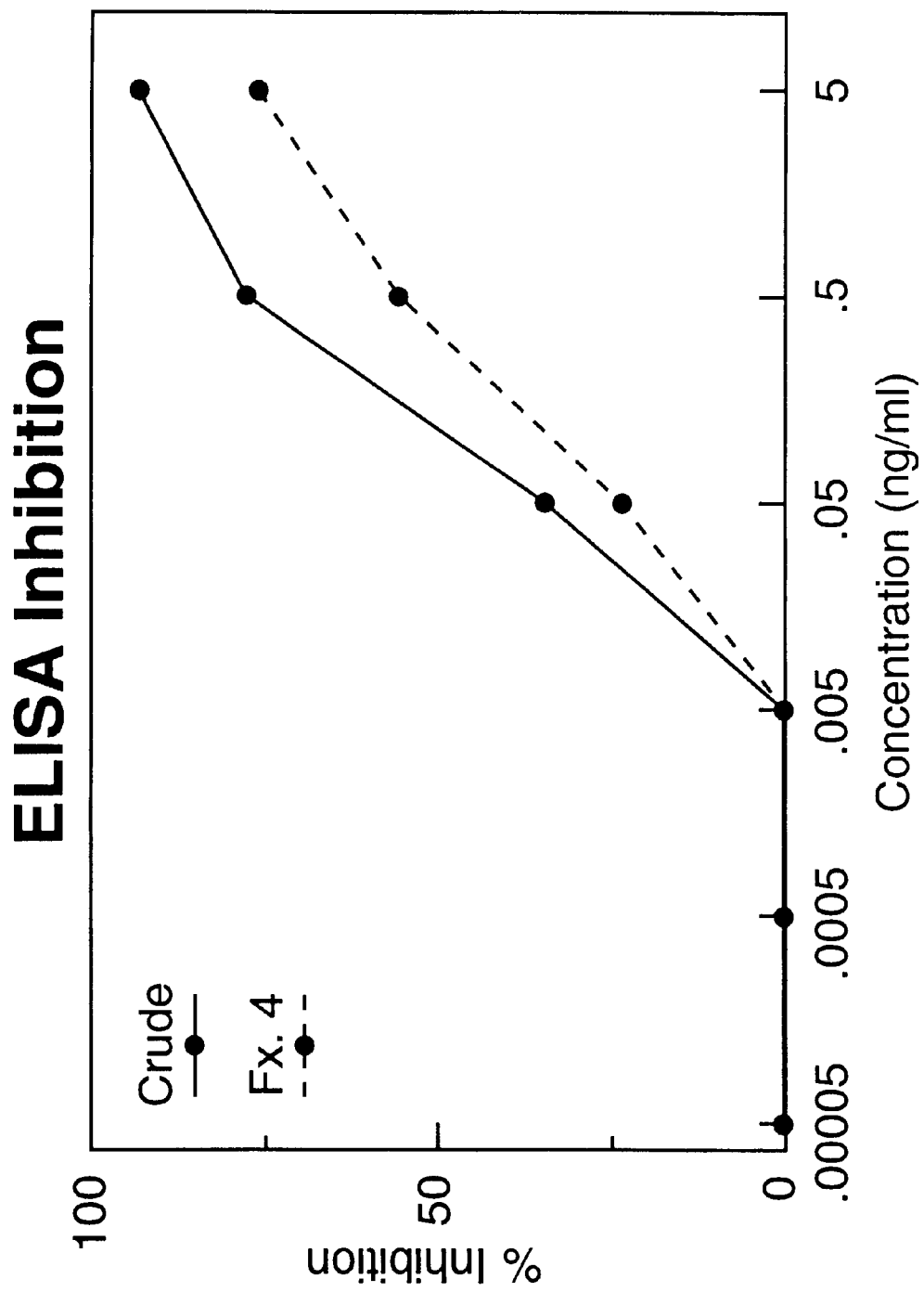

The ELISA inhibition results are shown in FIG. 13. The concentration of the 17 kD fraction required to produce 50% inhibition was 0.4 ng/ml compared with 0.1 ng/ml of the crude peanut extract.[18]

Two-dimensional Gel Electrophoresis

Figure 14:
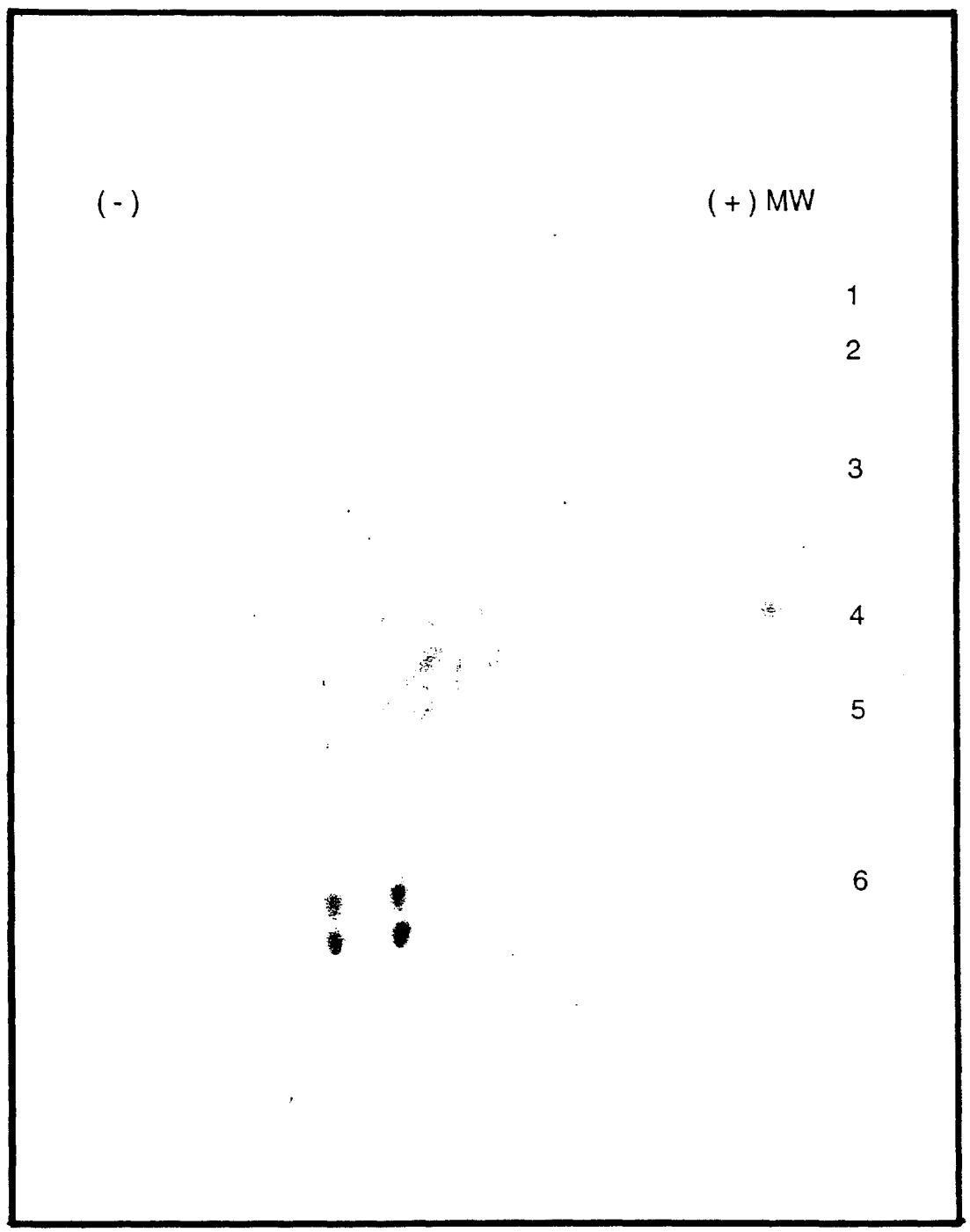

Because immunoblotting and ELISAs of the various anion-exchange fractions suggested that fraction 4 appeared to contain a major allergen, isoelectric focusing was done on this fraction. The two bands in this allergen, which migrated closely together at a mean molecular weight of 17 kD on SDS-PAGE stained with Coomassie brilliant blue, had a pI of 5.2 (gel not shown). FIG. 14 shows the Coomassie-stained gel of the 17 kD fraction. One can see the protein divided into four distinct areas at a mean molecular weight of 17 kD and a mean pI of 5.2.

Amino Acid Analysis, Amino Acid Sequencing, and Carbohydrate Analysis

Table 11 shows the complete amino acid analysis of the purified peanut fraction. The fraction was particularly rich in glutamic acid, aspartic acid, qlycine, and arginine.

The amino acid sequence for both 17 kD bands is shown in Table 12. The sequence for the second 17 kD band was essentially identical. Molecular weight discrepancies may be a result of carbohydrate composition in the two isoallergens. There are no known similar N-terminal sequences found in PIR, GEN-BANK, or SWISS-PROTEIN.

The 17 kD fraction was found to be 20% carbohydrate with significant levels of galacuronic acid, arabinose, and xylose (Table 13).

DISCUSSION

Individuals are genetically prone to produce IgE to specific antigens and to have allergic disease. No known features have been found to distinguish allergens as unique antigens.[19] The route of allergen administration, the dosage, the frequency of exposure, and genetic factors all determine the type and severity of the individual's allergic response. Three seemingly distinct foods account for approximately 80% of positive food challenges in children.[5-7] It is apparent that in addition to the fact that these foods are consumed frequently in the diet of children, other factors in either the allergen (food) itself or in the processing of these allergens cause these foods to be responsible for most food hypersensitivity reactions.

Most allergens are low molecular weight proteins or glycoproteins (5 to 50 kD) 20 Recent knowledge about the amino acid sequence of known allergens has not revealed any special features that would be associated with IgE antibody formation.[19] To first identify and then purify the allergens is crucial to a better understanding of the allergic response. Various biochemical techniques have been used to purify allergens from pollen, mite, and animal dander. These techniques include gel filtration, anion-exchange chromatography, and isoelectric focusing.[19] Recent advances in chromatography, including the FPLC (Pharmacia) and immunoaffinity columns with monoclonal antibodies specific for the purified allergens, has allowed easier and faster identification and purification of allergens.

House dust mite, ragweed, and venom allergens are among those allergens that have been isolated and well characterized. Food allergens have been less studied. The food allergens that have been identified and characterized include Gad c I (cod), Gal d II (ovalbumin), and antigen I (shrimp).[1,2]

Because of the prevalence and severity of adverse reactions to peanuts, several previous studies have examined the possibly relevant peanut allergens.[21-27] Multiple molecular weight peanut proteins have been identified from these various studies. Meier-Davis et al.[24] identified three major allergenic fractions, one of which had a molecular weight of 15 kD, which is close to the molecular weight of the allergen Ara h II we have identified. No further identification or characterization of this protein is available.

In a previous study we identified Ara h I, a 63.5 kD allergen from peanuts with a pI of 4.55.[7] This allergen was similarly purified and identified with a combination of anion-exchange chromatography, SDS-PAGE, ELISA, TLIEF, and ELISA inhibition. The allergen described in this report has two major bands, with an apparent mean molecular weight of 17 kD on SDS-PAGE and a mean pI of 5.2. This fraction bound specific antipeanut IgE from the peanut-positive pool in the ELISA and in the immunoblotting experiments. When used in the ELISA-inhibition studies, the 17 kD fraction significantly inhibited the IgE binding from the peanut-positive pool. In preliminary studies we have used the 17 kD allergen to inhibit binding from the pooled peanut-positive IgE serum to our previously described Ara h I. There does appear to be a moderate amount of inhibition of IgE binding to Ara h I produced by the 17 kD allergen. Amino acid sequencing of Ara h I will help to resolve the identity of similar epitopes for IgE between the unique allergens.

According to recent recommendations by a recent international committee (IUIS) for proper identification of allergens we have designated this fraction Ara h II.[20] This fraction has been purified from a crude peanut extract from Florunner peanuts (*Arachis hypogaea*) by anion-exchange chromatography. The fraction was identified as a major allergen by SDS-PAGE, ELISA, ELISA inhibition, TLIEF, amino acid analysis and sequencing, carbohydrate analysis, and two-dimensional gels.

As we have previously speculated, Ara h II is likely to be the second of several major and minor allergens isolated from peanuts. The identification of the allergenic components in foods will allow new studies to elucidate more comprehensively the body's immune response to these allergens. Future work in this area will be directed toward molecular identification and characterization of both B- and T-cell epitopes.

In accordance with the present invention, isolated and purified peanut allergen Ara h II is used as an antigen to produce monoclonal antibodies having a specificity for the Ara h II allergen and to develop a monoclonal antibody enzyme linked immunosorbent assay or the peanut allergen Ara h II using the same methods and procedures as described above with respect to the development of monoclonal antibodies and assays for the peanut allergen Ara h I. In accordance with one example of the present invention, a method for detecting the presence and quantity of the peanut allergen Ara h II in a sample using a two-site monoclonal antibody enzyme linked immunosorbent assay includes the steps of: coating an assay test surface with a layer of capture monoclonal antibodies having a specificity for the Ara h II allergen, incubating the coated test surface to allow the capture monoclonal antibodies to adhere to the test surface, washing the coated test surface to remove any unadhered capture monoclonal antibodies, adding a sample to the coated test surface, incubating the coated test surface to allow the adhered capture monoclonal antibodies to capture any Ara h II peanut allergen present in the sample, washing the coated test surface to remove the uncaptured peanut allergen and remaining sample, adding a layer of biotinylated monoclonal antibodies having a specificity for the Ara h II allergen to the coated test surface, incubating the coated test surface to allow the biotinylated monoclonal antibodies to bind to the captured peanut allergen, washing the coated test surface to remove unbound biotinylated monoclonal antibodies, adding horseradish peroxidase-avidin conjugate to the coated test surface, allowing the horseradish-peroxidase, avidin conjugate to bind to the biotinylated monoclonal antibodies, washing the coated test surface to remove any unbound horseradish peroxidase-avidin conjugate, adding citric acid substrate to the coated test surface to develop a color change indicative of the quantity of bound horseradish peroxidase, adding a stopping agent to stop the development of the color change, and reading the assay to determine the presence and/or quantity of the peanut allergen Ara h II. Also, in accordance with a more particular method, the capture monoclonal antibodies and biotinylated monoclonal antibodies demonstrate specificity for different binding sites on the peanut allergen Ara h II.

Moreover, in accordance with another embodiment of the present invention, test kits for detecting and quantifying the peanut allergens Ara h I and Ara h II include an ELISA test tray, the capture and biotinylated monoclonal antibodies, allergen standards, and the necessary reagents for practicing the described assay method.

Thus, it will be appreciated that as a result of the present invention, two major peanut allergens have been isolated and a highly effective two-site monoclonal antibody enzyme-linked immunosorbent assay and method is provided by which the principal objective, among others, is completely fulfilled. It is contemplated, and will be apparent to those skilled in the art from the preceding description and accompanying drawings, that modifications and/or changes may be made in the illustrated embodiments without departure from the present invention. Accordingly, it is expressly intended that the foregoing description and accompanying drawings are illustrative of preferred embodiments only, not limiting, and that the true spirit and scope of the present invention be determined by reference to the appended claims.

LIST OF ABBREVIATIONS

| | |
|---|---|
| DBPCFC: | Double-blind, placebo-controlled, food challenge |
| SDS: | Sodium dodecyl sulfate |
| PAGE: | Polyacrylamide gel electrophoresis |
| NBT: | 30 mg nitro blue tetrazolium in 70% dimethylformamide |
| BCIP: | 15 mg of 5-bromo-4-chloro-3-indolyl-phosphate in 70% dimethylformamide |
| TLIEF: | Thin-layer isoelectric focusing |
| ELISA: | Enzyme-linked immunosorbent assay |
| AD: | Atopic dermatitis |
| pI: | Isoelectric point |
| CRIE: | Crossed radioimmunoelectrophoresis |
| Ab: | Antibody |
| IUIS: | International Union of Immunological Societies |
| FPLC: | Fast protein liquid chromatography |
| PAS: | Periodic acid-Schiff |
| MAb: | Monoclonal antibody |
| IEF: | Isoelectric focusing |
| Con A: | Concanavalin A |
| PBS: | Phosphate-buffered saline |
| RIA: | Radioimmunoassay |

REFERENCES

1. Anderson J A, Sogn D D, eds. Adverse reactions to foods. Hyattsville, Md.: 1984; NIH publication no. 84-2442:7-26.
2. Metcalfe D D. Food allergens. Clin Rev Allergy 1985;3:331–49.
3. Lemanske R F, Taylor S L. Standardized extracts, foods. Clin Rev Allergy 1987;5:23–36.
4. Sampson H A. Peanut anaphylaxis. J ALLERGY CLIN IMMUNOL 1990;86:1–3.
5. Sampson H A. Role of immediate food hypersensitivity in the pathogenesis of atopic dermatitis. J ALLERGY CLIN IMMUNOL 1983;71:473–80.
6. Sampson H A, McCaskill C C. Food hypersensitivity in atopic dermatitis: evaluation of 113 patients. J Pediatr 1095; 107:669–75.
7. Burks A W, Williams L W, Helm R M, Connaughton C, Cockrell G, O'Brien T. Identification of a major peanut allergen, Ara h I, in patients with atopic dermatitis and positive peanut challenges. J ALLERGY CLIN IMMUNOL 1991;88:172–9.
8. Burks A W, Mallory S B, Williams L W, Shirrell M A. Atopic dermatitis: clinical relevance of food hypersensitivity reactions. J Pediatr 1988;113:447–51.
9. Yunginger J W, Jones R T. A review of peanut chemistry; implications for the standardization of peanut extracts. In: Proceedings of the Fourth International Paul Ehrlich Seminar on the Regulatory Control and Standardization of Allergenic Extracts. Bethesda, Md.: Oct. 16–17, 1985. Stuttgart: Gustav Fischer Verlag, 1987:251–64.
10. Laemmli U K. Cleavage of structural proteins during the assembly of the head of bacteriophage T4. Nature 1970;227:680–5.
11. Sutton R, Wrigley C W, Baldo B A, Detection of IgE and IgG binding proteins after electrophoresis transfer from polyacrylamide gels. J Immunol Methods 1982;52:183–6.
12. Kapitany R, Zebrowski E J. A high resolution PAS strain for polyacrylamide gel electrophoresis. Anal Biochem 1973; 65:361–9.
13. Towbin H, Staehelin T, Gordan J. Electrophoretic transfer of proteins from polyacrylamide gels to nitrocellulose sheets: procedure and some applications. Proc Natl Acad Sci U S A 1979;76:4350–4.
14. Burks A W, Sampson H A, Buckley R H. Anaphylactic reactions following gammaglobulin administration in patients with hypogammaglobulinemia: detection of IgE antibodies to IgA. N Engl J Med 1986;314:560–4.
15. Burks A W, Brooks J R, Sampson H A. Allergenicity of major component proteins of soybean determined by enzyme-linked immunosorbent assay (ELISA) and immunoblotting in children with atopic dermatitis and positive soy challenges. J ALLERGY CLIN IMMUNOL 1988;81:1135–42.
16. Burks A W, Williams L W, Casteel H B, Fiedorek S C, Connaughton C A. Antibody response to milk proteins in patients with milk-protein intolerance documented by challenge. J ALLERGY CLIN IMMUNOL 1990;85:921–7.
17. O'Farrell P H. High resolution two-dimensional electrophoresis of proteins. J Biol Chem 1975;250:4007–21.
18. Jusko J W. Corticosteroid pharmacodynamics: models for a broad array of receptor-mediated pharmacologic effects. J Clin Pharmacol 1990;30:303–10.
19. Marsh D G. Allergens and the genetics of allergy. In: Sela M, ed. The antigens. New York: Academic Press, 1975:271–359.
20. Chapman M D. Purification of allergens. Curr Opin Immunol 1989;1:647–53.
21. Nordlee J A, Taylor S L, Jones R T, Yunginger J R. Allergeni-city of various peanut products as determined by RAST inhibition. J ALLERGY CLIN IMMUNOL 1981;68:376–82.
22. Heiner D C, Neucere N J. RAST analyses of peanut allergens [Abstract]. J ALLERGY CLIN IMMUNOL 1975;55:82.
23. Barnett D, Baldo B A, Howden M E H. Multiplicity of allergens in peanuts. J ALLERGY CLIN IMMUNOL 1983;72:61–8.
24. Meier-Davis S, Taylor S L, Nordleie J, Bush R. Identification of peanut allergens by immunoblotting [Abstracts]. J ALLERGY CLIN IMMUNOL. 1987;79:218.
25. Barnett D, Howden M E H, Bonham B, Burley R W. Aspects of legume allergy research. Proc Sydney Allergy Group 1985;4:104–18.
26. Taylor S L, Nordlee J A, Yunginger J W, Jones R T, Sach M I, Bush R K. Evidence for the existence of multiple allergens in peanuts [Abstract]. J ALLERGY CLIN IMMUNOL 1982;69:128.

27. Sachs M I, Jones R T, Yunginger R W. Isolation and partial characterization of a major peanut allergen. J ALLERGY CLIN IMMUNOL 1981;67:27–34.

TABLE 1

Individual IgE-antibody to peanut allergens (ng/ml)

| Pt | Crude peanut | Ara h Ii | Ara h I |
|---|---|---|---|
| #1 | 4.2 | 21.0 | 14.6 |
| #2 | 7.0 | 11.4 | 13.0 |
| #3 | 285.2 | 285.8 | 380.0 |
| #4 | 1.0 | 2.0 | 3.2 |
| #5 | 11.4 | 19.4 | 17.0 |
| #6 | 5.8 | 12.0 | 9.8 |
| Normals (x2) | <0.05 | <0.05 | <0.05 |

TABLE 2

ELLISA inhibition for 7 monoclonal antibodies to Ara h I

| Biotinylated monoclonal | Inhibiting antibody | | | | | | | |
|---|---|---|---|---|---|---|---|---|
| | 8F10 | 8D9 | 2E9 | 7B3 | 1B6 | 6B5 | 6F9 | Alt 1 |
| 8F10 | 71% | 10% | 11% | 11% | 2% | 5% | 5% | 0% |
| 8D9 | 31% | 82% | 34% | 0% | 28% | 26% | 5% | 0% |
| 2E9 | 26% | 35% | 53% | 15% | 29% | 27% | 10% | 0% |
| 7B3 | 22% | 4% | 0% | 50% | 16% | 13% | 10% | 0% |
| 1B6 | 0% | 43% | 39% | 0% | 55% | 34% | 6% | 0% |
| 6B5 | 22% | 52% | 35% | 18% | 52% | 75% | 8% | 0% |
| 6F9 | 20% | 20% | 12% | 12% | 35% | 27% | 54% | 0% |

TABLE 3

SAMPLES

| Peanut | Others | Oils |
|---|---|---|
| Plain M&M | Twix | Olive |
| Peanut M&M | Skor | Garlic |
| Whatchamacalit | Nestle Crunch | Vegetable |
| Snickers | 3 Musketeers | Canola |
| Peanut Butter M&M | Kit Kat | Corn |
| | | Peanut |

TABLE 4

63.5 Kd Two-site Immunometric Assay (Candy)

| Peanut | (ng/ml) | Others | (ng/ml) |
|---|---|---|---|
| Plain M&M | 7.35 | Twix | 0 |
| Snickers | 219.00 | Skor | 0 |
| Peanut M&M | 221.00 | Nestle Crunch | 0 |
| Whatchamacalit | 233.00 | 3 Musketeers | 0 |
| Peanut Butter M&M | 299.00 | Kit Kat | 0 |

TABLE 5

63.5 kD Two-site Immunometric Assay

| Oils | (ng/ml) |
|---|---|
| Olive | 0 |
| Garlic | 0 |
| Vegetable | 0 |

TABLE 5-continued 63.5 kD Two-site Immunometric Assay

| Oils | (ng/ml) |
|---|---|
| Canola | 0 |
| Corn | 0 |
| Peanut | 0 |

TABLE 6

Individual IgE Ab to peanut allergens (nanograms per milliliter)

| Patient | Crude peanut | 63.5 kd |
|---|---|---|
| 1 | 4.21 | 4.6 |
| 2 | 7.0 | 13.0 |
| 3 | 285.2 | 380.0 |
| 4 | 1.0 | 3.2 |
| 5 | 11.4 | 17.0 |
| 6 | 5.8 | 9.8 |
| 7 | ND | ND |
| 8 | ND | ND |

TABLE 7

ELISA - IgE (pooled peanut positive serum)

| PROTEIN | CAPTURE ANTIBODY | | | |
|---|---|---|---|---|
| | 8D9 | 8F10 | 2E9 | 7B3 |
| Peanut Positive IgE Serum Pool | | | | |
| 63.5 kD fraction | 4+ | 4+ | 4+ | 4+ |
| crude peanut | 4+ | 4+ | 4+ | 4+ |
| 17 kD fraction | 2+ | 2+ | 2+ | 2+ |
| soy | 0+ | 0+ | 0+ | 0+ |
| peas | 1+ | 1+ | 1+ | 1+ |
| chick peas | 1+ | 1+ | 1+ | 1+ |
| green beans | 0+ | 0+ | 0+ | 0+ |
| lima beans | 0+ | 0+ | 0+ | 0+ |
| ovalbumin | 0+ | 0+ | 0+ | 0+ |
| Normal serum pool | | | | |
| crude peanut | 0+ | 0+ | 0+ | 0+ |
| 63.5 kD fraction | 0+ | 0+ | 0+ | 0+ |

Table 7. We examined various proteins in the two-site immunometric assay with the mA as the capture antibody and the peanut positive IgE serum pool as the second antibody. Table 7 shows the results of this assay. The binding was graded from 0+ (none) to 4+ (significant).

TABLE 8

IgE (individual peanut positive serum)

| PATIENTS | CAPTURE ANTIBODY | | | |
|---|---|---|---|---|
| | 8D9 | IF10 | 2E9 | 7B3 |
| #1 | 38% | 28.3% | 35.3% | 32.3% |
| #2 | 227.8% | 156% | 282.2% | 164.3% |
| #3 | 61.6% | 82.9% | 38.7% | 27.4% |
| #4 | 18.2% | 14.4% | 13.6% | 13.1% |
| #5 | 21.2% | 24.8% | 38% | 23.1% |
| #6 | 57.8% | 71.9% | 56% | 64.8% |
| Peanut positive pool | 165% | 144% | 125.7% | 143% |
| #7 | 7.1% | 7.4% | 0.0% | 0.0% |
| #8 | 7.1% | 1.8% | 4.5% | 3.5% |

Table 8. Table 8 shows the results of individual peanut positive patients in a similar two-site assay. Patients with normal serum IgE (#7) or patients (#8) with elevated serum IgE but who were not challenge positive to peanut.

TABLE 9

Site specificity of Ara h I monoclonal antibodies

| (a) | A | B | C | D |
|---|---|---|---|---|
| | 8F10 | 8D9 | 7B3 | 6F9 |
| | | 2E9 | | |
| | | 1B6 | | |
| | | 7B3 | | |
| (b) | X | Y | | Z |
| | 8F10 | 8D9 | | 6F9 |
| | | 6B5 | | |

TABLE 10

Concentrations (ng/ml) of peanut-specific IgE binding to the crude peanut extract, Ara h I (63.5 kd allergen), and fraction 4 (from FPLC) (17 kd allergen)

| Patient | Crude peanut (ng/ml) | Ara h I (ng/ml) | Fraction 4 (ng/ml) |
|---|---|---|---|
| 1 | 4.2 | 21.0 | 14.6 |
| 2 | 7.0 | 11.4 | 13.0 |
| 3 | 285.2 | 285.8 | 380.0 |
| 4 | 1.0 | 2.0 | 3.2 |
| 5 | 11.4 | 19.4 | 17.0 |
| 6 | 5.8 | 12.0 | 9.8 |
| 7 | <0.05 | <0.05 | <0.05 |
| 8 | <0.05 | <0.05 | <0.05 |
| Normals | <0.05 | <0.05 | <0.05 |

Patients 1–6 are patients with AD and positive DBPCFCs to peanut.
Patient 7 is a patient with AD who had positive DBPCFC to milk and elevated serum IgE values but did not have positive skin test results or positive challenge to peanut (n = 2).
Patient 8 is a healthy control patient from the serum bank in the ACH Special Immunology Laboratory (n = 2).

TABLE 11

Amino acid analysis of Ara h II

| Amino acid | Residues/molecule |
|---|---|
| Asp | 12.2 |
| Glu | 24.8 |
| Ser | 9.8 |
| His | 1.3 |
| Gly | 11.3 |
| Thr | 2.2 |
| Arg | 10.8 |
| Ala | 5.4 |
| Tyr | 3.9 |
| Met | 2.7 |
| Val | 2.4 |
| Phe | 2.4 |
| Ile | 2.9 |
| Leu | 7.9 |

TABLE 12

Sequencing of upper band (SEQ ID NO: 1) and lower band (SEQ ID NO: 2) of electroluted 17 kd peanut allergen

| Upper Band | * | — | Gln | — | Gln | — | * | — | Glu | — | Leu |
| Lower Band | * | — | Gln | — | Gln | — | * | — | Glu | — | Leu |
| Upper Band | — | Gln | — | Ser | — | Gln | — | Leu | — | Glu | — | Arg |
| Lower Band | — | Gln | — | Ser | — | Gln | — | Leu | — | Glu | — | Asp |
| Upper Band | — | Glu | — | Gln | — | * | — | Leu | — | Met | — |
| Lower Band | — | Glu | — | Gln | — | * | — | Leu | — | Met | — |
| | | | | | | | | | | | |
| Upper Band | — | Gln | — | * | — | Asp | — | * | — | * | — | * |
| Lower Band | — | Gln | — | Asp | — | Leu | — | Glu | — | * | — | * |
| Upper Band | — | Ala | — | Asp | — | Leu | — | Arg | — | Pro | — | (Gly) |
| Lower Band | — | Ala | — | Asn | — | Leu | — | Arg | — | Pro | — | Arg |
| Upper Band | * | — | Lys | — | Ile | | | | | | |
| Lower Band | * | — | Lys | — | Ile | | | | | | |

*Unable to identify amino acid.

TABLE 13

Glycosyl composition analysis of 17 kd allergen

| Glycosyl residue | Ara h II (μg/total) |
|---|---|
| Arabinose | 14.0 |
| Rhamose | 2.8 |
| Fucose | 0.58 |
| Xylose | 9.3 |
| Mannose | 2.5 |
| Galactose | 4.4 |
| Glucose | 5.0 |
| Galacuronic acid | 41.0 |
| Galactosamine | ND |

ND, None detected.

Peanuts are a common cause of food hypersensitivity reactions. The sera of 10 patients who had atopic dermatitis and a positive double-blind placebo-controlled food challenge to peanut were used to investigate the major allergens of peanut. Crude Florunner extracts were fractionated by anion-exchange chromatography using a step gradient (limit buffer, 0.05M BisTris/1.5M NaCl). One hundred microliters of each 2.0 ml fraction was dot-blotted onto nitrocellulose paper and IgE-binding activity assessed using the serum pool to select allergen-containing fractions. A protein peak (OD 280) which eluted at 10% NaCl and demonstrated intense IgE-binding was further analyzed by two-dimensional SDS-PAGE/immunoblot analysis. The majority of this fraction is a protein which has a molecular weight of 17 kD and a pI of 5.2. Sequencing data from the N-terminus revealed the following initial 9 amino acids: (*)-Q-Q-(*)-E-L-Q-D-L. Based on IgE-binding activity and no known amino acid sequence identity to other allergens, this allergen is designated Ara h II.

Figure Legends

FIG. 1—Logit: Abs vs. Log (conc)

Figure 2:
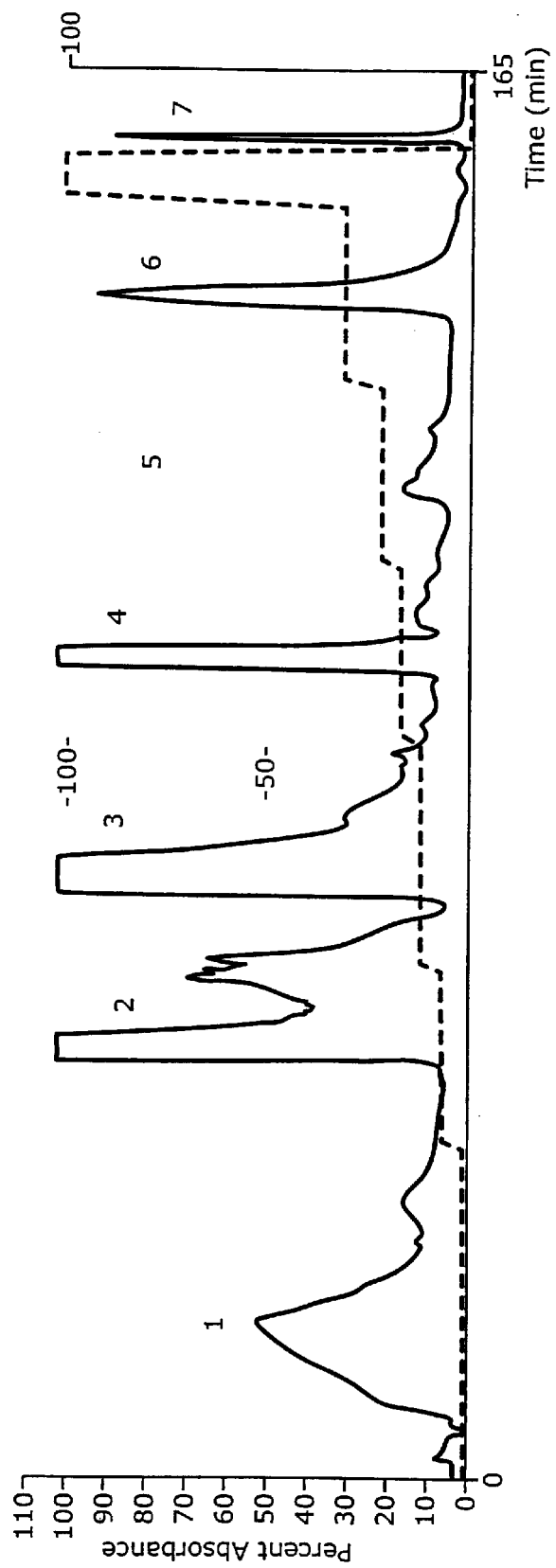

FIG. 2—Anion exchange chromatogram of the defatted crude peanut extract fractionated over the FPLC Mono Q 10/10. The elution pattern of proteins ($A_{280}$) is illustrated by the solid line. A stepwise salt gradient of 0 to 1.5 mol/L of NaCl is illustrated by the dotted line. Fractions were pooled as numbered (fraction 2 is divided into 2a and 2b) and applied to SDS-PAGE for analysis.

FIG. 3—Antipeanut IgE-specific ELISA (nanograms per milliliter) to the defatted crude peanut extract and the pooled fractions from the anion-exchange column. The results are from the peanut-positive serum pool.

FIG. 4—IgE ELISA-inhibition results of crude peanut extract and anion-exchange fraction 3 (63.5 kd fraction) in ELISA for crude peanut.

FIG. 10—Anion-exchange chromatogram of the defatted crude peanut extract fractionated over the FPLC PL-SAX column. Elution pattern of proteins ($A_{280}$) shown by the solid line. Stepwise salt gradient of 0 to 1.5 mol/L NaCl shown by the dotted line. Fractions were pooled as numbered and applied to SDS-PAGE for analysis.

Figure 11:
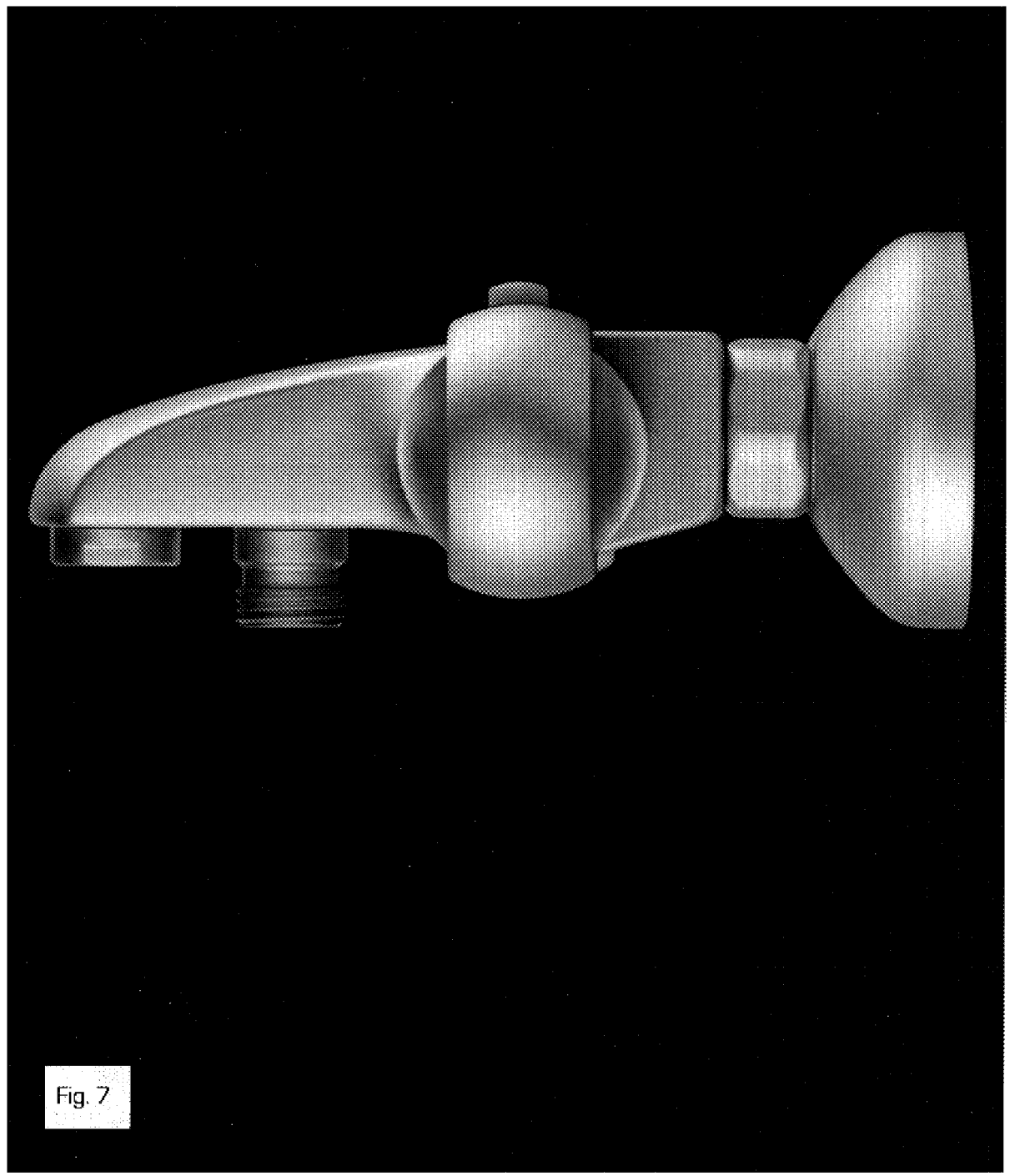

FIG. 11—SDS-PAGE (14 cm×12 cm) analysis of the defatted crude peanut extract stained with Coomassie brilliant blue (lane 1) and immunoblotted for antipeanut specific IgE (lane 2) with pooled serum from patients with AD and positive DBPCFCs to peanut. Molecular weights: 1, 50,000; 2, 39,000; 3, 27,500; 4, 14,500.

FIG. 12—Antipeanut IgE-specific ELISA (ng/ml) to defatted crude peanut extract and pooled fractions from the anion-exchange column. Results are from the peanut positive serum pool.

FIG. 13—IgE ELISA inhibition results of crude peanut extract and anion-exchange fraction 4 in the ELISA for crude peanut.

FIG. 14—Coomassie brilliant blue stain of two-dimensional gel with fraction 4. (anion exchange column) containing the 17 kd allergen. Molecular weights: 1, 112,000; 2, 75,000; 3, 50,000; 4, 39,000; 5, 27,500; 6, 17,000.

With respect to Table 12, the upper band corresponds to SEQ ID NO:1, and the lower band corresponds to SEQ ID NO:2.

Sequencing data from the N-terminus of the lower band revealed the following initial 9 amino acids: (*)-Q-Q-(*)-E-L-Q-D-L (SEQ ID NO:3).

RECOMBINANT PEANUT ALLERGEN Ara h I EXPRESSION AND IgE BINDING IN PATIENTS WITH PEANUT HYPERSENSITIVITY

Acknowledgments

This work was supported in part by grants from the National Institutes of Health R29AI26695-05, the Asthma and Allergy Foundation of America, and the United States Department of Agriculture—AMD:9402890.

INTRODUCTION

Peanut allergy is a significant health problem because of the potential severity of the allergic reaction, the chronicity of the allergic sensitivity, and the ubiquity of peanut products. Peanuts, fish, tree nuts, and shellfish account for the majority of food hypersensitivity reactions in adults, while peanuts, milk, and eggs cause over 80% of food hypersensitivity reactions in children (1,2). Peanut hypersensitivity reactions often tend to be quite severe in nature, sometimes resulting in episodes of fatal anaphylaxis (3,4). Unlike the food hypersensitivity reactions to milk and eggs, peanut hypersensitivity reactions usually persist into adulthood and last for a lifetime (5). Despite the significant prevalence of peanut hypersensitivity reactions and several fatalities annually, the identification of the clinically relevant antigens and an understanding of the immunobiology of peanut hypersensitivity is just beginning (6).

Recently a number of allergens have been identified which stimulate IgE production and cause IgE mediated disease (7). The identification and purification of these allergens is essential for the immunological studies necessary to understand their role in stimulating IgE antibody, formation. Significant information now exists on the identification and purification of inhaled allergens from pollens, dust mites, animal danders, insects, and fungi (7). By comparison, few food allergens known to cause IgE-mediated reactions have been similarly identified and purified (8–10).

Recombinant methodology to clone allergens provides an efficient means of producing pure polypeptides which, in their native source, form complex mixtures and are often represented in only very small amounts. Several inhaled allergens have been cloned, including the allergens of house dust mites (11) and pollen grains (12), in comparison little work has been directed toward producing recombinant food allergens.

Because of the prevalence and severity of peanut hypersensitivity reactions in both children and adults, coupled with the recent identification of two major peanut allergens that are involved in this process (6,13), we set out to clone and characterize the Ara h I peanut allergen. In this communication we report the isolation and characterization of the Ara h I mRNA and the identification of this allergen as belonging to the vicilin seed storage protein family. In addition, this recombinant allergen can be produced in *E. coli* cells and is recognized by serum IgE from patients, with documented peanut hypersensitivity reactions.

METHODS

Patients. Serum from eighteen patients with documented peanut hypersensitivity (mean age—25 years) was used to identify peanut allergens. Each of these individuals had a positive immediate prick skin test to peanut and either a positive double blind, placebo controlled, food challenge (DBPCFC) or a convincing history of peanut anaphylaxis (laryngeal edema, severe wheezing, and/or hypotension). One individual with elevated serum IgE levels (who did not have peanut specific IgE or peanut hypersensitivity) was used as a control in these studies. Details of the challenge procedure and interpretation have been discussed previously (6). At least five mls: of venous blood were drawn from each patient and allowed to clot, and the serum was collected. All studies were approved by the Human Use Advisory Committee at the University of Arkansas for Medical Sciences.

Isolation and Amino Acid Sequence Analysis of Peanut Allergen Ara h I. Ara h I was purified to near homogeneity from whole peanut extracts according to the methods of Burks et al (6). Purified Ara h I was electrophoresed on 12.5% acrylamide mini-gels (Bio-Rad, Hercules, Calif.) in Tris glycine buffer. The gels were stained with 0.1% Coomassie blue in 10% acetic acid, 50% methanol, and 40% water for 3 hours with continuous shaking. Gel slices containing Ara h I were sent to the W.M. Keck Foundation (Biotechnology Resource Laboratory, Yale University, New Haven, Conn.) for amino acid sequencing. Initial sequencing indicated that the amino terminal end of Ara h I was blocked. In order to obtain protein sequencing data Ara h I was treated with trypsin and peptides were selected for further analysis. Amino acid sequencing of tryptic peptides was performed on an Applied Biosystems sequencer with an on-line HPLC column that was eluted with increasing concentrations of acetonitrile.

Peanut RNA Isolation and Northern (RNA) Gels. Three commercial lots from the 1979 crop of medium grade peanut species, Arachis hypogaea (Florunner) were obtained from North Carolina State University for this study. Total RNA was isolated from one gram of this material according to procedures described by Larsen (14). Poly A+ RNA was isolated using a purification kit supplied by Collaborative Research (Bedford, Mass.) according to manufacturer's instructions. Poly A+ RNA was subjected to electrophoresis in 1.2% formaldehyde agarose gels, transferred to nitrocellulose, and hybridized with $^{32}$P-labeled probes according to the methods of Bannon et al (15).

cDNA Expression Library Construction and Screening. Peanut poly A+ RNA was used to synthesize double stranded cDNA according to the methods of Watson and Jackson (16) and Huynh et al (17). The cDNA was treated with Eco R1 methylase and then ligated with Eco R1 and Xho I linkers. The DNA was then ligated with Eco R1-Xho I cut, phosphatase treated Lambda ZAP XR phage arms (Stratagene, Lajolla, Calif.) and in vitro packaged. The library was 95% recombinants carrying an average insert size of >400 bp as determined by sizing of randomly selected clones. The library was screened using an IgE antibody pool consisting of an equal volume of serum from each patient with peanut hypersensitivity. Detection of the primary antibody was either with alkaline phosphatase labeled anti-IgE or I$^{125}$-labeled anti-IgE antibody performed according to manufacturer's instructions. Positive plaques were subjected to subsequent screens using the same pooled serum until all non-reacting plaques were removed. The remaining positive plaques were then re-screened with serum from a patient with elevated total serum IgE who did not have peanut specific IgE to ensure that we were not isolating non-specific, IgE binding clones.

PCR Amplification of the Ara h I mRNA Sequence. Using the oligonucleotide GA(TC)AA(AG)GA(TC)AA(TC)GTNAT(TCA)GA(TC)CA derived from amino acid sequence analysis of the Ara h I (63.5 kD) peanut allergen as one primer and a 27 nucleotide long oligo dT stretch as the second primer a portion of the nucleotide sequence that encodes this protein was amplified from peanut cDNA. Reactions were carried out in a buffer containing 3 mM MgCl$_2$, 500 mM KCl, 100 mM Tris-HCl, pH-9.0. Each cycle of the polymerase chain reaction consisted of one minute at 94° C., followed by two minutes at 42° C., and three minutes at 72° C. Thirty cycles were performed with both primers present in all cycles. From this reaction a 400 bp fragment was amplified and subsequently cloned into a TA vector by standard protocols (Promega, Madison, Wis.).

DNA Sequencing and Analysis. Sequencing was done according to the methods of Sanger et al (18) using a series of clones constructed by Exo III digestion of the original DNA isolate or oligonucleotide primers directed to different regions of the clone. Sequence analysis was done on the University of Arkansas for Medical Science's Vax computer using the Wisconsin DNA analysis software package.

Production of Recombinant Ara h I Protein. The Ara h I cDNA was ligated into the Eco R 1 site of a pBluescript vector (Stratagene, LaJolla, Calif.). This vector contains 111 nucleotides of the Beta galactosidase gene prior to the Eco R1 site. When E. coli JM109 cells carrying this construct are induced with IPTG they produce a fusion protein consisting of 37 amino acids derived from Beta galactosidase followed by the Ara h I protein. Exponentially growing cells are induced with 1 mM IPTG for 4 hrs at 37° C. Cells are then pelleted and resuspended in SDS-sample buffer, placed in a boiling water bath for 5 minutes and then either used immediately for immunoblot analysis or stored at −20° C. until needed.

IgE Immunoblot Analysis. SDS-polyacrylamide gel electrophoresis was performed by the method of Laemmli (19). All gels were composed of a 10% acryla,mide resolving gel and 4% acrylamide stacking gel. Electrophoretic transfer and immunoblotting on nitrocellulose paper were performed by the procedures of Towbin et al (20). The blots were incubated with antibodies diluted in a solution containing TBS and 1% bovine serum albumin for at least 12 hr at 4° C. or for 2 hours at room temperature. Detection of the primary antibody was with I$^{125}$-labeled anti-IgE antibody.

RESULTS

Isolation and Partial Amino Acid Sequence Determination of Peptides Derived From the Ara h I Protein. Purified Ara h I protein was treated with trypsin and the peptide products separated from one another by high performance liquid chromatography. Three peptide fractions, selected on the basis of their separation from each other and other fractions in the mix, were used for amino acid sequence determination. During the course of sequencing it was noted that fraction I and III consisted of a single peptide species (peptide I and peptide III, respectively). Fraction II consisted of one major peptide (peptide II) with numerous minor peptide contaminants which complicated sequence determination. However, it was possible to determine the first 16 residues of the major peptide in fraction I and II and the first 10 residues of the major peptide in fraction III. The amino acid sequence determined for each peptide is noted in Table 14.

Isolation of Clones That Produce Antigens Recognized By Peanut Specific IgE From Patients With Peanut Hypersensitivity. RNA isolated from the peanut species, Arachis hypogaea (Florunner) was used to construct an expression library for screening with serum IgE from patients with peanut hypersensitivity. Numerous IgE-binding clones were isolated from this library after screening 10$^6$ clones with serum IgE from a pool of patients with reactivity to most peanut allergens by western blot analysis. Since the number of plaques reacting with serum IgE was too large to study all in detail we randomly selected a small portion of the positive plaques for further purification. Phage positive for IgE binding were plaque purified to homogeneity and then tested for their ability to react with serum IgE collected from a patient without peanut hypersensitivity. All of the selected clones were intensely positive when incubated with serum IgE from patients with peanut hypersensitivity. In contrast, these same clones did not react with control serum IgE. These results show that we have isolated numerous clones capable of producing IgE recognizable antigens specific to patients who have peanut,hypersensitivity.

Identification and Characterization of Clones That Encode Peanut Allergen Ara h I. To help identify which of the many IgE positive clones encoded the Ara h I allergen, a hybridization probe was constructed using an oligonucleotide developed from Ara h I amino acid sequence and PCR technology. The oligonucleotide sequence GA(TC)AA(AG)

GA(TC)AA(TC)GTNAT(TCA)GA(TC)CA was derived from amino acid residues located within peptide I (Table 14) of the Ara h I peanut allergen. Utilizing this oligonucleotide as one primer and a 27 nucleotide oligo dT stretch as the second primer a portion of the mRNA sequence that encodes this protein was amplified from peanut cDNA. This 400 bp DNA fragment was subsequently cloned and sequenced by the Sanger dideoxy (18) method. DNA sequence analysis revealed that the 400 bp DNA fragment contained a poly A stretch on one end and the Ara h I specific nucleotide sequence on the other end. In addition, this clone contained nucleotide sequence correctly encoding the remaining carboxy terminal portion of peptide I. Thus, an Ara h I specific clone has been isolated and it can be used as a hybridization probe to identify which of the many IgE positive clones selected encodes the Ara h I allergen.

We hybridized a Southern blot containing four of the IgE selected cloned DNAs with a $^{32}$P-labeled, Ara h I PCR amplification product to determine which of the isolated clones encoded the Ara h I peanut allergen. All of the clones were positive for hybridization with this probe. In addition we screened 200,000 clones from the peanut cDNA library using $^{32}$P-labeled Ara h I clone as a probe. From this screen, over 100 Ara h I positive clones were identified (data not shown). These results indicate that the mRNA encoding the Ara h I allergen is an abundant message within this library.

Figure 15:

In order to determine what size mRNA these clones identify, 32P-labeled insert from one of the largest cDNA clones (41B) was used as a hybridization probe of a Northern blot containing peanut poly A+ RNA (FIG. 15). This insert hybridized to an ~2.3 kb mRNA indicating that this insert probably represented the entire mRNA.

Peanut Allergen Ara h I is a Vicilin-Like Seed Storage Protein. The primary DNA sequence of two of the largest cDNA clones selected (41B and P17) was determined by Sanger dideoxy sequencing using oligonucleotide primers directed to different regions on the insert or a series of subclones constructed by Exo III digestion of the inserts. Clone 41B carried a 2,050 base insert while clone P17 carried a 1,972 base insert. The first ATG protein synthesis start codon was located at nucleotide position 50–53. The sequence around this codon agrees with the translation initiation sequence found in most eukaryotic mRNAs (21). Each of the inserts contained a large open reading frame starting with this codon and ending with a TGA codon at nucleotide position 1928–1930. Overall, there was greater than 97% DNA sequence homology between the two inserts.

Both clones were capable of encoding a protein of ~68 kD. The amino acid sequence that was determined from Ara h I peptides I and III is found in both of these clones. The only difference between the derived and predicted amino acid sequence of both clones occurs at position seven of peptide II in clone P17. At this position there is a glycine residue in the peptide that is missing in the P17 DNA sequence. In addition, both proteins have a signal peptide at the amino terminus (22) and a single glycosylation addition site (NAS) at amino acid position 521–523. These data confirm and extend our conclusion that these clones encode the Ara h I allergen (FIG. 16).

A search of the GenBank database revealed significant sequence homology between the Ara hI cDNA clones and a class of seed storage proteins called vicilins. There was 60–65% homology over greater than 750 bases when the Ara h I DNA sequences were compared with the broad bean and pea vicilins (Table 15). These results indicate that the Ara h I allergen belongs to a vicilin-like multi-gene family encoding very similar but not identical proteins.

Figure 17:
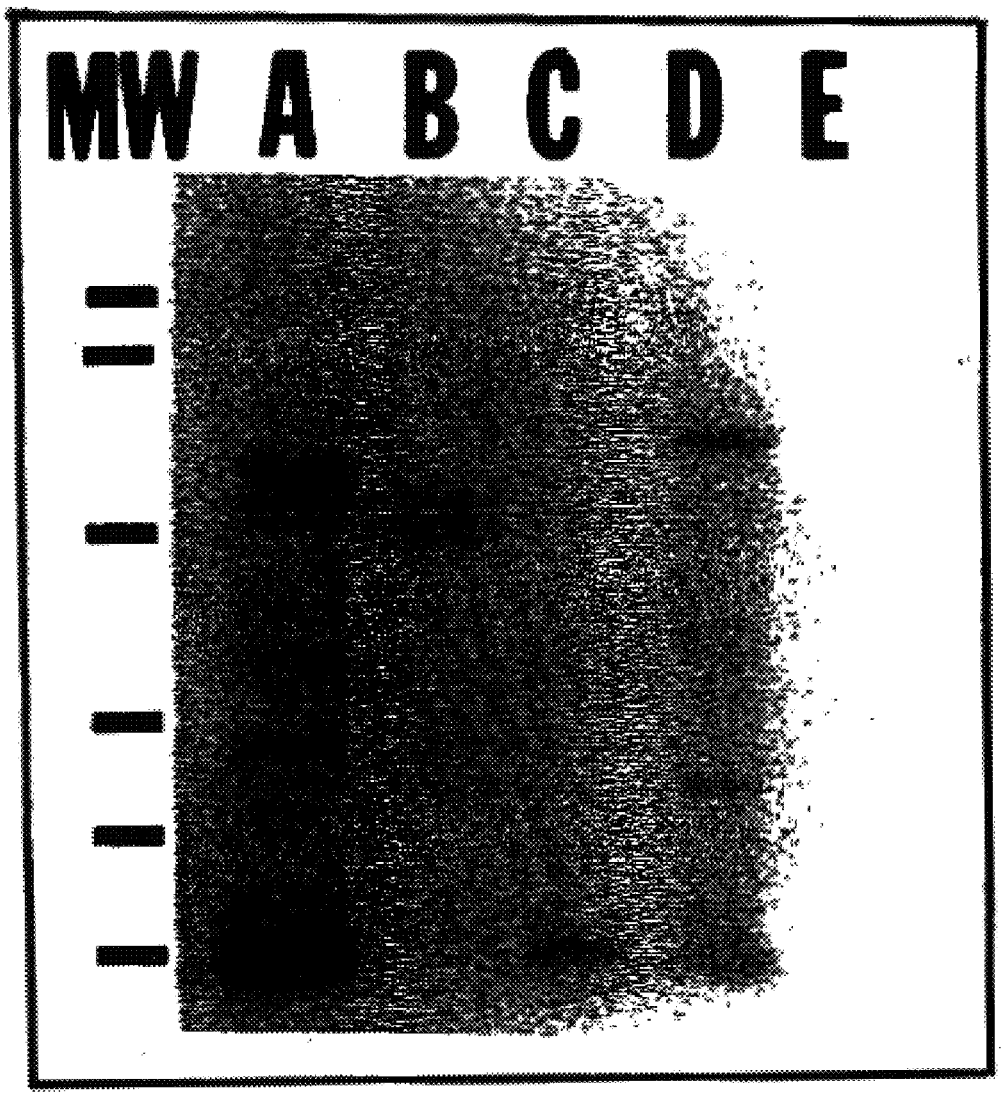

Recognition of Recombinant Ara h I by Patient Sera in an IgE Immunoblot Assay. IgE immunoblot analysis was initially performed using serum IgE from a pool of patients with peanut hypersensitivity to determine the molecular weight of the recombinant protein and the specificity of the IgE recognition reaction. FIG. 17 (lanes A and B) shows that the IgE pool recognized whole peanut extract and purified native Ara h I protein as expected, but did not react with any proteins from an E. coli lysate that was prepared from cells carrying vector alone (FIG. 17, lane E). However, instead of the IgE pool recognizing a 68 kD protein produced from clone P17, an unexpectedly small protein was identified (FIG. 17, lane C). On further analysis, we noted that by eliminating the first 93 bases (31 amino acids, 5% of Ara h I) of this clone we could produce full length Ara h I protein (68 kD) with numerous truncated products that migrated as smaller IgE reactive peptides (FIG. 17, lane D). The presence of truncated Ara h I products could be the result of inefficient translation of the amino terminal portion of this protein (23,24) caused by rare codons, numerous cysteine residues, or secondary structure of the mRNA.

Figure 18:
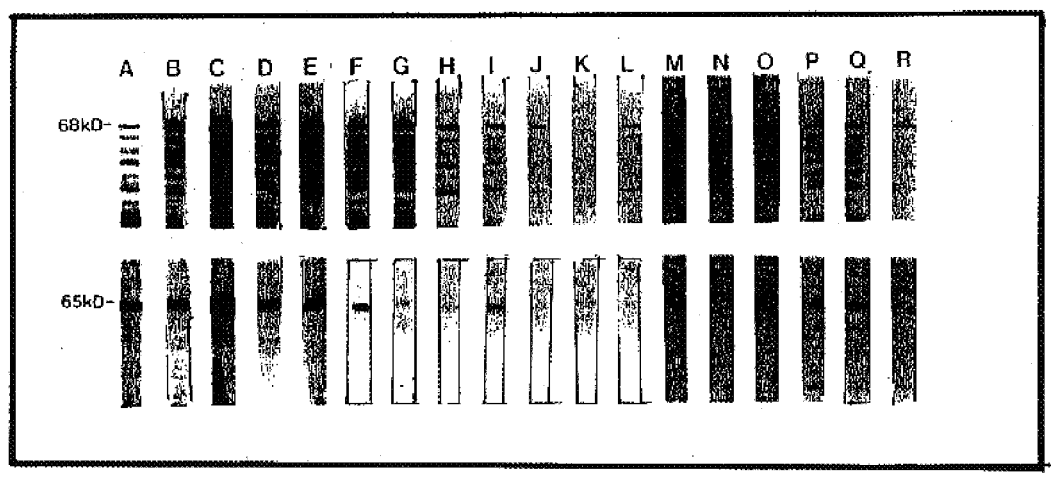

FIG. 18 shows eighteen immunoblot strips of recombinant Ara h I (Upper Panel) or native Ara h I (Lower Panel) that have been incubated with different patient sera. Ninety-four percent (17/18) of the patients that showed IgE binding to the native allergen also showed some level of binding to the recombinant Ara h I protein. Of the 18 patient sera tested in this manner there were varying intensities of IgE binding to the recombinant and native allergen. In general, there was good agreement between the level of IgE binding of recombinant and native Ara h I for any individual patient. For example, patients who had high levels of IgE which bound native protein (FIG. 18, Lower panel, lanes A–F) also showed high immunoreactivity with recombinant Ara h I protein (FIG. 18, Upper panel, lanes A–F) Patients who had low levels of IgE which bound native allergen (FIG. 18, Lower panel, lanes L–R) showed low reactivity with the recombinant protein (FIG. 4, Upper panel, lanes L–R). One peanut sensitive individual (lane K) who had serum specific IgE to native Ara h I had no detectable IgE which recognized the recombinant protein (FIG. 18, Upper Panel, lane K). The differences we have noted between peanut hypersensitive patients could be due to the amount of peanut-specific IgE in individual patients, differences in affinity of patient-specific IgE for peanut, or that some patients recognize only certain peanut proteins.

DISCUSSION

Peanuts are one of the most allergenic foods (25). Sensitive individuals may experience symptoms ranging from urticaria to anaphylaxis (25). Multiple cases of fatal anaphylaxis have been reported (4). Peanut sensitivity appears early in life and often persists indefinitely. Because of the significance of the allergic reaction and the widening use of peanuts as protein extenders in processed foods, the risk to the peanut-sensitive individual is increasing.

Various studies over the last several years have examined the nature and location of the multiple allergens in peanuts (26). Taylor et al demonstrated that the allergenic portion of peanuts was in the protein portion of the cotyledon (27). Our laboratory recently identified two major allergens from peanut extracts, designated Ara h I (6) and Ara h II (13). Greater than 90% of our patients who were challenge positive to peanut had specific IgE to these proteins.

The Ara h I nucleotide sequences identified in this report have significant sequence homology with the vicilin family of seed storage proteins of other legumes (soybean, pea, common bean, etc.). The major seed storage proteins of legumes are globulins that are represented in most legumes by two different types of polypeptides, the nonglycosylated legumins and glycosylated vicilins. The genes for the glycosylated seed storage proteins of higher plants code for proteins that are classified by their size into small (50 kD) and large (70 kD) vicilins (28). A comparison of the vicilin amino acid sequences reveals considerable amino acid homology between the small and large vicilins in the carboxy terminal portion of these molecules. The major difference between the large and small vicilin preproteins is the existence of an additional tract of amino acids at the amino terminal end of the large vicilins (29). The information generated in our laboratory demonstrating that the major peanut allergens are vicilin-like proteins may explain why patients with peanut hypersensitivity and peanut-specific IgE tend to have serum IgE to multiple other legume proteins. Since the vicilins of most major plants share significant sequence homology in their carboxy terminal portion, it is not surprising that serum specific IgE would tend to bind to several vicilin proteins from different sources. However, despite patients with legume hypersensitivity having IgE to multiple legume proteins (peanuts, soybeans, peas, etc.) they generally have clinical food hypersensitivity to only one food in the legume family. Because the amino terminal domains of the large glycosylated (vicilin) proteins share little or no homology, the immune response to this portion of the protein may be responsible for the severe and chronic hypersensitivity response characteristic of peanuts.

We have demonstrated that the cloned Ara h I gene is capable of producing a protein product in procaryotic cells that is recognized by serum IgE from a large proportion of individuals with documented peanut hypersensitivity. These results are significant in that they indicate that some of the allergenic epitopes responsible for this reaction are linear amino acid sequences that do not include a carbohydrate component. These findings may provide the basis for the improving diagnosis and therapy of persons with food hypersensitivity.

Current diagnosis of food hypersensitivity relies on a significant clinical history plus evidence of specific IgE to the food allergen in question. The absence of specific IgE to a food means there is a greater than 95% probability that the ingestion of the food will not lead to clinical symptoms. However, the presence of specific IgE to a particular food has only at best a 50% positive predictive value when correlated with a positive food challenge (1). One explanation of this low predictive value is the current use of crude allergen mixtures. The utilization of recombinant allergens should make it possible to obtain diagnostics with optimal concentrations of each allergen or to develop panels of mixtures of large numbers of recombinant allergens and then test for individual components. The disadvantages of recombinant allergens are that the IgE binding capacity of some may not be that of the corresponding natural allergen and that the number of recombinant allergens to be produced for any one food may need to be quite large.

Another possible use for recombinant peanut allergens is in immunotherapy. Allergen immunotherapy is an effective therapeutic modality for patients with insect sting hypersensitivity when they have experienced significant systemic symptoms (30). Because allergen immunotherapy can down-regulate the specific IgE response and the cellular response to allergens, treatment of patients with peanut immunotherapy is now being studied as a possible option (31). Immunotherapy with specific recombinant allergen epitopes rather than the crude allergen mixture could prove to be a more effective treatment modality. Another utilization of immunotherapy could be the modification of the molecular structure of the recombinant allergen in order to reduce the IgE binding capacity while retaining the T-cell reactivity or the production of specific T-cell epitopes designed for immunotherapy. The use of recombinant allergens in standard allergen immunotherapy would have several advantages over natural allergens, including better control of the batch to batch variability of the specific allergens and the assurance of the representation of minor allergens in standard amounts. Our finding that recombinant Ara h I is recognized by a large proportion of people with peanut hypersensitivity will allow these immunotherapeutic approaches to be rigorously tested.

In the last several years the primary structure of a number of important inhaled allergens have been defined by cDNA cloning, including the house dust mite Group I allergen Der p I (32), the Birch pollen allergen Bet v I (33), and one of the ragweed allergens Amb a II (34). Similar work with foods has identified the major allergen in shrimp as a 34 kD heat-stable protein that has greater than 85% homology with tropomyosin for Drosophila melanogaster (35). Additionally, two different cDNA clones have been isolated in maize that share significant homology to several flower-expressed gene products, including short ragweed (36). Recent work by Valenta et al. (37,38) has shown that plant profilins are prominent allergens that can be isolated from pollens of birch, grass, and weeds. There has now been isolated a wheat profilin by cDNA cloning that appears to be a major food allergen (39).

The information we have gathered about the peanut Ara h I allergen and the recent identification of other recombinant food allergens should allow our understanding of the pathophysiologic and immunologic mechanisms involved in food hypersensitivity reactions to move forward. Future studies with the recombinant peanut allergens will allow a better understanding of the relevant allergens in peanuts, the human immune response involved in this hypersensitivity reaction, and the possible diagnostic and therapeutic capabilities of recombinant food allergens.

TABLE 14

Amino Acid Sequence of Ara h I Peptides

| Peptide | Amino Acid Sequence |
|---|---|
| I | I-F-L-A-G-D-K-D-N-V-I-D-Q-I-E-K |
| II | K-G-S-E-E-E-G-D-I-T-N-P-I-N-L-R |
| III | N-N-P-F-Y-F-P-S-R-R |

Table 14. The amino acid sequence of three tryptic peptides derived from purified Ara h I protein was determined. The sequence is shown as the one letter amino acid code.

TABLE 15

Homology of the Ara h I Gene to Plant Vicilins

| | Clone 41B | | Clone P17 | |
|---|---|---|---|---|
| | bp overlap | % homology | bp overlap | % homology |
| Broad Bean | 1,081 | 64.3 | 985 | 62.3 |
| Pea | 1,078 | 64.2 | 961 | 62.5 |
| Soybean | 323 | 65.9 | 815 | 61.2 |

Table 15. The Wisconsin DNA analysis software package was used to search for homology between the Ara h I nucleotide sequence and any DNA sequence contained in the data base. Significant homology was observed between Ara h I and the plant vicilins.

Figure Legends

FIG. 15. An Ara h I clone hybridizes to a 2.3 kb peanut mRNA. Peanut poly A+ RNA wasisolated from Arachis hypogaea (Florunner) species and 10 micrograms were electrophoresed on denaturing formaldehyde agarose gels. Insert from 41B was purified, labeled with alpha-$^{32}$P-dCTP, and used as a hybridization probe of a Northern blot of this gel. Sizes of known RNA species are expressed in kilobases along the right side of the figure.

FIG. 16. Nucleotide sequence of an Ara h I cDNA clone. The nucleotide sequence of clone 41B is shown on the first line. The second line depicts clone P17 DNA sequence with dots (.) representing nucleotides that are the same, dashes (-) nucleotides that are missing, and A,C,G, or T nucleotides that differ between the two DNA sequences. The protein synthesis start (ATG) and stop (TGA) sites are underlined along with a consensus polyadenylation signal (AATAAA). Bold amino acid residues are those areas which correspond to the determined amino acid sequence of peptides I, II, and III of Ara h I (Table I). The numbers on the left of the figure indicate the nucleotide sequence, and those on the right correspond to the deduced amino acid sequence.

GenBank accession #L34402.

FIG. 17. Serum IgE from a pool of peanut hypersensitive patients recognize recombinant Ara h I. Serum IgE from a pool of patients with reactivity to most peanut allergens was used to detect whole peanut extract (lane A), purified native Ara h I (lane B), recombinant Ara h I (lanes C and D), or *E. coli* extract (lane E). In preliminary experiments, we noted that full length clone P17 made small quantities of truncated recombinant protein (lane C). We found that by eliminating the first 93 bases of this clone we could produce large quantities of nearly full length Ara h I protein (lane D). The recombinant Ara h I (lane D; 68 kD) is larger than the native Ara h I (lane B; 65 kD) because the recombinant protein includes 37 amino acids of Beta galactosidase (See Material and Methods for details of the expression system). Note that the serum IgE pool does not recognize any proteins in the *E. coli* extract (lane E) and therefore the other bands in lane D are truncated versions of Ara h I. MW.—molecular weight standards expressed in kilodaltons.

FIG. 18. Serum IgE from individual patients with peanut hypersensitivity recognize recombinant and native Ara h I protein in an immunoblot assay. Upper Panel: *E. coli* XL1-Blue cells carrying clone P172C were induced to express the recombinant Ara h I protein and lysates were prepared for immunoblot analysis. Each lane (A–R), represents a different patient with peanut hypersensitivity. Lower Panel: Lanes A–R, purified, native Ara h I protein was used in.an immunoblot assay with serum IgE from the same individuals in the Upper Panel.

REFERENCES

1. Sampson H A. 1983. Role of immediate food hypersensitivity in the pathogenesis of atopic dermatitis. J. Allergy Clin. Immunol. 71:473–480.
2. Sampson H A. 1985. Food hypersensitivity and atopic dermatitis: evaluation of 113 patients. J. Pediatr. 107:669–675.
3. Yunginger J W, D L Squillace, R T Jones, and R M Helm. 1989. Fatal anaphylactic reactions induced by peanuts. Allergy Proc. 10:249–253.
4. Sampson H A, L Mendelson, and J P Rosen. 1992. Fatal and near-fatal anaphylactic reactions to food in children and adolescents. N. Engl. J. Med. 327:380–384.
5. Bock S A and F M Atkins. 1989. The natural history of peanut allergy. J. Allergy Clin. Immunol. 83:900–904.
6. Burks A W, L W Williams, R M Helm, C Connaughton, G Cockrell, and T J O'Brien. 1991. Identification of a major peanut allergen, Ara h I, in patients with atopic dermatitis and positive peanut challenges. J. Allergy Clin. Immunol. 88:172–179.
7. Chapman M D. 1989. Purification of allergens. Curr. Opin. Immunol. 1:647–653.
8. Anderson J A and D D Sogn, eds. 1984. Adverse reactions to foods. NIH Publication No. 84-2442, July, pp 1–6.
9. Metcalfe D D. 1985. Food allergens. Clin. Rev. Allergy. 3:331–349.
10. Lemanske R F and S L Taylor. 1987. Standardized extracts, Foods. Clin. Rev. Allergy. 5:23–36.
11. Thomas W R, G A Stewart, R J Simpson, K Y Chua, T M Plozza, R J Dilworth, A Nisbet, and K J Turner. 1987. Cloning and expression of DNA coding for the major house dust mite allergen Der p I in *Escherichia coli*. Int. Arch. Allergy Appl. Immunol. 85:127–129.
12. Knox R B, M B Singh, T Hough, and P Theerakulpisut. 1989. The rye grass pollen allergen Lol p I. In Allergy and Molecular Biology, Adv. Biosci. 74: 161–171.
13. Burks A W, L W Williams, C Connaughton, G Cockrell, T O'Brien, and R M Helm. 1992. Identification and characterization of a second major peanut allergen, Ara h II, utilizing the sera of patients with atopic dermatitis and positive peanut challenge. J. Allergy Clin. Immunol. 90: 962–969.
14. Larsen J N, P Stroman, and H Ipsen. 1992. PCR based cloning and sequencing of isogenes encoding the tree pollen major allergen Car b I from Carpinus betulus, Hornbeam. Mol. Immunol. 29:703–711.
15. Bannon G A, F J Calzone, J K Bowen, C D Allis, and M A Gorovsky. 1983. Multiple, independently regulated, polyadenylated messages for histone H3 and H4 in Tetrahymena. Nuc. Acids Res. 11:3903–3917.
16. Watson C J, and R F Jackson. In DNA Cloning, Vol I, DM Glover (editor), IRL Press pp 79–88.
17. Huynh T Y, R A Young, and R W Davies. 1985. Constructing and screening of cDNA libraries in lambda gt10 and lambda gt11; In DNA Cloning, A Practical Approach Vol I, DM Glover (ed), Oxford Press, pp 49–78.
18. Sanger F, S Nicklen, and A R Coulson. 1977. DNA sequencing with chain-terminating inhibitors. Proc. Natl. Acad. Sci., USA. 74:5463–5467.
19. Laemmli UK. 1970. Cleavage of structural proteins during the assembly of the head of bacteriophage T4. Nature. 227:680–685.
20. Towbin H, T Staehelin, and J Gordon. 1979. Electrophoretic transfer of proteins from polyacrylamide gels to nitrocellulose sheets: procedures and some applications. Proc. Natl. Acad. Sci., USA. 76:4350–4354.
21. Kozak, M. 1984. Compilation and analysis of sequences upstream from the translational start site in eukaryotic mRNAs. Nuc. Acids Res., 12:857–872.
22. Coleman, J., M. Inukai, and M. Inouye. 1985. Dual functions of the signal peptide in protein transfer across the membrane. Cell, 43:351–360.
23. Shatzman, A. R. and M. Rosenberg. 1987. Expression, identification, and characterization of recombinant gene products in *Escherichia coli*. Methods Enzymology, 152:661.
24. Wood, C. R., M. A. Boss, T. P. patel, and J. S. Engle. 1984. The influence of messenger RNA secondary structure on expression of an immunoglobulin heavy chain in *Escherichia coli*. Nucleic Acids Res., 12:3937.

25. Yunginger J W, and R T Jones. 1987. A review of peanut chemistry: Implications for the standardization of peanut extracts. In Regulatory control and standardization of allergenic extracts. Proceedings of The Fourth International Paul Ehrlich Seminar, M Schaeffer, Sisk C, Brede H D (eds) Washington D.C., pp. 251–264.

26. Bush R K, S L Taylor, and J A Nordlee. 1989. Peanut sensitivity. Allergy Proc. 10:261–264.

27. Taylor S L, W W Busse, M I Sachs, J L Parker, and J W Yunginger. 1981. Peanut oil is not allergenic to peanut-sensitive individuals. J. Allergy Clin. Immunol. 68:372–375.

28. Chee P P, and J L Slightom. 1991. Molecular biology of legume vicilin-type seed storage protein genes. Sub-Cellular Biochemistry. 17:31–52.

29. Dure L. 1990. An unstable domain in the vicilin genes of higher plants. The New Biologist. 2(5):487–493.

30. Valentine M D, K C Schuberth, A Kagey-Sobotka, D F Graft, K A Kwiterovich, M Szlko, and L M Lichtenstein. 1990. The value of immunotherapy with venom in children with allergy to insect stings. N. Engl. J. Med. 323:1601–1604.

31. Oppenheimer J J, H S Nelson, S A Bock, F Christensen, and D Y M Leung. 1992. Treatment of peanut allergy with rush immunotherapy. J. Allergy Clin. Immunol. 90:256–262.

32. Chua K Y, G A Stewart, W R Thomas, R J Simpson, R J Dilworth, T M Plozza, and K J Turner. 1988. Sequence analysis of cDNA coding for a major house dust mite allergen, Der p I. Homology with cysteine proteases. J. Exp. Med. 167:175–182.

33. Breiteneder H, K Petternburger, A Bito, R Valenta, D Kraft, H Rumpold, O Scheiner, and M Breitenbach. 1989. The gene coding for the major birch pollen allergen Bet v I, is highly homologous to a pea disease resistance response gene. EMBO J 8:1935–1938.

34. Rogers B L, J P Morgenstern, I J Griffith, X B Yu, C M Counsell, A W Brauer, T P King, R D Garman, and M C Kuo. 1991. Complete sequence of the allergen Amb a II. Recombinant expression and reactivity with T cells from ragweed allergic patients. J. Immunol. 147:2547–2552.

35. Shanti K N, Nartin B M, Nagpal S, Metcalf D D, Rao P V. 1993. Identification of tropomyosin as the major shrimp allergen and characterization of its IgE-binding epitopes. J. Immunol. 151(10):5354–5363.

36. Turcich M P, Hamilton D A, Mascarenhas J P. 1993. Isolation and characterization of pollen-specific maize genes with sequence homology to ragweed allergens and pectate lyases. Plant Molecular Biology 23(5):1061–1065.

37. Valenta R, Duchene M, Pettenburger K, Sillaber C H, Valent P, Bettelheim P, Breitenbach M, Rumpold H, Kraft D, ScheinerO. 1991. Identification of profilin as a novel pollen allergen: IgE autoreactive in sensitized individuals. Science 253:557–560.

38. Valenta Duchene M Ebner C, Valent P, Sillaber C, Deviller P, Ferreira F, Tejkl M, Edelmann H, Kraft D, Scheiner O. 1992. Profilins constitute a novel family of functional plant pan-allergens. J Exp Med 175:377–385.

39. Rihs H P, Rozynek, May-Taube K, Welticke B, Baur X. 1994. Polymerase chain reaction based cDNA cloning of wheat profilin: a potential plant allergen. Int Arch Allergy Immunol 105:190–194.

PEANUT HYPERSENSITIVITY: IgE BINDING CHARACTERISTICS OF A RECOMBINANT ARA h I PROTEIN

Peanut allergy is a significant health problem because of the potential severity of the allergic reaction, the life-long nature of the allergic hypersensitivity, and the ubiquitous use of peanut products. Milk, eggs, and peanuts are three foods which cause over 80% of food hypersensitivity reactions in children (1,2). Unlike the food hypersensitivity reactions to milk and eggs, peanut hypersensitivity reactions usually persists into adulthood and last for a lifetime (3). Despite the prevalence of peanut hypersensitivity reactions and several fatalities annually, the identification of the clinically relevant antigens is incomplete and an understanding of the immunobiology of peanut hypersensitivity is very limited (4–6).

Figure 19:
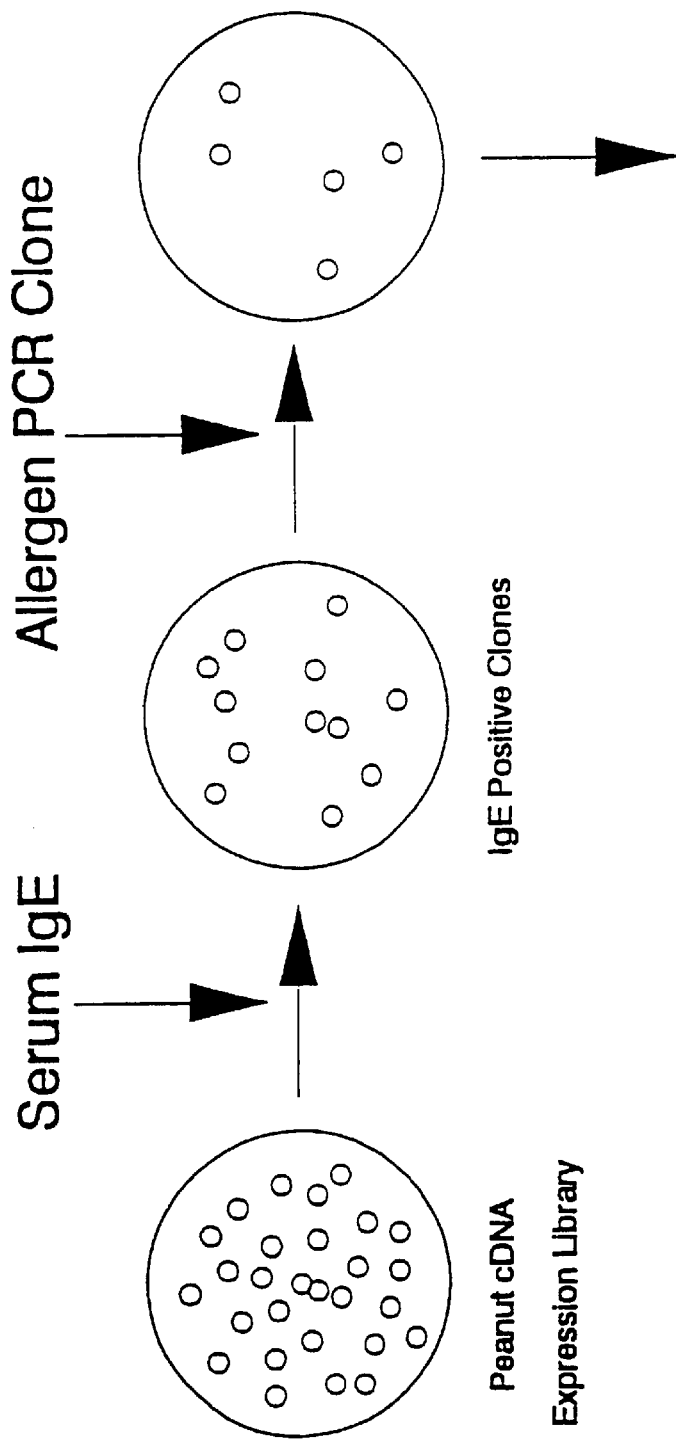

Recombinant methodology to clone allergens provides an efficient means of producing pure polypeptides which, in their native source, form complex mixtures and are often represented in only very small amounts (7). Several inhaled allergens have been cloned, including the allergens of house dust mites (8) and pollen grains (9,10), in comparison little work has been directed toward producing recombinant food allergens. Because of the prevalence and severity of peanut hupersensitivity reactions in both children and adults, coupled with the recent identification of two peanut allergens (Ara h I and Ara h II) that are involved in this process (11, 12), we set out to clone and characterize the Ara h I peanut allergen. Using serum IgE from peanut hypersensitive individuals, IgE reactive clones were isolated from a peanut cDNA expression library. Ara h I clones were then selected from this group of potential recombinant allergens by probing with a $^{32}$P-labeled Ara h I PCR clone constructed by amplifying peanut mRNA with an Ara h I oligonucleotide and oligo dT (FIG. 19). After identification of a full-length Ara h I cDNA clone, the frequency of IgE binding by individual patients sera to the recombinant protein and purified, native Ara h I from whole peanut extracts was determined by immunoblot analysis. Of the 18 patients tested in this manner, 17 had IgE which recognized recombinant Ara h (Table 16). In general, there was good agreement between the level of IgE binding of recombinant and native Ara h I for each individual. For example, patients who had high levels of IgE binding to native allergen also showed high immunoreactivity with recombinant Ara h I protein. Patients who had low levels of IgE binding to native allergen showed low reactivity with the recombinant protein. Only one peanut sensitive individual who had serum IgE specific to native Ara h I had no detectable IgE which recognized the recombinant protein.

Figure 20:
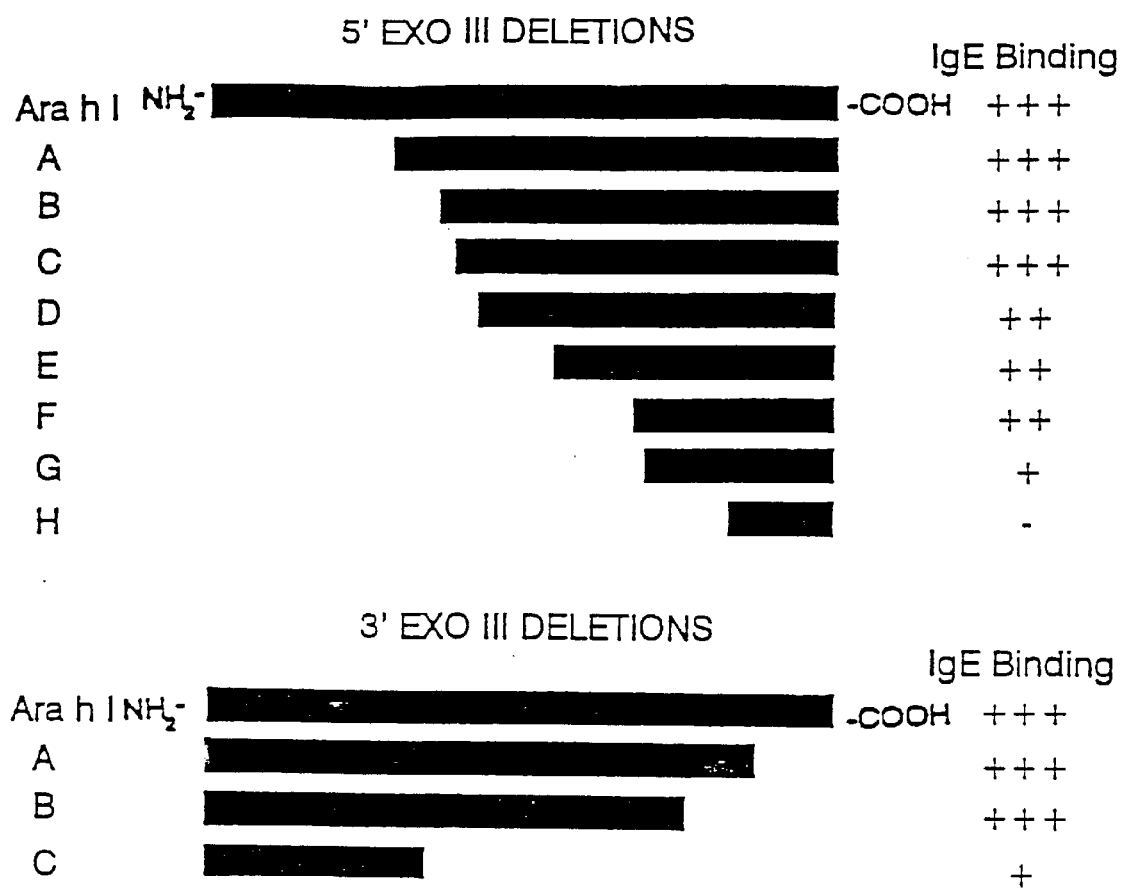

Since it appeared that the recombinant Ara h I protein bound IgE with the same degree/intensity as native allergen, we set out to map the major IgE binding domanin(s) on the recombinant molecule. Exo III digestion from the 5' or 3' end of the full length Ara h I cDNA clone was used to produce shortened clones whose protein products could then be tested for IgE binding by immunoblot analysis (FIG. 20).

The pluses (+) on the right side of this figure indicate the extent of IgE binding to the protein product of each construct. All constructs bound IgE until they were reduced to the extreme carboxyl terminal (5' Exo III) or amino terminal (3' Exo III) end of the molecule. These results indicate that there are multiple IgE epitopes on the Ara h I allergen. These results are significant in that they indicate the utility of using recombinant peanut allergens for studying peanut hypersensitivity.

ACKNOWLEDGMENTS

This research was supported by the Allergy and Asthma Foundation of America.

TABLE 16

Comparison of Serum IgE Binding to Native and Recombinant Ara h I Protein

| Patient | Native Ara h I | Recombinant Ara h I |
|---|---|---|
| 1 | +++ | +++ |
| 2 | +++ | +++ |
| 3 | +++ | +++ |
| 4 | +++ | +++ |
| 5 | +++ | +++ |
| 6 | ++ | +++ |
| 7 | +++ | +++ |
| 8 | ++ | ++ |
| 9 | ++ | ++ |
| 10 | + | + |
| 11 | + | − |
| 12 | + | + |
| 13 | + | + |
| 14 | + | + |
| 15 | + | + |
| 16 | + | + |
| 17 | + | + |
| 18 | + | + |
| 19 | − | − |

Table 16. Purified Ara h I from whole peanut extracts or recombinant Ara h I protein was electrophoresed on denaturing polyacrylamide gels, blotted to nitrocellulose, and then probed with serum IgE from patients with peanut hypersensitivity (A–R) or serum IgE from an individual who is not peanut allergic (S). Patients were scored for the presence (+) or absence (−) of serum IgE to recombinant or native Ara h I.

REFERENCES

1. Sampson H A. Food hypersensitivity and atopic dermatitus: evaluation of 113 patients. J. Pediatr 1985; 107:669–675.
2. Yunginger J W, Squillace D L, Jones R T, Helm R M. Fatal anaphylactic reactions induced by peanuts. Allergy Proc 1989; 10:249–253.
3. Sampson H A, Mendelson L, Rosen J P. Fatal and near-fatal anaphylactic reactions to food in children and adolescents. New Engl J. med 1992; 327:380–384.
4. Metcalfe D D. Food allergens. Clin Rev Allergy 1985; 3:331–349.
5. Yunginger J W, Sweeney K G, Sturner W Q, Giannandrea L A, Teigland J D, Bray M, Benson P A, Biedrzycki L, Squillace D L, Helm R M. Fatal food-induced anaphylaxis. JAMA 1988; 260: 1450–1452.
6. Hoffman, D R, Haddad Z H, Diagnosis of IgE mediated reactions to food antigens by radioimmunoassay. J. Allergy Clin Immunol 1974; 54:165–173.
7. Donovan G R, Baldo B A. Recombinant DNA approaches to the study of allergens and allergenic determinants. Monogr Allergy 1990; 28:52–83.
8. Thomas W R, Stewart G A, Simpson R J, Chua K Y, Plozza T M, Dilworth R J, Nisbet A, Turner K J. Cloning and expression of DNA coding for the major house dust mite allergen Der p I in *Escherichia coli*. Int. Arch. Allergy Appl. Immunol 1988, 85:127–129.
9. Valenta R, Vitala S, Ebner C, Kraft D, Scheiner O. Diagnosis of grass pollen allergy with recombinant timothy grass (Phleum pratense) pollen allergens. Int. Archives Allergy Immunol 1992; 736:287.
10. Larsen, J N, Stroman P, Ipsen H. PCR based cloning and sequencing if isogenes encoding the tree pollen major allergen Car b I from Carpinus betulus, Hornbeam. Mol. Immunol 1992; 29:703–711.
11. Burks A W, Williams L W, Helm R M, Connaughton C, Cockrell G, O'Brien T J. Identification of a major peanut allergen, Ara h I, in patients with atopic dermatitis and positive challenges. J Allergy Clin Immunol 1991; 88:172–179.
12. Burks A W, Williams L W, Connaughton C, Cockrell G, O'Brien T J, Helm R M. Identification and characterization of a second major peanut allergen, Ara h II, utilizing the sera of patients with atopic dermatitis and positive peanut challenge. J Allergy Clin Immunol 1992; 90: 962–969.
13. Burks W, Cockrell G, Stanley J S, Helm R, Bannon G A. Isolation, identification, and characterization of clones encoding antigens responsible for peanut hypersensitivity. Inter Arch Aller Immunol 1995 (In Press).

FIG. 19. Strategy for isolation of ARA h I cDNA clones that produce IgE recognized proteins. Using Serum IgE from peanut hypersensitive individuals, IgE reactive clones were isolated from a peanut cDNA expression library as described by Burks et al. (13). Ara h I was then selected from this group of potential recombinant allergens by probing with a $^{32}$P labeled Ara h I PCR clone.

FIG. 20. EXO III deletions of the intact Ara h I cDNA clone indicate multiple IgE binding domains. Exo III digestion from the 5' or 3' end of the full length Ara h I cDNA clone was used to produce shortened clones whose protein products could then be tested for IgE binding by immunoblot analysis. The pluses (+) on the right side of this figure indicate the extent of IgE binding to the protein product of each construct. All constructs bound IgE until they were reduced to the extreme carboxyl terminal (5' Exo III) or amino terminal (3' Exo III) end of the molecule. These results indicate that there are multiple IgE epitopes on the Ara h I allergen.

THE IDENTIFICATION OF A FAMILY OF VICILIN-LIKE GENES ENCODING ALLERGENS RESPONSIBLE FOR PEANUT HYPERSENSITIVITY

Peanut allergy is a significant health problem because of the potential severity of the allergenic reaction and the chronicity of the allergic sensitivity. Two major peanut allergens, Ara h I and Ara h II, have been previously isolated and characterized. The gene encoding the Ara h I allergen has been cloned, sequenced, and found to have a high degree of homology with plant vicilin seed storage proteins. DNA hybridization analysis using $^{32}$P. labeled Ara h I insert as a probe of a peanut cDNA library identified numerous clones with enough sequence similarity to cross-hybridize with this allergen. DNA sequence analysis of these clones revealed that there are at least two classes of genes encoding Ara h I-like proteins. Northern blot analysis of peanut poly A-RNA using representative clones from the two Ara h I classes as probes showed that they recognized the same size (2.3 kb) mRNA. In addition, each of the Ara h I like clones produces a recombinant peanut protein that is significantly bound by serum IgE from patients with peanut hypersensitivity. These results indicate that a family of vicilin-like genes in peanut are responsible for producing IgE binding proteins. The identification of this family of vicilin-like proteins as allergens may explain in part the reason that patients with peanut hypersensitivity produce IgE to multiple legumes containing similar vicilin proteins.

SERUM IgE ANTIBODIES FROM WHEAT-ALLERGIC PATIENTS BIND A 50 kD WHEAT PROTEIN

Wheat is a major cause of food hypersensitivity, but information concerning specific wheat allergens is limited. The focus of this study was to isolate and characterize the clinically relevant allergens in wheat protein. Whole wheat extracts were prepared (1 10 w/y in PBS). The extracts (1 mg/ml) were separated with 10% SDS-PAGE and 10 Coomasie-stained protein bands (range: 16–65 kD) were obtained. The crude wheat extract was separated with a stepwise salt gradient (0–1.5 M NaCl) on a Mono-Q/FPLC anion exchange column resulting in two major protein peaks. SDS-PAGE (10%) analysis of Peak I revealed protein bands ranging from 16–40 kD, while Peak II contained wheat proteins greater than 45 kD. A 50 kD protein band was isolated from Peak II using 8% preparative cell-SDS-PAGE. An ELISA was designed to screen for serum-specific IgE antibodies to the isolated 50 kD wheat protein band. Seven wheat-allergic patients (ages: 1–17 yr. median 2 yr.) confirmed by prick skin tests, blinded challenges and/or convincing histomes of anaphylaxis after wheat ingestion were studied. Sera from 3 patients without food allergy served as controls. Four of the 7 patient sera had significant IgE binding to the 50 kD wheat protein in the ELISA when compared to a negative control (range: 160–1200%, median 365%). IgE, immunoblotting studies revealed that serum-specific IgE antibodies from all the wheat-allergic patients bound to this 50 kD protein. No binding was demonstrated with normal control sera. These studies demonstrate that serum IgE antibodies from wheat-allergic, pediatric patients binds a 50 kD protein from crude wheat extracts. Further characterization of this protein is needed to delineate its significance in the pathogenesis of wheat hypersensitivity.

Ara h I, A MAJOR ALLERGEN INVOLVED IN PEANUT HYPERSENSITIVITY, HAS MULTIPLE IGE BINDING DOMAINS

Peanuts are one of the most allergenic foods. Peanut-allergic individuals may experience symptoms ranging from uricaria to anaphylaxis. Ara h I, a vicilin-like protein derived from the cotyledon, is a major peanut allergen involved in peanut hypersensitivity reactions. The gene encoding the Ara h I protein has been previously cloned and characterized. This gene has been used to produce recombinant Ara h I protein that retains IgE binding characteristics similar to the native protein. To understand the role of this allergen in causing IgE mediated disease, the IgE binding epitope(s) on the protein must be identified. To begin this process the Ara h I gene was digested with Eno III for varying lengths of time to produce a sub-library of clones with progressively shorter inserts. Clones produced in this manner were sequenced around the deletion point in order to ensure that the shortened, re-ligated clones were in frame and would produce the appropriate peanut peptide. These clones were then expressed in E. coli and their protein products tested for IgE binding by immunoblot analysis. All of the peptides produced by the shortened clones retained some level of IgE binding indicating that there are multiple Ara h I epitopes involved in peanut hypersensitivity. We are currently in the process of mapping the exact location of these epitopes within the Ara h I allergen.

PRODUCTION OF MURINE MONOCLONAL (mAb) ANTIBODIES TO ARA h I, A 63.5 kD ALLERGEN IN PEANUTS

Our previous study has identified a 63.5 kD allergen, Ara h I from peanuts, utilizing the serum of patients with atopic dermatitis and positive double-blind, placebo-controlled food challenges to peanut. This allergen isolated from crude extracts of Florunner peanuts was used as an immunogen to produce mAbs. Spleen cells from hyperimmunized BALB/c mice were fused with mouse myeloma cells using standard procedures. Hybridoma cell lines were screened for secretion of mAb by ELISA using insolubilized Ara h I. Culture supernatants from thirty subclones were further screened for Ara h I binding activity by SDS-PAGE/immunoblot analysis. Four clones were then selected for expansion and production of ascites in pristane-primed BALB/c mice. All four mabs subtyped as lambda chain $IgG_1$. Epitope specificity of the four mAb determined in a competitive binding ELISA of each clone against a biotinylated mAb and Ara h I revealed four different epitopes. In direct ELISA studies, these four mAbs recognized antigens in extracts of 2 other varieties of peanut tested, Spanish and Virginia, but did recognize antigens in soybean extracts.

Current work is underway to purify peanut allergens by mAb-affinity chromatography. These mAbs should allow for easier isolation of major allergens and provide reagents for the future standardization of peanut extracts.

IDENTIFICATION OF A SECOND MAJOR PEANUT ALLERGEN IN PATIENTS WITH ATOPIC DERMATITIS AND PEANUT HYPERSENSITIVITY

Peanuts are a common cause of food hypersensitivity reactions. We used the sera of 10 patients who had atopic dermatitis and a positive double-blind placebo-controlled food challenge to peanut to investigate the major allergens of peanut. Crude Florunner extracts were fractionated by anion exchange chromatography using a step gradient (limit buffer, 0.05M BisTris/1.5M NaCl). One hundred microliter of each 2.0 ml fraction was dot-blotted onto nitrocellulose paper and IgE-binding activity assessed using our serum pool to select all-ergen-containing fractions. A protein peak (OD 280) which eluted at 10% NaCl and demonstrated intense IgE-binding was further analyzed by two-dimensional SDS-PAGE/immunoblot analysis. The majority of this fraction is a protein which has a molecular weight of 17 kD and a pI of 5.2. Sequencing data from the N-terminus revealed the following initial 9 amino acids: G-Q-G-(W)-E-L-Q-G-D.

Based on IgE-binding activity and no known amino acid sequence identity to other allergens, we have designated this allergen Ara h II.

MONOCLONAL ANTIBODY ENZYME-LINKED IMMUNOSORBENT ASSAY (ELISA) FOR Ara h I, A MAJOR PEANUT ALLERGEN

Ara h I is a previously described major allergen in peanuts. Over 90% of our patients with documented food hypersensitivity reactions to peanut demonstrate specific -IgE to this allergen. $IgG_2$ products from 2 of 20 hybridoma cell lines produced against Ara h I were used to develop a 2-site monoclonal antibody ELISA. Monoclonal antibody 8D9 was used as the capture antibody and monoclonal antibody 8F10 was biotinylated to use as the 2nd antibody. A crude Florunner peanut extract was used as the standard. We chose 5 food products with peanuts on the label (including plain M&m's®), 5 food products without peanuts on the label, 3 commercial peanut oils and 2 commercial soy oils as extract source material. The amount of Ara h I in the peanut-labelled products varied from 1.4 μg/ml to 1777 μg/ml. No Ara h I allergen could be detected in peanut oil, soy oil or in any of the non-peanut food extracts. The specificity for the Ara h I ELISA should be useful for screening food products for this peanut allergen and correlating the amount of peanut allergen which might cause significant clinical reactions.

PRODUCTION OF MURINE MONOCLONAL (MaB) ANTIBODIES TO ARA h II, A 17 KD ALLERGEN IN PEANUTS

In a previous study we identified a 17 kD peanut allergen, Ara h II utilizing the serum of patients with atopic dermatitis and positive food challenges to peanuts. This allergen was used as an immunogen to produce mabs. Spleen cells from hyperimmunized BALB/c mice were fused with mouse myeloma cells using standard procedures. Hybridoma cell lines were screened for secretion of mAb by ELISA using insolubilized Ara h II. Culture supernatants from 40 subclones were further screened for Ara h II binding activity by SDS-PAGE/immunoblot analysis. Four clones were then selected for expansion and production of ascites in pristane-primed BALB/c mice. All four mAbs subtyped as lambda chain IgG1. Epitope specificity of the four mAb was determined in competitive binding ELISAs. Using Ara h II as a solid phase antigen, serial dilution inhibition of each mAb with a biotinylated mAb revealed at least 2 different epitopes. In a similar assay using our peanut-positive serum IgE pool, solid-phase Ara h II, and the four mAbs, we identified at least 2 different IgE-binding epitopes. In a direct ELISA, these 4 mAbs recognized antigens in extracts of 2 other varieties of peanuts tested, but did not recognize antigens in soybean extracts. Production of, these mAbs against Ara h II will allow definitive studies on the epitopes responsible for IgE binding.

CLONING OF THE ARA H II PEANUT ALLERGEN BY POLYMERASE CHAIN REACTION (PCR) AMPLIFICATION

Peanut allergy is a relatively common and sometimes fatal food allergy. Previous work has documented at least two major allergens in peanuts. The Ara h II allergen is composed of two proteins whose apparent molecular weights on SDS-PAGE are at 16.5 kD and 17.5 kD. These proteins were purified and N-terminal sequence analysis was used to determine the first 35 amino acids of each. Interestingly, their sequences were identical at 30 of the 345 amino acids determined for each protein. A set of oligonucleotide probes representing all of the possible coding sequences for the first 7 common amino acids was then constructed. This set of oligonucleotide probes and a poly-dT sequence were used as primers in the PCR to amplify Ara h II sequences from first strand cDNA synthesized from peanut mRNA. Analysis of the products of this amplification revealed two DNA bands at approximately 475 and 525 base pairs in length. These DNAs roughly correspond to the size required to encode the 16.5 kD and 17.5 kD Ara h II proteins, respectively. Northern analysis using total peanut RNA and alpha-32P-dCTP labelled PCR ,products as a probe revealed that the amplified DNAs represented the nearly full length mRNAs. We are currently cloning and characterizing these DNAs. Once completed we will use these cloned sequences to synthesize the Ara h II proteins to allow the antigenic portions of these molecules to be mapped and studied.

EPITOPE SPECIFICITY OF THE MAJOR PEANUT ALLERGEN, Ara h II

Peanuts are considered one of the most allergenic foods.[1] Peanut allergy is a significant health problem because of the potential severity of the allergic reaction, the chronicity of the allergic sensitivity, and the ubiquity of peanut products. Individuals sensitive to peanuts may experience symptoms ranging from mild urticaria to severe, systemic anaphylaxis.[1] In food-induced, fatal anaphylaxis, peanuts are the food most commonly implicated in causing the reaction.[2,3] Sensitivity to peanuts often appears early in life, and unlike most other food allergies, tends to persist indefinitely.[4]

To elucidate the exact mechanism of IgE-mediated reactions, the identification and purification of the precise allergens are necessary. Significant information has accumulated in allergen characterization from a wide variety of sources, including pollens, dust mite, animal danders, and insects.[5] In comparison, allergen characterization for even the most common food allergens is much less defined. Despite the significant prevalence of peanut hypersensitivity reactions and several deaths annually, the identification of the clinically relevant antigens and an understanding of the immunobiology of peanut hypersensitivity is just beginning.

Monoclonal antibodies are being increasingly used to define and characterize the allergenic epitopes of many allergens. Multiple allergens including the dust mite allergen, Der f I,[6] and the grass pollen allergen, Lol p I,[7] have been studied by using monoclonal antibodies. Murine monoclonal antibodies to these allergens have been shown to be quite effective in defining their allergenic epitopes.

In this report we have investigated the epitope specificity of Ara h II,[8] a major peanut allergen, by using monoclonal antibodies as probes for mapping the possible antigenic determinants. We have produced and characterized a panel of monoclonal antibodies specific to Ara h II. The Ara h II monoclonal antibodies allowed us to define at least two antigenic sites on Ara h II. Inhibition assays were used to determine the IgE-binding sites on Ara h II.

METHODS

Patients With Positive Peanut Challenge Responses

Approval for this study was obtained from the Human Use Advisory Committee at the University of Arkansas for Medical Sciences. Twelve patients with atopic determatitis and a positive immediate prick skin test response to peanut had either a positive response to double-blind placebo-controlled food challenge (DBPCFC) or a convincing history of peanut anaphylaxis (the allergic reaction was potentially life-threatening, that is with laryngeal edema, severe wheezing, and/or hypotension). Details of the challenge procedure and interpretation have been previously discussed.[9] Five milliliters of venous blood was drawn from each patient and allowed to clot, and the serum was collected. An equal volume of serum from each donor was mixed to prepare a peanut-specific IgE antibody pool.

Crude Peanut Extract

Three commercial lots of Southeastern Runners peanuts (Arachis hypogaea), medium grade, from the 1979 crop (North Carolina State University) were used in this study. The peanuts were stored in the freezer at −18° C. until they were roasted. The three lots were combined in equal proportions and blended before defatting. The defatting process (defatted with hexane after roasting for 13 to 16 minutes at 163° C. to 177° C.) was done in the laboratory of Dr. Clyde Young (North Carolina State University). The powdered crude peanut was extracted in 1 mol/L NaCl, 20 mmol/L sodium phosphate (pH 7.0)[1] and 8 mol/L urea for 4 hours at 4° C. The extract was clarified by centrifugation at 20,000 g for 60 minutes at 4° C. The total protein determination was done by the bicinchoninic acid method (Pierce Laboratories, Rockville, Ill.).

Monoclonal Antibodies

Mouse hybridoma cell lines were prepared by standard selection after polyethylene glycol-mediated cell fusion was carried out as previously described.[10] $Sp^2/0-Ag^{14}$ mouse/myeloma cells were fused with immune splenocytes from female BALB/c mice hyperimmunized with Ara h II. Hybridoma cell supernatants were screened by ELISA and Western blotting, and cell lines were cloned by limiting dilution. The antibodies secreted by the monoclonal hybridoma cell lines were isotyped according the directions provided (Screen Type; Boehringer Mannhein, Indianapolis, Ind.). Ascites fluid produced in BALB/c mice was purified with Protein G Superose, as outlined by the manufacturer (Pharmacia, Uppsala, Sweden). Purified monoclonal antibodies were used in ELISA and ELISA inhibition assays.

ELISA for IgE

A biotin-avidin ELISA was developed to quantify IgE anti-peanut protein antibodies with modifications from an assay previously described.[11] The upper 2 rows of a 96-well microtiter plate (Gibco, Santa Clara, Calif.) were coated with 100 μl each of equal amounts (1 μg/ml) of anti-human IgE monoclonal antibodies, 7.12 and 4.15 (kindly provided by Dr. Andrew Saxon). The remainder of the plate was coated with the peanut protein at a concentration of 1 μg/ml in coating buffer (0.1 mol/L sodium carbonate-bicarbonate buffer, pH 9.6). The plate was incubated at 37° C. for 1 hour and then washed five times with rinse buffer (phosphate-buffered saline, pH 7.4, containing 0.05% Tween 20, Sigma Chemical Co., St. Louis, Mo.) immediately and between subsequent incubations. A secondary IgE reference standard was added to the upper 2 rows to generate a curve for IgE, ranging from 0.05 to 25 ng/ml.

The serum pool and patient serum samples were diluted (1:20 vol/vol) and dispensed into individual wells in the lower portion of the plate. After incubation for 1 hour at 37° C. and washing, biotinylated, affinity-purified goat anti-human IgE (KPL, Gaithersburg, Md.) (1:1000 vol/vol bovine serum albumin) was added to all wells. Plates were incubated for 1 hour at 37° C. and washed, and 100 μl horseradish peroxidase-avidin conjugate (Vector Laboratories, Burlingame, Calif.) was added for 5 minutes. After washing, the plates were developed by the addition of a citrate buffer containing O-phenylenediamine (Sigma Chemical Co.). The reaction was stopped by the addition of 100 μl 2N hydrochloric acid to each well, and absorbance was read at 490 nm (Bio-Rad Microplate reader model 450; Bio-Rad Laboratories Diagnostic Group, Hercules, Calif.). The standard curve was plotted on a log-logit scale by means of simple linear regression analysis, and values for the pooled serum and individual samples were read from the curve.[8,9]

ELISA Inhibition

An inhibition ELISA was developed to examine the site. specificity of the monoclonal antibodies generated to Ara h II. One hundred microliters of Ara h II protein (1 mg/ml) was added to each well of a 96-well microtiter plate (Gibco). in coating buffer (carbonate buffer, pH 9.6) for 1 hour at 37° C. Next, 100 μl of differing concentrations (up to 1000-fold excess) of each of the monoclonal antibodies was added to each well for 1 hour at 37° C. After washing, a standard concentration of the biotinylated monoclonal antibody preparation was added for 1 hour at 37° C. The assay was developed by the addition of the avidin substrate as in the ELISA above.

A similar ELISA inhibition was performed with the peanut-positive serum IgE pool instead of the biotinylated monoclonal antibody to determine the ability of each monoclonal antibody to block specific IgE binding.

RESULTS

Hybridomas Specific for Ara h II

Cell fusions between spleen cells obtained from female BALB/c mice immunized with Ara h II and the mouse myeloma cells resulted in a series of hybridomas specific for Ara h II. Seven monoclonal antibody-producing lines were chosen for further study. In preliminary studies all seven hybridoma-secreting cell lines had antibodies that bound Ara h II, as determined by ELISA and immunoblot analysis.[12,13] On the basis of different binding studies, four of the hybridomas were used for further analysis. As determined by isotype immunoglobulin-specific ELISA, all four hybridoma-secreting cell lines typed as $IgG_1$.

ELISA With Monoclonal Antibody as Solid Phase

Four monoclonal antibody preparations (4996D6, 4996C3, 5048B3, and 4996D5) were used as capture antibodies in an ELISA with Ara h Ii as the antigen. Serum from individual patients, who had positive challenge responses to peanut, was used to determine the amount of IgE binding to each peanut fraction captured by the Ara h II-specific monoclonal antibody (Table 17). A reference peanut-positive serum pool was used as the control serum for 100% binding. Seven patients who had positive DBPCFC responses to peanut were chose. All seven patients had significant amounts of anti-peanut-specific IgE to the peanut antigen presented by each of the four monoclonal antibodies compared with the control sera (patient 8 without peanut sensitivity who had elevated serum IgE values, patient 9 without peanut sensitivity who had normal serum IgE values). Titration curves were performed to show that limited amounts of antigen binding were not responsible for similar antibody binding. There were no significant differences in the levels of anti-peanut-specific IgE antibody to the peanut antigens presented by each monoclonal antibody. Most patients had their highest value for IgE binding to the peanut antigen presented by either 4996D6 or 4996C3, whereas no patient had his or her highest percent of IgE binding to the peanut antigen presented by monoclonal antibody 4996D5.

Food Antigen Specificity of Monoclonal Antibodies to Ara h II

To determine whether the Ara h II monoclonal antibodies would bind to only peanut antigen, an ELISA was developed with the pooled peanut-specific IgE from patients who had positive DBPCFC responses to peanut. All four monoclonal antibodies that were fully characterized bound only peanut antigen (Table 18). In the ELISA no binding to soy, lima beans, or ovalbumin occurred. When the normal serum pool was used in the ELISA, no peanut-specific IgE to either Ara h II or crude peanut could be detected.

In the United States, three varieties of peanuts are commonly consumed: Virginia, Spanish, and Runner. In an ELISA, we attempted to determine whether there were differences in monoclonal antibody binding to the three varieties of peanuts. There was only a minor variation with the ability of the peanut-specific IgE to bind to the captured peanut antigen (data not shown).

Site Specificity of Four Monoclonal Antibodies

An inhibition ELISA was used to determine the site specificity of the four monoclonal antibodies to Ara h II (Table 19). As determined by ELISA inhibition analysis, there are at least two different epitomes on Ara h II, which could be recognized by the various monoclonal antibodies (epitope 1-4996C3, epitope 2-4996D6, 5048B3, 4996D5). Seven different monoclonal antibodies generated to Ara h I, a 63.5 kd peanut allergen,9 were used to inhibit the binding of the four Ara h II monoclonal antibodies to the Ara h Ii protein. None of the Ara h I monoclonal antibodies inhibited any binding of the Ara h II monoclonal antibodies.

Site Specificity of Peanut-specific Human IgE

Results of inhibition assays with monoclonal antibodies to inhibit IgE binding from the IgE pool (from patients with peanut hypersensitivity) to Ara h Ii are shown in Table 20. Monoclonal antibodies 4996C3 and 4996D5 inhibited the peanut-specific IgE up to approximately 25%. Monoclonal antibodies 4996D6 and 5048B3 did not inhibit peanut-specific IgE binding. These two inhibition sites correspond with the two different IgG epitopes recognized by the monoclonal antibodies in the inhibition experiments.

DISCUSSION

The route of allergen administration, dosage, frequency of exposure, and genetic factors all determine the type and severity of an individual's allergic response.[14] To date, no distinct features, which would distinguish allergens as unique antigens, have been identified.[14] In contrast, only three foods in the United States (milk, eggs, and peanuts) account for approximately 80% of positive responses to food challenges in children.[15]

Although clinical sensitivity to most foods is typically lost as a patient ages, clinical sensitivity to peanut is rarely lost. For this reason, it is important to examine the peanut allergens to determine whether they have distinct features that would cause the persistence of clinical reactions.

Two major peanut allergens, Ara h I and Ara h II, have recently been identified and characterized.[8,9] Ara h I has two major bands as determined by sodium dodecylsulfate-polyacrylamide gel electrophoresis with a mean molecular weight of 63.5 kd and an isoelectric point of 4.55. Ara h II has a mean molecular weight of 17 kd and an isoelectric point of 5.2. Individual sequencing of Ara h I and Ara h II indicates that they are probably isoallergens.[8] Other peanut allergens have been identified including peanut 1[16] and concanavalin A-reactive glycoprotein.[17]

In this study four monoclonal antibodies to Ara h II were extensively characterized. All four monoclonal antibodies produced to Ara h II, when used as capture antibodies in an ELISA, presented antigens that bound IgE from patients with positive challenge responses to peanut. No significant differences were detected in the binding of IgE from any one patient to the allergen presented by the individual monoclonal antibodies. In separate ELISA experiments, the four monoclonal antibodies generated to Ara h II did not bind to other legume allergens and did not bind to one variety of peanuts preferentially.

To determine the epitope site specificity of these monoclonal antibodies, inhibition ELISAs were done. At least two different and distinct IgG epitopes could be identified in experiments with the allergen, Ara h II. In related experiments done with pooled serum from patients with positive DBPCFC responses to peanut, two similar IgE epitopes were identified. The results of this study are comparable to those with monoclonal antibodies to Der f I[18] in which five nonoverlapping antigenic sites and three IgE-binding epitopes were identified. In our previous studies with Ara h I monoclonal antibodies,[19] four different antigenic sites were recognized, and three of these sites were IgE-binding epitopes.

In related experiments with other allergens, a variety of solid-phase inhibition assays have been used to block the polyclonal IgE response to the allergen being studied.[6] The interpretation of the level of inhibition that should be regarded as significant has varied from 15% to 80%.[6] The Ara h II monoclonal antibodies inhibited the polyclonal IgE response by up to 25%.

The characterization of these Ara h II monoclonal antibodies will allow future studies to better define the exact amino acid sequence that is responsible for IgE binding. Additionally, these monoclonal antibodies should make purification of the Ara h II allergen much simpler and more efficient. Immunoaffinity purification of allergens, such as that completed with the cockroach allergens[6] and with the Ara h I peanut allergen,[19] has produced a technique to purify allergens from a heterogeneous crude source material.

Future studies on the antigenic and allergenic structure of allergens will likely use monoclonal antibody techniques, in addition to recombinant DNA technology. Monoclonal antibodies will be used to map these epitopes and to identify cDNA clones specific for the allergens. Together, recombinant DNA technology and monoclonal antibody production will be used to examine the role of specific T-cell epitopes in the induction and regulation of the allergenic response.[20]

REFERENCES

1. Yunginger J. W., Jones R T. A review of peanut chemistry: implications for the standardization of peanut extracts. In: Schaeffer M, Sisk C, Brede H I, eds. Proceedings of the Fourth International Paul Ehrlich Seminar on the Regulatory Control and Standardization of Allergenic Extracts, Oct. 16–17, 1985; Bethesda, Md. Stuttgart: Gustav Fischer Verlag, 1987;251–64.
2. Yunginger J W, Sweeney K G, Sturner W Q, et al. Fatal food-induced anaphylaxis. JAMA 1988;260:1450–2.
3. Sampson H A, Mendelson L, Rosen J P. Fatal and near-fatal anaphylactic reactions to food in children and adolescents. N Engl J Med 1992;327:380–4.
4. Hoffman D R, Haddad Z H. Diagnosis of IgE-mediated reaction to food antigens by radioimmunoassay. J ALLERGY CLIN IMMUNOL 1974;54:165–73.
5. Chapman M D. Purification of allergens. Curr Opin Immunol 1989;1:647–53.
6. Chapman M D. Monoclonal antibodies as structural probes for mite, cat, and cockroach allergens. J Immunol 1987; 139:1479–84.
7. Mourad W, Mecheri S, Peltre G, David B, Hebert J. Study of the epitope structure of purified Dac g I and Lol p I, the major allergens of Dactylis glomerata and Lolium perenne pollens, using monoclonal antibodies. J Immunol 1988;141:3486–91.
8. Burks A W, Williams L W, Connaughton C, Cockrell G, O'Brien T J, Helm R M. Identification and haracterization of a second major peanut allergen, Ara h II, with use of the sera of patients with atopic dermatitis and positive peanut challenges. J ALLERGY CLIN IMMUNOL 1992;90:962–9.
9. Burks A W, Williams L W, Helm R M, Connaughton C A, Cockrell G, O'Brien T J. Identification of a major peanut allergen, Ara h I, in patients with atopic dermatitis and positive peanut challenges. J ALLERGY CLIN IMMUNOL 1991;88:172–9.
10. Rouse D A, Morris S L, Karpas A B, Probst P G, Chaparas S D. Production, characterization, and species specificity of monoclonal ant ibodies to Mycobacterium avium complex protein antigens. Infect Immun 1990;58:1445–99.
11. Burks A W, Sampson H A, Buckley R H. Anaphylactic reactions following gammaglobulin administration in patients with hypogammaglobulinemia; detection of IgE antibodies to IgA. N Engl J Med 1986;314:560–4.
12. Sutton R, Wrigley C W, Baldo B A. Detection of IgE and IgG binding proteins after electrophoresis transfer from polyacrylamide gels. J Immunol Methods 1982;52:183–6.
13. Towbin H, Staehelin T, Gordan J. Electrophoretic transfer of proteins from polyacrylamide gels to nitrocellulose sheets; procedure and some applications. Proc Natl Acad Sci U S A 1979;76:4350–4.
14. Marsh D G. Allergens and the genetics of allergy. In: Sela M. ed. The antigens. New York: Academic Press. 1975;3:271–359.
15. Sampson H A, McCaskill C C. Food hypersensitivity in atopic dermatitis: evaluation of 113 patients. J Pediatr 1985;107:669–75.
16. Sachs M I, Jones R T, Yunginger J W. Isolation and partial characterization of a major peanut allergen. J ALLERGY CLIN IMMUNOL 1981;67:27–34.
17. Barnett D, Howden, M E H, Bonham B, Burley R W. Aspects of legume allergy research. proc Sydney Allergy Group 1985; 4:104–18.
18. Chapman M D, Heyman P W, Platts-Mills T A E. Epitope mapping of two major inhalant allergens, Der p I and Der f I, from mites of the genus Dermatophagoides. J Immunol 1987;139:1479–84.
19. Burks A W, Cockrell G, Connaughton C, Helm R M. Epitope specificity and immunoaffinity purification of the major peanut allergen, Ara h I. J ALLERGY CLIN IMMUNOL 1994;93:743–50.
20. O'Hehir R E, Young D B, Kay A B, Lamb J R. Cloned human T lymphocytes reactive with Dermatophagoides farina (house dust mite): a comparison of T- and B-cell antigen recognition. Immunology 1987;62:635–40.

ISOLATION, IDENTIFICATION, AND CHARACTERIZATION OF CLONES ENCODING ANTIGENS RESPONSIBLE FOR PEANUT HYPERSENSITIVITY

Figure 21:
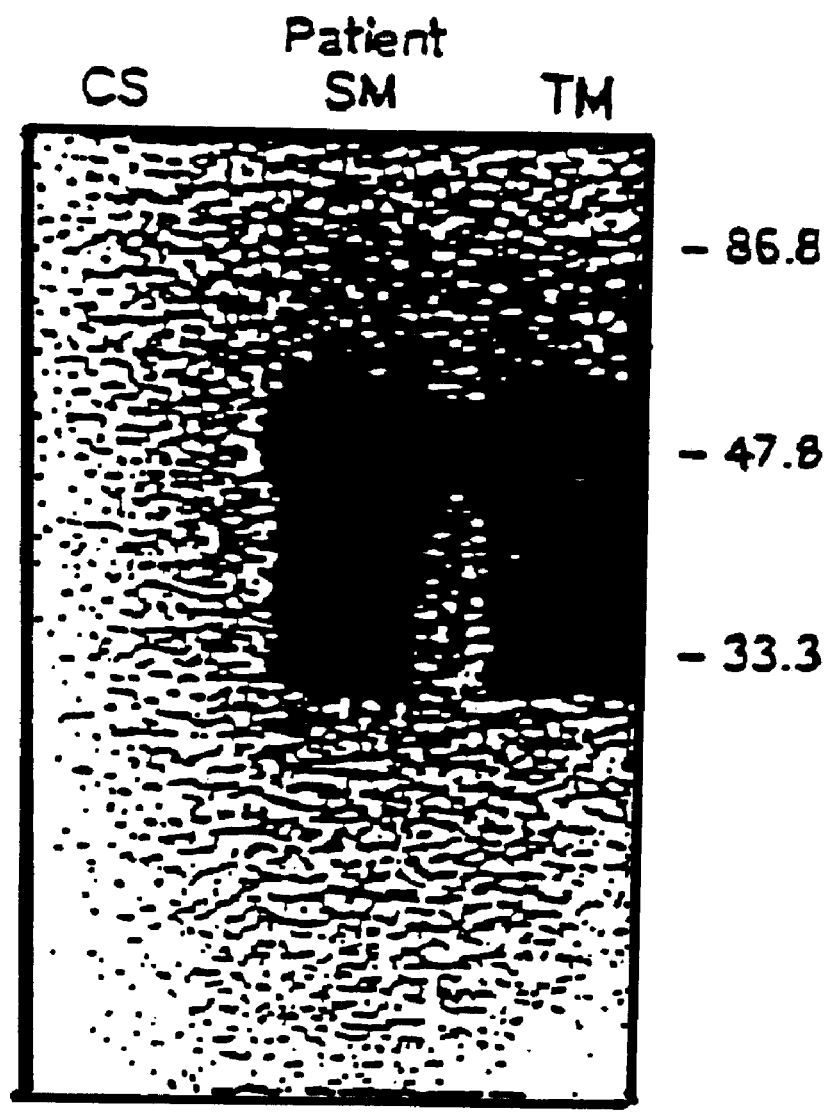

Peanut allergy is a significant health problem because of the frequency, the potential severity, and the chronicity of the allergic sensitivity. Peanut hypersensitivity reactions often tend to be quite severe, sometimes resulting in episodes of fatal anaphylaxis [1,2]. Despite the significant prevalence of peanut hypersensitivity reactions and several fatalities annually, the identification of the clinically relevant antigens and an understanding of the immunobiology of peanut hypersensitivity are just beginning [3]. The identification and purification of allergens is essential for the immunological studies necessary to understand their role in stimulating IgE antibody formation. Because of the prevalence and severity of peanut hypersensitivity reactions in both children and adults, coupled with the recent identification of two major peanut allergens that are involved in this process [3,4], we set out to clone and characterize the Ara h I peanut allergen. Serum IgE from patients with documented peanut hypersensitivity reactions and a peanut cDNA expression library were used to identify clones that encode peanut allergens. One of the major peanut allergens, Ara h I, was selected from these clones using Ara h I-specific oligonucleotides and polymerase chain reaction technology. Using the oligonucleotide GA(TC)AA(AG)GA(TC)AA(TC)GTNAT(TCA)GA(TC)CA derived from amino acid sequence analysis of the Ara h I (63.5 kD) peanut allergen as one primer and a 27-nucleotide-long oligo-dT stretch as the second primer, a portion of the mRNA that encodes this protein was amplified from peanut cDNA. To determine if this clone (5Ala) represented the entire Ara h I, a $^{22}$P-labeled insert from this clone was used as a hybridization probe of a Northern blot containing peanut poly A+RNA. This insert hybridized to a single-size mRNA of approximately 2.3 kb. The insert contained 1,360 bases not including the poly A tail. The sequence beginning at position 985 and extending through to position 1032 encodes an amino acid sequence identical to that determined from Ara h I peptide I. DNA sequence analysis of the cloned insert revealed that the Ara h I allergen has significant homology with the vicilin seed storage protein family found in most higher plants [5,6]. There were 64% homology over more than 1,000 bases when the clone SAla sequence was compared with the broad bean and pea vicilins. IgE immunoblot analysis was performed using serum IgE from patients with peanut hypersensitivity and Ara h I protein expressed from clone 5Ala in *Escherichia coli* XL1-Blue cells to address the question of how frequently recombinant Ara h I was recognized by these individuals. FIG. 21 shows three representative immunoblot strips that have been incubated with different patient sera. Two of the patients showed strong IgE binding to the recombinant Ara h I protein while one patient had no detectable IgE binding to this protein. Of the 11 patient sera tested in this manner, 8 (73%) had IgE which recognized recombinant Ara h I (Table 21). We have demonstrated that the cloned Ara h I gene is capable of producing a protein product in prokaryotic cells that is recognized by serum IgE from a large number of individuals with documented peanut hypersensitivity. These results are significant in that they indicate that some of the allergenic epitopes responsible for this reaction are linear amino acid sequences that do not include a carbohydrate component. These findings may provide the basis for improving diagnosis and therapy of persons with food hypersensitivity. With the production of the recombinant peanut protein it will now be possible to address the pathophysiologic and immunologic mechanisms regarding peanut hypersensitivity reactions specifically and food hypersensitivity in general.

REFERENCES

1. Yunginger J W, Squillace D L, Jones R T, Helm R M: Fatal anaphylactic reactions induced by peanuts. Allergy Proc 1989;10:249–253.
2. Sampson H A, Mendelson L, Rosen J P: Fatal and near-fatal anaphylactic reactions to food in children and adolescents. N Engl J. Med 1992;327:380–384.
3. Burks A W, Williams L W, Helm R M, Connaughton C, Cockrell G, O'Brien T J: Identification of a major peanut Allergen, Ara h I, in patients with atopic dermatitis and positive peanut challenges. J Allergy Clin Immunol 1991;88:172–179.
4. Burks A W, Williams L W, Connaughton C, Cockrell G, O'Brien T, Helm R M: Identification and characterization of a second major peanut allergen, Ara h II, utilizing the sera of patients with atopic dermatitis and positive peanut challenge. J Allergy Clin Immunol 1992;90:962–969.

5. Chee P P, Slightom J L: Molecular biology of legume vicilin-type seed storage protein genes. Subcell Bioch 1991;17:31–52.

6. Dure L: An unstable domain in the vicilin genes of higher plants. N Biol 1990;2:487–493.

TABLE 17

Peanut-specific IgE to antigen presented by four monoclonal antibodies

| Patient No. | Capture antibody | | | |
|---|---|---|---|---|
| | 4996D6 | 4996C3 | 5048B3 | 4996D5 |
| 1 | 95% | 80% | 80% | 91% |
| 2 | 94% | 66% | 72% | 90% |
| 3 | 96% | 114% | 87% | 96% |
| 4 | 98% | 116% | 76% | 96% |
| 5 | 97% | 74% | 130% | 107% |
| 6 | 94% | 63% | 76% | 86% |
| 7 | 109% | 123% | 104% | 116% |
| 8 | 0% | 0% | 0% | 0% |
| 9 | 0% | 0% | 0% | 0% |

Ara h II monoclonal antibodies used as capture antibodies in ELISA with Ara h II as the antigen. Values are expressed as a percent of binding compared with challenge-positive peanut pool. Patients 1 to 7 had positive DBPCFC responses to peanut; patient 8 is the patient without peanut sensitivity with elevated serum IgE; patient 9 is the patient without peanut sensitivity with normal serum IgE.

TABLE 18

IgE-specific binding to legumes captured by Ara h II monoclonal antibodies

| | Capture antibody | | | |
|---|---|---|---|---|
| | 4996D6 | 4996C3 | 5048B3 | 4996D5 |
| Pooled serum* | | | | |
| Ara h II (17 kd) | 0.451 | 0.565 | 0.235 | 0.381 |
| Crude peanut | 0.137 | 0.409 | 0.161 | 0.170 |
| Soy | 0.053 | 0.055 | 0.055 | 0.015 |
| Lima beans | 0.033 | 0.026 | 0.029 | 0.025 |
| Ovalbumin | 0.028 | 0.029 | 0.029 | 0.035 |
| Normal serum | | | | |
| Ara h II (17 kd) | 0.024 | 0.031 | 0.038 | 0.033 |
| Crude peanut | 0.017 | 0.027 | 0.028 | 0.024 |

Values are expressed as optical density units.
*Pooled serum is from patients with positive responses to peanut challenge.

TABLE 19

ELISA inhibition for four monoclonal antibodies to Ara h II

| Biotinylated mAb | Inhibitory antibody | | | | |
|---|---|---|---|---|---|
| | 4996C3 | 4996D6 | 5048B3 | 4996D5 | Alt 1 |
| 4996C3 | 99% | 8% | 6% | 3% | 1% |
| 4996D6 | 0% | 53% | 31% | 18% | 9% |
| 5048B3 | 30% | 83% | 100% | 100% | 3% |
| 4996D5 | 1% | 44% | 56% | 64% | 8% |

Site specificity of four Ara h II monoclonal antibodies as determined by ELISA inhibition analysis. Values are expressed as percent inhibition. mAb, Monoclonal antibody.

TABLE 20

Individual anti-peanut-specific IgE binding to Ara h II

| | Serum dilution | | | | | |
|---|---|---|---|---|---|---|
| | 1:320 | 1:100 | 1:80 | 1:40 | 1:20 | 1:5 |
| 4996D6 | 0% | 0% | 0% | 0% | 3% | 5% |
| 4996C3 | 14% | 10% | 10% | 12% | 10% | 24% |
| 5048B3 | 0% | 5% | 5% | 5% | 7% | 11% |
| 4996D5 | 0% | 10% | 10% | 22% | 23% | 25% |

Site specificity of four Ara h II monoclonal antibodies inhibiting anti-peanut-specific IgE (serum pool from patients with peanut hypersensitivity) binding to Ara h II. Values are expressed as percent of anti-peanut-specific IgE binding to Ara h II without inhibiting monoclonal antibody.

TABLE 21

Recognition of Ara h I protein by patient serum IgE from patients with peanut hypersensitivity.

| Patient | Recombinant Ara h I | Native Ara h I |
|---|---|---|
| AC | + | + |
| BE | − | + |
| L | + | + |
| AS | − | + |
| KS | + | + |
| KF | + | + |
| CS | − | + |
| SM | + | + |
| TM | + | + |
| TH | + | + |
| JH | + | + |

Recombinant or native Ara h I protein was electrophoresed on denaturing polyacrylamide gels, blotted to nitrocellulose, and then probed with serum IgE from patients with peanut hypersensitivity. Patients were scored for the presence (+ or absence (−) of serum IgE to recombinant or native Ara h I.

Mapping of the B-cell Epitopes on Ara h I, a Legume Vicilin Protein and a Major Allergen in Peanut Hypersensitivity

SUMMARY

Peanut allergy is a significant health problem because of the potential severity of the allergic reaction and the difficulty in the accurate diagnosis of this disease. Serum IgE from patients with documented peanut hypersensitivity reactions and overlapping peptides were used to identify the major IgE binding epitopes on the major peanut allergen, Ara h I. At least twenty-three different linear IgE binding epitopes, located throughout the length of the Ara h I protein, were identified. Two of the peptides appeared to be immunodominant IgE binding epitopes in that they were recognized by serum from >90% of the patients tested. No other peptide was recognized by greater than 50% of the peanut sensitive population tested. Mutational analysis of the immunodominant epitopes revealed that single amino acid changes within these peptides had dramatic effects on IgE binding characteristics. With the identification of the IgE binding epitopes on the Ara h I protein and the determination of the amino acids within these epitopes important to immunoglobulin binding it will now be possible to address the pathophysiologic and immunologic mechanisms regarding peanut hypersensitivity reactions specifically and food hypersensitivity in general.

INTRODUCTION

Approximately 8% of children and 1–2% of adults have some type of food allergy (1). Peanuts, fish, tree nuts, and shellfish account for the majority of food hypersensitivity reactions in adults, while peanuts, milk, and eggs cause over 80% of food hypersensitivity reactions in children (2). Unlike the food hypersensitivity reactions to milk and eggs, peanut hypersensitivity reactions usually persist into adulthood and last for a lifetime (3). In addition, hypersensitivity reactions to peanuts tend to be more severe than those to other food allergens. Allergic reactions to peanuts can produce symptoms ranging from urticaria to anaphylaxis in patients with peanut hypersensitivity. Several reports (4,5) have detailed fatal and near-fatal anaphylactic reactions occurring in adolescents and adults following the ingestion of peanuts or peanut products. Diagnosis of individuals with peanut hypersensitivity is often complicated by the presence of cross-reacting antibodies to other legumes (6). Currently, the only effective treatment for patients with peanut hypersensitivity is avoidance of any food products which contain the allergen. This is becoming more difficult due to the inclusion of peanuts and peanut products as protein extenders in many different foods.

Food hypersensitivity reactions occur shortly after contact of a specific allergen with its corresponding IgE antibodies which are bound to mast cells. Allergen-specific IgE when cross-linked by the respective allergen activates the mast cells to release histamine, heparin, and other mediators responsible for the clinical symptoms observed. Thus the IgE binding epitopes of the allergens play an important role in the disease process. Their characterization will provide a better understanding of the human immune response involved in food hypersensitivity reactions. If improved diagnostic and therapeutic capabilities are to be developed it is important to determine the primary structure and frequency of recognition of any IgE binding epitopes contained within the allergen.

Various studies have shown that the most allergenic portion of the peanut is the protein fraction of the cotyledon (7). A major allergen found in the cotyledon is the peanut protein, Ara h I (8). This protein is recognized by >90% of peanut sensitive patients, thus establishing it as an important allergen (8). The majority of serum IgE recognition of the Ara h I allergen appears to be due to epitopes within this protein that are linear amino acid sequences that do not contain significant amounts of carbohydrate (8,9). The Ara h I allergen belongs to the vicilin family of seed storage proteins (9). Previous results have demonstrated similarity between the level of IgE binding to recombinant Ara h I protein and the native form of this allergen when individual patient serum was tested (9). These results indicated that the recombinant protein could be considered for use in both diagnostic and immunotherapeutic approaches to peanut hypersensitivity.

Because of the prevalence and severity of peanut hypersensitivity reactions in both children and adults, coupled with the difficult nature of diagnosing this food allergy, we set out to map and characterize the major IgE epitopes of the Ara h I allergen. In this communication we report the primary structure of the Ara h I IgE-binding epitopes recognized by peanut hypersensitive individuals. Two epitopes that bound peanut specific serum IgE from >90% of patients tested were identified. The amino acids important to peanut-specific IgE recognition of these epitopes were then determined for the purpose of using them in future diagnostic and immunotherapeutic approaches to this disease.

MATERIALS AND METHODS

Patients. Serum from fifteen patients with documented peanut hypersensitivity reactions(mean age, 25 yr) was used to identify the Ara h I IgE binding epitopes. Each of these individuals had a positive immediate prick skin test to peanut and either a positive double blind, placebo controlled, food challenge (DBPCFC) or a convincing history of peanut anaphylaxis (laryngeal edema, severe wheezing, and/or hypotension). One individual with elevated serum IgE levels (who did not have peanut specific IgE or peanut hypersensitivity) was used as a control in these studies. In some instances a serum pool was made by mixing equal aliquots of serum IgE from each of the 15 patients with peanut hypersensitivity. This pool was then used in immunoblot analysis experiments to determine the IgE binding characteristics of the population. At least five mls of venous blood were drawn from each patient and allowed to clot, and the serum collected. All studies were approved by the Human Use Advisory Committee at the University of Arkansas for Medical Sciences.

Computer analysis of Ara h I sequence. Sequence analysis of the Ara h I gene (9) and peptide sequences was done on the University of Arkansas for Medical Science's Vax computer using the Wisconsin DNA analysis software package. The predicted antigenic regions on the Ara h I protein are based on algorithms developed by Jameson and Wolf (10) that relates antigenicity to hydrophilicity, secondary structure, flexibility, and surface probability.

Peptide synthesis. Individual peptides were synthesized on a cellulose membrane containing free hydroxyl groups using Fmoc-amino acids according to the manufacturer's instructions (Genosys Biotechnologies, The Woodlands, TX). Synthesis of each peptide was started by esterification of an Fmoc-amino acid to the cellulose membrane. After washing, all residual amino functions on the sheet were blocked by acetylation to render it unreactive during the subsequent steps. Each additional Fmoc-amino acid is esterified to the previous one by this same process. After addition of the last amino acid in the peptide, the amino acid side chains were de-protected using a, mixture of dichloromethane/trifluoroacetic acid/triisobutylsilane (1/1/0.05), followed by treatment with dichloromethane and washing with methanol. Membranes containing synthesized peptides were either probed immediately with serum IgE or stored at −20° C. until needed.

IgE binding assay. Cellulose membranes containing synthesized peptides were incubated with the serum pool or individual serum from patients with peanut hypersensitivity diluted (1:5) in a solution containing TBS and 1% bovine serum albumin for at least 12 h at 4° C. or 2 h at room temperature. Detection of the primary antibody was with $^{125}$I-labeled anti-IgE antibody (Sanofi Pasteur Diagnostics, Chaska, Minn.).

RESULTS

Figure 22:
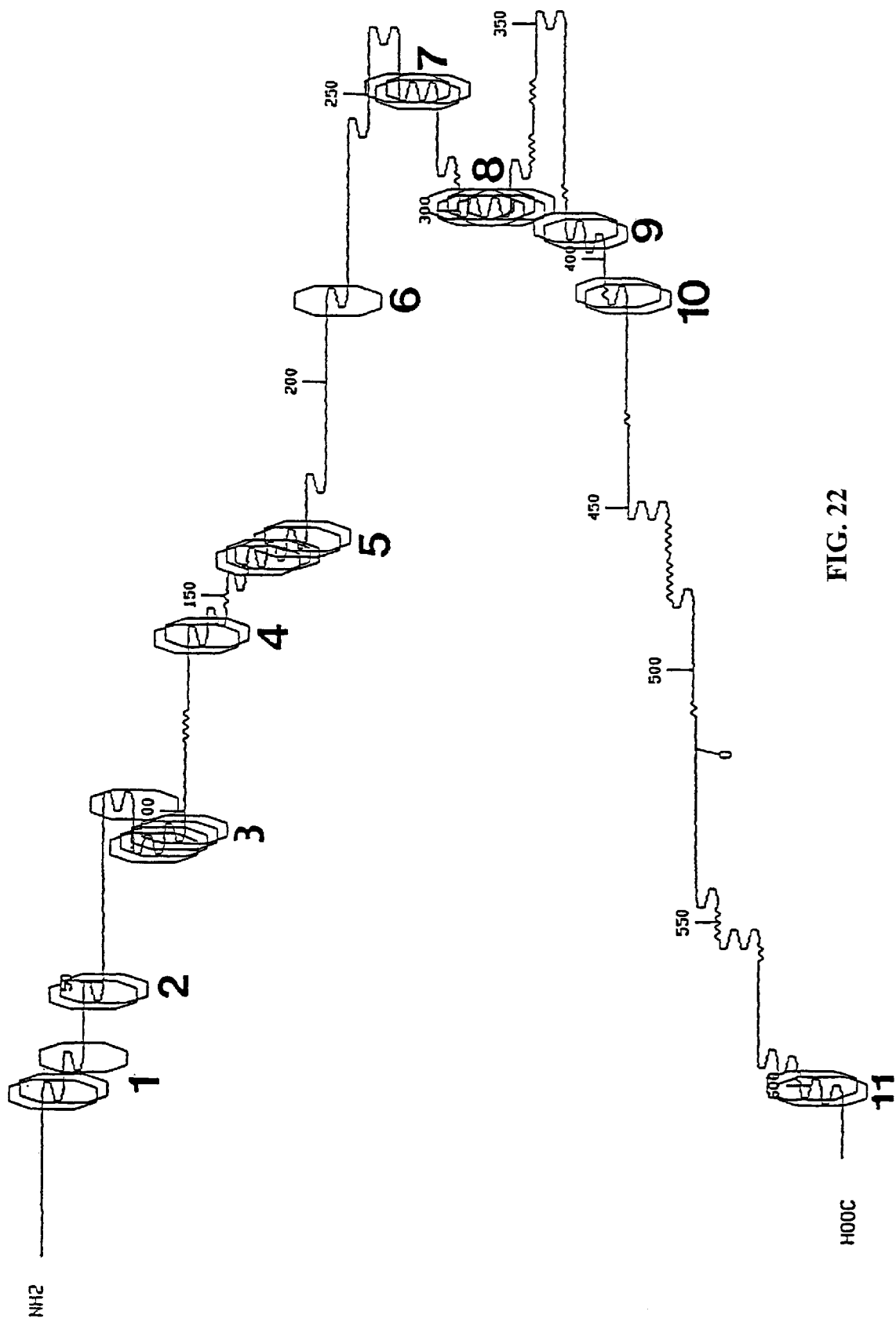

There are Multiple IgE Binding Regions Throughout the Ara h I Protein. The Ara h I protein sequence was analyzed using a computer program to model secondary structure and predict antigenicity based on the parameters of hydrophilicity, secondary structure, flexibility, and surface probability. Eleven antigenic regions, each containing multiple antigenic sites, were predicted by this analysis along the entire length of the molecule (FIG. 22).

Figure 23A:
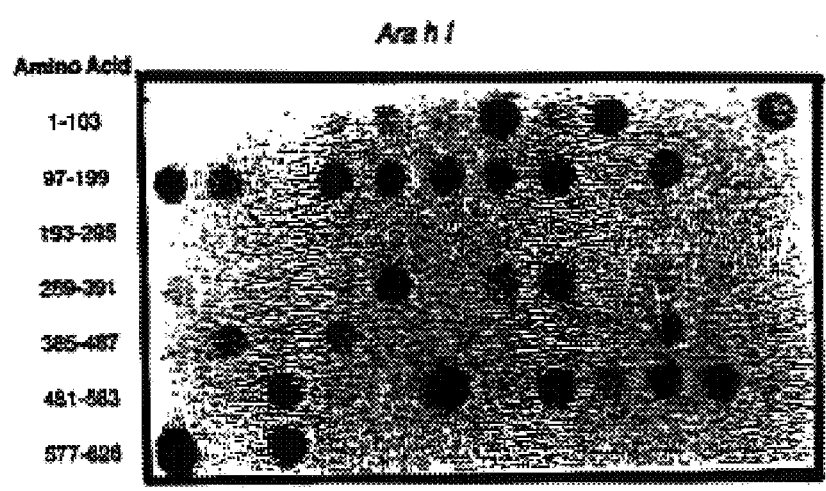

Seventy-seven overlapping peptides representing the entire length of the Ara h I protein were synthesized and probed with pooled serum to determine IgE binding to the predicted antigenic regions, or any other regions of the protein. Each peptide was 15 amino acids long and offset from the previous peptide by eight amino acids. These peptides were then probed with a pool of serum IgE from 15 patients with documented peanut hyper-sensitivity or with serum IgE from a control patient with no food allergy. FIG. 23A shows 12 IgE binding regions along the entire length of the Ara h I protein recognized by this population of peanut hypersensitive patients. Serum IgE from the control patient did not recognize any of the synthesized peptides (data not shown). In general, there was good agreement between the predicted antigenic regions (FIG. 23B, boxed areas P1–P11) and those that were determined (FIG. 23B, shaded areas D1–D12) by actual IgE binding. However, there were two predicted antigenic regions (AA221–230; AA263–278) that were not recognized by serum IgE from peanut hypersensitive individuals. In addition, there were numerous IgE binding regions found in the Ara h I protein between amino acids 450–600 (FIG. 23A).

Figure 24A:
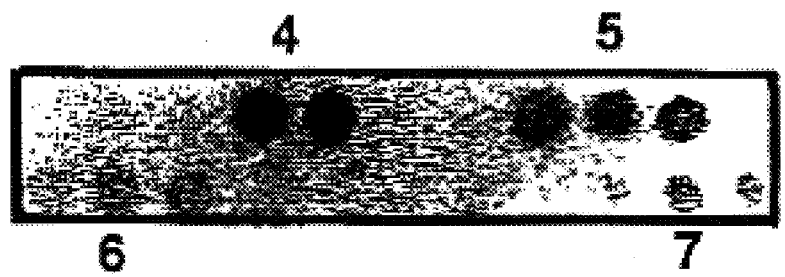

In order to determine the amino acid sequence of the IgE binding sites, small overlapping peptides spanning each of the larger IgE binding regions identified in FIG. 23 were synthesized. By synthesizing smaller peptides (10 amino acids long) that were offset from each other by only two amino acids it was possible to identify individual IgE binding epitopes within the larger IgE binding regions of the Ara h I molecule. FIG. 24 shows a representative immunoblot and the respective amino acid sequence of the binding region D2–D3 (AA82–133). Four epitopes (FIG. 24, numbers 4–7) were identified in this region. Similar blots were performed for the remaining IgE binding regions to identify the core amino acid sequences for each IgE epitope. Table 22 summarizes the 23 IgE epitopes (peptides 1–23) and their respective positions in the Ara h I molecule. The most common amino acids found were acidic (D,E) and basic (K,R) residues comprising 40% of all amino acids found in the epitopes. In addition, no obvious amino acid sequence motif was shared by the epitopes.

Figure 25:
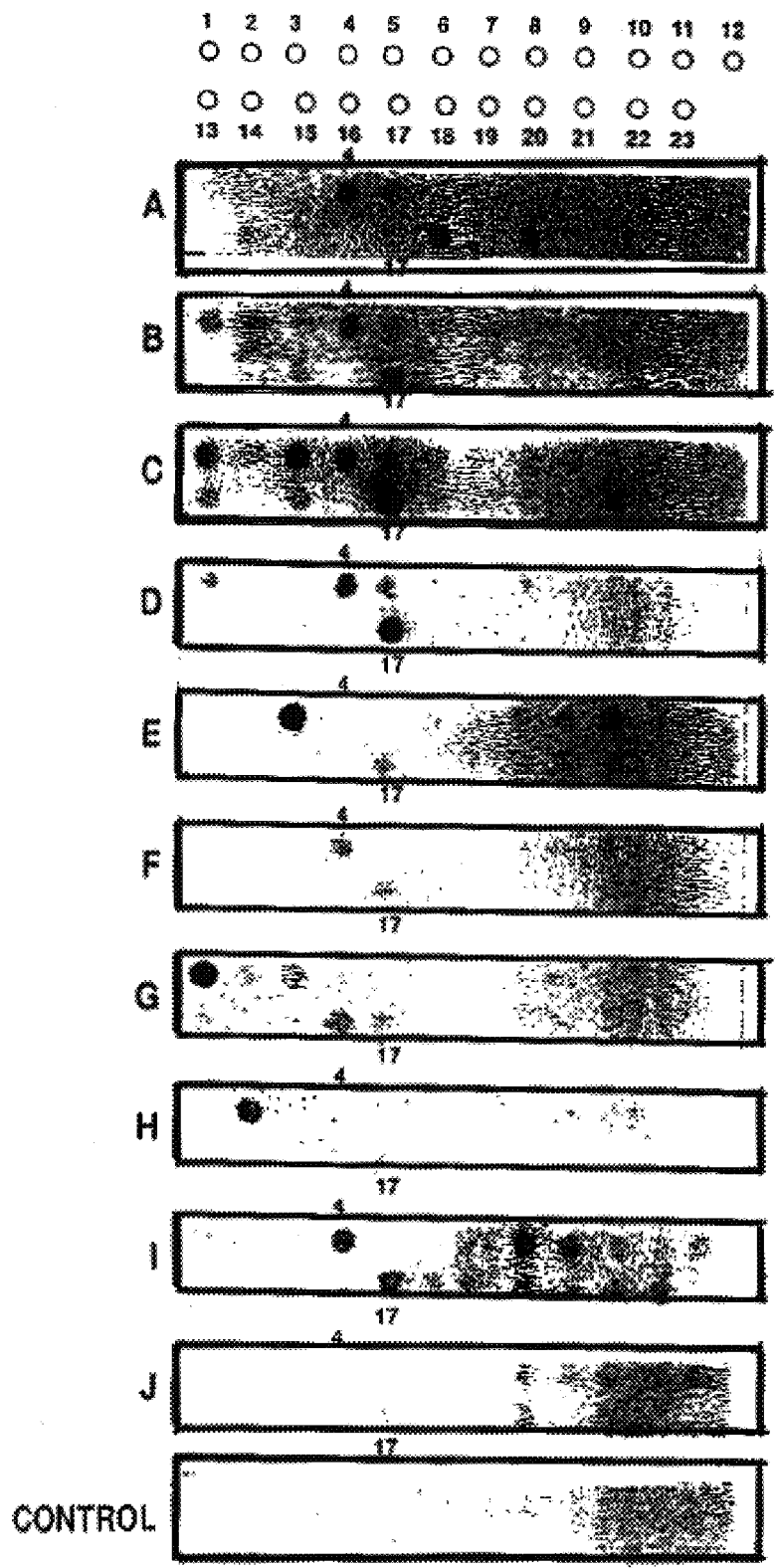

Identification of Common Ara h I Epitopes Recognized by Serum IgE from Patients With Peanut Hypersensitivity. Each set of twenty-three peptides was probed with serum IgE from 10 individuals to determine which of the twenty-three epitopes were recognized by serum IgE from patients with peanut hyper-sensitivity. Serum from five individuals randomly selected from the 15 patient serum pool and an additional five sera from peanut hypersensitive patients not represented in the serum pool were used to identify the common epitopes. FIG. 25 shows the IgE binding results of the 10 immunoblot strips (A–J) containing these peptides incubated with individual patient sera. All of the patient sera tested (10/10) recognized multiple epitopes. The average number of epitopes recognized was 6/patient sera, ranging from one serum recognizing only 2 epitopes to another patient's serum recognizing 12 epitopes. The results are summarized in Table 23. Interestingly, epitope 17 was recognized by all patient sera tested (10/10) and epitope 4 was recognized by 90% (9/10) of patient sera tested. No other epitope was recognized by more than 50% of the patient sera tested.

Figure 26:
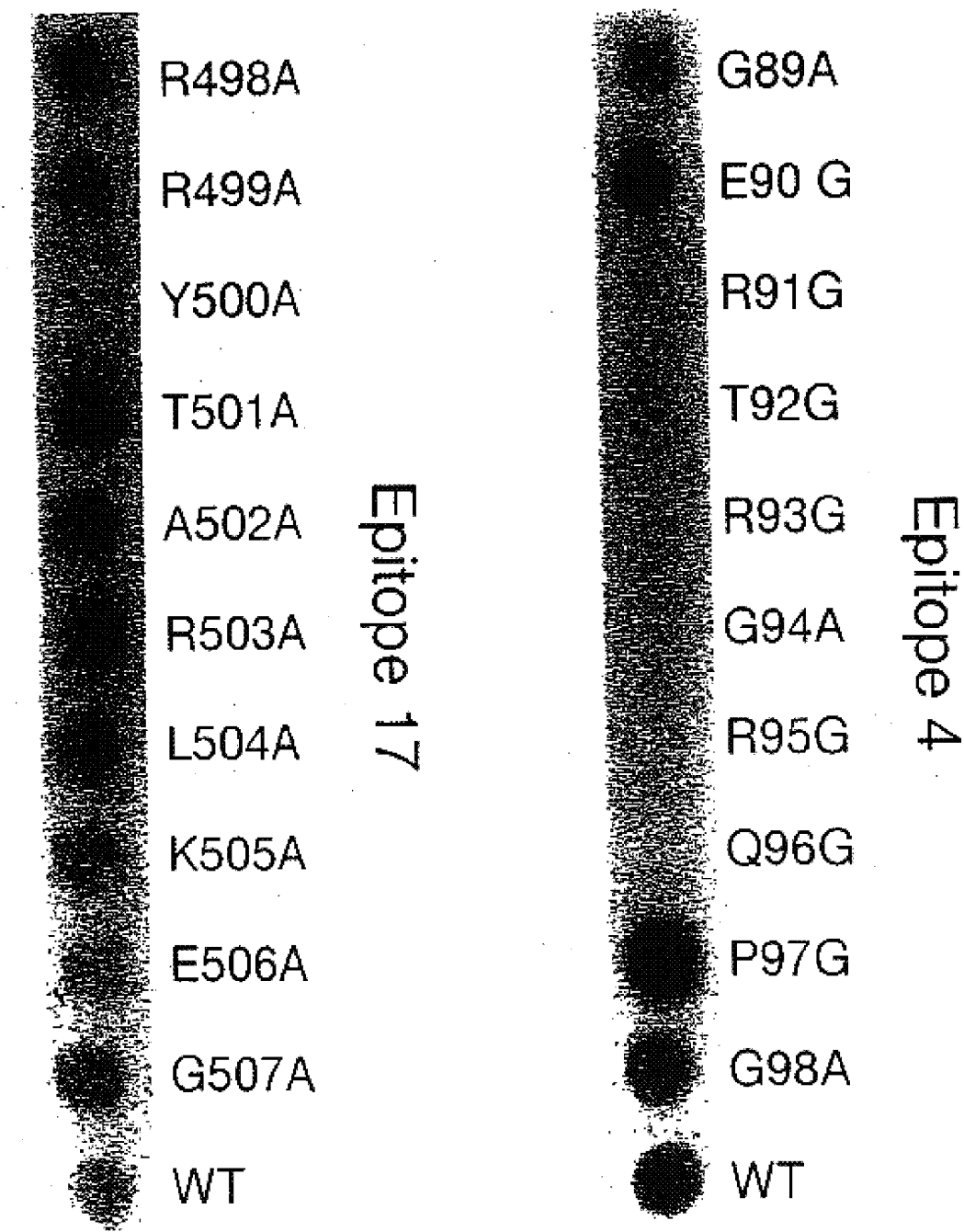

IgE hbinding Characteristics of Mutated Ara h I Epitopes. The amino acids essential to IgE binding in epitopes 4 and 17 were determined by synthesizing duplicate peptides with single amino acid changes at each position. The amino acids were changed to either an alanine or glycine residue because these amino acids have small, R groups. These peptides were then probed with pooled serum IgE from 15 patients with peanut hypersensitivity to determine if the change affected peanut-specific IgE binding. The results are shown in FIG. 26. Clearly, a single amino acid substitution has dramatic effects on the IgE binding characteristics of that peptide. Replacement of any amino acid in the 91–96 region of epitope 4 resulted in almost complete loss of IgE binding to this epitope. In epitope 17, replacement of the tyrosine residue at position 500 or replacement of the glutamic acid residue at position 506 also resulted in dramatic decreases in IgE binding.

Significant sequence homology between epitopes 4 and 17 and seed storage proteins from other plants could explain the presence of cross-reacting antibodies to other legumes which complicates diagnosis. To assess the prevalence of the amino acid sequences of epitope 4 and 17 in other seed storage proteins, the complete Ara h 1 amino acid sequence was first used to select all plant proteins that shared sequence homology with the peanut vicilin. There were 93 entries selected on this basis, representing amino acid sequences deposited in the protein data base from a variety of seed storage proteins. The amino acid sequence for epitope 17 was present in many of these proteins with sequence identity ranging from 20–60%. Interestingly, even in those proteins with only 20% identity the tyrosine at position 500 and the glutamic acid residue at position 506 were almost always conserved (Table 24). The amino acid sequence for epitope 4 was present in fewer of these proteins with sequence identity ranging from 20–30%. In every case, at least one of the amino acids at positions 91–96 were different from the peanut vicilin (Table 24).

DISCUSSION

The development of an IgE response to an allergen involves a series of interactions between T cells and B cells. B cells bearing appropriate antigen-specific receptors interact with proliferating allergen specific T-cells which leads to isotype switching and the generation of antigen-specific IgE. The antigen-specific IgE then binds to surface receptors of mast cells, basophils, macrophages, and other APCs enabling the immune system to respond to the next encounter with the specific antigen (B-cell epitope). Because antigen specific IgE plays such a critical role in the etiology of allergic disease, determination of allergen-specific, IgE binding epitopes is an important first step toward a better understanding of this complex disease process.

The vicilins are seed storage proteins found in most higher plants (11). A comparison of the vicilin amino acid sequences from different plant sources reveals that considerable sequence homology exists between the carboxyl two-thirds of all these molecules. The major difference between the vicilins is found in the amino terminal end of these proteins where little sequence homology is detected (11). In sequence comparison studies (9) with other legumes, the peanut vicilin, Ara h I conforms to this general rule with the highest similarity being found in the carboxyl two-thirds of this molecule.

In the present study we have determined that there were multiple antigenic sites predicted for the Ara h I allergen. In general, as has been found with other allergens (12,13), there was good agreement between those residues predicted by computer analysis and B-cell epitopes determined by experimental analysis of overlapping peptides. This strong correlation between predicted and determined epitopes is probably due to the ability of the computer model to predict which regions of the molecule are exposed on the surface of the allergen, making them accessible to immunoglobulin interactions. There are at least 23 different IgE recognition sites on the major peanut allergen Ara h I. These sites are distributed throughout the protein. The identification of multiple epitopes on a single allergen is not novel. Allergens from cow milk (14), codfish (15), hazel, (16), soy (17) and shrimp (18) have all been shown to contain multiple IgE binding epitopes. The observation that most of these proteins have multiple IgE binding sites probably reflects the polyclonal nature of the immune response to them and may be a necessary step in establishing a protein as an allergen.

The elucidation of the major IgE binding epitopes on Ara h I may also enable us to better understand the immunopathogenic mechanisms involved in peanut hypersensitivity. Recent evidence suggests that there is a preferential variable heavy chain usage in IgE synthesis and a direct switching from IgM production to IgE synthesis (19). This would suggest that epitopes responsible for antigen-specific IgE antibody production may differ from those promoting antigen-specific IgG antibodies. Immuno-therapeutic approaches utilizing peptides representing IgG epitopes may be able to shift the balance of antigen-specific antibody production from IgE to IgG. We are currently identifying which of the IgE binding epitopes also bind IgG to determine if this would be a feasible strategy for patients with peanut hypersensitivity.

Two of the Ara h I peptides appear to be immunodominant IgE binding epitopes in that they are recognized by >90% of patient sera tested. Interestingly, epitope 17 which is located in the carboxyl end of the protein (AA 498–507), is in a region that shares significant sequence homology with vicilins from other legumes. The amino acids important to IgE binding also appear to be conserved in this region and may explain the possible cross-reacting antibodies to other legumes that can be found in sera of patients with a positive DBPCFC to peanuts. Epitope 4, located in the amino terminal portion (AA 89–98) of the protein, appears to be unique to this peanut vicilin and does not share any significant sequence homology with vicilins from other legumes. In addition, the amino acids important to IgE binding in this region are not conserved. These findings may enable us to develop more sensitive and specific diagnostic tools and lead to the design of novel therapeutic agents to modify the allergic response to peanuts.

The only therapeutic option presently available for theprevention of a food hypersensitivity reaction is food avoidance. Unfortunately, for a ubiquitous food such as peanut, the possibility of an inadvertent ingestion is great. One therapeutic option used extensively for patients with allergic reactions to various aeroallergens and insect sting venoms is allergen desensitization immunotherapy. Allergen immunotherapy consists of injections of increasing amounts of allergens to which a patient has Type I immediate hypersensitivity (20,21). Allergens for immunotherapy are usually extracted from natural sources and represent mixtures of several different proteins, to many of which the patient is not allergic. These non-allergenic components could induce an IgE-response in hyposensitized patients (22) thus complicating their use as a therapeutic tool. One of the major improvements in allergen immunotherapy has been the use of standardized allergenic extracts which has been made possible by the use of recombinant allergens (23,24). While the absolute mechanism of immunotherapy is unknown, an increase in IgG or IgG4 antibody activity, a decrease in allergen-specific IgE levels, and a decrease in basophil activity have all been implicated (25–28) in mediating this response. Because allergen immunotherapy has been proven efficacious for treatment of some allergies, treatment with peanut immunotherapy is now being studied as a possible option (29). Our work showing the IgE binding epitopes of a major peanut allergen may allow for the use of immunodominant epitopes in this approach. One possible advantage of using peptides over using the whole allergen is the reduced danger of anaphylaxis. The degranulation of mast cells requires the cross-linking of IgE antibodies bound to the high affinity FceR I receptors (30). Peptides containing single IgE epitopes would be unable to bind to more than one IgE antibody and therefore unable to cross-link the bound IgE. We are currently exploring this possibility in in vitro and in vivo models.

REFERENCES

1. Jansen J. J., A. F. M. Kardinaal, G. Huijber, B. J. Vleig-Boerstra, B. P. Martens, and T. Ockhuizen. 1994. Prevalence of food allergy and intolerance in the adult Dutch population. J. Allergy Clin. Immunol. 93:446–456.
2. Sampson H. A. 1988. The role of food allergy and mediator release in atopic dermatitis. J. Allergy Clin. Immunol. 81:635–645.
3. Bock S. A., and F. M. Atkins. 1989. The natural history of peanut allergy. J. Allergy Clin. Immunol. 83:900–904.
4. Sampson H. A., I. Mendelson, and J. P. Rosen. 1992. Fatal and near-fatal anaphylactic reactions to food in children and adolescents. N. Engl. J. Med. 327:380–384.
5. Yunginger, J. W., K. G. Sweeney, W. Q. Sturner, L. A. Giannandrea, J. D. Teigland, M. Bray, P. A. Benson, J. A. York, L. Biedrzycki, D. L. Squillace, et al. 1988. Fatal food-induced anaphylaxis. JAMA, 260:1450–1452.
6. Bernhisel-Broadbent, J., S. Taylor, and H. A. Sampson. 1989. Cross-allergenicity in the legume botanical family in children with food hypersensitivity. II. Laboratory correlates J. Allergy Clin. Immunol. 84:701–709.
7. Taylor, S. L., W. W. Busse, M. I. Sachs, J. L. Parker, and J. W. Yunginger. 1981. Peanut oil is not allergenic to peanut sensitive individuals. J. Allergy Clin. Immunol. 68:372–375.
8. Burks A. W., L. W. Williams, R. M. Helm, C. Connaughton, G. Cockrell, T. O'Brien. 1991. Identification of a major peanut allergen Ara h I, in patients with atopic dermatitis and positive peanut challenge. J. Allergy Clin. Immunol. 88:172–179.
9. Burks A. W., G. Cockrell, J. S. Stanley, R. M. Helm, G. A. Bannon. 1995. Recombinant peanut allergen Ara h I expression and IgE binding in patients with peanut hypersensitivity. J. Clin. Invest. 96:1715–1721.
10. Jameson, B. A, and H. Wolf. 1988. The antigenic index: a novel algorithm for predicting antigenic determinants. Comput. Appl. Biosci. 4:181–186.
11. Gibbs, P. E., K. B. Strongin, and A. McPherson. 1989. Evolution of legume seed storage proteins—a domain common to legumins and vicilins is duplicated in vicilins. Mol. Biol. Evol. 6:614–623.
12. Van Kampen, V., W. M. Becker, Z. Chen, H. P. Rihs, G. Mazur, M. Raulf, V. Liebers, S. Isringhausen-Bley, and X. Baur. 1994. Analysis of B-cell epitopes in the N-terminal region of Chit I component III using monoclonal antibodies. Molecular Immunol., 31:1133–1140.
13. Breiteneder, H., F. Ferreira, A. Reikerstorfer, M. Duchene, R. Valenta, K. Hoffman-Sommergruber, C. Ebner, M. Breitenbach, D. Kraft, O. Scheiner. 1992. Complementary DNA cloning and expression in *Escherichia coli* of Aln g I, the major allergen in pollen of alder (Alnus glutinosa). J. Allergy Clin. Immunol., 90:909–917.
14. Ball G., M. J. Shelton, B. J. Walsh, D. J. Hill, C. S. Hosking, and M. E. Howden. 1994. A major continuous allergenic epitope of bovine bata-lactoglobulin recognized by human IgE binding. Clinical and Experimental Allergy. 24:758–764.
15. Aas, K. and S. Elsayed. 1975. Physico-chemical properties and specific activity of a purified allergen (codfish). Developments in Biological Standardization. 29:90–98.

16. Elsayed, S., E. Holen, and T. Dybendal. 1989. Synthetic allergenic epitopes from the amino-terminal regions of the major allergens of hazel and birch pollen. Int'l. Archives of Allergy & Applied Immunology, 89:410–415.
17. Herian, A. M., S. L. Taylor, and R. K. Bush. 1990. Identification of soybean allergens by immunoblotting with sera from soy-allergic adults. Int. Arch. Allergy Appl. Immunol., 92:193–198.
18. Shanti, K. N., B. M. Martin, S. Nagpal, D. D. Metcalf, and P. V. Rao. 1993. Identification of tropomyosin as the major shrimp allergen and characterization of its IgE-binding epitopes. J. of Immunology. 151:5354–5363.
19. Van der Stoep, N., W. Korver, and T. Logtenberg. 1994. In vivo and in vitro IgE isotype switching in human B lymphocytes: evidence for a predominantly direct IgM to IgE class switch program. European J. of Immunol., 24:1307–1311.
20. Reisman, R. E. 1994. Fifteen years of hymenoptera venom immunotherapy: changing concepts and lessons. Allergy Proceedings, 15:61–63.
21. Fitzsimons, T., and L. C. Grammer. 1990. Immunotherapy-definition and mechanism. Allergy Proc., 11:156.
22. Birkner, T., H. Rumpold, E. Jarolim, H. Ebner, M. Breitenbach, O. Scheiner, and D. Kraft. Evaluation of immunotherapy-induced changes in specific IgE, IgG, and IgG-subclasses in birch pollen-allergic patients by means of immunoblotting. Correlation with clinical response. Allergy, 45:418–426.
23. Scheiner, O. 1992. Recombinant allergens: biological, immunological and practical aspects. Int Arch Allergy Immunol., 98:93–96.
24. Gordon, B. R., 1.995. Future immunotherapy: what lies ahead? Otolaryngol Head Neck Surg., 113:603–605.
25. Sparholt, S. H., O. T. Olsen, and C. Schou. 1992. The allergen specific B-cell response during immunotherapy. Clinical and Experimental Allergy, 22:648–653.
26. Gieni, R. S., X. Yang, and K. T. Hayglass. 1993. Allergen-specific modulation of cytokine synthesis patterns and IgE responses in vivo with chemically modified allergen. The Journal of Immunol., 150:302–310.
27. Secrist, H., C. J. Chelen, Y. Wen, J. D. Marshall, and D. T. Umetsu. 1993. Allergen immunotherapy decreases interleukin 4 production in CD4+ T cells from allergic individuals. J. Exp. Med., 178:2123–2130. 28. Garcia, N. M., N. R. Lynch, M. C. Di Prisco, and R. I. Lopez. 1995. Nonspecific changes in immunotherapy with house dust extract. J Invest. Allergol. Clin. Immunol., 5:18–24.
29. Oppenheimer, J. J., H. S. Nelson, S. A. Bock, F. Christensen, and D. Y. Leung. 1992. Treatment of peanut allergy with rush immunotherapy. J. Allergy Clin. Immunol., 90:151–152.
30. Fung-Leung, W. P., J. DeSousa-Hitzler, A. Ishaque, L. Zhou, J. Pang, K. Ngo, J. A. Panakos, E. Chourmouzis, F. T. Liu, and C. Y. Lau. 1996. Transgenic mice expressing the human high-affinity immunoglobulin (Ig) E receptor alpha chain respond to human IgE in mast cell degranulation and in allergic reactions. J. of Exp. Med., 183:49–56.

ACKNOWLEDGEMENTS

This work was supported in part by grants from the National Institute of Health (AI33596) and the Clarissa Sosin Research Foundation.

FIGURE LEGENDS

FIG. 22. There Are Multiple Predicted Antigenic Sites on the Ara h I Allergen. The amino acid sequence of the Ara h I protein was analyzed for potential antigenic sites by the Jameson and Wolf (1988) algorithm. These predictions are based on a model that relates antigenicity to hydrophilicity, secondary structure, flexibility, and surface probability. There were 11 (1–11) predicted regions that contained multiple antigenic sites (octagons) along the entire length of the molecule. Amino acid residues (small numbers) are represented as alpha-helical (sinusoidal curve), Beta-sheet (saw tooth curve), and coil (flat sinusoidal curve) conformations. Beta turns are denoted by chain reversals.

FIG. 23. Multiple IgE Binding Regions Identified on the Ara h I Allergen. FIG. 23A; Upper Panel: Epitope mapping was performed on the Ara h I allergen by synthesizing the entire protein in 15 amino acid long overlapping peptides that were offset from each other by 8 amino acids. These peptides were then probed with a pool of serum IgE from 15 patients with documented peanut hypersensitivity. The position of the peptides within the Ara h I protein are indicated on the left hand side of this panel. FIG. 23B Lower Panel: The amino acid sequence of the Ara h I protein is shown in the lower panel. The numbered boxes correspond to the predicted antigenic regions (P1–P11) The hatched boxes (D1–D12) correspond to the IgE binding regions shown in FIG. 2A.

FIGURE 24. Core IgE Binding Epitopes Identified on the Ara h I Allergen. Panel A: Detailed epitope mapping was performed on IgE binding regions identified in FIG. 23 by synthesizing 10 amino acid long peptides offset from each other by two amino acids. These peptides were then probed with a pool of serum IgE from 15 patients with documented peanut hypersensitivity. The data shown represents regions D2 and a portion of D3 encompassing amino acid residues 82–133. Numbers corre spond to peptides as shown in Table 22. Panel B: The amino acid sequence (residues 82–133) of Ara h I that was tested in Panel A is shown. Shaded areas of boxes correspond to IgE binding peptides in Panel A.

FIG. 25. Commonly Recognized Ara h I Epitopes. Core IgE binding epitopes were synthesized (10 amino acids long) and then probed individually with serum IgE from 10 patients-with documented peanut hypersensitivity. The top panel represents where each of the Ara h I peptides (1–23) were placed on the membrane. Panels A–J show the peptides that bound serum IgE from patients with peanut hypersensitivity. The control panel was probed with sera from a patient with elevated IgE but who does not have peanut hypersensitivity.

FIG. 26. Amino Acids Involved in IgE Binding. Epitope 4 and 17 were synthesized with a glycine (G) or alanine (A) substituted for one of the amino acids in each of these peptides and then probed with a pool of serum IgE from 15 patients with documented peanut hypersensitivity. The letters across the top of each panel indicate the one letter amino acid code for the residue normally at that position and the amino acid that was substituted for it. The numbers indicate the psition of each residue in the Ara h I protein.

TABLE 22

Ara h I IgE binding epitopes.

| PEPTIDE | AA SEQUENCE | Ara h I POSITION |
|---|---|---|
| 1 | AKSSPYQKKT | 25–34 |
| 2 | QEPDDLKQKA | 48–57 |
| 3 | LEYDPRLVYD | 65–74 |
| 4 | GERTRGRQPG | 89–98 |
| 5 | PGDYDDDRRQ | 97–105 |

TABLE 22-continued

Ara h I IgE binding epitopes.

| PEPTIDE | AA SEQUENCE | Ara h I POSITION |
|---|---|---|
| 6 | PR<u>REEGGRW</u>G | 107–116 |
| 7 | R<u>EREEDWRQ</u>P | 123–132 |
| 8 | <u>EDWRRPSHQQ</u> | 134–143 |
| 9 | <u>QPRKIRPEGR</u> | 143–152 |
| 10 | TPG<u>QFEDFFP</u> | 294–303 |
| 11 | S<u>YLQEFSRNT</u> | 311–320 |
| 12 | <u>FNAEFNEIRR</u> | 325–334 |
| 13 | <u>EQEERGORRW</u> | 344–353 |
| 14 | <u>DITNPINLRE</u> | 393–402 |
| 15 | NN<u>FGKLFEVK</u> | 409–418 |
| 16 | GT<u>GNLELVAV</u> | 461–470 |
| 17 | <u>RRYTARLKEG</u> | 498–507 |
| 18 | <u>ELHLLGFGIN</u> | 525–534 |
| 19 | <u>HRIFLAGDKD</u> | 539–548 |
| 20 | <u>IDQIEKQAKD</u> | 551–560 |
| 21 | <u>KDLAFPGSGE</u> | 559–568 |
| 22 | <u>KESHFVSARP</u> | 578–587 |
| 23 | <u>PEKESPEKED</u> | 597–606 |

The underlined portions of each peptide are the smallest IgE binding sequences as determined by the analysis as described in FIG. 24.

TABLE 23

IgE binding of core Ara h I epitopes by serum from peanut hypersensitive individuals.

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | Epitopes/Patient |
|---|---|---|---|---|---|---|---|---|---|---|---|---|---|---|---|---|---|---|---|---|---|---|---|---|
| A | | | | X | X | | | | | | | | | | X | | X | X | | X | | | | 6 |
| B | X | X | | X | X | | | | | | | | | | | X | | X | | | | | | 6 |
| C | X | X | X | X | X | X | | X | | | X | X | | X | | X | | | | | | X | | 12 |
| D | X | | | X | X | | | | | | | | | X | | X | | X | | | | | | 6 |
| E | | | X | X | | | | X | X | X | X | X | | | | | X | | X | X | X | | | 11 |
| F | X | | X | | | | | | X | | | | | | | | X | | | | | | | 4 |
| G | X | X | X | | | | | | | | | | | X | | | X | X | | | | | | 6 |
| H | X | | X | | | | | | | | | | | | | | X | | | | | | | 3 |
| I | | X | | | | X | X | | | | | | | | | | X | X | X | X | | X | | 8 |
| J | | X | | | X | X | | X | | | | | | | | | X | | X | | X | | | 7 |
| Pts/epitope | 4 | 5 | 3 | 9 | 4 | 1 | 0 | 3 | 4 | 2 | 1 | 3 | | 3 | 1 | 3 | 1 | 10 | 2 | 1 | 4 | 1 | 3 | 1 |

Patients are indicated by letters (A–J) on the left hand side of the table. Ara h I peptides are indicated by number (1–23) across the top of the table. The number of epitopes recognized by each patient (epitopes/patient) is shown on the right hand side of the table. The number of patients that recognized each epitope (pts/epitope) is shown across the bottom of the table. An X indicates that a peptide bound IgE.

TABLE 24

Amino acid comparison of Ara h I epitopes 4 and 17 with similar regions in other seed storage proteins.

| | EPITOPE 4 | | EPITOPE 17 |
|---|---|---|---|
| <u>Ara h 1</u> | GERTRGRQPG | <u>Ara h I</u> | RRYTARLKEG |
| <u>Soy</u> | FPRPQPRQEE | <u>Soy</u> | RKYRAELSEQ |
| <u>Cacao</u> | -EQCEQRCER | <u>Jack bean</u> | RRYAATLSEG |
| <u>Pea</u> | EEHEEEKQKY | <u>Pea</u> | QRYEARLADG |
| <u>Maize</u> | WEDDNHHHHH | <u>Fava bean</u> | QNYKAKLSPG |

The peptides representing Ara h I epitopes 4 and 17 were compared with similar regions from other seed storage proteins. The amino acids residues important to IgE binding are indicated as bold underlined letters. Those amino acids that are identical to the Ara h I sequence are underlined.

The that are linear amino acid sequences that do not contain significant amounts of carbohydrate. The gene encoding the Ara h 1 allergen has been cloned, sequenced, and identified as a seed storage protein belonging to the vicilin family of legume storage proteins.

The major peanut allergen, Ara h 2, has now been cloned and the nucleotide sequence determined. The derived amino acid sequence has been used to construct synthetic peptides and perform a detailed examination of the linear IgE binding epitopes of this protein.

EXPERIMENTAL PROCEDURES

Patients. Serum from 15 patients with documented peanut hypersensitivity (mean age, 25 yr) was used to identify peanut allergens. Each of these individuals had a positive immediate skin prick test to peanut and either a positive double-blind, placebo controlled, food challenge or a convincing history of peanut anaphylaxis (laryngeal edema, severe wheezing, and/or hypotension). Details of the challenge procedure and interpretation have been discussed previously. One individual with elevated serum IgE levels (who did not have peanut specific IgE or peanut hypersensitivity) was used as a control in these studies. At least five mls of venous blood were drawn from each patient and allowed to clot, and the serum was collected. All studies were approved by the Human Use Advisory Committee at the University of Arkansas for Medical Sciences.

Isolation and amino acid sequence analysis of peanut allergen Ara h 2. Ara h 2 was purified to near homogeneity from whole peanut extracts according to the methods of Burks et al. Purified Ara h 2 was electrophoresed on 12.5% acrylamide mini-gels (Bio-Rad. Hercules, Calif.) in Tris glycine buffer. The gels were stained with 0.1% Coomassie blue in 10% acetic acid, 50% methanol, and 40% water for 3 h with continuous shaking. Gel slices containing Ara h II were sent to the W.M. Keck Foundation (Biotechnology Resource Laboratory, Yale University, New Haven Conn.) for amino acid sequencing. Amino acid sequencing of intact Ara h 2 and tryptic peptides of this protein was performed on an Applied Biosystems sequencer with an on-line HPLC column that was eluted with increasing concentrations of acetonitrile.

Peanut RNA isolation and northern (RNA) gels. Three commercial lots from the 1979 crop of medium grade peanut species, Arachis hypogaea, (Florunner) were obtained from North Carolina State University for this study. Total RNA was isolated from one gram of this material according to procedures described by Larsen. Poly A+ RNA was isolated using a purification kit supplied by collaborative Research (Bedford Mass.) according to manufacturer's instructions. Poly A+ RNA was subjected to electrophoresis in 1.2% formaldehyde agarose gels, transferred to nitrocellulose, and hybridized with $^{32}$P-labeled probes according to the methods of Bannon et al.

Computer analysis of Ara h II sequence. Sequende analysis of the Ara h 2 gene was done on the University of Arkansas for Medical Science's Vax computer using the Wisconsin DNA analysis software package. The predicted Ara h 2 epitopes are based on a algorithms developed by Jameson and Wolf (1988) that relates antigenicity to hydophilicity, secondary structure, flexibility, and surface probability.

cDNA expression library construction and screening. Peanut poly A+ RNA was used to synthesize double-stranded cDNA according to the methods of Watson and Jackson and Huynh et al. The cDNA was treated with EcoRI methylase and then ligated with EcoRI and XhoI linkers. The DNA was then ligated with EcoRI-XhoI cut, phosphatase treated Lambda ZAP XR phage arms (Stratagene, LaJolla, Calif.) and in vitro packaged. The library was 95% recombinants carrying insert sizes >400 bp. The library was screened using an IgE antibody pool consisting of an equal volume of serum from each patient with peanut hypersensitivity. Detection of primary antibody was with $I^{125}$-labeled anti-IgE antibody performed according to the manufacturer's instructions (Sanofi, Chaska, Minn.).

PCR amplification of the Ara h 2 mRNA sequence. Using the oligonucleotide CA(AG)CA(AG)TGGGA(AG)TT(AG) CA(AG)GG(N).GA(TC)AG derived from amino acid sequence analysis of the Ara h 2 peanut allergen as one primer and a 23 nucleotide long primer which hybridizes to the Bluescript vector, the cDNA that encodes Ara h 2 was amplified from the IgE positive clones. Reactions were carried out in a buffer containing 3 mM $MgCl_2$, 500 mM KCl, 100 mM Tris-HCl, pH 9.0. Each cycle of the polymerase chain reaction consisted of 1 min at 94° C., followed by 2 min at 42° C., and three minutes at 72° C. Thirty cycles were performed with both primers present in all cycles. From this reaction, a clone carrying an approximately 700 bp insert was identified.

DNA sequencing and analysis. DNA Sequencing was done according to the methods of Sanger et al. using either $^{32}$P-end labeled oligonucleotide primers or on a automated ABI model 377 DNA sequencer using fluorescent tagged nucleotides. Most areas of the clone were sequenced at least twice and in some cases in both directions to ensure an accurate nucleotide sequence for the Ara h 2 gene.

Peptide synthesis. Individual peptides were synthesized on a derivatised cellulose membrane using Fmoc amino acid active esters according to the manufacturer's instructions (Genosys Biotechnologies, Woodlands, Tex.). Fmoc-amino acid derivatives were dissolved in 1-methyl-2-pirrolidone and loaded on marked spots on the membrane. Coupling reactions were followed by acetylation with a solution of 4% (v/v) acetic anhydride in N,N-Dimethylformamide (DMF). After acetylation, Fmoc groups were removed by incubation of the membrane in 20% (v/v) piperdine in DMF. The membrane was then stained with bromophenol blue to identify the location of the free amino groups. Cycles of coupling, blocking, and deprotection were repeated until the peptides of the desired length were synthesized. After addition of the last amino acid in the peptide, the amino acid side chains were deprotected using a solution containing a 1/1/ 0.5 mixture of dichloromethane/ trifluoroacetic acid/ triisobutlysilane. Membranes were either probed immediately or stored at −20° C.until needed.

IgE binding assay. Cellulose membranes containing synthesized peptides were washed with Tris-buffered saline (TBS) and then incubated with blocking solution overnight at room temperature. After blocking, the membranes were incubated with serum from patients with peanut hypersensitivity diluted (1:5) in a solution containing TBS and 1% bovine serum albumin for at least 12 h at 4° C. or 2 h at room temperature. Detection of the primary antibody was with $^{125}$I-labeled anti-IgE antibody (Sanofi, Chaska, Minn.).

RESULTS

Isolation and partial amino acid sequence determination of the Ara h 2 protein. The amino terminus of the purified Ara h 2 protein, or PePtides resulting from trypsin digestion of this protein, were used for amino acid sequence determination. It was possible to determine the first 17 residues from peptide I and the first 13 residues from peptide II of the major peptide in each fraction. The amino acid sequence representing the amino terminus of the Ara h 2 protein (peptide I) and a tryptic peptide fragment (peptide II) is noted in Table 25. These results confirm and extend previous amino acid sequence analysis of the Ara h 2 protein.

Identification and Characterization of Clones That Encode Peanut Allergen Ara h 2

RNA isolated from the peanut species, Arachis hypogaea (Florunner) was used to construct an expression library for screening with serum IgE from patients with peanut hypersensitivity. Numerous IgE binding clones were isolated from this library after screening $10^6$ clones with serum IgE from a pool of patients with reactivity to most peanut allergens by Western blot analysis. Since the number of plaques reacting with serum IgE was too large to study all in detail we randomly selected a small portion of the positive clones for further analysis.

To identify which of the clones encoded the Ara h 2 allergen, a hybridization probe was constructed using an oligonucleotide developed from Ara h 2 amino acid sequence and PCR technology. The oligonucleotide sequence CA (AG) CA (AG) TGGGA (AG)TT(AG)CA (AG)GG(N)GA(TC)AG was derived from the amino terminus of the Ara h 2 peanut allergen (peptide I). Utilizing this oligonucleotide, an ~700-bp cDNA clone was identified. DNA sequence revealed that the selected clone carried a 741-base insert which included a 21-base poly A tail and a 240 base 3' non-coding region. This insert contained a large open reading frame starting with an ACG codon and ending with a TAA stop codon at nucleotide position 480 (FIG. 27). The calculated size of the protein encoded by this open reading frame was ~17.5 kD, which is in good agreement with the molecular weight of Ara h 2 that has been determined experimentally. The amino acid sequence that was determined from the amino terminus and a tryptic peptide from purified Ara h 2 (Table 25) were found in this clone. The additional coding region on the amino terminal end of this clone probably represents a signal peptide which would be cleaved from the mature Ara h 2 allergen.

Figure 28:
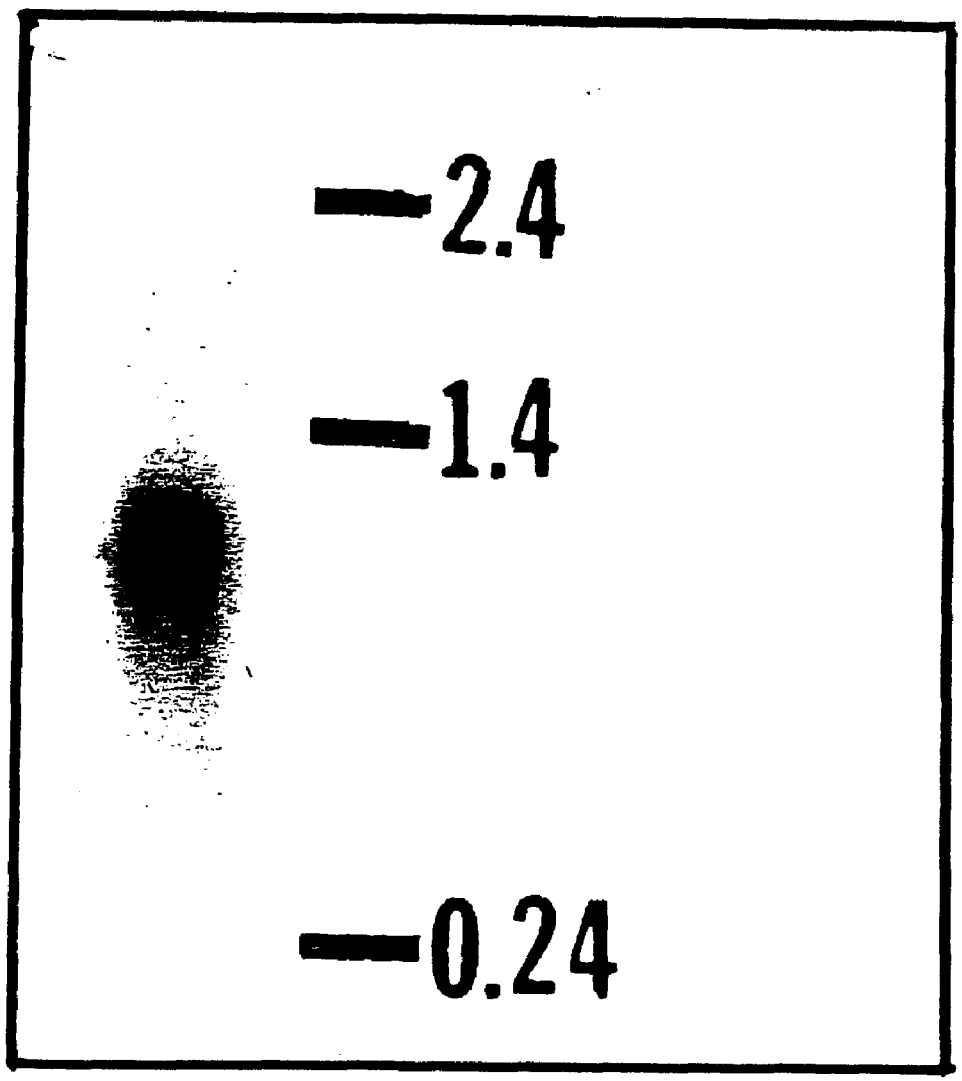

To determine what size mRNA this clone identified, $^{32}$P-labeled insert was used as a hybridization probe of a Northern blot containing peanut poly(A)+ RNA (FIG. 28). This insert hybridized to an ~0.7-kb mRNA. Since the size of the cloned insert and the size of the mRNA were in good agreement, coupled with the good agreement in both the calculated and determined size of the Ara h 2 protein and the identity of the determined amino acid sequence with that which was determined from the clone, we concluded that an Ara h 2 specific clone had been isolated.

Peanut Allergen Ara h 2 is a Conglutin-like Seed Storage Protein

A search of the GenBank database revealed significant amino acid sequence homology between the Ara h 2 protein and a class of seed storage proteins called conglutins. There was =32% identity with the Ara h 2 protein and a delta conglutin from the lupin seed. These results indicate that the Ara h 2 allergen belongs to a conglutin-like family of seed storage proteins.

Figure 29:
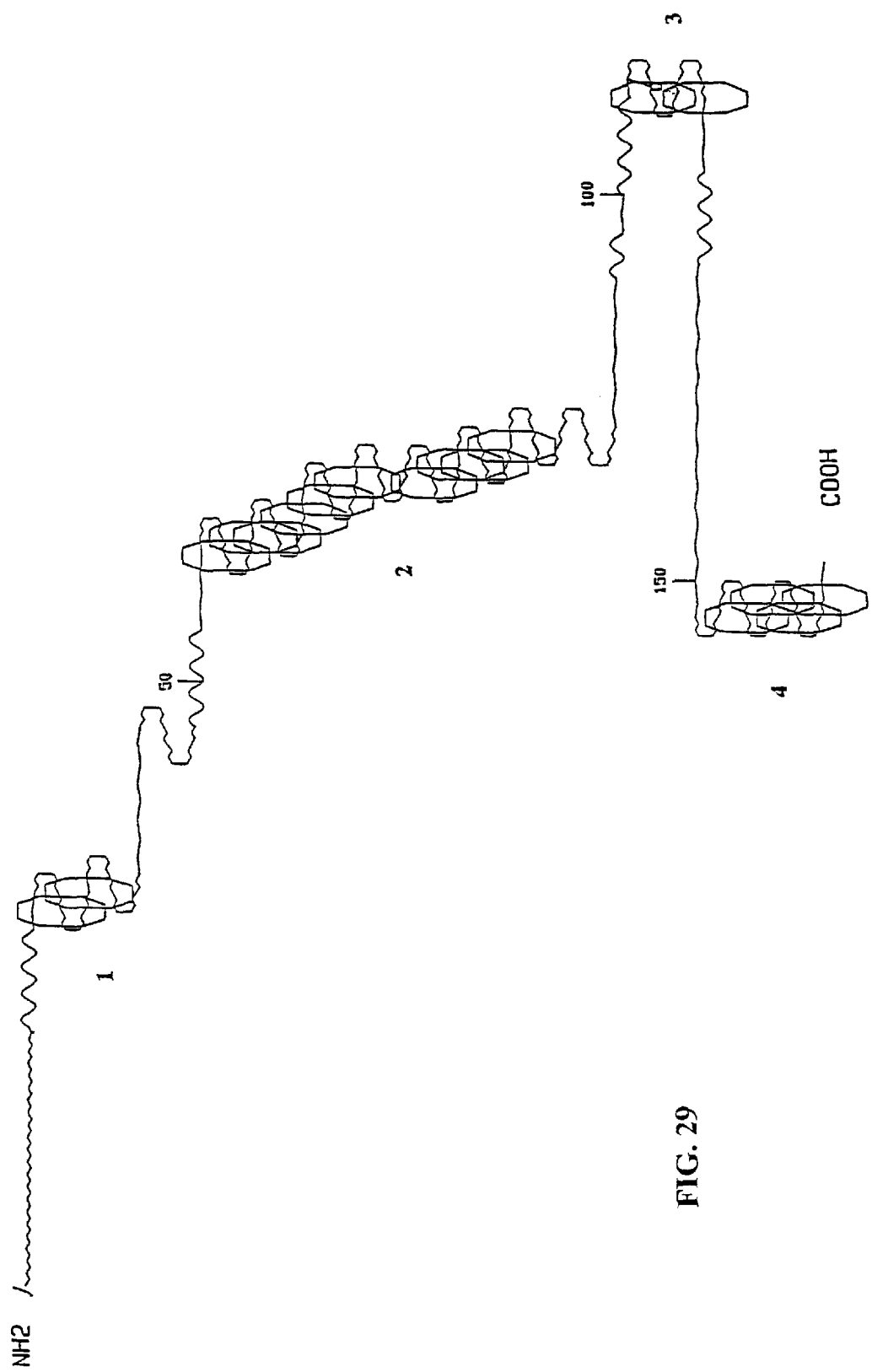

Multiple IgE binding epitopes on the Ara h 2 protein. The Ara h 2 protein sequence was analyzed for potential antigenic epitopes by algorithms designed to determine which portion(s) of this protein could be responsible for antibody binding. There were four possible antigenic regions predicted by this analysis along the entire length of the molecule (FIG. 29).

Nineteen overlapping peptides representing the derived amino acid sequence of the Ara h 2protein were synthesized to determine if the predicted antigenic regions, or any other regions, were recognized by serum IgE. Each peptide was 15 amino acids long and was offset from the previous peptide by eight amino acids. In this manner, the entire length of the Ara h 2 protein could be studied in large overlapping fragments. These peptides were then probed with a pool of serum from 12 patients with documented peanut hypersensitivity or serum from a control patient with no peanut hypersensitivity. Serum IgE from the control patient did not recognize any of the synthesized peptides (data not shown). In contrast, FIG. 30 shows that there are five IgE binding regions along the entire length of the Ara h 2 protein that are recognized by this population of patients with peanut hypersensitivity. These IgE binding regions were amino acid residues 17–38, 41–62, 57–78, 113–134, and 129–154.

Figure 31:

In order to determine the exact amino acid sequence of the IgE binding epitopes, small peptides (10 amino acids long offset by two amino acids) representing the larger IgE binding regions were synthesized. In this manner it was possible to identify individual IgE binding epitopes within the larger IgE binding regions of the Ara h 2 molecule (FIG. 31). The ten IgE binding epitopes that were identified in this manner are shown in Table 26. The size of the epitopes ranged from 6–10 amino acids in length. Three epitopes (aa17–26, aa23–32, aa29–38), which partially overlapped with each other, were found in the region of amino acid residues 17–38. Two epitopes (aa41–50, aa51–60) were found in region 41–62. Two epitopes (aa59–68, aa67–76) were also found in region 57–78. Finally, three epitopes (aa117–126, aa129–138, aa145–154) were found in the overlappings regions represented by amino acid residues 113–134 and 129–154. Sixty-three percent of the amino acids represented in the epitopes were either polar or apolar uncharged residues. There was no obvious amino acid sequence motif that was shared by all the epitopes, with the exception that epitopes 6 and 7, which contained the sequence DPYSPS.

In an effort to determine which, if any, of the ten epitopes were recognized by the majority of patients with peanut hypersensitivity each set of ten peptides was probed individually with serum IgE from 10 different patients. Five patients were randomly selected from the pool of 12 patients used to identify the common epitopes and five patients were selected from outside this pool. An immunoblot strip containing these peptides was. incubated with an individual's patient serum. The remaining patients were tested in the same manner and the intensity of IgE binding to each spot was determined as a function of that patient's total IgE binding to these ten epitopes (FIG. 32) All of the patient sera tested (10/10) recognized multiple epitopes (Table 27). The average number of epitopes recognized was about 4–5/patient ranging from two sera recognizing only 3 epitopes and one patients' sera recognizing as many as 7 epitopes. Interestingly, epitopes 3, 6, and 7 were recognized by all patients tested (10/10). No other epitope was recognized by more than 50% of the patients tested.

DISCUSSION

Peanuts are one of the most common food allergens in both children and adults. In addition, peanut hypersensitivity is less likely to resolve spontaneously and more likely to result in fatal anaphylaxis. Because of the significance of the allergic reaction and the widening use of peanuts as protein extenders in processed food, the risk to the peanut-sensitive individual is increasing.

Various studies over the last several years have examined the nature and location of the multiple allergens in peanuts. Taylor et al. demonstrated that the allergenic portion of peanuts was in the protein portion of the cotyledon. Our laboratory recently identified two major allergens from peanut extracts, designated Ara h 1 and Ara h 2. Greater than 90% of our patients who were challenge positive to peanut had specific IgE to these proteins. The Ara h 1 allergen has been identified as a seed storage protein with significant homology to the vicilins, a family of proteins commonly found in many higher plants. The Ara h 2 nucleotide sequence identified in this report has significant sequence homology with another class of seed storage proteins called conglutins. It is interesting to note that two of the major peanut allergens thus far identified are seed storage proteins that have significant sequence homology with proteins in other plants. This may explain the cross-reacting antibodies to other legumes that are found in the sera of patients that manifest clinical symptoms to only one member of the legume family.

In the present study we have determined that there were multiple antigenic sites predicted for the Ara h 2 allergen. As has been found for another peanut allergen Ara h 1, and other allergens in general, there was good agreement between those residues predicted by computer analysis and B-cell epitopes determined by experimental analysis of overlapping peptides. This strong correlation between predicted and determined epitopes is probably due to the ability of the computer model to predict which regions of the molecule are accessible to immunoglobulin interactions In fact 3D structural models of the Ara h 1 protein indicate that most of the peptides identified by computer modeling and experimental analysis as IgE binding epitopes are located on the surface of the molecule (unpublished observation).

There are at least 10 IgE recognition sites distributed throughout the major peanut allergen Ara h 2. The identification of multiple epitopes on a single allergen is not novel, there being reports of multiple IgE binding epitopes on allergens from many foods that cause immediate hypersensitivity reactions. The observation that most of these proteins have multiple IgE binding sites probably reflects the polyclonal nature of the immune response to them and may be a necessary step in establishing a protein as an allergen.

Recent evidence suggests that there is a preferential variable heavy chain usage in IgE synthesis and a direct switching from IgM production to IgE synthesis. This would suggest that epitopes responsible for antigen-specific IgE antibody production may differ from those promoting antigen-specific IgG antibodies and that there may be some structural similarity between peptides that elicit IgE antibody production. However, there was no obvious sequence motif that was shared by the 23 different IgE binding epitopes of the peanut allergen Ara h 1. In the present study, two epitopes share a hexameric peptide (DPYSPS). It is significant to note that these peptides are recognized by serum IgE from all the peanut-hypersensitive patients tested in this study. In addition, serum IgE that recognize these peptides represent the majority of Ara h 2 specific IgE found in these patients. Whether there is any further structural similarity between the IgE binding epitopes of Ara h 2 remains to be determined.

The elucidation of the major IgE binding epitopes on Ara h 2 may enable us to design better therapeutic options for the prevention of anaphylaxis as a result of peanut hypersensitivity. The only therapeutic option presently available for the prevention of a food hypersensitivity reaction is food avoidance. Unfortunately, for a ubiquitous food such as peanut, the possibility of an inadvertent ingestion is great. One therapeutic option used extensively for patients with allergic reactions to various aeroallergens and insect sting venoms is allergen desensitization immunotherapy. Allergen immunotherapy consists of injections of increasing amounts of allergens to which a patient has Type I immediate hypersensitivity. While the absolute mechanism of immunotherapy is unknown, an increase in IgG or $IgG_4$ antibody activity, a decrease in allergen-specific IgE levels, and a decrease in basophil activity have all been implicated in mediating this response. Because allergen immunotherapy has been proven efficacious for treatment of some allergies, treatment with peanut immunotherapy is now being studied as a ppssible option. Our work showing the IgE binding epitopes of a major peanut allergen may allow for the use of immunodominant epitopes in this approach.

Another potential immunotherapeutic approach that has-recently attracted much attention is the use of DNA vaccines. In this approach a promoter region is placed 5' to the cDNA encoding the allergen and then introduced to the whole animal via intramuscular injection or intradermal application. Early work with a dust mite allergen, Der p 1, indicates that this approach can both prevent the development of an immunogenic response to a specific protein and dampen the response to a protein to which the animal has already been sensitized. We are currently exploring this possibility with the Ara h 2 allergen.

TABLE 25

| AMINO ACID SEQUENCE OF Ara h 2 PEPTIDES | |
|---|---|
| Peptide | Amino Acid Sequence |
| I | X-Q-Q-W-E-L-Q-G-D-R-R-Q-S-Q-L-E-R |
| II | A-N-L-R-P-C-E-Q-H-L-M-Q-K |

The amino acid sequence of the amino terminus (I) and a tryptic peptide (II) derived from Ara h 2 protein was determined. The sequence is shown as the one letter amino acid code.

TABLE 26

| Ara h 2 IgE BINDING EPITOPES | | |
|---|---|---|
| PEPTIDE | AA SEQUENCE | Ara h 2 POSITION |
| 1 | HASARQQWEL | 17–26 |
| 2 | QWELQGDRRC | 23–32 |
| 3 | DRRCQSQLER | 29–38 |
| 4 | LRPCEQHLMQ | 41–50 |
| 5 | KIQRDEDSYE | 51–60 |
| 6 | YERDPYSPSQ | 59–68 |
| 7 | SQDPYSPSPY | 67–76 |
| 8 | DRLQGRQQEQ | 117–126 |
| 9 | KRELRNLPQQ | 129–138 |
| 10 | QRCDLDVESG | 145–154 |

TABLE 27

IgE BINDING TO Ara h 2 EPITOPES

| | 1 | 2 | 3 | 4 | 5 | 6 | 7 | 8 | 9 | 10 | Epitopes/Pt |
|---|---|---|---|---|---|---|---|---|---|---|---|
| A | | X | | | X | X | X | | | | 4 |
| B | X | | X | X | | X | X | | | | 5 |
| C | X | | X | X | | X | X | | | | 5 |
| D | | | X | | | X | X | X | | | 4 |
| E | | X | X | | | X | X | | | | 4 |
| F | X | | X | X | | X | X | X | | X | 7 |
| G | | | X | | | X | X | | | | 3 |
| H | | | X | X | X | X | X | X | | | 6 |
| I | | | X | | | X | X | | | | 3 |
| J | X | | X | | | X | X | | X | | 5 |
| Pts/Epitope | 4 | 1 | 10 | 4 | 1 | 10 | 10 | 4 | 1 | 1 | |

Patients are indicated by letters (A–J) on the left hand side of the table. Ara h 2 peptides are indicated by number (1–10) across the top of the table. The number of epitopes recognized by each patient (epitopes/patient) is shown on the right hand side of the table. The number of patients that recognized each epitope is shown across the bottom of the table. An X indicates that a peptide bound IgE.

FIGURE LEGENDS

FIG. 27. Nucleotide Sequence of an Ara h II CDNA Clone. The nucleotide sequence is shown on the first line. The second line is the derived amino acid sequence. Bold amino acid residues. are those areas which correspond to the determined amino acid sequence of peptide I and II of Ara h II (Table 25). The numbers on the right of the figure indicate the nucleotide sequence.

FIG. 28. An Ara h II Clone Hybridizes to a 700 b Peanut mRNA. Peanut poly A+ RNA was isolated from Arachis hypogaea (Florunner) species and 10 μg were electrophoresed on formaldehyde denaturing agarose gels. Insert from an Ara h II clone was purified, labeled with alpha-$^{32}$P-dCTP, and used as a hybridization probe for Northern blot analysis of this gel. Sizes of known RNA species are expressed in kilobases along the right side of the figure.

FIG. 29. Multiple Predicted Antigenic Sites are Present in the Ara h 2 Allergen. The amino acid sequence of the Ara h 2 protein was analyzed for potential antigenic epitopes by the Jameson and Wolf (1988) algorithm. These predictions are based on a model that relates antigenicity to hydrophilicity, secondary structure, flexibility, and surface probability. There were 4 predicted regions (1–4) that contained multiple antigenic sites (octagons) along the entire length of the molecule. Amino acid residues (small numbers) are represented as alpha-helical (sinusoidal curve), Beta-sheet (saw tooth curve), and coil (flat sinusoidal curve) conformations. Beta turns are denoted by chain reversals.

FIG. 30. Multiple IgE Binding Sites Identified in the Ara h 2 Allergen. Epitope analysis was performed on the Ara h 2 allergen by synthesizing 15 amino acid long peptides, offset from each other by 8 amino acids for the entire protein molecule. These peptides, represented as spots 1–19, were then probed with a serum pool consisting of 15 patients with documented peanut hypersensitivity.

FIG. 31. Core IgE Binding Epitopes Identified on the Ara h 2 Allergen. Epitope analysis was performed on the IgE binding sites identified in FIG. 30 by synthesizing 10 amino acid long peptides offset by two amino acids. These peptides were then probed with the 18 patient serum pool. FIG. 31A is the peptide analysis of Ara h II amino acid residues 49–70. FIG. 31B identifies the amino acid sequence of this region.

Figure 32:
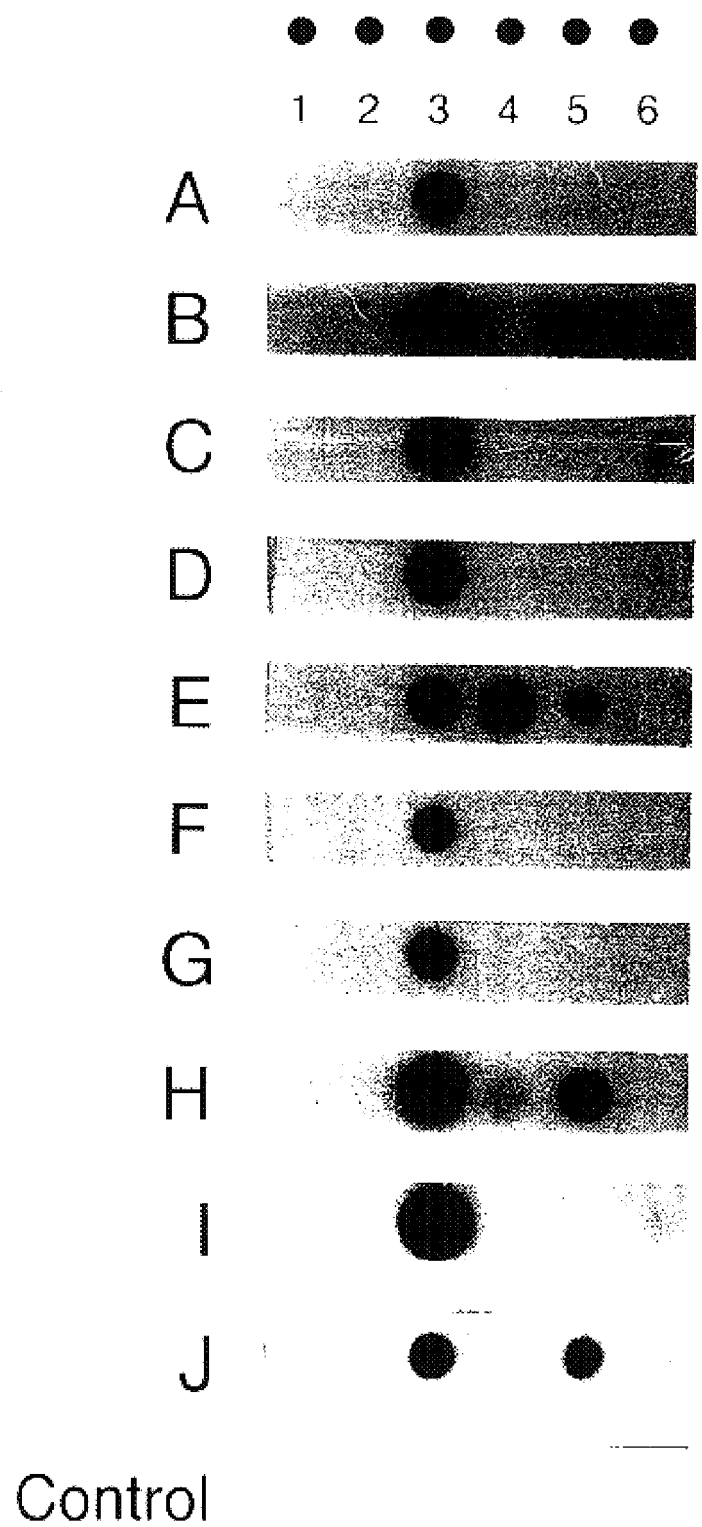

FIG. 32. Of the 10 patients five were selected at random from the 18 patient serum pool and five were patients with peanut hypersensitivity that were not included in the pool. Patient K represents a non-peanut sensitive (negative) control.

Characterization of a Major Peanut Allergen: Mutational Analysis of the Ara h 1 IgE Binding Epitopes Immediate hypersensitivity reactions to foods occur in about 6–8% of young children and 1% of adults. These reactions are mediated by the production of IgE antibodies to glycoproteins found in the food. Peanuts are a major cause of serious allergic reactions in both adults and children. Ara h 1, a major peanut allergen, has been extensively characterized and shown to contain 23 linear IgE binding epitopes. We set out to determine the amino acids critical to their binding and to determine the location of these epitopes on the 3-D structure of the Ara h 1 molecule. To accomplish this, mutational analysis of each epitope was performed by synthesizing 10 amino acid long peptides with single amino acids changed at each position to alanine, followed by determination of the IgE binding capacity of each mutated epitope relative to wild-type. It was determined that changes in those amino acids located at positions, 4, 5, and 6 of the epitope have a greater influence than residues located on either end. In addition, the substitution of most apolar, charged residues resulted in the loss of IgE. More importantly, 21/23 epitopes could be mutated to non-IgE binding by a single amino acid substitution. The 3-D model of the Ara h 1 protein indicates that the majority of the IgE binding epitopes are located on the surface of the molecule. Currently, we are determining what effect the amino acid substitutions that lead to loss of IgE binding will have on the tertiary structure of the protein.

Cloning, Epitope Mapping, and Mutational Analysis of Ara h 2, a Major Peanut Allergen A major peanut allergen, Ara h 2, is recognized by serum IgE from 90% of patients with peanut hypersensitivity. Biochemical characterization of this allergen indicates that it is a glycoprotein of ~17.5 kDa. Using N-terminal amino acid sequence data from purified Ara h 2, oligonucleotide primers were synthesized and used to identify a clone (700 bp) from a peanut cDNA library. This clone was capable of encoding a 17.5 kDa protein with homology to the conglutin family of seed storage proteins. The major linear IgE binding epitopes of this allergen were mapped using overlapping peptides synthesized on an activated cellulose membrane and pooled serum IgE from 15 peanut sensitive patients. Ten IgE binding epitopes were identified, distributed throughout the length of the Ara h 2 protein. The size of the epitopes ranged from 6–10 amino acids in length. Sixty-three percent of the amino acids represented in the epitopes were either polar or apolar uncharged residues. In an effort to determine which, if any, of the ten epitopes were recognized by the majority of patients with peanut hypersensitivity, each set of ten peptides was;probed individually with serum IgE from 10 different patients. All of the patient sera tested recognized multiple epitopes. Three epitopes (aa29–38, aa59–68, and 67–76) were recognized by all patients tested. Mutational analysis of these immunodominant epitopes indicate that single amino acid changes result in loss of IgE binding. Both epitopes contained in region aa59–76 contained the amino acid sequence DPYSPS that appears to be necessary for IgE binding. These results may allow for the design of improved diagnostic and therapeutic approaches to peanut hypersensitivity.

Ara h 3, a Peanut Allergen Identified by Using Peanut Sensitive Patient Sera Adsorbed With Soy Proteins Peanuts and soybeans are members of the legume family and share several common antigenic fractions. Patients allergic to one of these foods have serum IgE antibodies which immunologically cross-react with other legumes. However, ingestion of other legumes generally does not induce an allergic reaction, suggesting that cross-reacting antibodies to soy were removed from the sera of patients clinically allergic to peanuts. Adsorbed sera were then used to identify specific IgE binding to peanut immunoblots. Several peanut proteins ranging in size from 5 kDa to 49 kDa, were identified. A ~14 kDa protein identified in this manner was purified and prepared for amino acid sequence analysis. Amino terminal sequencing determined the first 23 amino acids of this protein. A search of the Genbank protein database with this peptide revealed that it had 61% identity with a soybean gene for glycinin subunit G3. A degenerate oligonucleotide primer was then designed from this data to use in conjunction with vector primers to amplify the clones that encode this protein from a peanut cDNA library. DNA sequencing of these clones also revealed ~70% homology with the soybean gene for glycinin subunit G3. These data indicate that while there is significant homology between the peanut and soybean glycinins there must be peanut-specific epitopes responsible for the binding of the soy-adsorbed serum IgE. Subsequent characterization of this allergen will include determination of the IgE binding epitopes and testing of the clinical relevance of this protein in peanut hypersensitivity. If this strategy is successful it will not only identify proteins that bind IgE but also those allergens and epitopes important in the disease process.

MAPPING OF THE B-CELL EPITOPES ON Ara h I AND Ara h II LEGUME STORAGE PROTEINS AND MAJOR ALLERGENS INVOLVED IN PEANUT HYPERSENSITIVITY

Approximately 8% of children and 1–2% of adults suffer from some form of food allergy. Reactions to peanuts are more likely than other food allergies to give rise to fatal or near fatal anaphylaxis in sensitized patients. Ara h I (MW= 63.5 kD) and Ara h II (MW=17 kD) are peanut proteins recognized by serum IgE from 90% of peanut sensitive patients, thus establishing them as clinically important allergens. Overlapping peptides representing the entire Ara h I and Ara h II molecules were constructed and IgE immunoblot analysis performed to determine which portions of these allergens were responsible for IgE binding. Utilizing a pool (n=15) of patients with peanut hypersensitivity, 23 IgE binding epitopes were identified on Ara h I and 6 epitopes were identified on Ara h II. Even though there were multiple epitopes identified on each allergen, two epitopes on Ara h I and one epitope on Ara h II were recognized by 90% of individual patient sera tested (n=l0). The amino acids important for IgE binding in these immunodominant epitopes were determined by mutational analysis. The identification of the major Ara h I and Ara h II IgE binding epitopes may lead to improved diagnosis of peanut hypersensitivity and eventually to an improved therapeutic regimen for this disease. SUPPORTED IN PART BY THE NATIONAL INSTITUTE OF HEALTH, CLARISSA SOSIN ALLERGY RESEARCH FOUNDATION, AND ARKANSAS SCIENCE AND TECHNOLOGY AUTHORITY.

INTRODUCTION

Approximately 1–2% of USA population suffers from some for of food allergy. Peanuts, fish, tree nuts, and shell fish account for the majority of food hypersensitivity reactions in adults; while peanuts, milk, and eggs cause over 80% of food hypersensitivity reactions in children. Unlike the food hypersensitivity reactions to milk and eggs, peanut hypersensitivity reactions usually persist into adulthood and last for a lifetime. In addition, hypersensitivity reactions to peanuts tend to be more severe than those to other food allergens, sometimes resulting in death. Several reports have detailed the fatal and near-fatal anaphylactic reactions occurring in adolescents and adults. Currently, avoidance is the only effective means of dealing with food allergy, but the use of peanuts and peanut by-products as supplements in many different foods makes accidental consumption almost inevitable.

Two major allergens involved in peanut hypersensitivity are the peanut proteins, Ara h I and Ara h II. These proteins are recognized by 90% of peanut positive patients, thus establishing them as clinically important allergens. Both proteins are seed storage proteins. Ara h I shares significant sequence homology with vicilin proteins from other plants while Ara h II is a conglutin like protein.

Food hypersensitivity reactions occur shortly after contact of a specific allergen with its corresponding IgE antibodies which are bound to mast cells. IgE, when complexed with antigen, will activate mast cells to release histamine, heparin, and other substances which are responsible for the clinical symptoms observed. Thus the IgE binding epitopes of the allergens play an important role in the disease process and their elucidation will lead to a better understanding of the human immune response involved in food hypersensitivity reactions and to improved diagnostic and therapeutic capabilities.

FIGS. 22 and 29. Multiple Predicted Antigenic Sites in the Ara h I and Ara h II Allergens The amino acid sequences of the Ara h I and Ara h II proteins were analyzed for potential antigenic epitopes. These predictions are based on a model that relates antigenicity to hydrophilicity, secondary structure, flexibility, and surface probability. There were 11 (1–11) predicted regions that contained multiple antigenic sites (octagons) along the entire length of the Ara h I protein and 4 (1–4) predicted regions on the Ara h II protein. Amino acid residues (small numbers) are represented as alpha-helical (sinusoidal curve), Beta sheet (saw tooth curve), and coil (flat sinusoidal curve) conformations. Beta turns are denoted by chain reversals.

FIGS. 23 and 30. Multiple IgE Binding Regions Identified in the Ara h I and Ara h II Allergens Upper Panels: Epitope mapping was performed on the Ara h I and Ara h II allergens by synthesizing each of these proteins in 15 amino acid long overlapping peptides that were offset from each other by 8 amino acids. These peptides were then probed with a pool of serum IgE from 15 patients with documented peanut hypersensitivity. The position of the peptides within the Ara h I and Ara h II proteins are indicated on the left hand side of each panel. Lower Panels: The amino acid3 sequences of the Ara h I and Ara h II proteins are shown in the lower panels. The numbered boxes correspond to the predicted antigenic regions (P1–P11; P1–P4). The hatched boxes (D1–D12; D1–4) correspond to the IgE binding regions shown in the upper panels.

FIGS. 24 and 31. Core IgE Binding Epitopes Identified in the Ara h I and Ara h II Allergens Detailed epitope mapping was performed on IgE binding regions identified in FIG. 23 and 30 by synthesizing 10 amino acid long peptides offset from each other by two amino acids. These peptides were then probed with pool of serum IgE from 15 patients with documented peanut hypersensitivity. The data shown represents regions D2 and a portion of D3 from Ara h I and region D2 from Ara h II. Numbers correspond to peptides as shown in Table 28. The amino acid sequences of Ara h I and Ara h II that were tested in the upper panels are shown. Shaded areas of boxes correspond to IgE binding peptides.

FIGS. 25 and 32. Conmonly Recognized Ara h I Epitopes

Core IgE binding epitopes were synthesized (10 amino acids long) and then probed individually with serum IgE from 10 patients with documented peanut hypersensitivity. The top panels represent where each of Ara h I peptides (1–23) and Ara h II peptides (1–6) were placed on the membrane. Panels A–J show the peptides that bound serum IgE from each patient. The control panels were probed with sera from a patient with elevated IgE but who does not have peanut hypersensitivity.

FIGS. 26 and 33. Amino Acids Involved in IgE Binding

Epitopes 4 and 17 from Ara h I and epitope 3 from Ara h II were synthesized with a glycine (G) or alanine (A) residue substituted for one of the amino acids in each of these peptides and then probed with a pool of serum IgE from 15 patients with documented peanut hypersensitivity. The letters across the top of each panel indicate the one letter amino acid code for the residue normally at that position and the amino acid that was substituted for it. The numbers indicate the position of each residue in the Ara h I and Ara h II proteins.

SUMMARY

The major peanut allergens Ara h I and Ara h II have been cloned, sequenced, and identified as seed storage proteins.

B-cell epitopes of Ara h I and 6 B-cell epitopes of Ara h II were mapped using synthetic peptides probed with serum IgE from a population of peanut hypersensitive patients.

Epitope #4 (AA89–98) and #17 (AA498–507) of Ara h I and epitope #3 (AA59–66) of Ara h II.were recognized by 90% of peanut hypersensitive patients tested.

Amino acids important to IgE binding of the immunodominant epitopes of Ara h I and Ara h II were determined.

FIG. 34 is the same as FIG. 16 with peptides I, II, III corresponding to the peptides in Table 14 highlighted by rectangular boxes.

Table 32 is a partial Ara h I Beta sequence (clone 5Ala).
Table 33 is an Ara h I Alpha sequence (clone p17).
Table 34 is the Ara h II sequence (clone Ara h II p38).
Table 35 is the Ara h I Beta sequence (clone p41b).
Table 36 is the Ara h II p38 translation of Ara h II p38.

TABLE 28

Ara h I IgE Binding Epitopes

| PEPTIDE | AA SEQUENCE* | Arah I POSITION |
|---|---|---|
| 1 | A K S S P Y Q K K T | 25–34 |
| 2 | Q E P D D L K Q K A | 48–57 |
| 3 | L E Y D P R L V Y D | 65–74 |
| 4 | G E R T R G R Q P G | 89–98 |
| 5 | P G D Y D D D R R Q | 97–105 |
| 6 | P R R E E G G R W G | 107–116 |
| 7 | R E R E E D W R Q P | 123–132 |
| 8 | E D W R R P S H Q Q | 134–143 |
| 9 | Q P R K I R P E G R | 143–152 |
| 10 | T P G Q F E D F F P | 294–303 |
| 11 | S Y L Q E F S R N T | 311–320 |
| 12 | F N A E F N E I R R | 325–334 |
| 13 | E Q E E R G Q R R W | 344–353 |
| 14 | D I T N P I N L R E | 393–402 |
| 15 | N N F G K L F E V K | 409–418 |
| 16 | G T G N L E L V A V | 461–470 |
| 17 | R R Y T A R L K E G | 498–507 |
| 18 | E L H L L G F G I N | 525–534 |
| 19 | H R I F L A G D K D | 539–548 |
| 20 | I D Q I E K Q A K D | 551–560 |
| 21 | K D L A F P G S G E | 559–568 |
| 22 | K E S H F V S A R P | 578–587 |
| 23 | P E K E S P E K E D | 597–606 |

Ara h II IgE Binding Epitopes

| PEPTIDE | AA SEQUENCE* | Arah II POSITION |
|---|---|---|
| 1 | L L A A H A S A R Q | 14–23 |
| 2 | Q G D R R C Q S Q L | 27–36 |
| 3 | Y E R D P Y S P S Q | 60–69 |
| 4 | A G S S Q H Q E R C | 81–90 |
| 5 | C N E L N E F E N N | 91–100 |
| 6 | Q R C D L D V E S G | 105–159 |

*The underlined portions of each peptide are the smallest IgE binding sequences as determined by the analysis as described in FIG. 31.

TABLE 29

Ara h I Epitopes
IgE binding of core Ara h I epitopes by serum from peanut hypersensitive individuals.

| Patients | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | Epitopes/Patient |
|---|---|---|---|---|---|---|---|---|---|---|---|---|---|---|---|---|---|---|---|---|---|---|---|---|
| A |  |  |  | X | X |  |  |  |  |  |  |  |  | X |  | X | X |  | X |  |  |  |  | 6 |
| B | X | X |  | X | X |  |  |  |  |  |  |  |  |  | X |  | X |  |  |  |  |  |  | 6 |
| C | X | X | X | X | X | X |  |  | X |  |  | X | X |  | X |  | X |  |  |  |  | X |  | 12 |
| D | X |  |  | X | X |  |  |  |  |  |  |  |  | X |  | X |  |  |  |  |  |  |  | 6 |

TABLE 29-continued

Ara h I Epitopes
IgE binding of core Ara h I epitopes by serum from peanut hypersensitive individuals.

| Patients | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | Epitopes/Patient |
|---|---|---|---|---|---|---|---|---|---|---|---|---|---|---|---|---|---|---|---|---|---|---|---|---|
| E | | | X | X | | | | X | X | X | X | X | | | | | X | | | X | X | X | | 11 |
| F | | X | | X | | | | | X | | | | | | | | X | | | | | | | 4 |
| G | X | X | X | | | | | | | | | | X | | | X | X | | | | | | | 6 |
| H | | X | | X | | | | | | | | | | | | | X | | | | | | | 3 |
| I | | | | X | | | | X | X | | | | | | | | X | X | X | X | | | X | 8 |
| J | | | | X | | | | X | X | | X | | | | | | X | | X | | X | | | 7 |
| Patients/Epitope | 4 | 5 | 3 | 9 | 4 | 1 | 0 | 3 | 4 | 2 | 1 | 3 | 3 | 1 | 3 | 1 | 10 | 2 | 1 | 4 | 1 | 3 | 1 | |

Ara h II Epitopes

IgE binding of core Ara h II epitopes by serum from peanut hypersensitive individuals

| Patients | 1 | 2 | 3 | 4 | 5 | 6 | Epitopes/Patient |
|---|---|---|---|---|---|---|---|
| A | | X | | | | | 1 |
| B | | X | | X | | | 2 |
| C | | X | | | X | | 2 |
| D | | X | | | X | | 2 |
| E | | X | X | X | | | 3 |
| F | | X | | | | | 1 |
| G | | X | | | | | 1 |
| H | | X | X | X | | | 3 |
| I | | X | | | X | | 2 |
| J | | X | | X | X | | 3 |
| Patients/Epitope | 0 | 0 | 10 | 2 | 4 | 4 | |

Patients are indicated by letters (A–J) on the left hand side of the table. Ara h I & II peptides are indicated by number across the top of the table. The number of epitopes recognized by each patient (epitopes/patient) is shown on the right hand side of the table. The number of patients that recognized each epitope (patients/epitope) is shown across the bottom of the table. An X indicates that a peptide bound IgE.

TABLE 30

IDENTIFICATION OF NATIVE AMINO ACID SEQUENCES IN THE DEDUCED
AMINO ACID SEQUENCE OF CLONE ARA H 2 P38
THE FOLLOWING AMINO ACID SEQUENCE WAS TRANSLAED
FROM THE ARA H 2 P39 GENE
(NUCLEOTIDE SEQUENCE) ISOLATED FROM OUR cDNA LIBRARY.
TRANSLATION of GENE: arah2p38

```
                                          N-terminal sequence
1    LTILVALALF LLAAHASAR  QWELQGDRRC QSQLER ANLR PCEOHLMQKI
                                                  peptide 45 peptide 37
51   QRDEDSYERD PYSPSQDPYS PSPYDRRGAG SSQHQERCCN ELNEFENNQR peptide 20
101  CMCEALQQIM ENQSDRLQGR QQEQQFKREL RNLPQQCGLR APQRCDLDVE

151  SGGRDRY
```

TABLE 31

The following information was obtained by
physicochemical measures and used
to confirm the deduced amino acid sequence
from clone Ara h 2 p 38.

17 5 kD N-TERMINAL SEQUENCE: gene sequence 19---48

| 1 | 2 | 3 | 4 | 5 | 6 | 7 | 8 | 9 | 10 | 11 | 12 | 13 |
|---|---|---|---|---|---|---|---|---|---|---|---|---|
| GLY | GLN | GLN | TRP | GLU | LEU | GLN | GLY | ASP | ARG | ARG | ARG | GLN |

TABLE 31-continued

The following information was obtained by
physicochemical measures and used
to confirm the deduced amino acid sequence
from clone Ara h 2 p 38.

| 14 | 15 | 16 | 17 | 18 | 19 | 20 | 21 | 22 | 23 | 24 | 25 | |
|----|----|----|----|----|----|----|----|----|----|----|----|---|
| Q  | Q  | W  | E  | L  | Q  | G  | D  | R  | R  | R  | Q  |   |
| SER| GLN| LEU| GLU| ARG| ALA| ASN| LEU| X  | PRO| X  | GLU|   |
| S  | Q  | L  | E  | R  | A  | N  | L  | R  | P  | C  | E  |   |
| 26 | 27 | 28 | 29 | 30 |    |    |    |    |    |    |    |   |
| GLN| X  | LEU| MET| X  |    |    |    |    |    |    |    |   |
| Q  | H  | K  | M  |    |    |    |    |    |    |    |    |   |

PEPTIDE 20: identified in gene sequence 121---128:

| 1 | 2 | 3 | 4 | 5 | 6 | 7 | 8 |
|---|---|---|---|---|---|---|---|
| GLN | GLN | GLU | GLN | GLN | PHE | LYS | ARG |
| Q | Q | E | Q | Q | F | K | R |

PEPTIDE 37: identified in gene sequence 60–76:

| 1 | 2 | 3 | 4 | 5 | 6 | 7 | 8 | 9 | 10 | 11 | 12 | 13 |
|---|---|---|---|---|---|---|---|---|----|----|----|----|
| ASP | PRO | TYR | SER | PRO | SER | GLN | ASP | PRO | TYR | SER | PRO | SER |
| D | P | Y | S | P | S | Q | D | P | Y | S | P | S |
| 14 | 15 | 16 | 17 |
| PRO | TYR | ASP | ARG |
| P | Y | D | R |

PEPTIDE 45: identified in gene sequence 37–49:

| 1 | 2 | 3 | 4 | 5 | 6 | 7 | 8 | 9 | 10 | 11 | 12 | 13 |
|---|---|---|---|---|---|---|---|---|----|----|----|----|
| ALA | ASN | LEU | ARG | PRO | CMC | GLU | GLN | HIS | LEU | MET | GLN | LYS |
| A | N | L | R | P | C | E | Q | H | L | M | Q | K |

TABLE 32

```
LOCUS       ARQARAHI    1340 bp ss-mRNA            PLN
DEFINITION  Arachis hypogea (clone 5 Ala) Ara h I mRNA, complete cds.
ACCESSION   L34402
KEYWORDS    .
SOURCE      Arachis hypogea (strain Florunner) seed CDNA to mRNA.
ORGANISM    Arachis hypogea
            Eukaryota; Plantae; Embryobionta; magnoliophyta; Magnoliopsida;
            Rosidae; Fabales; Fabaceae.
REFERENCE   1  (bases 1 to 1340)
AUTHORS     Burks,A.W., Cockrell,G., Stanley,J.S., Helm,R.M. and Bannon,G.A.
TITLE       Recombinant peanut allergen Ara h I expression and IgE binding
            in patients with peanut hypersensitinity
JOURNAL     Unpublished (1994)
STANDARD    full automatic
COMMENT     NCBI gi: 508640
FEATURES              Location/Qualifiers
     source           1.1340
                      /organisims = "Arachis hypogea"
                      /strain = "Florunner"
                      /dev_stage = "seed"
                      /sequenced_mol = "cDNA to mRNA"
     CDS              231..1238
                      /gene = "Ara h I"
                      /note = "NCBI gi: 508641"
                      /codon_start = 1
/translation = "MPVNTPGQFEDFFPASSRDQSSYLQGFSRNTLEAAFNAEFNEIR
RVLLEENAGGEQEERGQRRWSTRSSENNEGVIVKVSKEHVEELTKHAKSVSKKGSEEE
GDITNPINLREGEPDLSNNFGKLFEVKPDKKNPQLQDLDMMLTCVEIKEGALMLPHFN
SKAMVIVVVNKGTGNLELVAVRKEQQQRGRREEEEDEDEEEEGSNREVRRYTARLKEG
DVFIMPAAHPVAINASSELHLLGFGINAENNHRIFLAGDKDNVIDQIEKQAKDLAFPG
SGEQVEKLIKNQKESHFVSAQSQSQSPSSPEKESPEKEDQEEENQGGKGPLLSILKAF
N"
BASE COUNT   422 a    296 c    340 g    282 t
ORIGIN
Arqarahi   Length: 1340          05:04   Type: N   Check: 8329
       1    GTATTGTGCA GATCGAGGCC AAACCTAACA CTCTTGTTCT TCCCAAGCAC
      51    GCTGATGCTG ATAACATCCT TGTTATCCAG CAAGGGCAAG CCACCGTGAC
     101    CGTAGCAAAT GGCAATAACA GAAAGAGCTT TAATCTTGAC GAGGGCATG
     151    CACTCAGAAT CCCATCCGGT TTCATTTCCT ACATCTTGAA CCGCCATGG
     201    AACCAGAACC TCAGAGTAGC TAAAATCTCC ATGCCCGTTA ACACACCCGG
     251    CCAGTTTGAG GATTTCTTCC CGGCGAGCAG CCGAGACCAA TCATCCTACT
     301    TGCAGGGCTT CAGCAGGAAT ACGTTGGAGG CCGCCTTCAA TGCGGAATTC
     351    AATGAGATAC GGAGGGTGCT GTTAGAAGAG AATGCAGGAG GTGAGCAAGA
```

TABLE 32-continued

```
 401    GGAGAGAGGG CAGAGGCGAT GGAGTACTCG GAGTAGTGAG AACAATGAAG
 451    GAGTGATAGT CAAAGTGTCA AAGGAGCACG TTGAAGAACT TACTAAGCAC
 501    GCTAAATCCG TCTCAAAGAA AGGCTCCGAA GAAGAGGGAG ATATCACCAA
 551    CCCAATCAAC TTGAGAGAAG GCGAGCCCGA TCTTTCTAAC AACTTTGGGA
 601    AGTTATTTGA GGTGAAGCCA GACAAGAAGA ACCCCCAGCT TCAGGACCTG
 651    GACATGATGC TCACCTGTGT AGAGATCAAA GAAGGAGCTT TGATGCTCCC
 701    ACACTTCAAC TCAAAGGCCA TGGTTATCGT CGTCGTCAAC AAAGGAACTG
 751    GAAACCTTGA ACTCGTGGCT GTAAGAAAAG AGCAACAACA GAGGGGACGG
 801    CGGGAAGAAG AGGAGGACGA AGACGAAGAA GAGGAGGGAA GTAACAGAGA
 851    GGTGCGTAGG TACACAGCGA GGTTGAAGGA AGGCGATGTG TTCATCATGC
 901    CAGCAGCTCA TCCAGTAGCC ATCAACGCTT CCTCCGAACT CCATCTGCTT
 951    GGCTTCGGTA TCAACGCTGA AAACAACCAC AGAATCTTCC TTGCAGGTGA
1001    TAAGGACAAT GTGATAGACC AGATAGAGAA GCAAGCGAAG GATTTAGCAT
1051    TCCCTGGGTC GGGTGAACAA GTTGAGAAGC TCATCAAAAA CCAGAAGGAA
1101    TCTCACTTTG TGAGTGCTCA ATCTCAATCT CAATCTCCGT CGTCTCCTGA
1151    GAAAGAGTCT CCTGAGAAAG AGGATCAAGA GGAGGAAAAC CAAGGAGGGA
1201    AGGGTCCACT CCTTTCAATT TTGAAGGCTT TTAACTGAGA ATGGAGGCAA
1251    CTTGTTATGT ATCGATAATA AGATCACGCT TTTGTACTCT ACTATCCAAA
1301    AACTTATCAA TAAATAAAAA CGTTTGTGCG TTGTTTCTCC
```

TABLE 33

```
LOCUS         ARQARAH         1949 bp    mRNA                PLN
DEFINITION    Arachis hypogea (clone P17) Ara h I mRNA, complete cds.
ACCESSION     L38853
NID           g620024
KEYWORDS      peanut hypersensitivity.
SOURCE        Arachis hypogea (strain Florunner) seed cDNA to mRNA.
ORGANISM      Arachis hypogea
              Eukaryota; Plantae; Embryobionta; magnoliophyta; Magnoliopsida;
              Rosidae; Fabales; Fabaceae.
REFERENCE     1 (bases 1 to 1949)
AUTHORS       Burks,A.W., Cockrell,G., Stanley,J.S., Helm,R.M. and Bannon,G.A.
TITLE         Recombinant peanut allergen Ara h I expression and IgE binding in
              patients with peanut hypersensitivity
JOURNAL       Unpublished (1994)
COMMENT       NCBI gi: 620024
FEATURES              Location/Qualifiers
     source           1..1949
                      /organism = "Arachis hypogea"
                      /strain = "Florunner"
                      /dev_stage = "Seed"
                      /sequenced_mol = "cDNA to mRNA"
     5'UTR            1..2
     CDS              3..1847
                      /gene = "Ara h I"
                      /note = "NCBI gi: 620025"
                      /codon_start = 1
                      /db_xref="PID:g620025"
                      /translation = "MRGRVSPLMLLLGILVLASVSATQAKSPYRKTENPCAQRCLQSC
                      QQEPDDLKQKACESRCTKLEYDPRCVYDTGATNQRHPPGERTRGRQPGDYDDDRRQPR
                      REEGGRWGPAEPREREREEDWRQPREDWRRPSHQQPRKIRPEGREGEQEWGTPGSEVR
                      EETSRNNPFYFPSRRFSTRYGNQNGRIRVLQRFDQRSKQFQNLQNHRIVQIEARPNTL
                      VLPKHADADNILVIQQGQATVTVANGNNRKSFNLDEGHALRIPSGFISYILNRHDNQN
                      LRVAKISMPVNTPGQFEDFFPASSRDQSSYLQGFSRNTLEAAFNAEFNEIRRVLLEEN
                      AGGEQEERGQRRRSTRSSDNEGVIVKVSKEHVQELTKHAKSVSKKGSEEEDITNPINL
                      RDGEPDLSNNFGRLFEVKPDKKNPQLQDLDMMLTCVEIKEGALMLPHFNSKANVIVVV
                      NKGTGNLELVAVRKEQQQRGRREQEWEEEEEDEEEEGSNREVRRYTARLKEGDVFIMP
                      AAHPVAINASSELHLLGFGINAENNHRIFLAGDKDNVIDQIEKQAKDLAFPGSGEQVE
KLIKNQRESHFVSARPQSQSPSSPEKEDQEEENQGGKGPLLSILKAFN"
     3'UTR            1848..1949
     polyA_site       1949
BASE COUNT       599 a    455 c    517 g    378 t
ORIGIN
Arqarah       Length: 1949      1996 16:44  Type: N  Check: 6409
    1    CAATGAGAGG GAGGGTTTCT CCACTGATGC TGTTGCTTGG GATCCTTGTC
   51    CTGGCTTCAG TTTCTGCAAC GCAGGCCAAG TCACCTTACC GGAAAACAGA
  101    GAACCCCTGC GCCCAGAGGT GCCTCCAGAG TTGTCAACAG GAACCGGACG
  151    ACTTGAAGCA AAAGGCATGC GAGTCTCGCT GCACCAAGCT CGAGTATGAT
  201    CCTCGTTGTG TCTATGACAC TGGCGCCACC AACCAACGTC ACCCTCCAGG
  251    GGAGCGGACA CGTGGCCGCC AACCCGGAGA CTACGATGAT GACGCCGTC
  301    AACCCCGAAG AGAGGAAGGA GGCCGATGGG GACCAGCTGA ACCGAGGGAG
  351    CGTGAAAGAG AAGAAGACTG GAGACAACCA AGAGAAGATT GGAGGCGACC
  401    AAGTCATCAG CAGCCACGGA AAATAAGGCC CGAAGGAAGA GAAGGAGAAC
  451    AAGAGTGGGG AACACCAGGT AGCGAGGTGA GGGAAGAAAC ATCACGGAAC
  501    AACCCTTTCT ACTTCCCGTC AAGGCGGTTT AGCACCCGCT ACGGGAACCA
```

TABLE 33-continued

```
 551    AAACGGTAGG ATCCGCGTCC TGCAGAGGTT TGACCAAAGG TCAAAGCAGT
 601    TTCAGAATCT CCAGAATCAC CGTATTGTGC AGATCGAGGC CAGACCTAAC
 651    ACTCTTGTTC TTCCCAAGCA CGCTGATGCT GATAACATCC TTGTTATCCA
 701    GCAAGGACAA GCCACCGTGA CCGTAGCAAA TGGCAATAAC AGAAAGAGCT
 751    TTAATCTTGA CGAGGGCCAT GCACTCAGAA TCCCATCCGG TTTCATTTCC
 801    TACATCTTGA ATCGACATGA CAACCAGAAC CTCAGAGTAG CTAAAATCTC
 851    CATGCCCGTT AACACGCCCG GCCAGTTTGA GGATTTCTTC CCGGCGAGCA
 901    GCCGAGACCA ATCATCCTAC TTGCAGGGAT TCAGCAGGAA TACTTTGGAG
 951    GCCGCCTTCA ATGCGAATT CAATGAGATA CGGAGGGTGC TGTTAGAAGA
1001    GAATGCAGGA GGAGAGCAAG AGGAGAGAGG GCAGAGGCGA CGGAGTACTC
1051    GGAGTAGTGA TAATGAAGGA GTGATAGTCA AAGTGTCAAA GGAGCACGTT
1101    CAAGAACTTA CTAAGCACGC TAAATCCGTC TCAAAGAAAG GCTCCGAAGA
1151    GGAAGATATC ACCAACCCAA TCAACTTGAG AGATGGCAG CCCGATCTTT
1201    CTAACAACTT TGGGAGGTTA TTTGAGGTGA AGCCAGACAA GAAGAACCCC
1251    CAGCTTCAGG ACCTGGACAT GATGCTCACC TGTGTAGAGA TCAAAGAAGG
1301    AGCTTTGATG CTCCCACACT TCAACTCAAA GGCCATGGTC ATCGTCGTCG
1351    TCAACAAAGG AACTGGAAAC CTTGAACTCG TAGCTGTAAG AAAAGAGCAA
1401    CAACAGAGGG GACGGCGGGA ACAAGAGTGG AAGAAGAGG AGGAAGATGA
1451    AGAAGAGGAG GGAAGTAACA GAGAGGTGCG TAGGTACACA GCGAGGTTGA
1501    AGGAAGGCGA TGTGTTCATC ATGCCAGCAG CTCATCCAGT AGCCATCAAC
1551    GCTTCCTCCG AACTCCATCT GCTTGGCTTC GGTATCAACG CTGAAAACAA
1601    CCACAGAATC TTCCTTGCAG GTGATAAGGA CAATGTGATA GACCAGATAG
1651    AGAAGCAAGC GAAGGATTTA GCATTCCCTG GTTCGGGTGA ACAAGTTGAG
1701    AAGCTCATCA AAACCAGAG GGAGTCTCAC TTTGTGAGTG CTCGTCCTCA
1751    ATCTCAATCT CCGTCGTCTC CTGAAAAAGA GGATCAAGAG GAGGAAAACC
1801    AAGGAGGGAA GGGTCCACTC CTTTCAATTT TGAAGGCTTT TAACTGAGAA
1851    TGGAGGAAAC TTGTTATGTA TCCATAATAA GATCACGCTT TTGTAATCTA
1901    CTATCCAAAA ACTTATCAAT AAATAAAAAC GTTTGTGCGT TGTTTCTCC
```

TABLE 34

```
LOCUS       ARQALLII      717 bp     DNA                  PLN
DEFINITION  Arachis hypogea (clone Ara h II p38) allergen II gene, polyA
            signal.
ACCESSION   L77197
NID         g1236995
KEYWORDS    allergen; conglutin; seed storage protein.
SOURCE      Arachis hypogea (strain Florunner) (clone: Ara h II p38) DNA.
ORGANISM    Arachis hypogea
            Eukaryotae; mitochondrial eukaryotes; Viridiplantae;
            Charophyta/Embryophyta group; Embryophyta; Magnoliophyta;
            Magnoliopsida; Rutanae; Sapindales; Fabaceae; Papilionoideae;
            Arachis.
REFERENCE   1  (bases 1 to 717)
AUTHORS     Stanley, J. S.
TITLE       The major peanut allergen Ara h II is a seed storage protein with multiple
            IgE-binding epitopes
JOURNAL     Unpublished (1996)
FEATURES             Location/Qualifiers
     source          1..717
                     /organism = "Arachis hypogea"
                     /strain = "Florunner"
                     /clone = "Ara h II p38"
     polyA_signal    562..567
BASE COUNT     217 a      152 c      184 g     164 t
ORIGIN
Argallii    Length: 717            1996 14:32  Type: N  Check: 3606
  1         GCTCACCATA CTAGTAGCCC TCGCCCTTTT CCTCCTCGCT GCCCACGCAT
 51         CTGCGAGGCA GCAGTGGGAA CTCCAAGGAG ACAGAAGATG CCAGAGCCAG
101         CTCGAGAGGG CGAACCTGAG GCCCTGCGAG CAACATCTCA TGCAGAAGAT
151         CCAACGTGAC GAGGATTCAT ATGAACGGGA CCCGTACAGC CTAGTCAGG
201         ATCCGTACAG CCCTAGTCCA TATGATCGGA GAGGCGCTGG ATCCTCTCAG
251         CACCAAGAGA GGTGTTGCAA TGAGCTGAAC GAGTTTGAGA CAACCAAAG
301         GTGCATGTGC GAGGCATTGC AACAGATCAT GGAGAACCAG AGCGATAGGT
351         TGCAGGGGAG CAACAGGAG CAACAGTTCA GAGGGAGCT CAGGAACTTG
401         CCTCAACAGT GCGGCCTTAG GGCACCACAG CGTTGCGACT GGACGTCGA
451         AAGTGGCGGC AGAGACAGAT ACTAAACACC TATCTCAAAA AAGAAAAGA
501         AAAGAAAAGA AAATAGCTTA TATATAAGCT ATTATCTATG GTTATGTTTA
551         GTTTTGGTAA TAATAAAGAT CATCACTATA TGAATGTGTT GATCGTGTTA
601         ACTAAGGCAA GCTTAGGTTA TATGAGCACC TTTAGAGTGC TTTTATGGCG
651         TTGTCTATGT TTTGTTGCTG CAGAGTTGTA ACCATCTTGA AATAATATAA
701         AAAGATCATG TTTTGTT
```

TABLE 35

```
LOCUS        ARQARAHI     2032 bp    mRNA              PLN
DEFINITION   Arachis hypogea (clone P41b) Ara h I mRNA, complete cds.
ACCESSION    L34402
NID          g602435
KEYWORDS     allergen.
SOURCE       Arachis hypogea (strain Florunner) seed cDNA to mRNA.
ORGANISM     Arachis hypogea
             Eukaryota; Plantae; Embryobionta; Magnoliophyta; Magnoliopsida;
             Rosidae; Fabales; Fabaceae.
REFERENCE    1  (bases 1 to 2032)
AUTHORS      Burks,A.W., Cockrell,G., Stanley,J.S., Helm,R.M. and Bannon,G.A.
TITLE        Recombinant peanut allergen Ara h I expression and IgE binding in patients
             with peanut hypersensitinity
JOURNAL      unpublished (1994)
STANDARD     full automatic
COMMENT      NCBI gi: 602435
FEATURES             Location Qualifiers
     source          1..2032
                     /organism = "Arachis hypogea"
                     /strain = "Florunner"
                     /dev_stage = "seed"
                     /sequenced_mol = "cDNA to mRNA"
                     /clone = "P41b"
     5'UTR           <1..49
     CDS             50..1930
                     /gene = "Ara h I"
                     /note = "NCBI gi: 602436"
                     /codon start = 1
                     /db_ref = "PID:g602436"
                     /translation = "MRGRVSPLMLLLGILVLASVSATHAKSSPYQKKTENPCAQRCLQ
                     SCQQEPDDLKQKACESRCTKLEYDPRCVYDPRGHTGTTNQRSPPGERTRGRQPGDYDD
                     DRRQPRREEGGRWGPAGPREREREEDWRQPREDWRRPSHQQPRKIRPEGREGEQEWGT
                     PGSHVREETSRNNPFYFPSRRFSTRYGNQNGRIRVLQRFDQRSRQFQNLQNHRIVQIE
                     AKPNTLVLPKHADADNILVIQQGQATVTVANGNNRKSFNLDEGHALRIPSGFISYILN
                     RHDNQNLRVAKISMPVNTPGQFEDFFPASSRDQSSYLQGFSRNTLEAAFNAEFNEIRR
                     VLLEENAGGEQEERGQRRWSTRSSENNEGVIVKVSKEHVEELTKHAKSVSKKGSEEEG
                     DITNPINLREGEPDLSNNFGKLFEVKPDKKNPQLQDLDMMLTCVEIKEGALMLPHFNS
                     KAMVIVVVNKGTGNLELVAVRKEQQQRGRREEEEDEDEEEEGSNREVRRYTARLKEGD
                     VFIMPAAHPVAINASSELHLLGFGINAENNHRIFLAGDKDNVIDQIEKQAKDLAFPGS
                     GEQVEKLIKNQKESHFVSARPQSQSQSPSSPEKESPEKEDQEEENQGGKGPLLSILKA
                     FN"
     3'UTR           1931..2032
     polyA_signal    2005..2010
     polyA_site      2032
BASE COUNT       628 A     473 C      530 G      401t
ORIGIN
Araqarahi    Length: 2032          1996 16:36  Type: N  Check: 8370
    1        AATAATCATA TATATTCATC AATCATCTAT ATAAGTAGTA GCAGGAGCAA
   51        TGAGAGGGAG GGTTTCTCCA CTGATGCTGT TGCTAGGGAT CCTTGTCCTG
  101        GCTTCAGTTT CTGCAACGCA TGCCAAGTCA TCACCTTACC AGAAGAAAAC
  151        AGAGAACCCC TGCGCCCAGA GGTGCCTCCA GAGTTGTCAA CAGGAACCGG
  201        ATGACTTGAA GCAAAAGGCA TGCGAGTCTC GCTGCACCAA GCTCGAGTAT
  251        GATCCTCGTT GTGTCTATGA TCCTCGAGGA CACACTGGCA CCACAAACCA
  301        ACGTTCCCCT CCAGGGGAGC GGACACGTGG CCGCCAACCC GGAGACTACG
  351        ATGATGACCG CCGTCAACCC CGAAGAGAGG AAGGAGGCCG ATGGGGACCA
  401        GCTGGACCGA GGGAGCGTGA AGAGAAGAA GACTGGAGAC AACCAAGAGA
  451        AGATTGGAGG CGACCAAGTC ATCAGCAGCA ACGGAAAATA AGGCCCGAAG
  501        GAAGAGAAGG AGAACAAGAG TGGGGAACAA CAGGTAGCCA TGTGAGGGAA
  551        GAAACATCTC GGAACAACCC TTTCTACTTC CCGTCAAGGC GGTTTAGCAC
  601        CCGCTACGGG AACCAAAACG GTAGGATCCG GGTCCTGCAG AGGTTTGACC
  651        AAAGGTCAAG GCAGTTTCAG AATCTCCAGA ATCACCGTAT TGTGCAGATC
  701        GAGGCCAAAC CTAACACTCT TGTTCTTCCC AAGCACGCTG ATGCTGATAA
  751        CATCCTTGTT ATCCAGCAAG GGCAAGCCAC CGTGACCGTA GCAAATGGCA
  801        ATAACAGAAA GAGCTTTAAT CTTGACGAGG GCCATGCACT CAGAATCCCA
  851        TCCGGTTTCA TTTCCTACAT CTTGAACCGC ATGACAACC AGAACCTCAG
  901        AGTAGCTAAA ATCTCCATGC CCGTTACAC ACCCGGCCAG TTTGAGGATT
  951        TCTTCCCGGC GAGCAGCCGA GACCAATCAT CCTACTTGCA GGGCTTCAGC
 1001        AGGAATACGT TGGAGGCCGC CTTCAATGCG GAATTCAATG AGATACGGAG
 1051        GGTGCTGTTA GAAGAGAATG CAGGAGGTGA GCAAGAGGAG AGAGGGCAGA
 1101        GGCGATGGAG TACTCGGAGT AGTGAGAACA ATGAAGGAGT GATAGTCAAA
 1151        GTGTCAAAGG AGCACGTTGA AGAACTTACT AAGCACGCTA AATCCGTCTC
 1201        AAAGAAAGGC TCCGAAGAAG AGGGAGATAT CACCAACCCA ATCAACTTGA
 1251        GAGAAGGCGA GCCCGATCTT TCTAACAACT TTGGGAAGTT ATTTGAGGTG
 1301        AAGCCAGACA AGAAGAACCC CCAGCTTCAG GACCTGGACA TGATGCTCAC
 1351        CTGTGTAGAG ATCAAAGAAG GAGCTTTGAT GCTCCCACAC TTCAACTCAA
 1401        AGGCCATGGT TATCGTCGTC GTCAACAAAG GAACTGGAAA CCTTGAACTC
 1451        GTGGCTGTAA GAAAAGAGCA ACAACAGAGG GGACGGCGGG AAGAAGAGGA
 1501        GGACGAAGAC GAAGAAGAGG AGGGAAGTAA CAGAGAGGTG CGTAGGTACA
 1551        CAGCGAGGTT GAAGGAAGGC GATGTGTTCA TCATGCCAGC AGCTCATCCA
```

TABLE 35-continued

| | | | | |
|---|---|---|---|---|
| 1601 | GTAGCCATCA | ACGCTTCCTC | CGAACTCCAT | CTGCTTGGCT | TCGGTATCAA |
| 1651 | CGCTGAAAAC | AACCACAGAA | TCTTCCTTGC | AGGTGATAAG | GACAATGTGA |
| 1701 | TAGACCAGAT | AGAGAAGCAA | GCGAAGGATT | TAGCATTCCC | TGGGTCGGGT |
| 1751 | GAACAAGTTG | AGAAGCTCAT | CAAAAACCAG | AAGGAATCTC | ACTTTGTGAG |
| 1801 | TGCTCGTCCT | CAATCTCAAT | CTCAATCTCC | GTCGTCTCCT | GAGAAAGAGT |
| 1851 | CTCCTGAGAA | AGAGGATCAA | GAGGAGGAAA | ACCAAGGAGG | GAAGGGTCCA |
| 1901 | CTCCTTTCAA | TTTTGAAGGC | TTTTAACTGA | GAATGGAGGC | AACTTGTTAT |
| 1951 | GTATCGATAA | TAAGATCACG | CTTTTGTACT | CTACTATCCA | AAAACTTATC |
| 2001 | AATAAATAAA | AACGTTTGTG | CGTTGTTTCT | CC | |

TABLE 36

```
GENIE> type arah2p38.pep
TRANSLATE of: arah2p38.final check: 9822 from: 4 to: 480
generated symbols 1 to: 159.
Arah2p38.Pep  Length: 157        1996 15:24  Type: P  Check: 2859
     1 LTILVALALF LLAAHASARQ QWELQGDRRC QSQLERANLR PCEQHLMQKI
    51 QRDEDSYERD PYSPSQDPYS PSPYDRRGAG SSQHQERCCN ELNEFENNQR
   101 CMCEALQQIM ENQSDRLQGR QQEQQFKREL RNLPQQCGLR APQRCDLDVE
   151 SGGRDRY
```

In accordance with the present invention, it is contemplated that the discovery or identification of particular peptides or epitopes which bind IgE and cause an IgE response by a person having an allergy or sensitivity to that particular protein may be used to produce a DNA vaccine for immunization therapy to hopefully reduce the IgE response and thereby eliminate or reduce the negative effects of the allergy or sensitivity. For example, a protein, peptide, or epitope can be produced and injected into a patient as a DNA vaccine which hopefully will. have an immuno modulation effect of the IgE response and stimulate a different response, such as IgG, IgM, IgA, etc. and thereby down regulate IgE senthesis to the specific allergen.

Also in accordance with the present invention, similar peptides, epitopes and IgE binding proteins from other legumes, herbs, oil seeds, and the like, for example soybeans or wheat, can be isolated and identified, mutated so that they do not bind IgE, and used in a mutated DNA vaccine for immunization therapy.

Thus, it will be appreciated that as a result of the present invention, a highly effective improved immunization or vaccination therapy, immunoassay, amino acid or DNA sequence, peanut allergens, antibodies, cell lines, treatment compositions, and methods are provided by which the principal objective, among others is completely fulfilled. It is contemplated, and will be apparent to those skilled in the art from the preceding description and accompanying drawings, that modifications and/or changes may be made in the illustrated embodiments without departure from the present invention. Accordingly, it is expressly intended that the foregoing description and accompanying drawings are illustrative of preferred embodiments only, not limiting, and that the true spirit and scope of the present invention be determined by reference to the appended claims.

What is claimed is:

1. An isolated nucleic acid encoding peanut allergen Ara h 1.

2. The isolated nucleic acid of claim 1 comprising either one of SEQ ID NO 4 or 5, or a nucleotide molecule hybridizing thereto.

3. The isolated nucleic acid of claim 2 consisting essentially of SEQ ID NO 4.

4. The isolated nucleic acid of claim 2 consisting essentially of SEQ ID NO 5.

5. The isolated nucleic acid of claim 1, which isolated nucleic acid includes an expression vector.

6. The isolated nucleic acid of claim 1, or a fraction thereof, further including a diagnostic label.

* * * * *